(12) United States Patent
Doble et al.

(10) Patent No.: US 10,942,932 B2
(45) Date of Patent: *Mar. 9, 2021

(54) SYSTEM AND METHOD FOR GRADING AND SCORING FOOD

(71) Applicant: Everything Food, Inc., Orange, CA (US)

(72) Inventors: Daniel Edwin Doble, Irvine, CA (US); Peter B. Balsells, Orange, CA (US)

(73) Assignee: Everything Food, Inc., Orange, CA (US)

( * ) Notice: Subject to any disclaimer, the term of this patent is extended or adjusted under 35 U.S.C. 154(b) by 104 days.

This patent is subject to a terminal disclaimer.

(21) Appl. No.: 16/296,028

(22) Filed: Mar. 7, 2019

(65) Prior Publication Data

US 2019/0303374 A1 Oct. 3, 2019

Related U.S. Application Data

(63) Continuation-in-part of application No. 16/250,935, filed on Jan. 17, 2019.

(Continued)

(51) Int. Cl.
*G06F 16/2457* (2019.01)
*G06F 16/248* (2019.01)
(Continued)

(52) U.S. Cl.
CPC ...... *G06F 16/24578* (2019.01); *G06F 16/248* (2019.01); *G06F 16/284* (2019.01); *G16H 20/60* (2018.01); *G01N 33/02* (2013.01)

(58) Field of Classification Search
CPC .......... G09B 19/0092; G06F 16/24578; G06F 16/284
(Continued)

(56) References Cited

U.S. PATENT DOCUMENTS 5,832,446 A 11/1998 Neuhaus
6,180,934 B1 1/2001 Ishizaki et al.
(Continued)

FOREIGN PATENT DOCUMENTS

CN 101582102 A 11/2009
CN 103530496 A 1/2014
(Continued)

OTHER PUBLICATIONS

International Search Report and Written Opinion received in PCT Application No. PCT/US2019/014057, dated Apr. 2, 2019.
(Continued)

*Primary Examiner* — Hung T Vy
(74) *Attorney, Agent, or Firm* — Knobbe, Martens, Olson & Bear, LLP

(57) ABSTRACT

A system and method of providing food-related information is provided. The method includes receiving a user-generated food-related query regarding at least one food, accessing, in response to the query, at least one computer database having a plurality of nutrition values indicative of an amount per calorie in the food member of a corresponding substance, calculating a nutrition quotient for each food member, and transmitting, in response to the query, the nutrition quotients for the food members of the at least one selected table, to the user.

20 Claims, 88 Drawing Sheets

Related U.S. Application Data

(60) Provisional application No. 62/640,480, filed on Mar. 8, 2018, provisional application No. 62/620,358, filed on Jan. 22, 2018.

(51) Int. Cl.
  *G16H 20/60* (2018.01)
  *G06F 16/28* (2019.01)
  *G01N 33/02* (2006.01)

(58) Field of Classification Search
  USPC .......................................... 707/738; 434/127
  See application file for complete search history.

(56) References Cited

U.S. PATENT DOCUMENTS

| | | |
|---|---|---|
| 6,204,763 B1 | 3/2001 | Sone |
| 6,283,914 B1 | 9/2001 | Mansfield et al. |
| 6,553,386 B1 | 4/2003 | Alabaster |
| 6,585,516 B1 | 7/2003 | Alabaster |
| 6,872,077 B2 | 3/2005 | Yeager |
| 6,980,999 B1 | 12/2005 | Grana |
| 7,090,638 B2 | 8/2006 | Vidgen |
| 7,249,708 B2 | 7/2007 | McConnell et al. |
| 7,297,109 B2 | 11/2007 | Brown |
| 7,706,994 B2 | 4/2010 | Ramsden |
| 7,907,054 B1 | 3/2011 | Nguyen |
| 7,959,567 B2 | 6/2011 | Stivoric et al. |
| 7,974,881 B2 | 7/2011 | Culver et al. |
| 8,219,584 B2 | 7/2012 | Starr |
| 8,249,946 B2 | 8/2012 | Froseth et al. |
| 8,382,482 B2 | 2/2013 | Miller-Kovach et al. |
| 8,419,433 B2 | 4/2013 | Do et al. |
| 8,504,440 B1 | 8/2013 | Kolawa et al. |
| 8,647,121 B1 | 2/2014 | Witlin et al. |
| 8,690,578 B1 | 4/2014 | Nusbaum et al. |
| 8,740,060 B2 | 6/2014 | Aihara et al. |
| 8,768,727 B2 | 7/2014 | Schwarzberg et al. |
| 8,920,175 B2 | 12/2014 | Black et al. |
| 8,924,239 B1 | 12/2014 | Kurple |
| 8,990,274 B1 | 3/2015 | Hwang |
| 9,011,153 B2 | 4/2015 | Bennett et al. |
| 9,147,211 B2 | 9/2015 | Catlett |
| 9,212,996 B2 | 12/2015 | Watson et al. |
| 9,269,133 B2 | 2/2016 | Cho et al. |
| 9,449,208 B2 | 9/2016 | Luk et al. |
| 9,475,685 B2 | 10/2016 | Davenport et al. |
| 9,483,547 B1 | 11/2016 | Feller et al. |
| 9,519,620 B1 | 12/2016 | Pinel et al. |
| 9,536,449 B2 | 1/2017 | Connor |
| 9,552,461 B2 | 1/2017 | Harrison |
| 9,572,361 B2 | 2/2017 | Bordin |
| 9,734,182 B2 | 8/2017 | Bhatt et al. |
| 9,754,508 B2 | 9/2017 | Sharar et al. |
| 9,760,856 B2 | 9/2017 | Chouhan et al. |
| 2002/0046060 A1 | 4/2002 | Hoskyns |
| 2002/0049652 A1 | 4/2002 | Moore et al. |
| 2002/0120534 A1 | 8/2002 | Howard et al. |
| 2002/0157411 A1 | 10/2002 | Ishikawa et al. |
| 2002/0161652 A1 | 10/2002 | Paullin et al. |
| 2003/0200200 A1 | 10/2003 | Hughes |
| 2003/0204412 A1 | 10/2003 | Brier |
| 2005/0240434 A1 | 10/2005 | Wooten et al. |
| 2006/0017894 A1 | 1/2006 | Empel et al. |
| 2006/0199155 A1 | 9/2006 | Mosher |
| 2007/0152048 A1 | 7/2007 | Jung et al. |
| 2007/0191689 A1 | 8/2007 | Elitok |
| 2007/0269557 A1 | 11/2007 | Culver et al. |
| 2009/0144081 A1 | 6/2009 | Harlan |
| 2009/0177639 A1 | 7/2009 | Zerdoun |
| 2010/0187306 A1 | 7/2010 | Solomon |
| 2010/0198605 A1 | 8/2010 | Saulet |
| 2010/0216098 A1 | 8/2010 | Montgomery |
| 2010/0313768 A1 | 12/2010 | Koether et al. |
| 2011/0055044 A1 | 3/2011 | Wiedl |
| 2011/0160902 A1 | 6/2011 | Postins |
| 2011/0202359 A1 | 8/2011 | Rak |
| 2011/0213667 A1 | 9/2011 | Ierullo |
| 2012/0016781 A1 | 1/2012 | Hashimoto |
| 2012/0072842 A1 | 3/2012 | Yuan et al. |
| 2012/0096087 A1 | 4/2012 | Curcelli |
| 2012/0101876 A1 | 4/2012 | Turvey et al. |
| 2012/0209890 A1 | 8/2012 | Nowacki |
| 2012/0254196 A1 | 10/2012 | Abramski et al. |
| 2012/0260683 A1 | 10/2012 | Cheon et al. |
| 2012/0317505 A1 | 12/2012 | Schwartz et al. |
| 2012/0322032 A1 | 12/2012 | Smith |
| 2012/0323729 A1 | 12/2012 | Kline |
| 2013/0007615 A1 | 1/2013 | Goldman |
| 2013/0052616 A1 | 2/2013 | Silverstein et al. |
| 2013/0108993 A1 | 5/2013 | Katz |
| 2013/0110582 A1 | 5/2013 | Starkman |
| 2013/0117106 A1 | 5/2013 | Glassman et al. |
| 2013/0138656 A1 | 5/2013 | Wheaton |
| 2013/0149675 A1 | 6/2013 | Slone et al. |
| 2013/0149676 A1 | 6/2013 | Tokuda et al. |
| 2013/0149678 A1 | 6/2013 | Tokuda et al. |
| 2013/0149679 A1 | 6/2013 | Tokuda et al. |
| 2013/0171304 A1 | 7/2013 | Huntley |
| 2013/0183642 A1 | 7/2013 | Wan |
| 2013/0224694 A1 | 8/2013 | Moore et al. |
| 2013/0262995 A1 | 10/2013 | Howell |
| 2013/0280681 A1 | 10/2013 | Narayan et al. |
| 2014/0072936 A1 | 3/2014 | Herron et al. |
| 2014/0095479 A1 | 4/2014 | Chang et al. |
| 2014/0136368 A1 | 5/2014 | Brazell |
| 2014/0193783 A1 | 7/2014 | Jeong et al. |
| 2014/0200879 A1 | 7/2014 | Sakhai et al. |
| 2014/0220516 A1 | 8/2014 | Marshall et al. |
| 2014/0272817 A1 | 9/2014 | Park et al. |
| 2014/0379465 A1 | 12/2014 | Brazell |
| 2015/0079551 A1 | 3/2015 | Egan |
| 2015/0112759 A1 | 4/2015 | Hong et al. |
| 2015/0170543 A1 | 6/2015 | Sharar et al. |
| 2015/0212661 A1 | 7/2015 | Robberechts et al. |
| 2015/0220592 A1 | 8/2015 | Robberechts et al. |
| 2015/0323245 A1 | 11/2015 | Tan |
| 2016/0027330 A1 | 1/2016 | Briancon et al. |
| 2016/0066744 A1 | 3/2016 | Baxi et al. |
| 2016/0103834 A1 | 4/2016 | Altaf et al. |
| 2016/0103839 A1 | 4/2016 | Altaf et al. |
| 2016/0104225 A1 | 4/2016 | Stillman et al. |
| 2016/0140526 A1 | 5/2016 | Cummins et al. |
| 2016/0240101 A1 | 8/2016 | Rak |
| 2016/0253921 A9 | 9/2016 | Shrake |
| 2016/0372005 A1 | 12/2016 | Bajpai et al. |
| 2016/0379520 A1* | 12/2016 | Borel ................. G09B 19/0092 434/127 |
| 2016/0381742 A1 | 12/2016 | Banavara |
| 2017/0011649 A1 | 1/2017 | Lee et al. |
| 2017/0031995 A1 | 2/2017 | Bhatt et al. |
| 2017/0046980 A1 | 2/2017 | Mehta et al. |
| 2017/0116580 A1 | 4/2017 | Kim et al. |
| 2017/0162073 A1 | 6/2017 | Young et al. |
| 2017/0195542 A1 | 7/2017 | Thomas et al. |
| 2017/0206585 A1 | 7/2017 | Byron et al. |
| 2017/0213184 A1 | 7/2017 | Lee et al. |
| 2017/0316489 A1 | 11/2017 | Sampara et al. |

FOREIGN PATENT DOCUMENTS

| | | |
|---|---|---|
| CN | 104361039 A | 2/2015 |
| CN | 104573295 A | 4/2015 |
| CN | 105184719 A | 12/2015 |
| CN | 103062986 A | 1/2016 |
| CN | 105243614 A | 1/2016 |
| CN | 105276918 A | 1/2016 |
| CN | 205300106 U | 6/2016 |
| CN | 105989530 A | 10/2016 |
| CN | 106198900 A | 12/2016 |
| CN | 106296357 A | 1/2017 |
| CN | 106377153 A | 2/2017 |
| CN | 206056107 U | 3/2017 |
| EP | 1 176 377 A1 | 1/2002 |

(56) References Cited

FOREIGN PATENT DOCUMENTS

| | | |
|---|---|---|
| EP | 1 480 553 B1 | 1/2003 |
| EP | 2180299 A1 | 4/2010 |
| EP | 3100215 A2 | 12/2016 |
| EP | 3201807 A1 | 8/2017 |
| GB | 2368928 A | 5/2002 |
| JP | 2000-316492 A | 11/2000 |
| JP | 2002-115956 A | 4/2002 |
| JP | 2002-290955 A | 10/2002 |
| JP | 2004-348445 A | 12/2004 |
| JP | 2008-040778 A | 2/2008 |
| JP | 2011-203799 A | 10/2011 |
| JP | 5408891 B2 | 2/2014 |
| JP | 5811752 B2 | 11/2015 |
| JP | 2017-059021 A | 3/2017 |
| JP | 2017-068785 A | 4/2017 |
| JP | 6149233 B1 | 6/2017 |
| TW | 201437953 | 10/2014 |
| WO | WO 2001/020527 A1 | 3/2001 |
| WO | WO 2003/067373 A2 | 8/2003 |
| WO | WO 2003/079233 A1 | 9/2003 |
| WO | WO 2005/111955 A1 | 11/2005 |
| WO | WO 2006/066370 A1 | 6/2006 |
| WO | WO 2007/051049 A2 | 5/2007 |
| WO | WO 2007/077253 A1 | 7/2007 |
| WO | WO 2008/031163 A1 | 3/2008 |
| WO | WO 2010/136811 A1 | 12/2010 |
| WO | WO 2015/110925 A2 | 7/2015 |
| WO | WO 2015/135031 A1 | 9/2015 |
| WO | WO 2016/050958 A1 | 4/2016 |

OTHER PUBLICATIONS

Manual: "The Complete Guide to Eat This Much" Manual for Eat This Much in 29 pages. printed Sep. 5, 2017.
Press Release: LG Smart Instaview Refrigerator. http://www.lg.com/ca_en/press-release/lg-smart-instaview-refrigerator-features-voice-con-trol-webos-and-remote-viewing-capabilities; Toronto, Jan. 4, 2017.
Video: Learn More About What's Inside Smartlabel, http://www.smartlabel.org/about/learn-more-about-whats-inside-smartlabel; Published on Jul. 2, 2016.
Video: Liu, Sihan, et al, video: "What to Cook" https://www.youtube.com/watch?v=p9qLW-dHYuc; Published on Apr. 29, 2014.
Video: Murch, Steven, video: "BigOven: Cooking Simplified." https://www.youtube.com/watch?v=gcj-HWTpEXI; Published on May 31, 2016.
Video: Suresh, Prasanna, et al. Video: "What's for Dinner," https://www.slideshare.net/tommyroberts58910/pdf-34076215; Published on Apr. 29, 2014.
Webpage: Allrecipes, "Introducing a Cool New Way to Cook: Allrecipes on Amazon Alexa," http://dish.allrecipes.com/introducing-allrecipes-on-amazon-alexa/; printed Sep. 5, 2017.
Webpage: Be Food Smart, "Grading Scale." http://www.befoodsmart.com/ingredient-grading.php; printed Sep. 5, 2017.
Webpage: Check Ingredients, https://play.google.com/store/apps/details?id=com.anevar.ci&hl=en; printed Mar. 28, 2019.
Webpage: Diet Plan, https://play.google.com/store/apps/details?id=com.abma.dietplan&hl=en; printed Mar. 28, 2019.
Webpage: Diet Planner App Development, https://www.octalsoftware.com/diet-planner-app-development; printed Mar. 28, 2019.
Webpage: EWG's Food Scores, "Lay's Potato Chips Barbecue," http://www.ewg.org/foodscores/products/028400003001-LaysPotatoChipsBarbecueBarbecue: printed Nov. 29, 2017.
Webpage: EWG's Healthy Living, https://play.google.com/store/apps/details?id=com.skindeep.mobile; printed Mar. 28, 2019.
Webpage: Fitness Meal Planner, https://play.google.com/store/apps/details?id=com.fitnessmeals.fitnessmealplanner&hl=en; printed Mar. 28, 2019.
Webpage: Foodscanner, https://play.google.com/store/apps/details?id=com.ds.FoodScanner&hl=en; printed Mar. 28, 2019.
Webpage: Fooducate Weight Loss Coach, https://play.google.com/store/apps/details?id=com.fooducate.nutritionapp&referrer=utm_source%3Dfdct-redirect%26utm_campaign%3DFdct-Web-home-button-top%26utm_medium%3Dna; printed Apr. 5, 2019.
Webpage: Goodguide, https://itunes.apple.com/us/app/goodguide/id294447660?mt=8; printed Mar. 28, 2019.
Webpage: Grocery King: Android's Best Shopping List App, http://www.mobilemadly.com/2012/09/grocery-king-androids-best-shopping-list-app.html; printed Mar. 28, 2019.
Webpage: Grocery Shopping List Ease, https://www.verizonwireless.com/app-reviews/grocery-shopping-list-ease/; printed Mar. 28, 2019.
Webpage: ipiit—Scan Food Ingredients, https://play.google.com/store/apps/details?id=com.ipiit.ipiit&hl=en; Mar. 28, 2019.
Webpage: Is It Vegan? http://isitvegan.net/; printed Mar. 28, 2019.
Webpage: LG—New Food Management App That Averts Wastage of Food in Your Refrigerator, http://www.whatafuture.com/food-management-app-of-lg/; printed Mar. 28, 2019.
Webpage: Myfoodfacts (Know Your Food), http://www.myfoodfacts.com/; printed Mar. 28, 2019.
Webpage: Nutrition Made Simple, https://pinto.co/home; printed Mar. 28, 2019.
Webpage: Our Groceries, https://www.ourgroceries.com/user-guide; printed Mar. 28, 2019.
Webpage: Projects/Pantry Chef, http://courses.csail.mit.edu/6.831/wiki/index.php?title=Projects/PantryChef#Find_a_recipe; Printed Mar. 28, 2019.
Webpage: RecipeBook, https://recipebook.io/; printed Mar. 28, 2019.
Webpage: Recipe Software for Cooking, Diets& Nutrition, http://www.cooking-italian-food.com/recipewizard.html; printed Sep. 5, 2017.
Webpage: Safeeats: Allergen Alert, https://www.appannie.com/en/apps/ios/app/728374413/#; Mar. 28, 2019.
Webpage: Samsung Family-Hub Refrigerator. https://www.samsung.com/us/explore/family-hub-refrigerator/connected-hub/; Printed Mar. 28, 2019.
Webpage: Shopwell, http://www.shopwell.com/mobileapp; printed Mar. 28, 2019.
Webpage: Smart Foods Organic Diet Buddy, https://play.google.com/store/apps/details?id=com.saagara.organicbuddy&hl=en; printed Mar. 28, 2019.
Webpage: What is the Food Score or Food Grade?, https://www.mynetdiary.com/food-score.html; printed Mar. 28, 2019.
Webpage: Yuka Keeps Food Consumers Informed With Scandit Barcode Scanner Sdk, https://www.scandit.com/yuka-keeps-food-consumers-informed-with-scandit-barcode-scanner-sdk/; printed Mar. 28, 2019.
Bhatia, Aatish, "A New Kind of Food Science: How IBM Is Using Big Data to Invent Creative Recipes" https://www.wired.com/2013/11/a-new-kind-of-food-science/; WIRED. Nov. 16, 2013.
Freeman, Kate, "FoodSmart App Guides Consumers to Make Healthy, Delicious Choices," Mashable.com, Oct. 15, 2012. http://mashable.com/2012/10/15/foodsmart-app/#4IEpILDPOiqu.
Geleijnse, Gijs, "A Personalized Recipe Advice System to Promote Healthful Choices," IUI, Feb. 13, 2011.
Griffiths, Sarah, "Never run out of food again! Smart mat warns you when you're low on milk while Fridge Cam lets you remotely check what you already have during your weekly shop" DailyMail.com, Jan. 5, 2016.
Itzkovitch, Avi, "The Internet of Things and the Mythical Smart Fridge," UX Magazine, Sep. 18, 2013.
Kamieth, Felix, "Adaptive Implicit Interaction for Healthy Nutrition and Food Intake Supervision," Human-Computer Interaction. 2011.
Laczo, Lilla, "4 Healthy Eating Apps That Make You Want to Diet," https://shapescale.com/blog/health/4-healthy-eating-apps-that-make-you-want-to-diet/; Published Sep. 11, 2018.
Lardinois, Frederic, "Cooking with Google Home just got easier," https://techcrunch.com/2017/04/26/cooking-with-google-home-just-got-easier/; published Apr. 26, 2017.
Roeser, Mary Beth et al., "Oracle Database", Jul. 31, 2017, XP055573039, pp. 1-2, 8-4, and 9-1-9-3. retrieved from: https://docs.oracle.com/database/121/SQLRF/E41329-25.pdf.

(56) References Cited

OTHER PUBLICATIONS

Soper, Taylor, "Meet CookBrite: An app that recommends meals based on ingredients in your kitchen," GeekWire.com, Apr. 14, 2015.
Strom, Stephanie, "An App to Deconstruct Your Food," The New York Times, Jul. 18, 2016. https://well.blogs.nytimes.com/2016/07/18/an-app-to-deconstruct-your-food/, printed Mar. 28, 2019.
Teng, Chun-Yuen et al., "Recipe recommendation using ingredient networks," WebSci 2012, in 10 pgs.
Trujillo, Paul, "How Barcodes Are Revolutionizing Consumer Nutrition," Small Business Magazine, Jul. 19, 2016.
Wells, Jane, "A new cooking app that works like your car's GPS," https://www.cnbc.com/2014/11/25/cooking-app-for-smartphones-sidechef-app-like-a-gps-fo . . . ; published Nov. 26, 2014.
Brind, Mike, "Entity Framework Recipe: Hierarchical Data Management", https://www.mikesdotnetting.com/article/255/entity-framework-recipe-hierarchical-data-management [retrieved on Apr. 25, 2019] Oct. 24, 2014.
International Search Report and Written Opinion received in PCT Application No. PCT/US2019/021211, dated May 6, 2019.

* cited by examiner

FIG. 3:

| 350 → | 1 | 1 | 1 | 1 | 1 | 1 | 1 | 1 | 1 | 1 |
|---|---|---|---|---|---|---|---|---|---|---|
| 340 → |   |   |   |   |   |   |   | 2 | 2 | 2 |
| 340 → |   | 1 | 1 | 2 | 2 | 2 | 2 | 7 | 7 | 7 |
|   | Chicken | Cuts | Whole | Half | Quarter | Leg | Wing | Boneless with skin | Boneless and skinless | Skinless with bone |
| 330 → | 1 | 2 | 3 | 4 | 5 | 6 | 7 | 8 | 9 | 10 |

dbo.TemplateDefs

| TemplateDefID | Desc1 | TemplateRealmDesc1 | TemplateTierDesc1 |
|---|---|---|---|
| 1 | Food Class Alias Match | Food | Class |
| 2 | Food Primary Term Match | Food | Primary Term |
| 3 | Food Brand Match | Food | Brand |
| 4 | Food Manufacturer Match | Food | Manufacturer |
| 5 | Food Type Match | Food | Type |
| 6 | Equipment Class Alias Match | Equipment | Class |
| 7 | Equipment Type Match | Equipment | Type |
| 8 | Equipment Brand Match | Equipment | Brand |
| 9 | Equipment Manufacturer Match | Equipment | Manufacturer |
| 10 | Prep Def Alias Match | Preparation | Prep Defs |
| 11 | Prep Class Match | Preparation | Prep Class |
| 12 | Technique Match | Preparation | Technique |
| 13 | Recipe Class Alias Match | Recipe | Class |
| 14 | Recipe Primary Term Match | Recipe | Primary Term |
| 15 | Chef Match | Recipe | Chef |
| 16 | Restaurant Alias Match | Restaurant | Class |
| 17 | Restaurant Type Match | Restaurant | Type |

FIG. 5B:

dbo.TemplateBranchDefs

| TemplateDefID | TemplateBranchDefID1 | Desc1 |
|---|---|---|
| 1 | 1 | Other Forms within Same Top Level |
| 1 | 2 | Other Food Types, Same Form |
| 1 | 3 | List of Prep Defs |
| 1 | 4 | List of Equipment Classes |
| 1 | 5 | List of UPCs |
| 2 | 6 | List of Varieties for this Top Level |
| 2 | 7 | List of Forms for this Top Level |
| 2 | 8 | List of UPCs for this Top Level |
| 3 | 9 | List of Top Levels where this Brand Participates |
| 3 | 10 | List of Food Classes where this Brand Participates |
| 3 | 11 | List of UPCs for this Brand |

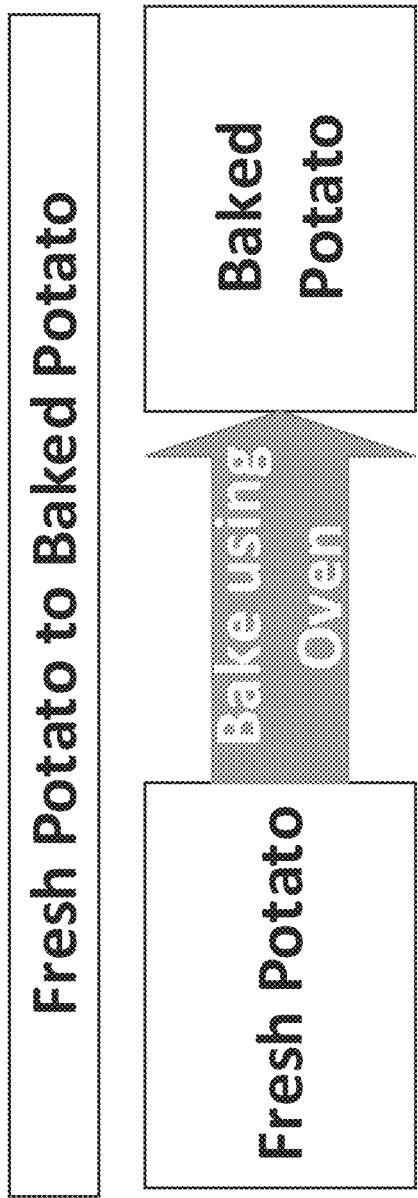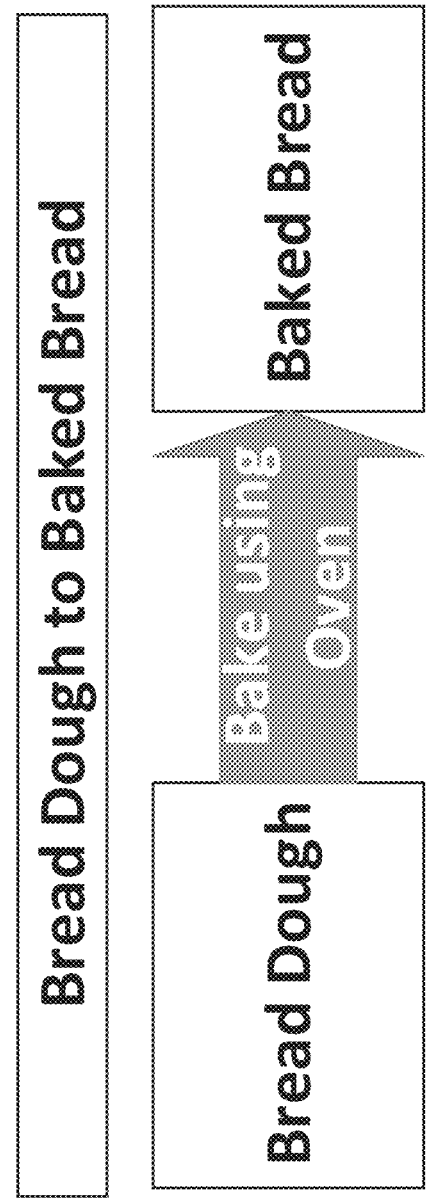

FIG. 12:

Node to Node: Basic Recipe

Fresh Apple Halves

Ingredients:

1) Fresh Apple

Steps:

1) Halve using a Chef Knife

Place the <ingredients/> onto the cutting board. Slice the item into two equal halves down its longest length.

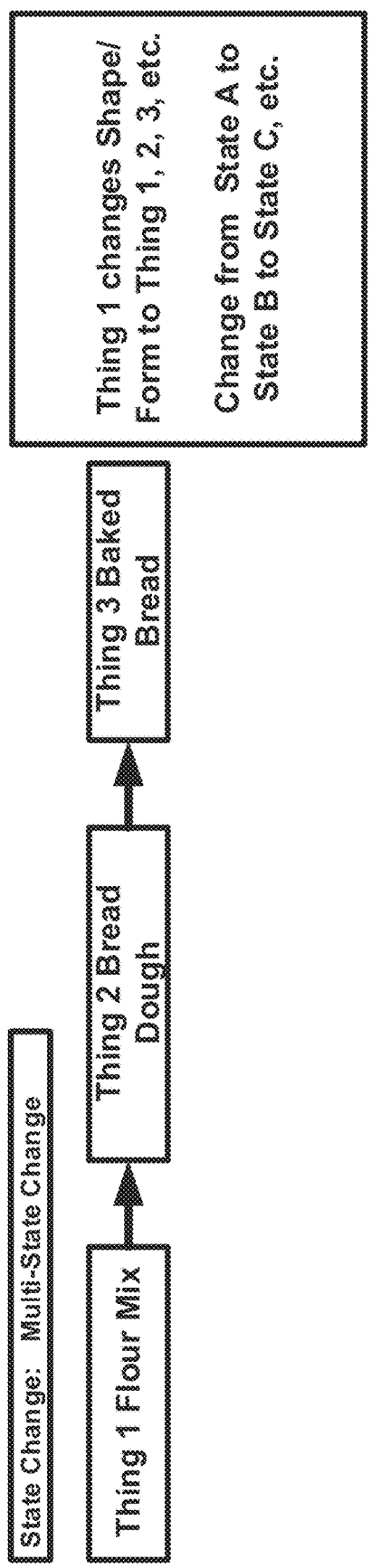
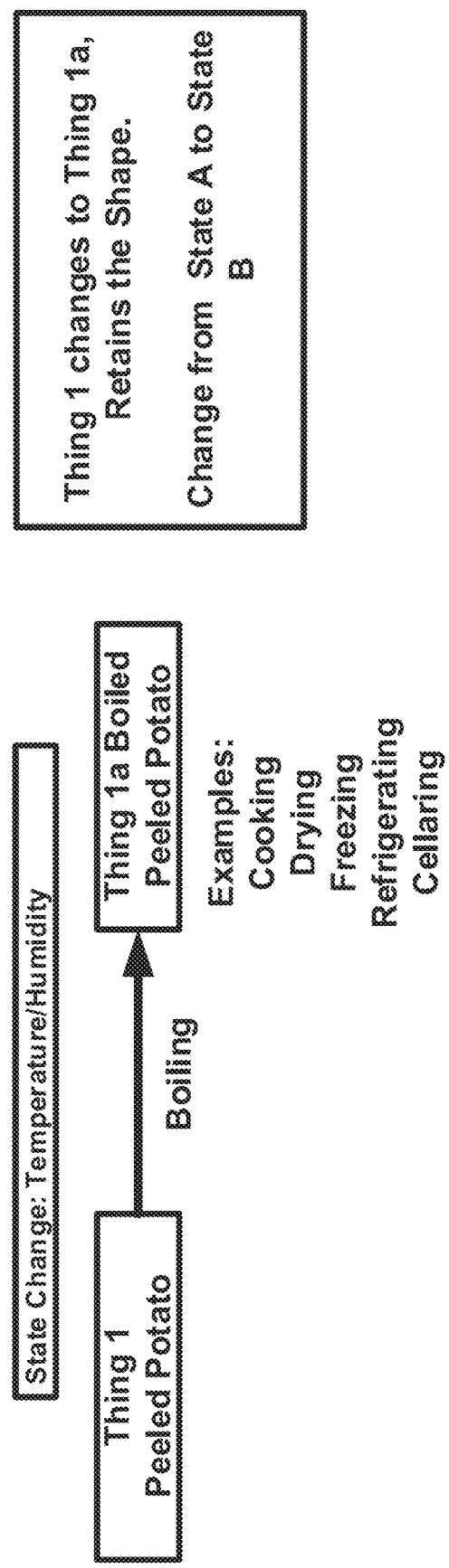
FIG. 17E:
FIG. 17F:

FIG. 18A:
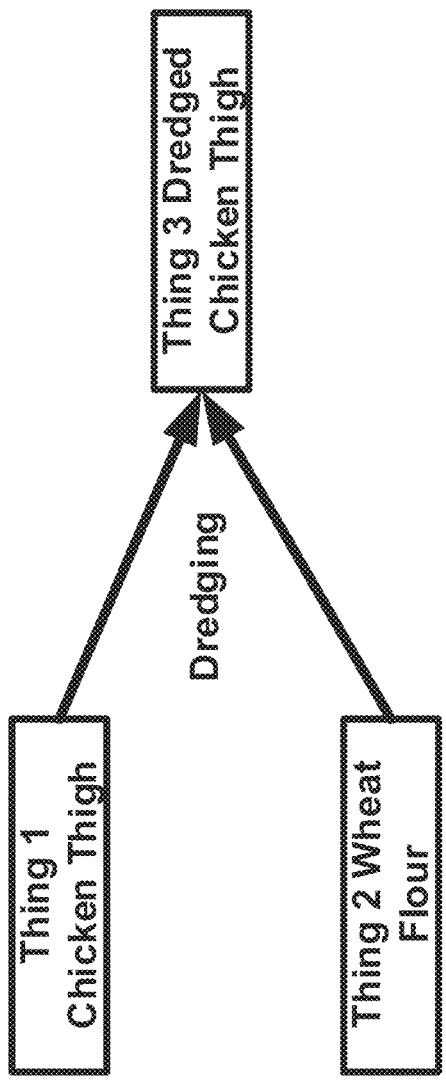
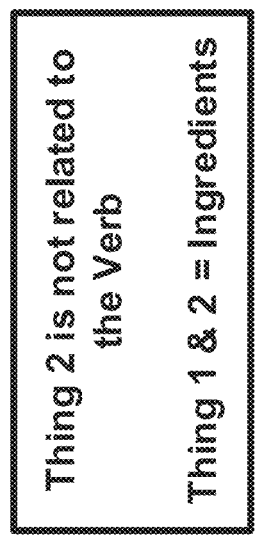
FIG. 18B:
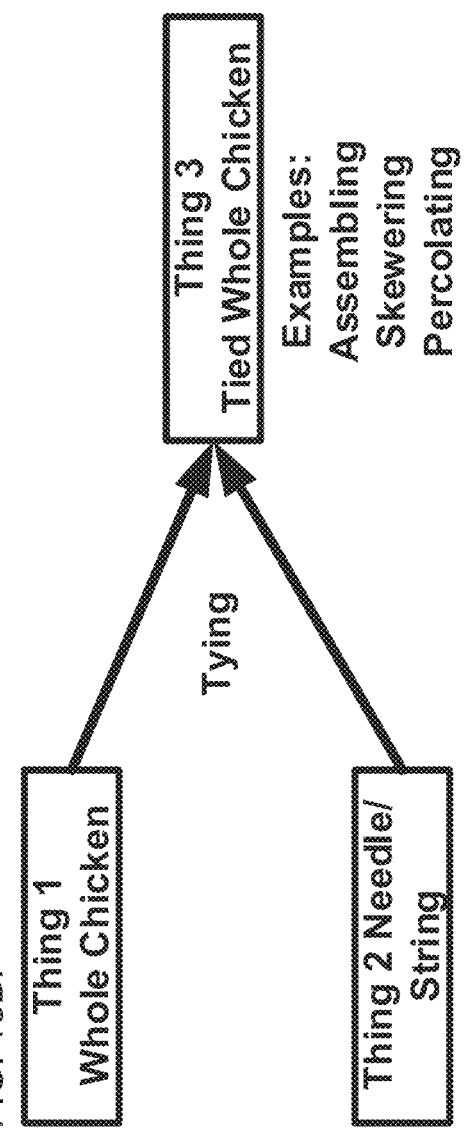
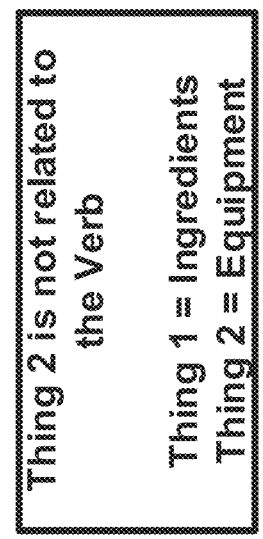

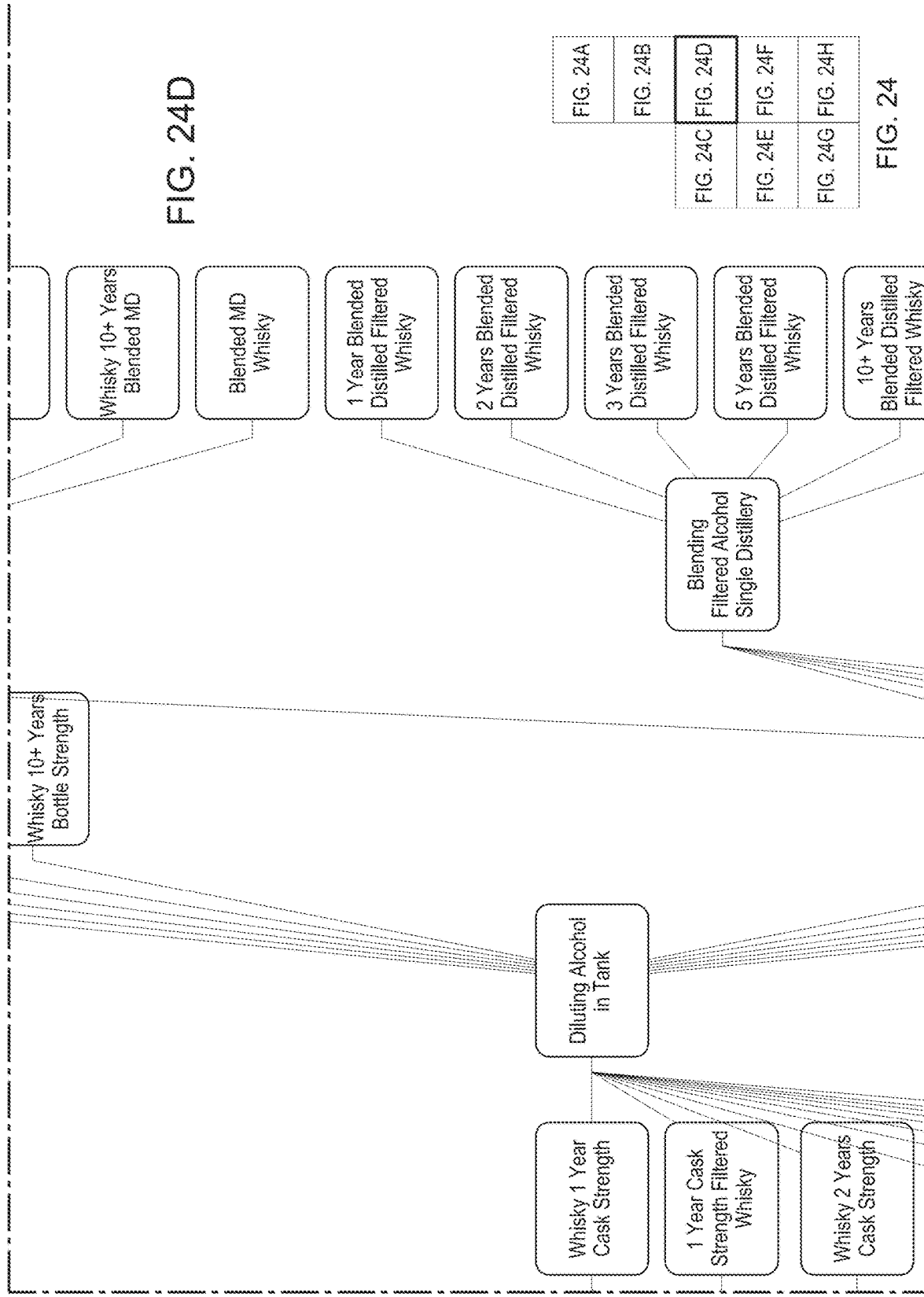

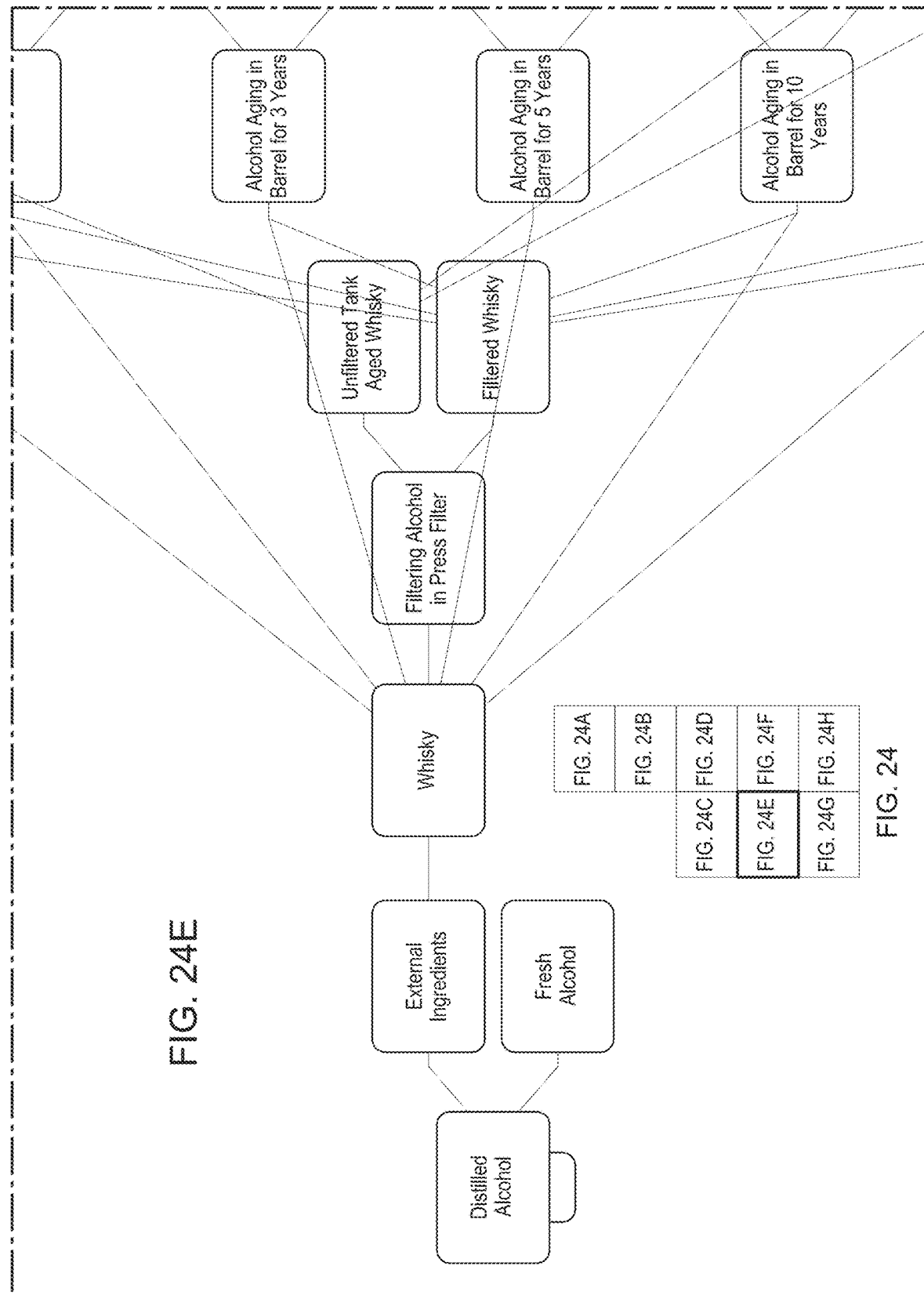

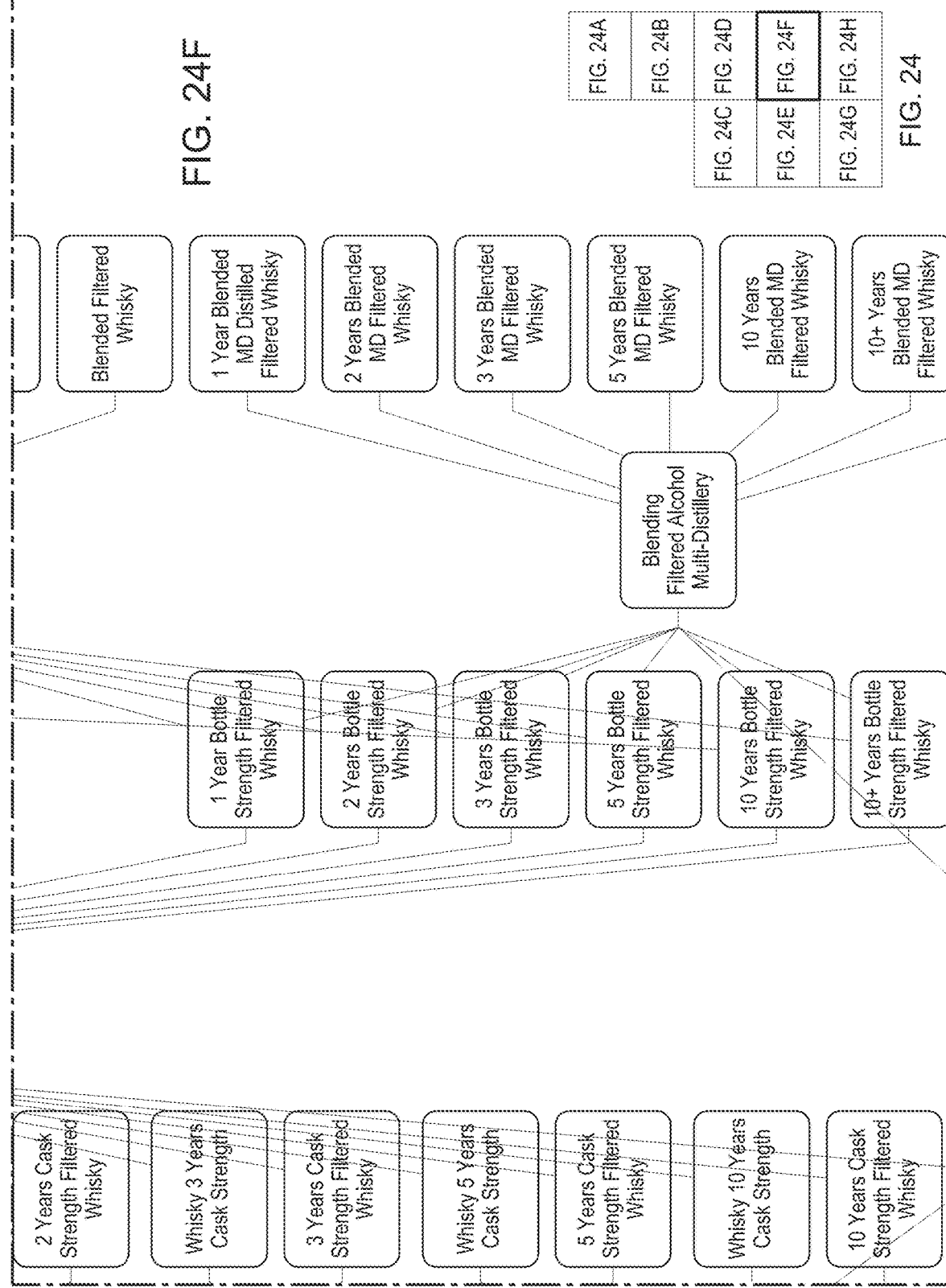

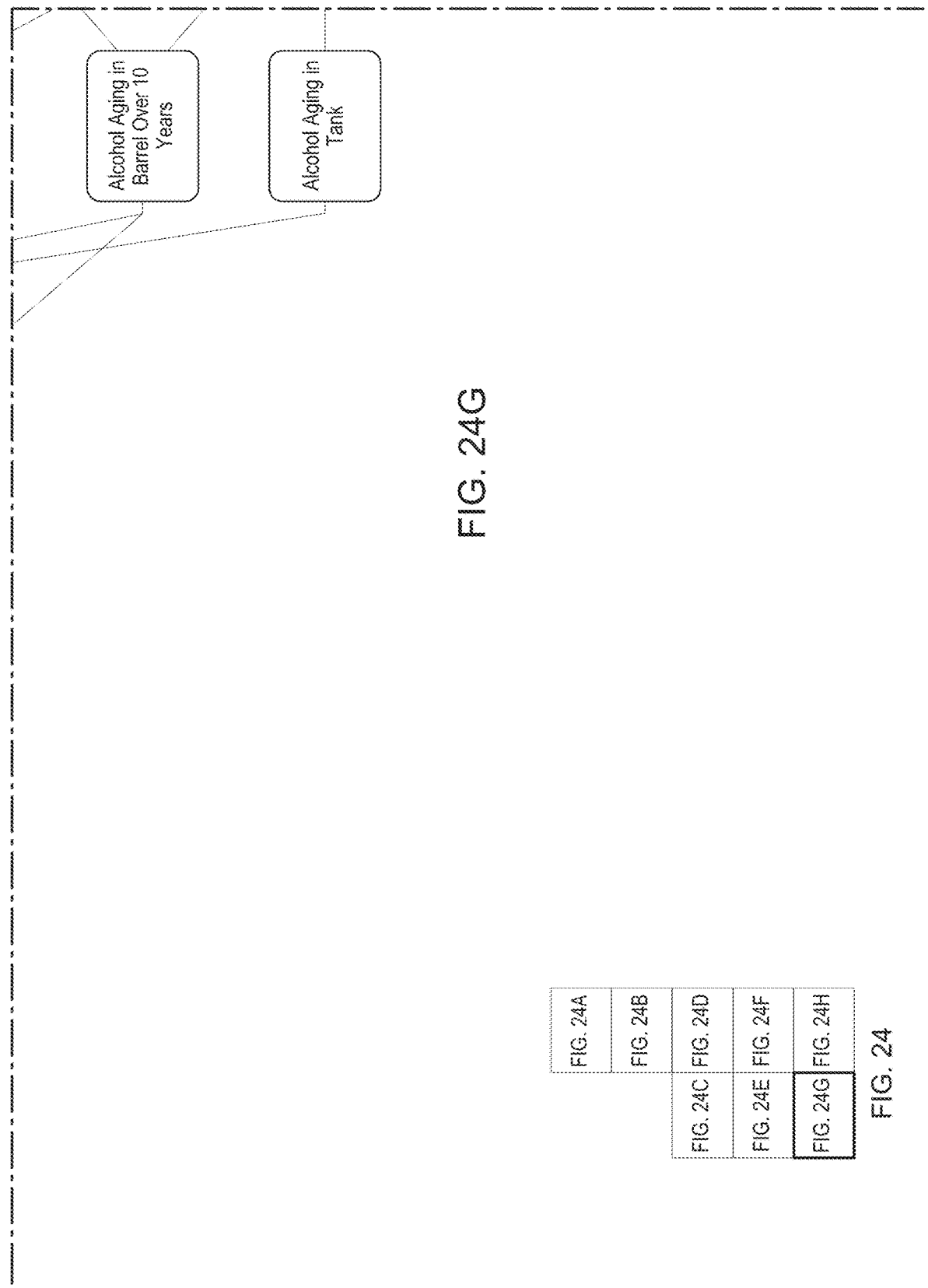

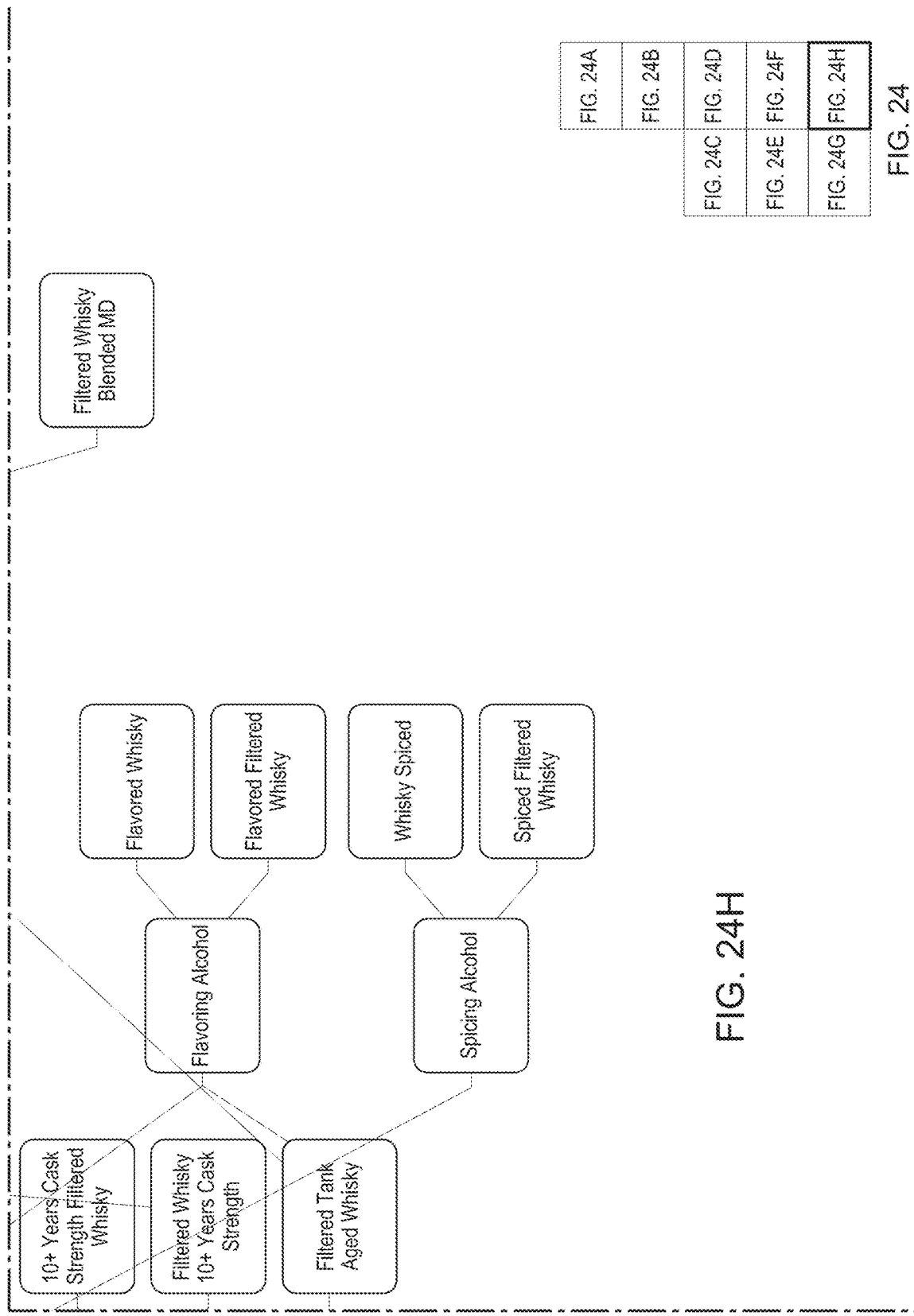

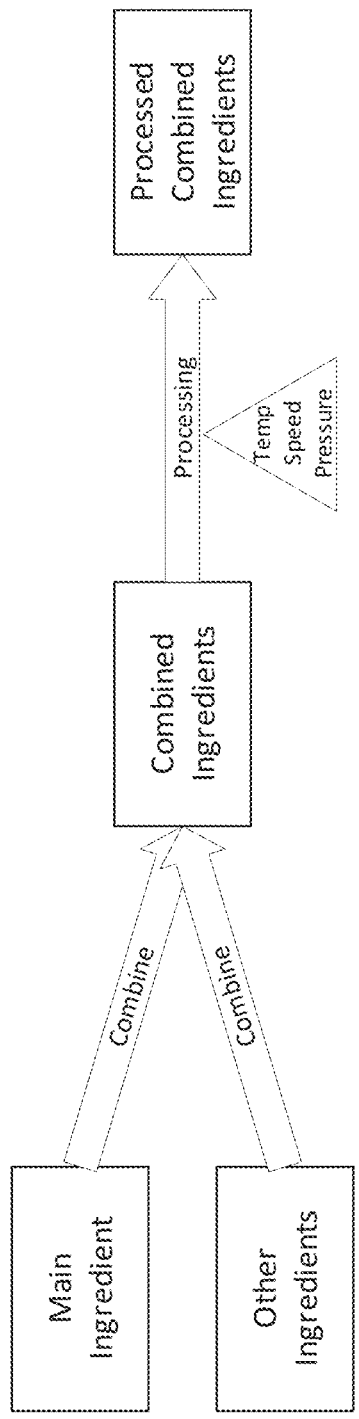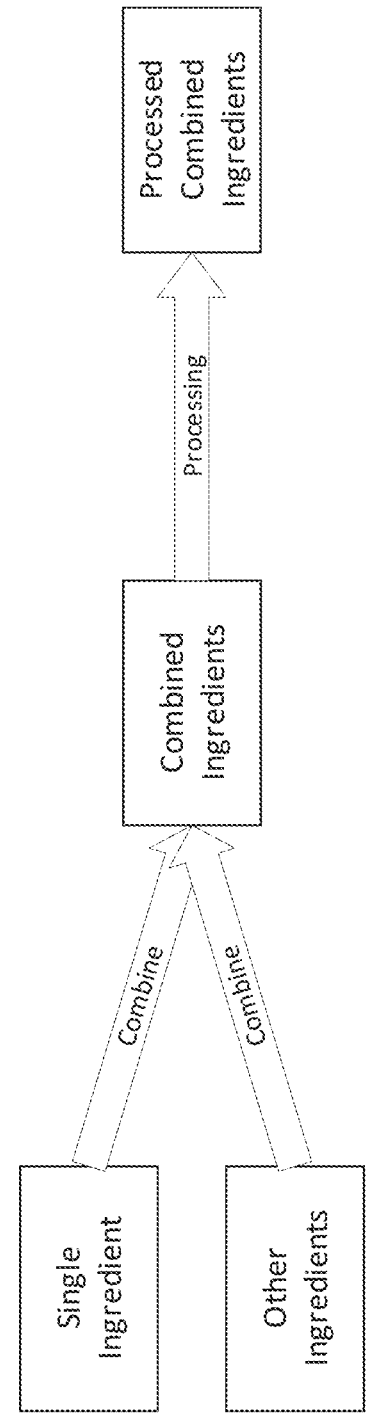

FIG. 37:

| Ingredient Quantity | Processing | Ingredient Category | Class | Method | Scoring Factors |
|---|---|---|---|---|---|
| Single | Ambient | Parent Food | Parent | A | Attributes |
| | | | | | Nutrition Levels |
| | | Derivative Food | Food | B | Attributes |
| | | | | | FDA Nutrition Levels |
| | | | CPG Food | C | Attributes |
| | | | | | CPG Nutrition Levels + FDA Nutrition Levels |
| | Impactful | | Food | B | Attributes |
| | | | | | FDA Nutrition Levels |
| | | Derivative Food | | D | Attributes |
| | | | | | FDA Nutrition Levels - Impact Chart |
| | | | CPG Food | C | Attributes |
| | | | | | CPG Nutrition Levels + FDA Nutrition Levels |
| | | | | E | Attributes |
| | | | | | CPG Nutrition Levels + FDA Nutrition Levels - Impact Chart |
| | | | | D | Attributes |
| | | | | | FDA Nutrition Levels - Impact Chart |

FIG. 39A:

| | Category | Nutrient | | Category | Nutrient | | Category | Nutrient |
|---|---|---|---|---|---|---|---|---|
| 1 | Calories | Total | 26 | Amino | Methionine | 51 | Fatty Acids | 4:00 |
| 2 | Calories | From Carbs | 27 | Amino | Phenylalanine | 52 | Fatty Acids | 6:00 |
| 3 | Calories | From Fat | 28 | Amino | Proline | 53 | Fatty Acids | 8:00 |
| 4 | Calories | From Protein | 29 | Amino | Serine | 54 | Fatty Acids | 10:00 |
| 5 | Calories | From Alcohol | 30 | Amino | Threonine | 55 | Fatty Acids | 12:00 |
| 6 | Protein | Total Protein | 31 | Amino | Tryptophan | 56 | Fatty Acids | 13:00 |
| 7 | Fats | Total Fats | 32 | Amino | Tyrosine | 57 | Fatty Acids | 14:00 |
| 8 | Fats | Total Omega 9 | 33 | Amino | Valine | 58 | Fatty Acids | 14:01 |
| 9 | Fats | Total Omega 6 | 34 | Carbs | Carbohydrate, by difference | 59 | Fatty Acids | 15:00 |
| 10 | Fats | Total Omega 3 | 35 | Carbs | Fiber, total dietary | 60 | Fatty Acids | 15:01 |
| 11 | Carbs | Total Carbs | 36 | Carbs | Fructose | 61 | Fatty Acids | 16:00 |
| 12 | Carbs | From Dietary Fiber | 37 | Carbs | Galactose | 62 | Fatty Acids | 17:00 |
| 13 | Carbs | From Starch | 38 | Carbs | Glucose (dextrose) | 63 | Fatty Acids | 17:01 |
| 14 | Carbs | From Sugar | 39 | Carbs | Lactose | 64 | Fatty Acids | 18:00 |
| 15 | Amino | Alanine | 40 | Carbs | Maltose | 65 | Fatty Acids | 18:04 |
| 16 | Amino | Arginine | 41 | Carbs | Starch | 66 | Fatty Acids | 20:00 |
| 17 | Amino | Aspartic acid | 42 | Carbs | Sucrose | 67 | Fatty Acids | 20:01 |
| 18 | Amino | Cystine | 43 | Carbs | Sugars, total | 68 | Fatty Acids | 21:05 |
| 19 | Amino | Glutamic acid | 44 | Fats | Fatty acids, total monounsaturated | 69 | Fatty Acids | 22:00 |
| 20 | Amino | Glycine | 45 | Fats | Fatty acids, total polyunsaturated | 70 | Fatty Acids | 22:04 |
| 21 | Amino | Histidine | 46 | Fats | Fatty acids, total saturated | 71 | Fatty Acids | 24:00:00 |
| 22 | Amino | Hydroxyproline | 47 | Fats | Fatty acids, total trans | 72 | Fatty Acids | 16:1 c |
| 23 | Amino | Isoleucine | 48 | Fats | Fatty acids, total trans-monoenoic | 73 | Fatty Acids | 16:1 t |
| 24 | Amino | Leucine | 49 | Fats | Fatty acids, total trans-polyenoic | 74 | Fatty Acids | 16:1 undifferentiated |
| 25 | Amino | Lysine | 50 | Fats | Total lipid (fat) | 75 | Fatty Acids | 18:1 c |

FIG. 39B:

| | Category | Nutrient | | Category | Nutrient | | Category | Nutrient |
|---|---|---|---|---|---|---|---|---|
| 76 | Fatty Acids | 18:1 t | 101 | Fatty Acids O6 | 20:4 n-6 | 126 | Sterols | Beta-sitosterol |
| 77 | Fatty Acids | 18:1 undifferentiated | 102 | Major | Alcohol, ethyl | 127 | Sterols | Campesterol |
| 78 | Fatty Acids | 18:1-11t (18:1t n-7) | 103 | Major | Ash | 128 | Sterols | Cholesterol |
| 79 | Fatty Acids | 18:2 CLAs | 104 | Major | Caffeine | 129 | Sterols | Phytosterols |
| 80 | Fatty Acids | 18:2 i | 105 | Major | Energy | 130 | Sterols | Stigmasterol |
| 81 | Fatty Acids | 18:2 t not further defined | 106 | Major | Theobromine | 131 | Vit A | Carotene, alpha |
| 82 | Fatty Acids | 18:2 t,t | 107 | Major | Water | 132 | Vit A | Carotene, beta |
| 83 | Fatty Acids | 18:2 undifferentiated | 108 | Mineral | Boron | 133 | Vit A | Cryptoxanthin, beta |
| 84 | Fatty Acids | 18:3 undifferentiated | 109 | Mineral | Calcium, Ca | 134 | Vit A | Lutein + zeaxanthin |
| 85 | Fatty Acids | 18:3i | 110 | Mineral | Chloride | 135 | Vit A | Lycopene |
| 86 | Fatty Acids | 20:3 undifferentiated | 111 | Mineral | Chromium | 136 | Vit A | Retinol |
| 87 | Fatty Acids | 20:4 undifferentiated | 112 | Mineral | Copper, Cu | 137 | Vit A | Vitamin A, IU |
| 88 | Fatty Acids | 22:1 c | 113 | Mineral | Fluoride, F | 138 | Vit A | Vitamin A, RAE |
| 89 | Fatty Acids | 22:1 t | 114 | Mineral | Iodine | 139 | Vit B1 | Thiamin |
| 90 | Fatty Acids | 22:1 undifferentiated | 115 | Mineral | Iron, Fe | 140 | Vit B12 | Vitamin B-12 |
| 91 | Fatty Acids | 24:1 c | 116 | Mineral | Magnesium, Mg | 141 | Vit B12 | Vitamin B-12, added |
| 92 | Fatty Acids O3 | 18:3 n-3 c,c,c (ALA) | 117 | Mineral | Manganese, Mn | 142 | Vit B2 | Riboflavin |
| 93 | Fatty Acids O3 | 20:3 n-3 | 118 | Mineral | Molybdenum | 143 | Vit B3 | Niacin |
| 94 | Fatty Acids O3 | 20:5 n-3 (EPA) | 119 | Mineral | Phosphorus, P | 144 | Vit B5 | Pantothenic acid |
| 95 | Fatty Acids O3 | 22:5 n-3 (DPA) | 120 | Mineral | Potassium, K | 145 | Vit B6 | Vitamin B-6 |
| 96 | Fatty Acids O3 | 22:6 n-3 (DHA) | 121 | Mineral | Selenium, Se | 146 | Vit B7 | Vitmamin B7-Biotin |
| 97 | Fatty Acids O6 | 18:2 n-6 c,c | 122 | Mineral | Sodium, Na | 147 | Vit B9 | Folate, DFE |
| 98 | Fatty Acids O6 | 18:3 n-6 c,c,c | 123 | Mineral | Zinc, Zn | 148 | Vit B9 | Folate, food |
| 99 | Fatty Acids O6 | 20:2 n-6 c,c | 124 | Protein | Adjusted Protein | 149 | Vit B9 | Folate, total |
| 100 | Fatty Acids O6 | 20:3 n-6 | 125 | Protein | Protein | 150 | Vit B9 | Folic acid |

FIG. 39C:

| | Category | Nutrient |
|---|---|---|
| 151 | Vit C | Vitamin C, total ascorbic acid |
| 152 | Vit D | Vitamin D |
| 153 | Vit D | Vitamin D (D2 + D3) |
| 154 | Vit D | Vitamin D2 (ergocalciferol) |
| 155 | Vit D | Vitamin D3 (cholecalciferol) |
| 156 | Vit E | Tocopherol, beta |
| 157 | Vit E | Tocopherol, delta |
| 158 | Vit E | Tocopherol, gamma |
| 159 | Vit E | Tocotrienol, alpha |
| 160 | Vit E | Tocotrienol, beta |
| 161 | Vit E | Tocotrienol, delta |
| 162 | Vit E | Tocotrienol, gamma |
| 163 | Vit E | Vitamin E (alpha-tocopherol) |
| 164 | Vit E | Vitamin E, added |
| 165 | Vit K | Dihydrophylloquinone |
| 166 | Vit K | Menaquinone-4 |
| 167 | Vit K | Vitamin K (phylloquinone) |
| 168 | Vitamin | Betaine |
| 169 | Vitamin | Choline, total |

FIG. 40A:

Standard intrinsic attributes for the ingredient categories

| Global Attributes | Water | Plants | Animals | Cultures | Hydrocarbons | Naturally Occurring | Artificial |
|---|---|---|---|---|---|---|---|
| Variety | Carbonation | Variety | Breed/Species | Microorganism | Hydrocarbons | Mineral | Groupings |
| Husbandry | Water Source | Cultivation | Husbandry | Bio Reactor | Refinery / Distillation | Extraction | Synthesized |
| Grade | Grade | USDA | USDA | Grade | Grade | Grade | Grade |
| Feed | Additive Type | Fertilizers | Animal Feed | Sugar Source | Distillates | Chemical Components | Chemical Components |
| Purity / Contamination | Treatment | Pesticides | Heavy Metals | Purity | Purity | Purity | Purity |
| Organic Product | None | Organic | Organic | Organic | Organic | Organic | Organic |
| Origin | Source Origin | Yes | Yes | Yes | Yes | Yes | Yes |
| Genetic Modification | GMO | GMO | GMO | GMO | GMO | GMO | GMO |
| Seasonality | Seasonal | Seasonal | Seasonal | Seasonal | Non Seasonal | Non Seasonal | Non Seasonal |
| Hormones | n/a | Hormones | Hormones | Hormones | n/a | n/a | n/a |
| Antibiotics | n/a | n/a | Antibiotics | n/a | n/a | n/a | n/a |
| Geographic Indication (GI) | GI | GI | GI | None | None | GI | None |

FIG. 40C:

| Non-Organic | USDA Grade | Low Contaminants | No Geo Indication | No Hormones | No Antibiotics |
|---|---|---|---|---|---|

| Wyoming | Piedmontese | Non-GMO | In Season | Grass Fed | Pasture Raised |
|---|---|---|---|---|---|

Attribute Score: 77

| Attribute Name | Value | Image/Icon | $AB_m$ | Impact Factor | Extended Score |
|---|---|---|---|---|---|
| Husbandry | Pasture Raised | | 100 | 5 | 500 |
| Organic | Yes | | 100 | 5 | 500 |
| Antibiotics | None | | 100 | 5 | 500 |
| Genetic Modification | GMO Free | | 100 | 1 | 100 |

FIG. 41B:
| Attribute Name | Value | Image/Icon | $AB_m$ | Impact Factor | Extended Score |
|---|---|---|---|---|---|
| Breed | Rhode Island Red |  | 1 | 5 | 5 |
| Contamination | POP Concern: Low |  | 100 | 3 | 300 |
| Feed | Pasture Foraging |  | 100 | 5 | 500 |
| Grade | USDA Grade A |  | 1 | 3 | 3 |

FIG. 41C:

| Attribute Name | Value | Image/Icon | $AB_m$ | Impact Factor | Extended Score |
|---|---|---|---|---|---|
| Hormone | None | | 100 | 1 | 100 |
| Seasonality | In Season | Calendar Function based Season and Current Month | 100 | 1 | 100 |
| Geo Indication | None | | 100 | 0 | 0 |
| Animal Origin | USA | | 80 | 1 | 80 |

| Attribute Value | Image/Icon | $AB_m$ |
|---|---|---|
| Caged | 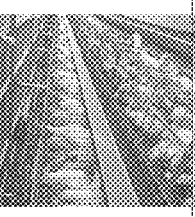 | 40 |
| Cage Free |  | 60 |
| Humanely Raised | 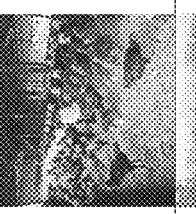 | 75 |
| Pasture Raised | 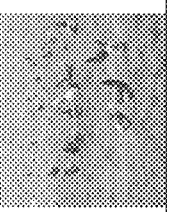 | 100 |
FIG. 41D:

FIG. 42A:

| Beef Husbandry | | Beef Feed | | Beef Breed | |
|---|---|---|---|---|---|
| Pasture Raised/Grass Foraged | | Grass Fed/Grass Finished | | Hereford | |
| Humanely Raised | | Silage/Hay | | Black Angus | |
| Feedlot | | Vegetarian Feed/Vegetarian Diet | | Piedmontese | |
| Unspecified | | Organic Feed | | Kobe | |
| | | Corn Fed | | Red Angus | |
| | | Grain Fed | | Angus | |
| | | Unspecified | | | |

FIG. 42B:
| Beef Grade | | Beef Origin | | Antibiotics | |
|---|---|---|---|---|---|
|  | U.S.D.A. Grass | | Farm, Estate or Chateau | 🚫 | No Antibiotics |
|  | U.S.D.A. Select | | County |  | Unspecified |
|  | U.S.D.A. Choice | ▪ | State | | |
|  | U.S.D.A. Prime | ≡ | Country | | |
| | | 🌐 | Unspecified | | |

FIG. 42C:

| Hormones | | GMO's | | Persistant Organic Pollutants (POPs) |
|---|---|---|---|---|
| No Hormones | | No Known GMOs | NO GMO | POP Low Concern |
| Unspecified | | | | POP Low Concern |
| | | | | POP Low Concern |

FIG. 42D:
| Organic | | Seasonality | | Geo Indication | |
|---|---|---|---|---|---|
| Organic |  | In Season | This is a calendar Function | Protected Designation of Origin |  |
| Non-Organic | 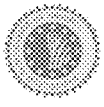 | Out of Season | Food is out of season locally | Protected Geographical Indication |  |
| | | | | Traditional Specialty Guaranteed |  |
| | | | | N/A | None |

FIG. 43

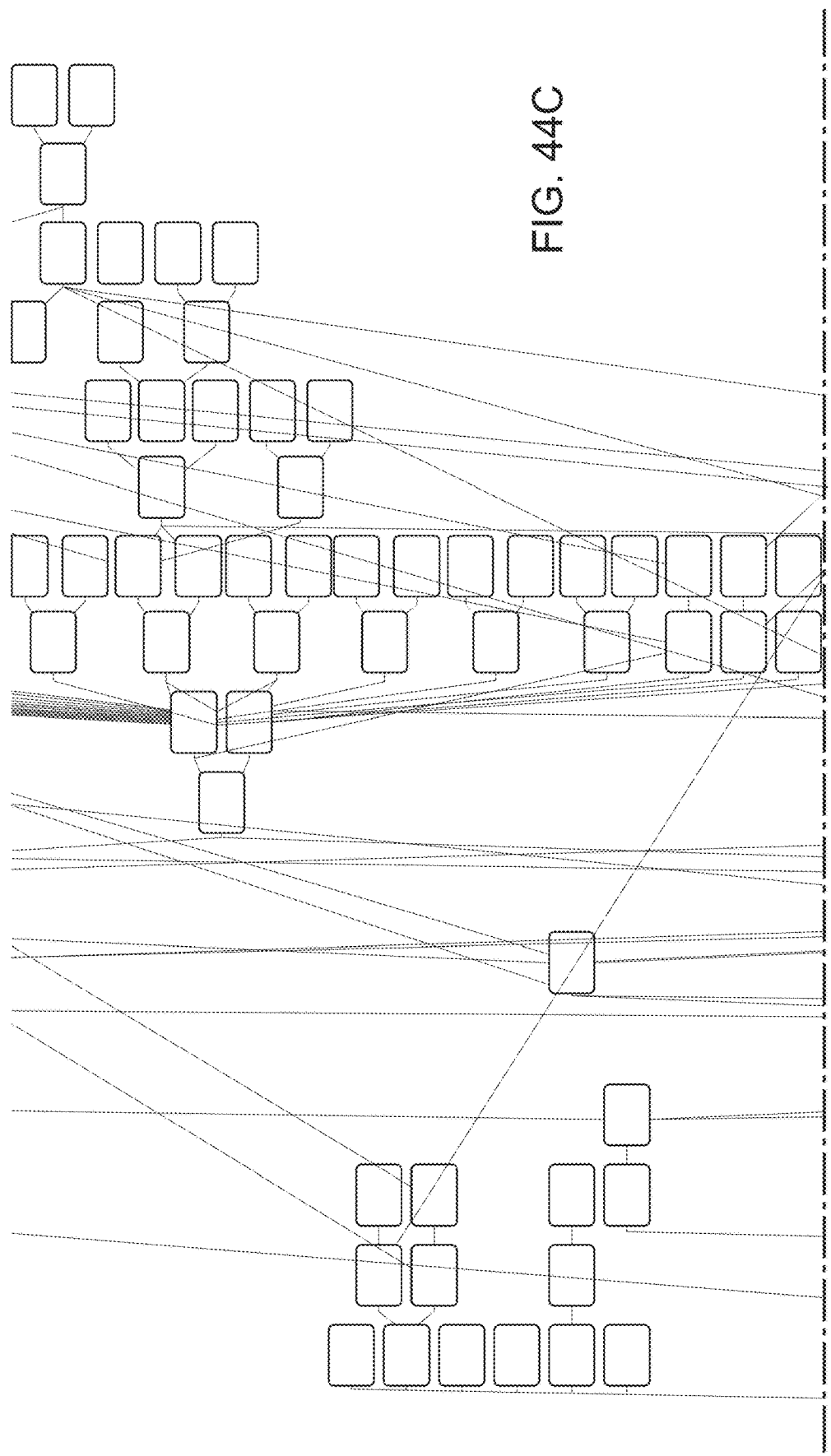

SYSTEM AND METHOD FOR GRADING AND SCORING FOOD

CLAIM OF PRIORITY

The present application is a continuation-in-part application from U.S. patent application Ser. No. 16/250,935 filed on Jan. 17, 2019 which claims the benefit of priority to U.S. Provisional Appl. No. 62/620,358 filed Jan. 22, 2018 and U.S. Provisional Appl. No. 62/640,480 filed Mar. 8, 2018, each of which is incorporated in its entirety by reference herein.

BACKGROUND

Field

This application relates generally to systems, methods, and databases for providing food-related information to a plurality of users that facilitate creation and modification of recipes, and more specifically to systems and methods for grading and scoring food.

Description of the Related Art

In conventional computer-based systems or databases, recipes are built to be stand-alone entities or a given recipe may sometimes be incorporated into a subsequent recipe. For example, to make a pie, the pie crust may be called out from a previous chapter of a cookbook in the pie recipe (e.g., the cookbook may say to use "Basic Pie Crust" from another page of the cookbook). Also, recipe websites generally do not reference other recipes, unless they are from the same author, but this is not very common. Most recipe websites are ad-based, so the author does not have an incentive to post all their recipes or to link them together. They also have no incentive to reference other chef's recipes as a sub-component of their recipe.

This stand-alone approach means that the author of the recipe creates one-off recipes with non-standard techniques. The techniques are all explained in different manners, making it extremely difficult to standardize. If it is not standardized, then each recipe has to be learned individually as well. This is a challenge for both human and robots. It can take years of experience to gain proficiency to wade through the multitude of non-standard techniques.

SUMMARY

In certain embodiments, a method of providing food-related information is provided. The method comprises receiving a user-generated query regarding at least one food. The method further comprises accessing, in response to the query, at least one computer database comprising a plurality of tables. Each table of the plurality of tables comprises a top-level record corresponding to a subject of the table and a plurality of lower-level records that correspond to food members of the subject of the table. Each lower-level record of the plurality of lower-level records comprises a plurality of nutrition values ($N_n$), each nutrition value indicative of an amount per calorie in the food member of a corresponding substance (n) of a plurality of substances. The method further comprises selecting at least one table of the plurality of tables. Each selected table comprises a lower-level record corresponding to a food of the at least one food. The method further comprises determining, for each food member of the at least one selected table, a plurality of substance base scores ($SB_n$), each substance base score indicative of a comparison of the nutrition value ($N_n$) of the corresponding substance in the food member to a nutrition value ($N_n^*$) of the corresponding substance in a benchmark food member of the table of the food member. The method further comprises determining, for each food member of the at least one selected table, a plurality of substance impact factors ($SIF_n$), each substance impact factor indicative of the nutrition value ($N_n^*$) of the corresponding substance in the benchmark food member relative to a dietary daily allowance of the corresponding substance per calorie ($DDA_n$) of the corresponding substance. The method further comprises calculating, for each food member of the at least one selected table, a nutrition quotient (NQ) given by: $NQ = \Sigma_n(SB_n \times SIF_n)/\Sigma_n(SIF_n)$, where $\Sigma_n(SB_n \times SIF_n)$ is a sum over the plurality of substances of the products of the substance base scores multiplied by the substance impact factors and $\Sigma_n(SIF_n)$ is a sum over the plurality of substances of the substance impact factors. The method further comprises transmitting, in response to the query, the nutrition quotients for the food members of the at least one selected table, to the user.

In certain embodiments, a computer system for providing food-related information, is provided. The system comprises at least one processor configured to provide food-related information to a plurality of user computing devices in response to food-related queries received from the plurality of user computing devices. The system further comprises at least one memory device in operative communication with the at least one processor. The at least one memory device is operative to store at least one computer database comprising a plurality of tables. Each table of the plurality of tables has a food-related subject. Each table of the plurality of tables comprises a top-level record corresponding to the subject of the table and a plurality of lower-level records that correspond to members of the subject of the table. Each lower-level record of the plurality of lower-level records comprises a plurality of nutrition values ($N_n$), each nutrition value indicative of an amount per calorie in the food member of a corresponding substance (n) of a plurality of substances. The at least one processor is configured to receive a user-generated query regarding at least one food and to access, in response to the query, the at least one computer database. The at least one processor is further configured to select at least one table of the plurality of tables, each selected table comprising a lower-level record corresponding to a food of the at least one food. The at least one processor is further configured to determine, for each food member of the at least one selected table, a plurality of substance base scores ($SB_n$), each substance base score indicative of a comparison of the nutrition value ($N_n$) of the corresponding substance in the food member to a nutrition value ($N_n^*$) of the corresponding substance in a benchmark food member of the table of the food member. The at least one processor is further configured to determine, for each food member of the at least one selected table, a plurality of substance impact factors ($SIF_n$), each substance impact factor indicative of the nutrition value ($N_n^*$) of the corresponding substance in the benchmark food member relative to a dietary daily allowance of the corresponding substance per calorie ($DDA_n$) of the corresponding substance. The at least one processor is further configured to calculate, for each food member of the at least one selected table, a nutrition quotient (NQ) given by: $NQ = \Sigma_n(SB_n \times SIF_n)/\Sigma_n(SIF_n)$, where $\Sigma_n(SB_n \times SIF_n)$ is a sum over the plurality of substances of the products of the substance base scores multiplied by the substance impact factors and $\Sigma_n(SIF_n)$ is a sum over the plurality of substances of the substance impact factors. The at least one processor is further configured to transmit, in response to the query, the nutrition quotients for the food members of the at least one selected table, to the user In certain embodiments, a non-transitory computer storage is provided which has stored thereon a computer program that instructs a computer system to provide food-related information. The food-related information is provided by at least receiving a user-generated query regarding at least one food and accessing, in response to the query, at least one computer database comprising a plurality of tables. Each table of the plurality of tables comprises a top-level record corresponding to a subject of the table and a plurality of lower-level records that correspond to food members of the subject of the table. Each lower-level record of the plurality of lower-level records comprises a plurality of nutrition values ($N_n$), each nutrition value indicative of an amount per calorie in the food member of a corresponding substance (n) of a plurality of substances. The food-related information is further provided by selecting at least one table of the plurality of tables, each selected table comprising a lower-level record corresponding to a food of the at least one food. The food-related information is further provided by determining, for each food member of the at least one selected table, a plurality of substance base scores ($SB_n$), each substance base score indicative of a comparison of the nutrition value ($N_n$) of the corresponding substance in the food member to a nutrition value ($N_n^*$) of the corresponding substance in a benchmark food member of the table of the food member. The food-related information is further provided by determining, for each food member of the at least one selected table, a plurality of substance impact factors ($SIF_n$), each substance impact factor indicative of the nutrition value ($N_n^*$) of the corresponding substance in the benchmark food member relative to a dietary daily allowance of the corresponding substance per calorie ($DDA_n$) of the corresponding substance. The food-related information is further provided by calculating, for each food member of the at least one selected table, a nutrition quotient (NQ) given by: $NQ=\Sigma_n(SB_n \times SIF_n)/\Sigma_n(SIF_n)$, where $\Sigma_n(SB_n \times SIF_n)$ is a sum over the plurality of substances of the products of the substance base scores multiplied by the substance impact factors and $\Sigma_n(SIF_n)$ is a sum over the plurality of substances of the substance impact factors. The food-related information is further provided by transmitting, in response to the query, the nutrition quotients for the food members of the at least one selected table, to the user.

BRIEF DESCRIPTION OF THE DRAWINGS

FIG. 3 schematically illustrates a segment of an example table in accordance with certain embodiments described herein.

FIG. 5A schematically illustrates an example list of templates in accordance with certain embodiments described herein.

FIG. 5B schematically illustrates a portion of a list of other tables in accordance with certain embodiments described herein.

FIGS. 9A-9D schematically illustrate example segments in accordance with certain embodiments described herein.

FIG. 12 schematically illustrates a basic recipe node-to-node network (e.g., instance) in accordance with certain embodiments described herein.

FIGS. 17A-17H schematically illustrate various examples of state change node-to-node structures in accordance with certain embodiments described herein.

FIGS. 18A-18D schematically illustrate various examples of convergent node-to-node structures in accordance with certain embodiments described herein.

FIGS. 36A-36E schematically illustrate various scenarios in which multiple ingredients are processed in accordance with certain embodiments described herein.

FIG. 37 illustrates various example combinations of factors relevant for the score calculation for single ingredients, based on ingredient type or category and type of processing in accordance with certain embodiments described herein.

FIG. 39A-39C show a table of 169 substances in accordance with certain embodiments described herein.

FIG. 40A shows twelve global attributes and the corresponding standard intrinsic attributes for each of the ingredient categories (e.g., Water, Plant, Animal, Culture, Hydrocarbon, Naturally Occurring, Artificial) in accordance with certain embodiments described herein.

FIG. 40C illustrates a graphical representation of the example intrinsic attribute values for a specific Consumer Package Goods (CPG) within a Universal Product Code (UPC) (e.g., beef filet mignon) in accordance with certain embodiments described herein.

FIGS. 41A-41C illustrate a graphical representation of an example scorecard for an example food (e.g., Handsome Brook Farm Grade A organic pasture-raised large chicken eggs) in accordance with certain embodiments described herein.

FIG. 41D illustrates a graphical representation of example attribute base scores corresponding to various attribute values for the "husbandry" attribute for chickens in accordance with certain embodiments described herein.

FIGS. 42A-42D schematically illustrate example beef attribute scoring parameters in accordance with certain embodiments described herein.

FIG. 43 schematically illustrates the nutrients for Apple Sauce and Fresh Apple expressed in terms of the recommended daily allowance (RDA) per calorie in accordance with certain embodiments described herein.

DETAILED DESCRIPTION

Figure 1:
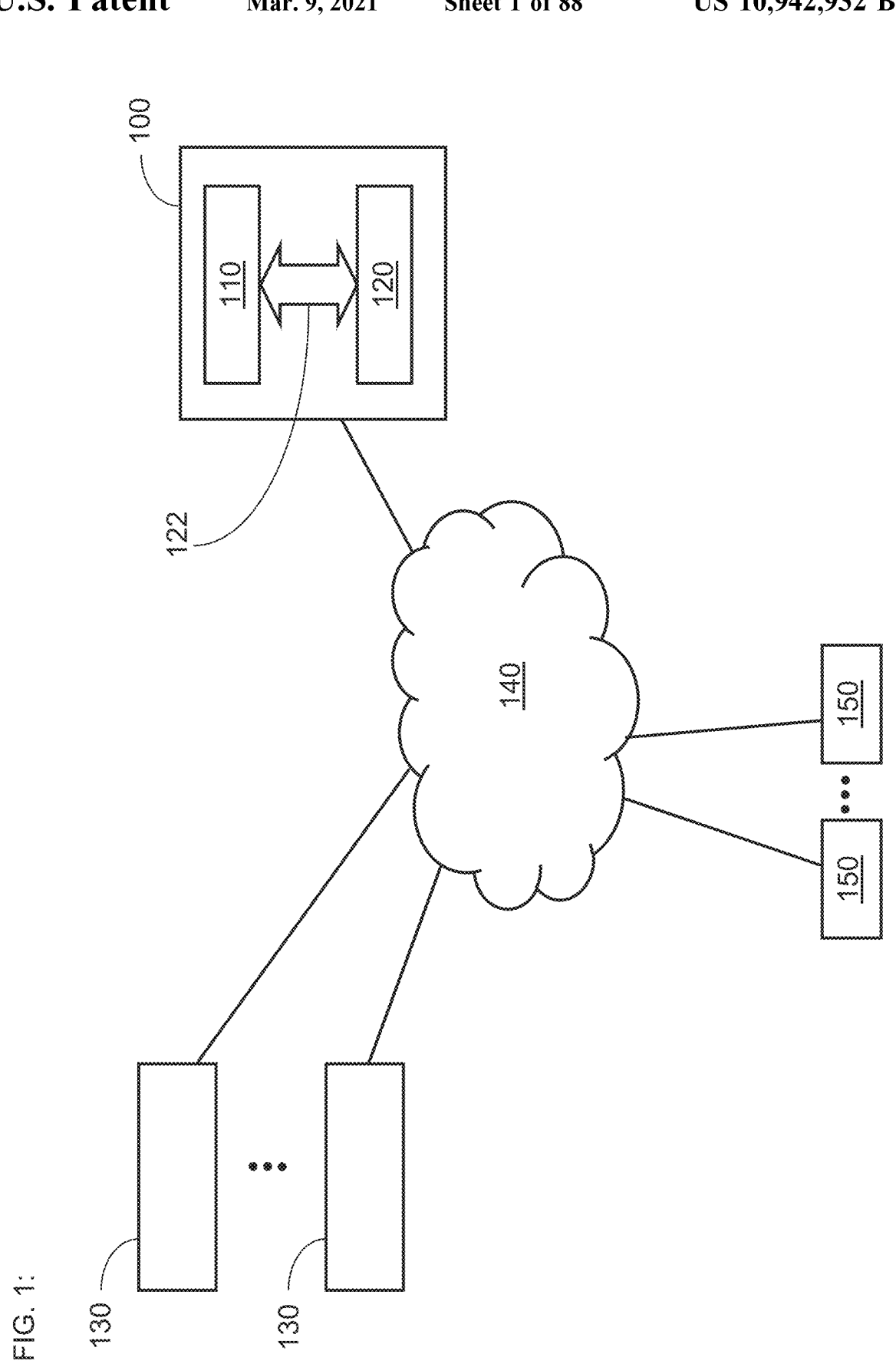
FIG. 1 schematically illustrates an example computer system for providing food-related information to a user computing device in accordance with certain embodiments described herein.

Certain embodiments described herein provide a computer-based system, method, and database (e.g., relational database) of food-related information configured to advantageously allow a user to leverage standardization to facilitate an enormous number of recipes and food-related information (e.g., ingredients, techniques, and equipment). In certain embodiments, the food-related information is organized in a node-to-node system comprising multiple food and recipe node-to-node networks. By way of analogy, the food and recipe node-to-node networks can be considered as the equivalent of standardized, interchangeable parts which facilitated the industrial revolution by avoiding the problem of individual craftsmanship as a hindrance to scaling up of industrial processes. While conventional recipe systems can be considered to be submitted by individual craftsmen and to not have interchangeable parts, in certain embodiments described herein, the node-to-node system and its food and recipe node-to-node networks provide a system utilizing "interchangeable" parts via ingredients, techniques, and equipment, and advantageously create an enormously efficient platform to enable interchangeable parts.

Certain embodiments described herein provide a computer-based system, method, and database (e.g., relational database) of food-related information configured to advantageously provide users with food-related information in a manner that facilitates the user creating recipes, making modifications to recipes, and evaluating the results of these recipes and/or modifications. For example, in certain embodiments described herein, the computer-based system is configured to quickly evaluate the user's initial request for information relevant to a recipe and its possible modifications, to determine the subject of the user's request, and to utilize a computer-based database that is structured such that the food-related information transmitted to the user includes sufficient information to allow the user to create recipes, make recipe modifications, and/or other desired operations without requiring that additional requests for additional information be transmitted to the computer-based system and database and without requiring that additional responses be processed by the computer-bases system and database. In certain embodiments, the food-related information transmitted to the user include an entire table (e.g., branch) of records corresponding to the subject of the user's request and a plurality of other entire tables (e.g., branches) of records corresponding to other subjects which correspond to potential modifications and/or other operations that the user may be expected to make. By transmitting these many tables, all in response to the initial request, certain such embodiments leverage fast transmission speeds and high bandwidths to advantageously avoid or reduce the number of subsequent information requests (e.g., dynamic, on-the-fly calls) sent by user devices to the computer-based system and database that would be needed in conventional systems in which each user modification and/or operation results in another information request send by the user device to the computer-based system and database. Certain such embodiments advantageously reduce the probability of excessive delays in receiving the information, potential crashes of the computer-based system and database, or other bottleneck-related performance degradations of the computer-based system.

FIG. 1 schematically illustrates an example computer system 100 for providing food-related information to a user computing device 150 in accordance with certain embodiments described herein. In certain embodiments, the computer system 100 comprises at least one processor 110 (e.g., server computer) and at least one memory device 120 (e.g., server computer data storage device; tangible storage; non-transitory storage; flash memory; hard-disk drive; non-volatile storage) that is in operative communication with the at least one processor 110. The at least one processor 110 is configured to provide food-related information 122 to a plurality of user computing devices 150 in response to food-related queries received from the plurality of user computing devices 150. The at least one memory device 120 is operative to store information (e.g., instructions; data; database) to be used by the at least one processor 110 and/or generated by the at least one processor 110, and to provide the stored information to the at least one processor 110. For example, the at least one memory device 120 can store food-related information 122 that is to be retrieved by the at least one processor 110 and provided to the user computing devices 150 (e.g., in response to queries received by the at least one processor 110 from the user computing devices 150).

In certain embodiments, the at least one processor 110 is in operative communication with one or more operator computing devices 130 (e.g., personal computers) via the internet 140. In certain embodiments, the one or more operator computing devices 130 are configured to provide operator input (e.g., commands; data) from one or more system operators (e.g., system administrators) to the at least one processor 110, to receive system output (e.g., data regarding system operations, analytics, and/or diagnostics) from the at least one processor 110, and to provide information (e.g., based on the system output) to the one or more system operators. The one or more operator computing devices 130 are configured to control and/or modify operation of the at least one processor 110 and/or create and/or modify the food-related information 122 stored by the at least one memory device 120. For example, the at least one processor 110 can communicate with an operator computing device 130 via the internet 140 so that a system operator using the operator computing device 130 can set up, access, diagnose, monitor, modify, and/or otherwise control the operation of the at least one processor 110.

In certain embodiments, the at least one processor 110 is in operative communication with one or more user computing devices 150 (e.g., smartphones; smart tablets; personal computers) via the internet 140. The one or more user computing devices 150 are configured to provide user input (e.g., queries; commands; data) from one or more users (e.g., resources; chefs; individuals) to the at least one processor 110, to receive food-related information 122 from the at least one processor 110, and to provide the food-related information 122 to the one or more users. For example, the at least one processor 110 can communicate with a user computing device 150 via the internet 140 so that a user using the user computing device 150 can transmit a query to the at least one processor 110 (e.g., via a user's account which is specified by a username and protected by a password) and the at least one processor 110 can receive the query. For another example, the at least one processor 110 can communicate with the user computing device 150 via the internet 140 so that the at least one processor 110 transmits food-related information 122 to the user computing device 150 (e.g., in response to the query). For still another example, the at least one processor 110 can communicate with the user computing device 150 via the internet 140 so that the user can set up, modify, and/or otherwise use the user's account to request and receive food-related information 112 from the at least one processor 110.

Figure 2:
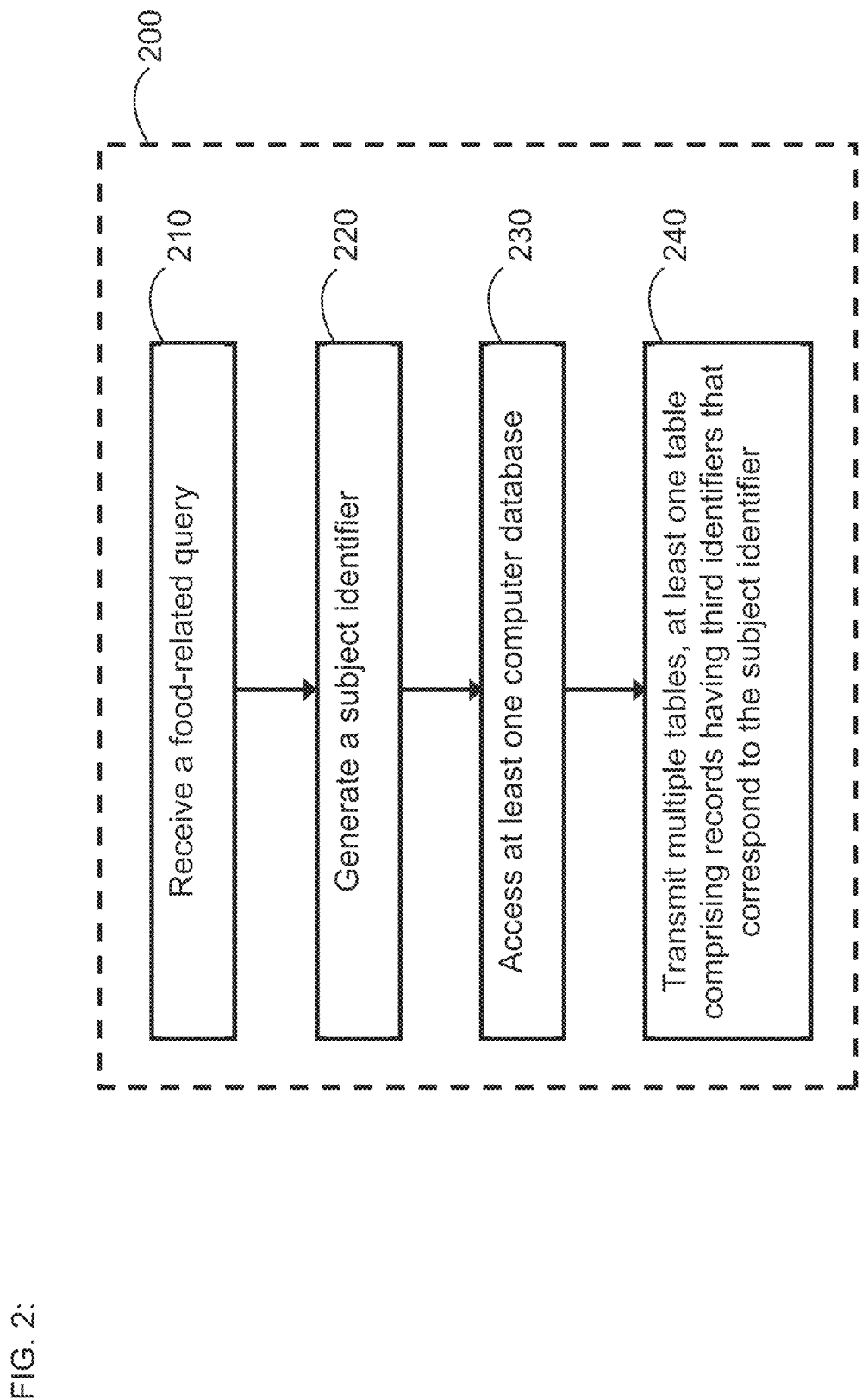
FIG. 2 is a flow diagram of an example method for providing food-related information in accordance with certain embodiments described herein.

FIG. 2 is a flow diagram of an example method 200 (e.g., performed by the example computer system 100) for providing food-related information (e.g., to a user computing device 150) in accordance with certain embodiments described herein. In certain embodiments, a software application is running on the user computing device 150, the software application configured to receive the food-related information transmitted from the computer system 100 to the user computing device 150 and to present the received food-related information to the user. In an operational block 210, the method 200 comprises receiving a food-related query (e.g., a user-generated food-related query from one of the plurality of user computing devices 150). In an operational block 220, the method 200 further comprises generating, in response to the query, a subject identifier indicative of a food-related subject of the query. In an operational block 230, the method 200 further comprises accessing at least one computer database comprising, inter alia, a plurality of tables (e.g., branches) (e.g., stored by the at least one memory device 120 of the computer system 100). In an operational block 240, the method 200 further comprises transmitting (e.g., from the computer system 100 to the user computing device 150 via the internet 140) multiple tables of the plurality of tables to the user (e.g., to the user computing device 150), the multiple tables comprising a primary table and at least one other table. The primary table comprises lower-level records having third identifiers that correspond to the subject identifier.

In certain embodiments, each table (e.g., branch) of the plurality of tables has a food-related subject. Examples of types of food-related subjects of a table include but are not limited to: a food class; a food preparation technique; a food preparation tool; a food brand; a food manufacturer; a food provider. Each table of the plurality of tables comprises a top-level record corresponding to the subject of the table and a plurality of lower-level records that correspond to members of the subject of the table and that are hierarchically organized within the table. Each lower-level record of the plurality of lower-level records comprises a first identifier indicative of the lower-level record, at least one second identifier corresponding to the first identifier of another record in the table, and a third identifier corresponding to the top-level record of the table.

FIG. 3 schematically illustrates a segment of an example table 300 in accordance with certain embodiments described herein. The example table 300 can be a portion of a larger table of the computer-based database. The example table 300 has a food-related subject (e.g., food class "chicken") and the table 300 comprises a top-level record 310 corresponding to the subject of the table 300. The example table 300 further comprises a plurality of lower-level records 320 that correspond to members of the subject of the table 300 and that are hierarchically organized within the table 300. These members can include derivative forms of the subject of the table 300 (e.g., different cuts; different seasonings; forms resulting from different preparation or processing techniques).

For example, the lower-level records 320 of the table 300 of FIG. 3 include records corresponding to various derivative forms of chicken (e.g., cuts; whole; half; quarter; leg; wing; boneless with skin; boneless and skinless; skinless with bone). Each lower-level record 320 comprises a first identifier 330 (e.g., primary key; alphanumeric identifier) indicative of the lower-level record 320, and at least one second identifier 340 (e.g., a foreign key; alphanumeric identifier) corresponding to the first identifier 330 of another record in the table 300. The second identifier 340 points (e.g., provides a link) to a higher-level record (e.g., a record from which the lower-level record 320 can be obtained). In conventional relational database structures with only first identifiers and second identifiers (e.g., only primary keys and foreign keys of a unique numeric indexing system), to navigate through the table 300 from a deep, lower-level record 320 to the top-level record 310 would require using the first and second identifiers to make multiple jumps amongst multiple lower-level records 320. For example, in a conventional relational database structure for aftermarket automobile parts, it may be desirable to identify a particular part (e.g., with a corresponding part number) and determine which automobile sub-assembly (e.g., body; engine; interior; exhaust system) is related to the part. In the conventional relational database structure, a database query would return only the first parent foreign key, which would point to the next most outer assembly (e.g., "engine mounting system," "rear seat") and the user would have to follow a series (e.g., 2, 3, or more) of parent level foreign keys (e.g., "stair-stepping" from a lower-level record to the next-higher-level record) before arriving at the top-level (e.g., "Interior Systems").

In certain embodiments, each lower-level record 320 further comprises a third identifier 350 (e.g., a sliding key or toplevelID; alphanumeric identifier) corresponding (e.g., pointing; providing a link) to the top-level record 310 of the table 300. In contrast to the second identifiers 340 which only point to other lower-level records 320, the third identifier 350 of each lower-level record 320 points (e.g., provides a link) to the top-level record 310 of the table 300. For example, as shown in FIG. 3, each lower-level record 320 has a third identifier 350 that identifies the subject of the table 300 ("chicken") for the lower-level record 320, regardless of the location of the lower-level record 320 within the table 300.

In certain embodiments, the third identifier 350 can be used to identify lower-level records 320 that correspond to members of the subject of the user's query (e.g., the third identifier 350 matches the subject identifier from the user's query) so that these lower-level records 320 are among those transmitted to the user. For example, if the subject identifier from the user's query corresponds to "broccoli" (e.g., the user seeks to develop recipes using broccoli), by transmitting a primary table including all the lower-level records 320 that have a third identifier 350 that matches the subject identifier for "broccoli," the records of the transmitted primary table will include all the various derivative forms of "broccoli" (e.g., chopped; spears; whole) that the user may be expected to use. Without the third identifier 350 (e.g., sliding key), traditional relational database structures have been burdened with a "many-to-many" design concept in which the foods (e.g., cucumber; apple; watermelon) were stored in an isolated table, and the possible "forms" or form definitions (e.g., sliced; chopped) were stored in another isolated table, and the intersection or relationships between the two tables (e.g., cucumber slices; chopped apple; etc.) were stored in yet another table, with multiple foreign keys. This structure would utilize an element-by-element maintenance which creates a burden on the database, the hardware, and the administrative staff managing the system. In addition, the absence of the third identifier 350 would require "stair-stepping" from a lower-level record to a top-level record to determine which food the lower-level record refers to (e.g., cucumbers; apples).

The third identifier 350 of certain embodiments described herein provides a means for identifying all the records (e.g., the entire table or branch of records corresponding to the subject of the user's request) that are expected to be potentially used by the user when creating recipes, making recipe modifications, and/or other desired operations. By using the third identifier 350 to identify the large number of records to be transmitted to the user, certain embodiments do not have to scale the computer-based system 100 to deal with many users, and can distribute the burden of further data operations to the user computing device 150. For example, by utilizing a computer-based database that is structured such that the lower-level records 320 each include a third identifier 350, certain embodiments transmit sufficient information to the user to allow the user to perform the desired operations without requiring that additional requests (e.g., dynamic, on-the-fly calls) for additional information be transmitted to the computer system 100 and without requiring the computer system 100 to respond to (e.g., process) these additional requests.

In certain embodiments, the received food-related query comprises a text string inputted by the user into the user computing device 150, which is running a software application that is configured to transmit the text string via the internet 140 to the computer system 100. The text string can comprise one or more words, phrases, sentences, and/or sentence fragments with which the user expresses a request for food-related information. For example, for a user seeking recipes that include a certain ingredient, the text string can mention the ingredient or a form of the ingredient, e.g., "whole chicken," "chicken breast," "apples," "fruit," In other examples, for a user seeking recipes that incorporate the use of a named piece of equipment (e.g., "barbeque"), the computer system 100 can return a set of recipes (e.g., comprising a predetermined number of recipes) using a barbeque. These recipes can be sorted by the number of barbequing minutes required by the recipe, which could be useful for users that may be running low on propane. In another example, the user can specify some description of a cooking or preparation method (e.g., soufflé; chopped; poaching), and the computer system 100 can return a set of recipes that utilize the specified cooking or preparation method or a list of equipment that can be used for the cooking or preparation method.

In certain embodiments, the query further comprises a realm identifier (e.g., an alphanumeric identifier) that identifies a realm (e.g., food-related topic) of the query. Examples of realms in accordance with certain embodiments described herein include but are not limited to: "Food," "Equipment," "Preparation," "Recipe," and "Restaurant." In certain embodiments, the software application running on the user computing device 150 is configured to include the realm identifier in the food-related query that is transmitted to the computer system 100. For example, the text string can be inputted by the user into a user interface field of the software application running on the user computing device 150, with the user interface field corresponding to a particular realm (e.g., separate user interface fields corresponding to different realms or a user interface field which corresponds to a user-selected one of the realms), and the software application includes the corresponding realm identifier in the query with the text string. The user interface field can be equipped with an "auto-complete feature" which provides suggested completions of partially-types words and/or phrases, and the resulting complete text strings can have a high likelihood of having at least a potion which matches an alias table term, as described more fully herein. For another example, the computer system 100 can be configured to derive the realm identifier from the text string (e.g., by examining the text string for a portion that corresponds to a word or phrase indicative of one of the realms).

Figure 4A:
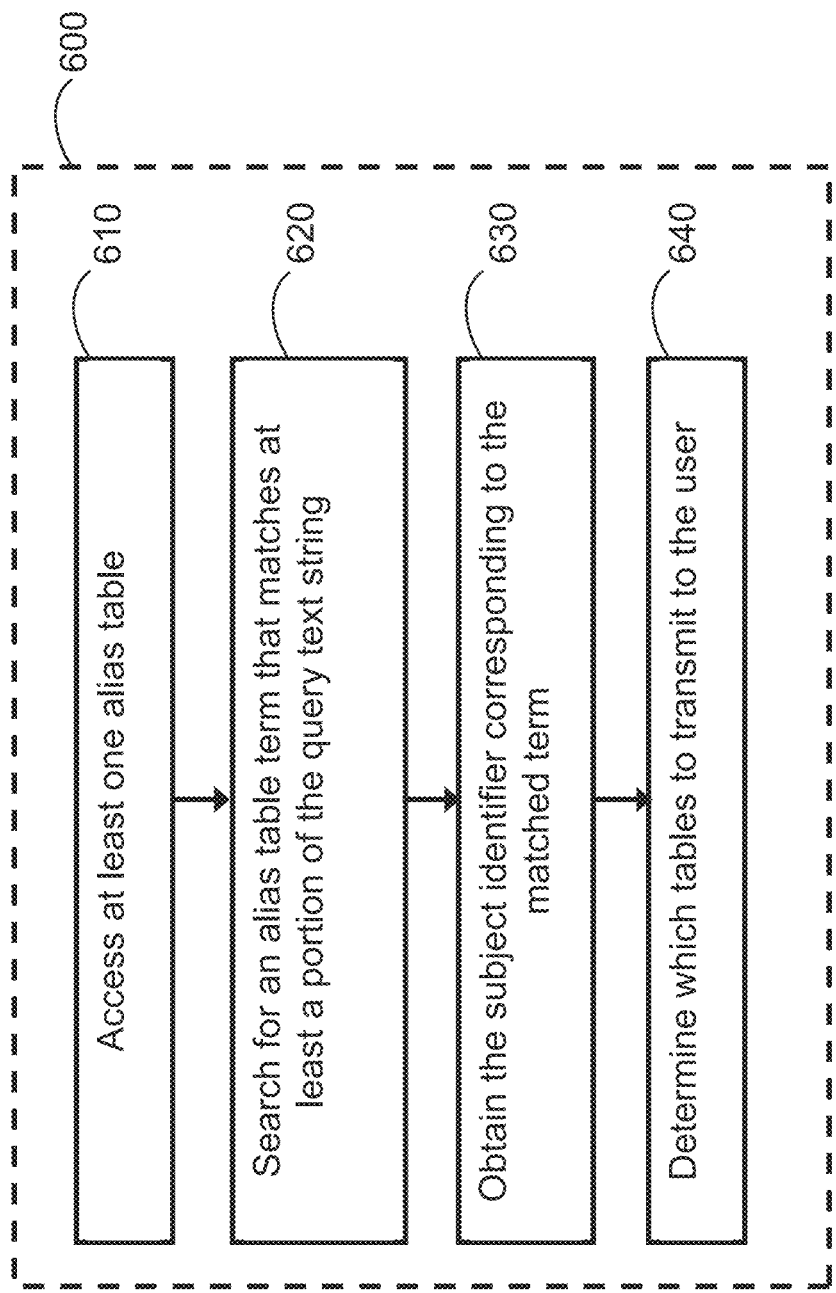
FIG. 4A is a flow diagram of an example method for generating the subject identifier in accordance with certain embodiments described herein.

FIG. 4A is a flow diagram of an example method 600 performed in the operational block 220 for generating the subject identifier in accordance with certain embodiments described herein. In an operational block 610, the method 600 comprises accessing at least one alias table (e.g., the at least one alias table stored by the at least one memory device 120). In an operational block 620, the method 600 further comprises searching for a term of the at least one alias table that matches at least a portion of a text string of the query received from a user computing device 150. In an operational block 630, the method 600 further comprises obtaining (e.g., retrieving from the at least one alias table) a subject identifier that corresponds to the matched term of the at least one alias table. In an operational block 640, the method 600 further comprises determining, based at least in part on the subject identifier, the primary table and the at least one other table to be transmitted to the user.

In certain embodiments, the at least one alias table comprises a listing of terms (e.g., words; phrases) that a user is expected to potentially include in a food-related query to identify the subject for which the user seeks information (e.g., from the computer system 100). The at least one alias table can comprise a single table or multiple tables that are concatenated (e.g., unioned) together. For example, the at least one alias table can comprise one or more alias tables for each realm (e.g., food-related topic) expected to be relevant to the food-related query and accessing the at least one alias table comprises accessing one or more alias tables corresponding to the realm identified by the realm identifier. For example, the alias table for the "food" realm can contain more than 1.2 million records, and the alias table for the "equipment" realm can contain more than 8,000 records.

Each realm can comprise a plurality of sub-realms (e.g., tiers) and each sub-realm can comprise a plurality of primary terms. For example, the realm of "food" can include a sub-realm of types (e.g., categories) of food (e.g., "fruit," "vegetable," "meat") and each type can include various primary terms (e.g., the type "fruit" can include primary terms such as "apple," "orange," "pear;" the type "vegetable" can include primary terms such as "broccoli," "cauliflower," "onion;" the type "meat" can include primary terms such as "chicken," "beef," "fish"). Other sub-realms of the "food" realm can include but are not limited to food brand (e.g., with primary terms corresponding to food brand names that the users may use in the queries), food manufacturer (e.g., with primary terms corresponding to names of food manufacturing companies that the users may use in the queries), and food providers (e.g., with primary terms corresponding to names of food selling companies that the users may use in the queries).

For another example, the realm of "equipment" can include a sub-realm of types (e.g., categories) of equipment (e.g., "oven," "stove," "pans," "blenders") and each type can include various primary terms (e.g., the type "oven" can include primary terms such as "convection," "broiler," "microwave"). For still another example, the realm of "preparation" can include a sub-realm of types (e.g., categories) of preparation techniques (e.g., "cutting," "mixing," "frying") and each type can include various primary terms (e.g., the type "cutting" can include primary terms such as "slicing," "dicing," "dividing"). Various realms, sub-realms, and primary terms are compatible with certain embodiments described herein.

In certain embodiments, the one or more alias tables for each realm can comprise an alias table comprising terms corresponding to the names of the various types (e.g., "fruit," "vegetable," "meat") and an alias table comprising terms corresponding to the primary terms (e.g., "apple," "orange," "pear," "broccoli," "cauliflower," "onion," "chicken," "beef," "fish"). In certain such embodiments, the terms corresponding to the names of the various types and/or the primary terms are configured to be searched separately (e.g., as described herein with regard to FIG. 4B).

Each term of the at least one alias table has a corresponding subject identifier (e.g., a numeric identifier; a class identification number) that identifies the subject with which the term is associated. Multiple terms can be "aliases" of one another, effectively denoting the same subject, and such aliases each have the same subject identifier as one another. These aliases can reflect one or more differences from one another, including but not limited to: singular/plural differences, word order differences, phrasing differences, punctuation differences, and spelling differences. For example, the at least one alias table can include the term "boneless skinless chicken breast" with a corresponding subject identifier and the at least one alias table can further other terms that are aliases of the term "boneless skinless chicken breast" with the same subject identifier. Examples of such aliases can include but are not limited to the following terms:

"boneless skinless chicken breasts" (e.g., singular/plural difference)

"skinless boneless chicken breast" (e.g., word order difference)

"boneless, skinless chicken breast" (e.g., punctuation difference)

"boneless and skinless breast of chicken" (e.g., phrasing difference)

"boneless chicken breast without skin" (e.g., phrasing difference)

"boneless skinless chiken breast" (e.g., spelling difference)

"breast of chicken (boned and skinned)" (e.g., multiple differences).

Figure 4B:
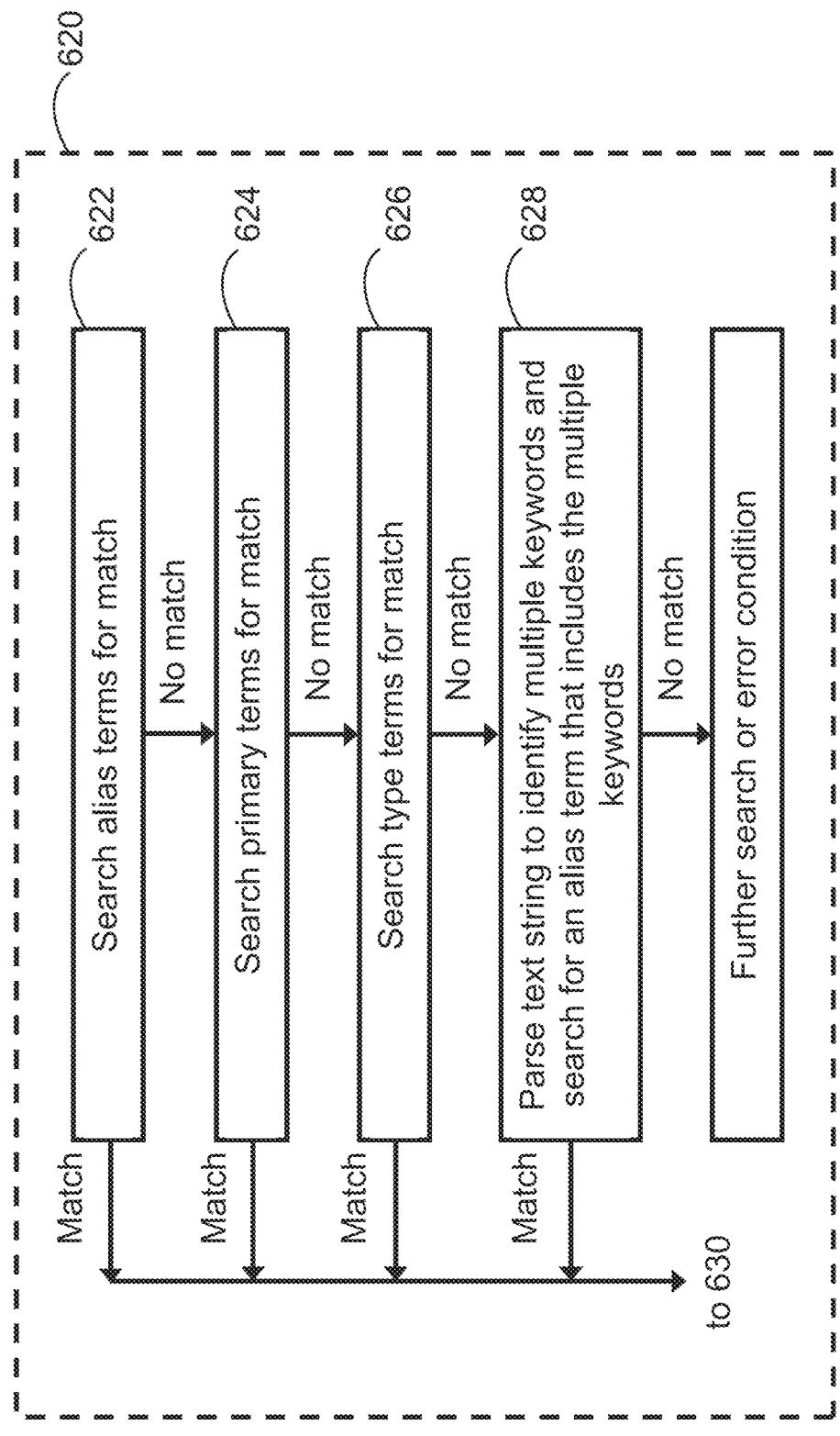
FIG. 4B is a flow diagram of an example search in accordance with certain embodiments described herein.

FIG. 4B is a flow diagram of an example search of the operational block 620 in accordance with certain embodiments described herein. In an operational block 622, the alias terms of the at least one alias table are searched for a match (e.g., an exact match; a literal match) of the text string of the query. If a match is found, then the search proceeds to the operational block 630, and if a match is not found, then the search proceeds to an operational block 624. In the operational block 624, the primary terms are searched for a match (e.g., an exact match; a literal match) of the text string of the query. If a match is found, then the search proceeds to the operational block 630, and if a match is not found, then the search proceeds to an operational block 626. In an operational block 626, the type terms are searched for a match (e.g., an exact match; a literal match) of the text string of the query. If a match is found, then the search proceeds to the operational block 630, and if a match is not found, then the search proceeds to an operational block 628. In the operational block 628, the text string is parsed into multiple keywords (e.g., parsing based on conjunctions and/or punctuation within the text string). For example, a text string of "steak and potatoes" can be parsed into a first keyword "steak" and a second keyword "potatoes." The alias terms of the at least one alias table are then searched for an alias term that matches the multiple keywords (e.g., includes each of the multiple keywords in any order). If a match is found, the search proceeds to the operational block 630, and if a match is not found, then the search either proceeds to further searches (e.g., parsing the text string in other ways) or to an error condition (e.g., "search failed").

In certain embodiments, the subject identifier of the matched term is obtained (e.g., retrieved from the at least one alias table) in the operational block 630 and based at least in part on the subject identifier, the multiple tables to be transmitted to the user are determined in the operational block 640. The multiple tables to be transmitted include (i) the table in which the lower-level records have third identifiers that correspond to the subject identifier of the matched term (e.g., the primary table) and (ii) at least one other table which includes records which are potentially useful to the user.

In certain embodiments, determining the at least one other table to be transmitted to the user is further based on other information (e.g., the realm identifier from the query; an identifier of the particular alias table in which the match was found). In certain embodiments, at least one template of a plurality of templates is accessed and used to determine this at least one other table (e.g., based on the subject identifier retrieved from the at least one alias table). Each template of the plurality of templates can specify a different set of other tables to be transmitted to the user, and this set of other tables can include tables which vary from the primary table in one or more attributes (e.g., type; variety; form; ingredients; preparation techniques; equipment to be used) that the user may seek to adjust while using the information.

FIG. 5A schematically illustrates an example list of templates (dbo.TemplateDefs) in accordance with certain embodiments described herein and FIG. 5B schematically illustrates a portion (e.g., corresponding to one of the templates) of a list of other tables (dbo.TemplateBranchDefs) in accordance with certain embodiments described herein. For each of the templates listed in FIG. 5A, the list of other tables (dbo.TemplateBranchDefs) of FIG. 5B can specify a corresponding different set of multiple other tables. These other tables can include but are not limited to: tables corresponding to other varieties of the subject of the primary table; tables corresponding to other forms of the subject of the primary table; tables corresponding to preparation definitions (e.g., techniques) compatible with the subject of the primary table; tables corresponding to equipment classes compatible with the subject of the primary table; tables corresponding to universal product codes (UPCs) relevant to the subject of the primary table. In certain embodiments, other information (e.g., static text files; image files), in addition to the primary table and the other tables, is transmitted to the user.

For example, in the food realm, if the subject identifier of the matched term is one of the food alias terms, then the template having TemplateDefID=1 is used to specify the at least one other table. As shown in FIG. 5B, for this template (TemplateDefID=1), the at least one other table includes (i) tables corresponding to other forms within the same top level as that of the primary table, (ii) tables corresponding to other food types with the same form as that of the primary table, (iii) tables corresponding to preparation definitions (e.g., techniques) compatible with the food of the primary table, (iv) tables corresponding to equipment classes compatible with the food of the primary table, and (v) tables corresponding to universal product codes (UPCs) relevant to the food of the primary table. For another example, if the subject identifier of the matched term is one of the food primary terms, then the template having TemplateDefID=2 is used to specify the at least one other table, which as shown in FIG. 5B, includes (i) tables corresponding to other varieties for the same top level as that of the primary table, (ii) tables corresponding to other forms for the same top level as that of the primary table, and (iii) tables corresponding to UPCs for the same top level as that of the primary table. For still another example, if the subject identifier of the matched term is one of the food brands, then the template having TemplateDefID=3 is used to specify the at least one other table, which as shown in FIG. 5B, includes (i) tables corresponding to other top levels with which the brand of the primary table participates, (ii) tables corresponding to other food classes with which the brand of the primary table participates, and (iii) tables corresponding to UPCs of the brand of the primary table.

If the subject identifier of the matched term is one of the food primary terms, then the template having TemplateDefID=2 is used to specify the at least one other table; if the subject identifier of the matched term is one of the food brand terms, then the template having TemplateDefID=3 is used to specify the at least one other table, etc. Various other sets of templates and sets of tables specified by each template are compatible with certain embodiments described herein.

In certain embodiments, once the primary table (e.g., the table with lower-level records having third identifiers that correspond to the at least one subject identifier) and the at least one other table (e.g., the tables specified by the appropriate template) are determined, the at least one computer database is accessed in the operational block 230 and all these tables are retrieved and transmitted (e.g., via the internet 140 from the computer system 100) to the user (e.g., the user computing device 150) in the operational block 240. For example, the transmitted data sets can be arranged in a series of JSON formatted responses, that are then transmitted via encrypted TCP packets to the client device (e.g., the user computing device 150). In certain embodiments, other information (e.g., static text files; image files), in addition to the primary table and the other tables, is transmitted to the user.

Node-to-Node Structure

The node-to-node system can provide a large amount of static, yet connected data, which can span tens of millions of connected records in a relational database. By spelling out the data points and their connections, the node-to-node system described herein can advantageously utilize less overhead in machine time to find requested data. In contrast, conventional text-based food and recipe systems search a database for text-based data using proximal estimates of the expected location of the data, and if the correct data is not found, then determining how best to proceed, and these multiple adjustments can create a massive burden on the computer hardware to keep up with all the searching.

In certain embodiments, the node-to-node system provides a "skeleton" structure which forms the backbone of supporting food and recipes. Each standard node-to-node segment can be set up one time and used many times. In certain embodiments, the node-to-node system supports a standard and a multiplicity of variants, e.g., between any two nodes, as an ending node, as a beginning node, a series of nodes, a network segment, and a series of network segments. In certain embodiments, individual users can specify their own standards and a multiplicity of variants.

In certain embodiments, one recipe has a multiplicity of methods/techniques and equipment that is customized for each user's unique preferences. In certain embodiments, standards enable recipes to be compared and contrasted based on the standard and/or any of its variants. They recipes can be compared or contrasted by the ingredients, methods/techniques, or the equipment used.

In addition to the node-to-node standards, in certain embodiments there is also an actor. The actor can be passive (e.g., an oven where heat is applied when baking in an Oven). The actor can be the device, person, robot, or equipment that takes some level of action in the specific conversion process from State A to State B. In the case of equipment, the actor may load or unload the food items into or out of the equipment, if the equipment doesn't have the capability.

The basic building blocks of the node-to-node structure are "States" and "Actions." The "state" of an item can comprise a form of an item and/or a temperature of the item. An "action" changes the state of an item, for example, by changing the form of the item and/or the temperature of the item. Each action of a node-to-node segment can have a time duration and, if appropriate, temperature, speed, humidity, and pressure.

Figure 6A:
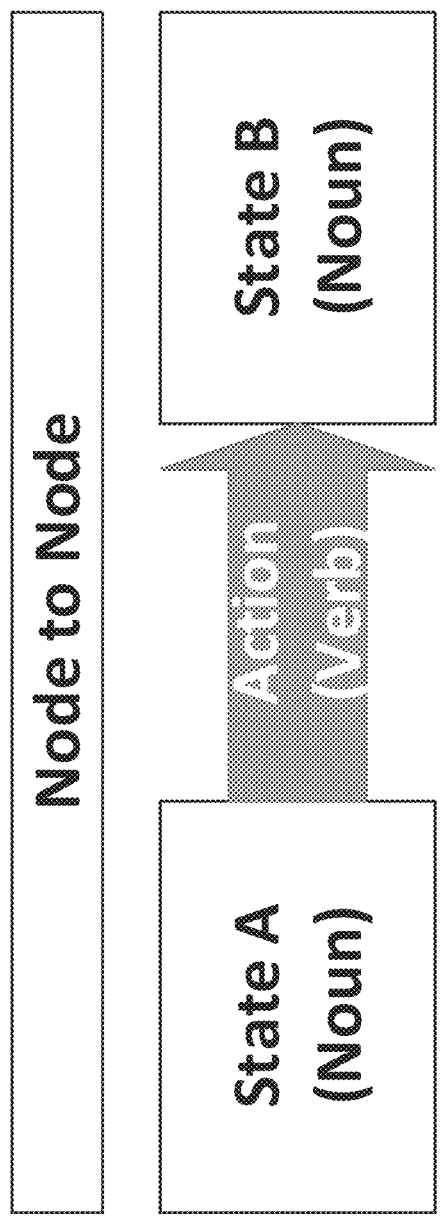
FIG. 6A schematically illustrates the relationship between states and actions for a general node-to-node segment in accordance with certain embodiments described herein.
Figure 6B:
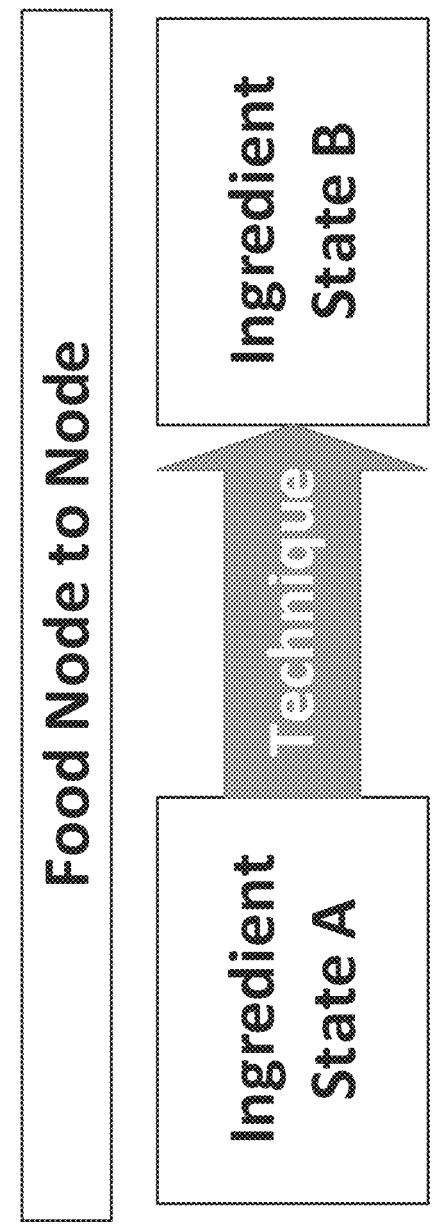
FIG. 6B schematically illustrates an example node-to-node segment for a food and recipe network in accordance with certain embodiments described herein.

FIG. 6A schematically illustrates the relationship between states and actions for a general node-to-node segment in accordance with certain embodiments described herein. The item is in State A and an Action changes the item into State B. FIG. 6B schematically illustrates an example node-to-node segment for a food and recipe network in accordance with certain embodiments described herein. The ingredient in State A is node 1 which is connected by the action to node 2 which is the ingredient in State B. In this example, the item (e.g., a food ingredient or a plurality of ingredients) is changed from State A to State B by the technique (e.g., action) that is performed to change the item from State A to State B. For example, a "Fresh Apple" (e.g., item in State A) can be changed to "Fresh Apple Halves" (e.g., item in State B). The technique (e.g., action) employed between State A and State B is "Halving with a Chef Knife." An action can be performed by hand, or in conjunction with a tool or plurality of tools (e.g., tools, containers, surfaces, equipment, etc.). In certain embodiments, the node-to-node segment for a food and recipe network includes inbound ingredients (Noun) in State A, applying a technique which includes using one or more tools (Verb) to produce an output (Noun) in State B. In certain embodiments, this Node B becomes the Node A in another subsequent instance of a node-to-node segment downstream of the node-to-node segment of FIG. 6B.

Figure 7:
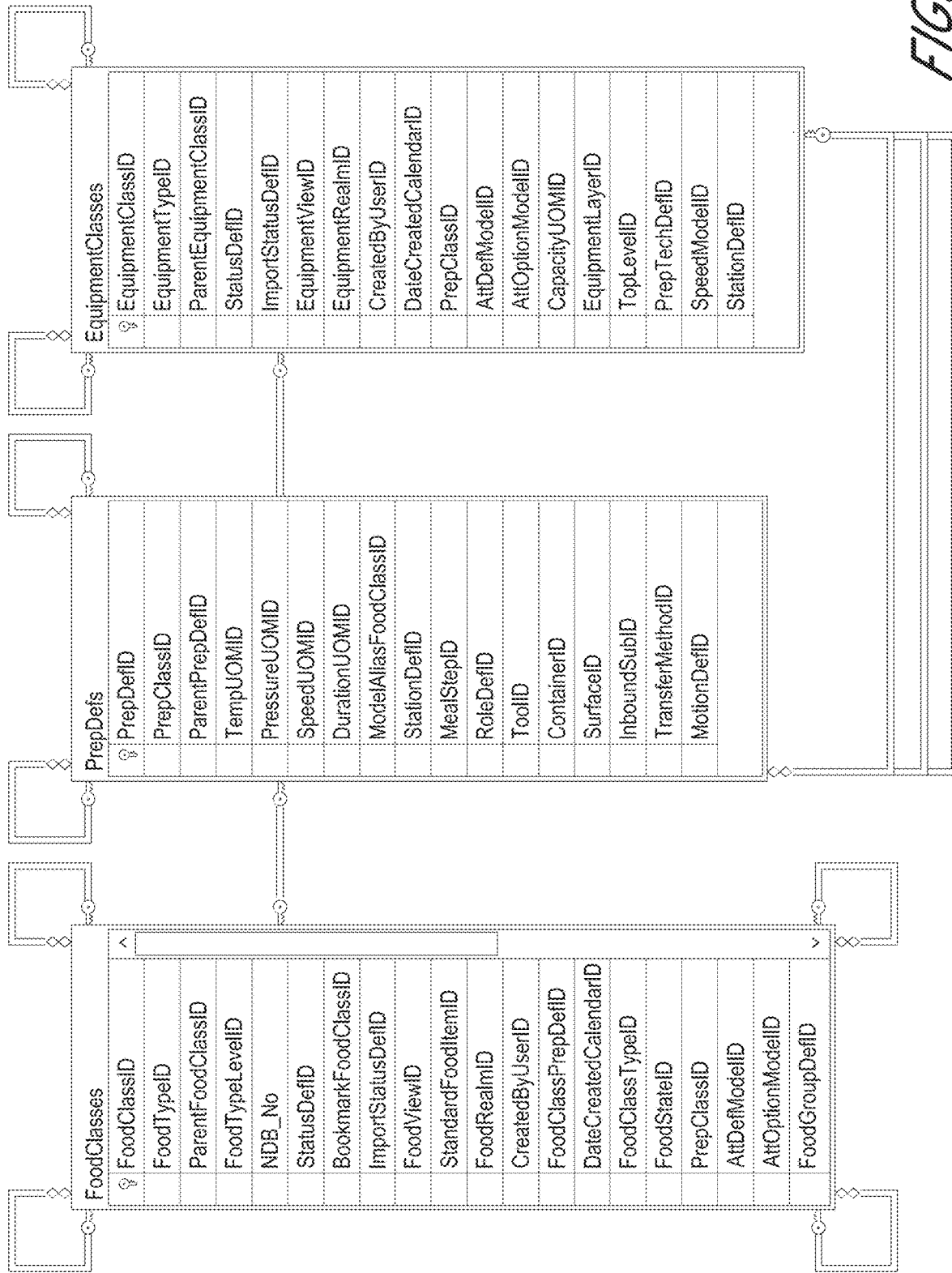
FIG. 7 schematically illustrates example multiple database tables and their relationships (e.g., associations) relative to one another that facilitates the node-to-node structure in accordance with certain embodiments described herein.

In certain embodiments, the at least one computer database organized in the node-to-node structure supports categorical definitions of the Foods, Preparation Methods, and Equipment that constitute the states and the actions of the node-to-node structure. For example, FIG. 7 schematically illustrates example multiple database tables and their relationships (e.g., associations) relative to one another that facilitates the node-to-node structure in accordance with certain embodiments described herein. As used herein, the terms "database table" and "table" have their broadest reasonable interpretation, including but not limited to, a set of cells or data elements (e.g., values) organized in a specified number of columns (e.g., vertical columns; identifiable by name) and any number of rows (e.g., horizontal rows), with each cell being where a row and a column intersect one another. As used herein, the term "database relationship" has its broadest reasonable interpretation, including but not limited to, the associations between the tables, and can include three types of relationships: (i) "one-to-one" in which both of two tables has only one record on either side of the relationship, and each primary key value relates to only one (or no) record in the related table; (ii) "one-to-many" in which the primary key table contains only one record that relates to none, one, or many records in the related table; and (iii) "many-to-many" in which each record in both tables can relate to any number of records (or no records) in the related table. As an analogy of the "many-to-many" relationship, if you have several siblings, each of your siblings also has many siblings. "Many-to-many" relationships can utilize a third table, known as an associate or linking table. As schematically illustrated in FIG. 7, the tables can have recursive relationships unto themselves, to support lower-level divergence, in both form and class. As used herein, the naming convention for the primary keys, in each table, is the Table name in its singular format concatenated with ID (e.g., dbo.FoodClasses and FoodClassID; dbo.PrepDefs and PrepDefID).

Figure 8A:
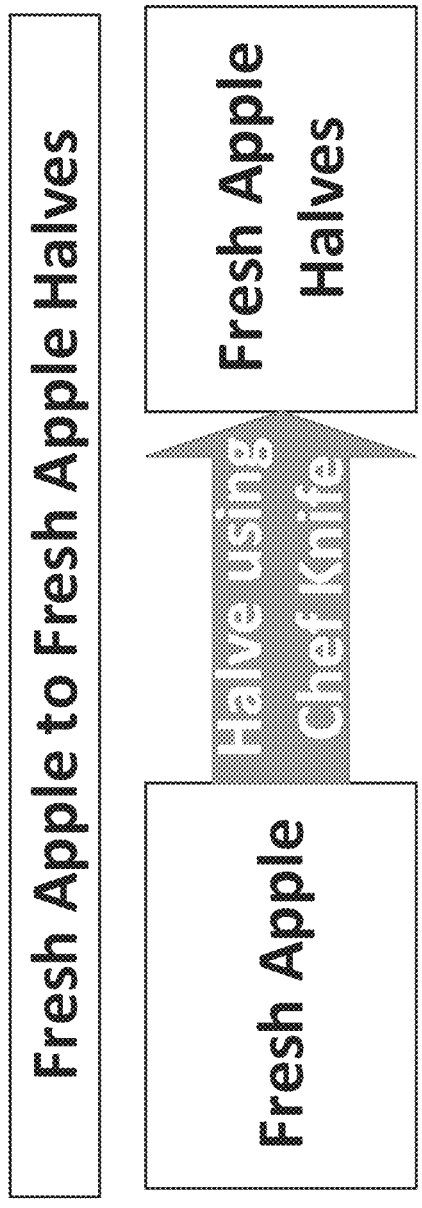
FIG. 8A schematically illustrates an example segment in which the nodes are connected by a single overall action/technique in accordance with certain embodiments described herein.
Figure 8B:
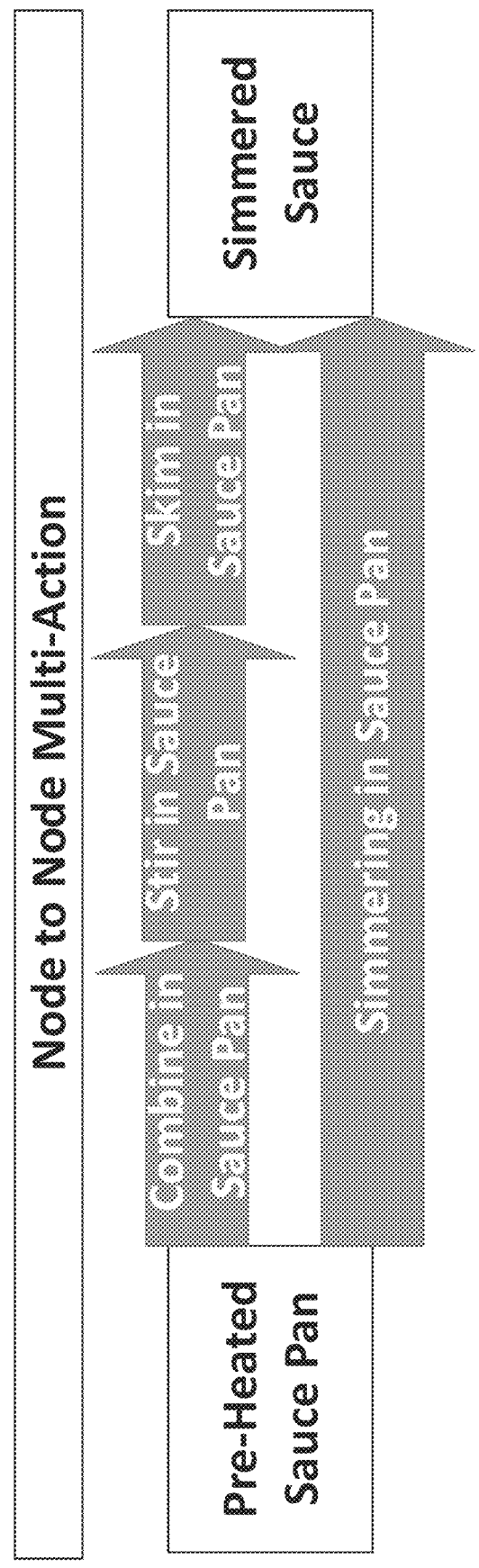
FIG. 8B schematically illustrates an example segment in which the nodes are connected by two or more separate, distinct actions/techniques in accordance with certain embodiments described herein.

FIG. 8A schematically illustrates an example segment in which the nodes are connected by a single overall action/technique in accordance with certain embodiments described herein. In FIG. 8A, the item "Fresh Apple" is changed to the item "Fresh Apple Halves" by the technique of "Halve using Chef Knife." FIG. 8B schematically illustrates an example segment in which the nodes are connected by two or more separate, distinct actions/techniques in accordance with certain embodiments described herein. In FIG. 8B, the sauce pan is preheated, then when hot, the ingredients are combined, then stirred and then skimmed until the items are made into a simmered sauce. The multiple actions can also be grouped (e.g., nested) together, effectively forming a single overall technique, e.g., the combining, stirring, and skimming can be grouped together as "simmering" as shown in FIG. 8B. In this example, there is a change in state of a cold sauce pan being brought up in temperature to become a "pre-heated sauce pan," and there is a series of actions that happen in sequence to create the sauce. For an example scenario, from State A, a first Oil can be pre-heated or butter melted, then various room temperature ingredients can be mixed in and allowed to simmer, creating the "simmered sauce" of State B. For another example scenario, from State A, the room temperature ingredients can be combined, brought to a boil, and then allowed to simmer, creating the "simmered sauce" of State B. There are a multitude of possible ways or scenarios to make a sauce, but the state change is happening to the main "Actor" in the recipe. The sauce pan may be viewed as the "Actor," the oil may be viewed as the "Actor," the mixed sauce may be viewed as the "Actor," and the simmered sauce may be viewed as the final result. In essence, what is changing from State A to State B can be the equipment or the ingredients.

Figure 9C:
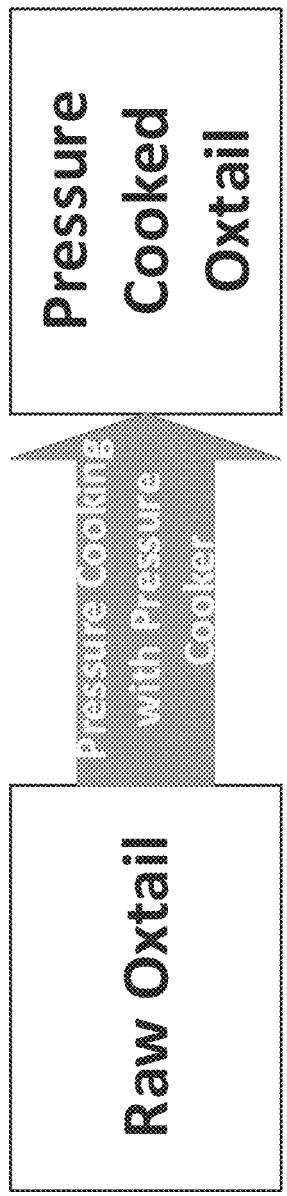
Figure 9D:
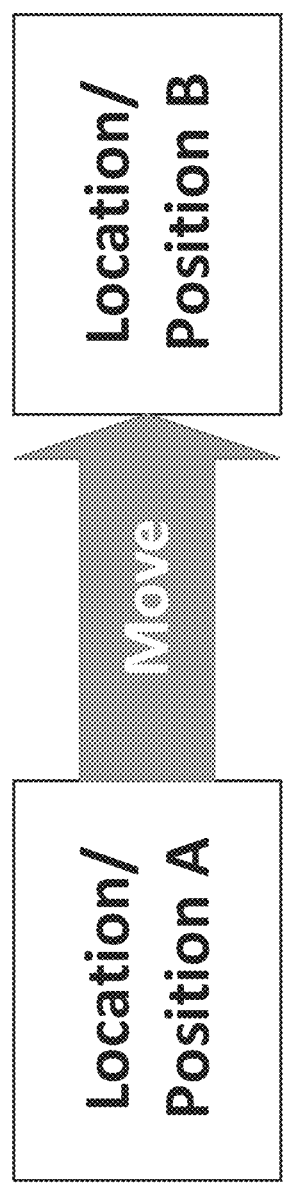

In certain embodiments, the change from State A to State B is a change of form, a change of temperature, a change of humidity, a change of pressure or vacuum, a change of location or position, or a combination thereof. FIGS. 8A and 9A-9D schematically illustrate example segments in accordance with certain embodiments described herein. FIG. 8A shows an example segment with a form change in which one Fresh Apple changes form by being cut in half using a chef knife which creates two Apple Halves (e.g., the form changed from a whole apple to two apple halves). FIG. 9A shows an example segment with a temperature change in which one Fresh Potato is baked in an oven which creates one Baked Potato. The temperature of the item is changed from room temperature to an internal temperature of 210° F. by baking it at 375° F. for 50 minutes. FIG. 9B shows an example segment with both a temperature and form change in which one pound of dough is baked in an oven until it transforms into baked bread. The dough is transformed into a new form from dough into baked bread. FIG. 9C shows an example segment with a pressure or vacuum change in combination with a temperature change in which one raw oxtail portion is cooked by Pressure Cooking with a Pressure Cooker to make a Pressure Cooked Oxtail. FIG. 9D shows an example segment with a location or position change (e.g., a grilled steak is positioned by Flipping with a Turner to cook the other side, and the location of the grilled steak is moved from the Barbecue Grill to the Serving Platter).

Figure 10:
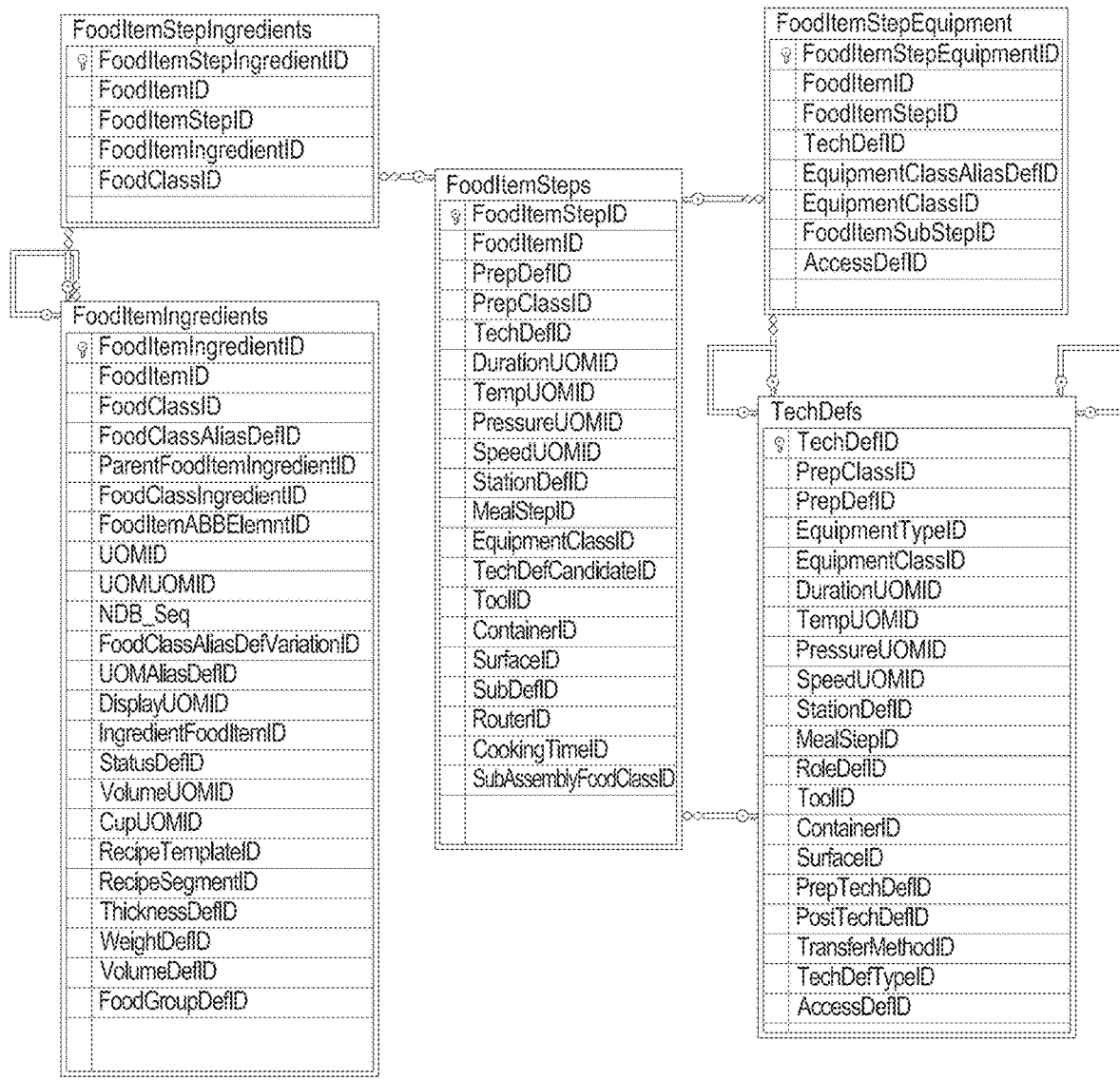
FIG. 10 schematically illustrates an example set of database tables in accordance with certain embodiments described herein.

In certain embodiments, the at least one computer database is configured to support a constant connection between Ingredients, Equipment, and Techniques used in a single step of a recipe. FIG. 10 schematically illustrates an example set of database tables in accordance with certain embodiments described herein. These database tables can be the inner-workings of the recipe instructions, making use of commonly-named foreign keys to extend back to their appropriate definitions tables. Each step in the recipe instructions can be assigned a "SeqOrder" or sequence order value (1 to Step 1, 2 to Step 2, etc.). Moreover, the gross list of ingredients can be correlated with the Recipe Step in which they are introduced.

Figure 11A:
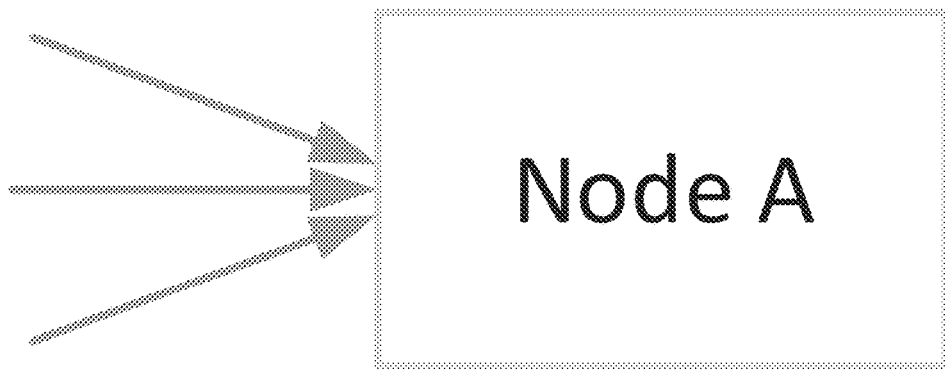
FIG. 11A schematically illustrates an example convergent connection in accordance with certain embodiments described herein.
Figure 11B:
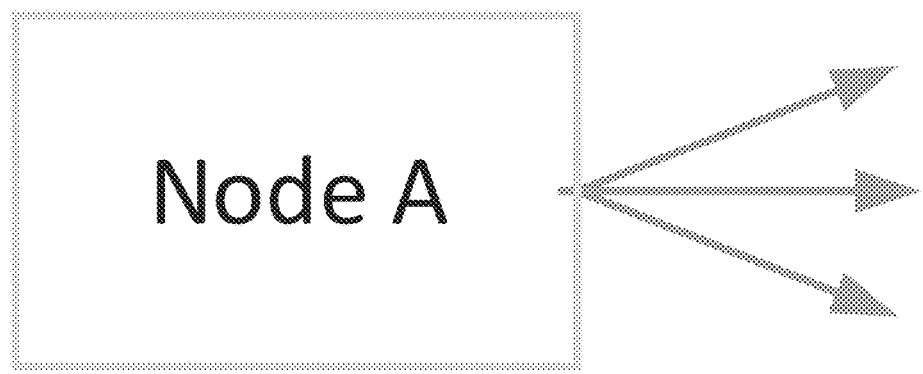
FIG. 11B schematically illustrates an example divergent connection in accordance with certain embodiments described herein.

In certain embodiments, the nodes are connected to each other by a technique or by a series of techniques that are used to convert the item or ingredient from State A to State B. For example, FIG. 11A schematically illustrates an example convergent connection in accordance with certain embodiments described herein, in which multiple nodes go into one or more techniques (e.g., one or more connectors converge into a node), producing a single node (Node A in FIG. 11A). For another example, FIG. 11B schematically illustrates an example divergent connection in accordance with certain embodiments described herein, in which one node (Node A in FIG. 11B) goes into one or more techniques (e.g., one or more connectors diverge from a node), resulting in multiple nodes leaving it.

The at least one computer database of certain embodiments couples (e.g., "stitches") single instances of a node-to-node model, with downstream instances of other node-to-node models, in a simple linear set of recipe instructions, an extended set of linear instructions, a convergent set of instructions, a divergent set of instructions, or any complex combination of linear, extended linear, convergent, and divergent set of instructions. For a set of simple linear instructions, the at least one computer database can create using a single node-to-node structure (e.g., the most basic model) which can include a single ingredient, a single technique, and a single set of tools, that result in a single ingredient. For example:

| Node A | Technique | Node B |
| --- | --- | --- |
| 1 lb Frozen Hamburger | Thaw in a Refrigerator | 1 lb Hamburger (thawed) |

For a set of extended linear instructions, the at least one computer database can use a single node-to-node structure that contains multiple steps and which can include a single ingredient, a series of multiple techniques, each with its own set of tools, that result in a single ingredient. For example:

| Node A | Technique 1 | Technique 2 | Technique 3 | Node B |
| --- | --- | --- | --- | --- |
| 1 lb Hamburger (thawed) | Place Hamburger on Clean Surface | Knead the Hamburger by hand. | Form the Hamburger into a Single Patty by hand | 1 Hamburger Patty (1 lb) |

For a convergent set of instructions, the at least one computer database can use multiple node-to-node networks (e.g., instances), each of which results in a single ingredient, which are then used as ingredients in a third node-to-node network, which results in a single ingredient. For the following example, Network I and Network II feed into Network III:

| Network I | | | | | | |
|---|---|---|---|---|---|---|
| Node A | Technique 1 | Technique 2 | Technique 3 | Technique 4 | Technique 5 | Node B |
| 1 Hamburger Patty (1 lb) | Preheat Gas Grill | Place Hamburger Patty on Preheated Grill | Grill Hamburger Patty for 3 minutes | Flip Hamburger Patty | Grill Hamburger Patty for 3 minutes | 1 Grilled Hamburger Patty |

| Network II | | | | |
|---|---|---|---|---|
| Node A | Technique 1 | Technique 2 | Technique 3 | Node B |
| 3 Mushrooms (halved) | Preheat lightly oiled Saute Pan | Place Mushroom Halves in the Preheated Saute Pan | Saute Mushroom Halves for 5 Minutes | 3 Mushrooms (halved and sauteed) |

| Network III | | | |
|---|---|---|---|
| Nodes A | Technique 1 | Technique 2 | Node B |
| A1 1 Grilled Hamburger Patty | Place Grilled Hamburger Patty on a Plate | Scoop the Sauteed Mushroom Halves on top of the Hamburger Patty | Grilled Hamburger and Mushrooms |
| A2 3 Mushrooms (halved and sauteed) | | | |

For a divergent set of instructions, the at least one computer database can use a single ingredient in one node-to-node network (e.g., instance), which results in multiple ingredients, which are then used, each individually, as single ingredient inputs to other node-to-node networks, each of which results in one or more ingredients. For the following example, Network I diverges into Network II and Network III:

| Network I | | | |
|---|---|---|---|
| Node A | Technique 1 | Nodes B | |
| 1 Fresh Apple | Core Apple with Corer | 1 Apple (cored) | B1 |
| | | 1 Apple Core | B2 |

| Network II | | | |
|---|---|---|---|
| Node A | Technique 1 | Node B | |
| 1 Apple (cored) | Peel with a Peeler | 1 Apple (cored and peeled) | B1 |
| | | Apple Peel | B2 |

| Network III | | | |
|---|---|---|---|
| Node A | Technique 1 | Node B | |
| 1 Apple Core | Seed Removal with Knife | Apple Seeds | B1 |
| | | Apple Core (seeded) | B2 |

For a set of complex combination instructions, the at least one computer database can use any single or multiple ingredients, feeding a combination of convergent, linear, and/or divergent structures, which collectively result in one or more ingredients. For the following example, multiple ingredients converge into a Sourdough Bread recipe, which is then halved, half for baking and half for storing (e.g., to be used as a starter mixture to make the next batch of sourdough):

| | | | | | |
|---|---|---|---|---|---|
| 1 tablespoon active dry yeast starter | Starter Mixture | Sourdough Dough | Halve | Half A | Bake | Sourdough Bread |
| 75 grams (½ cup) all- purpose flour | | | | | | |
| 75 grams (⅓ cup) water | | | | | | |
| 1 tablespoon salt | Dough Mixture | | | Half B | Store | Aged Sourdough Dough (Starter Mixture) |
| 525 grams (2½ cups) water | | | | | | |
| 700 grams (5½ cups) all-purpose flour | | | | | | |

FIG. 12 schematically illustrates a basic recipe node-to-node network (e.g., instance) in accordance with certain embodiments described herein. The network comprises a title (e.g., output) of the recipe, the ingredients (e.g., inputs) of the recipe, and the steps and description (e.g., actions) to turn the ingredient inputs into the recipe output.

Figure 13A:
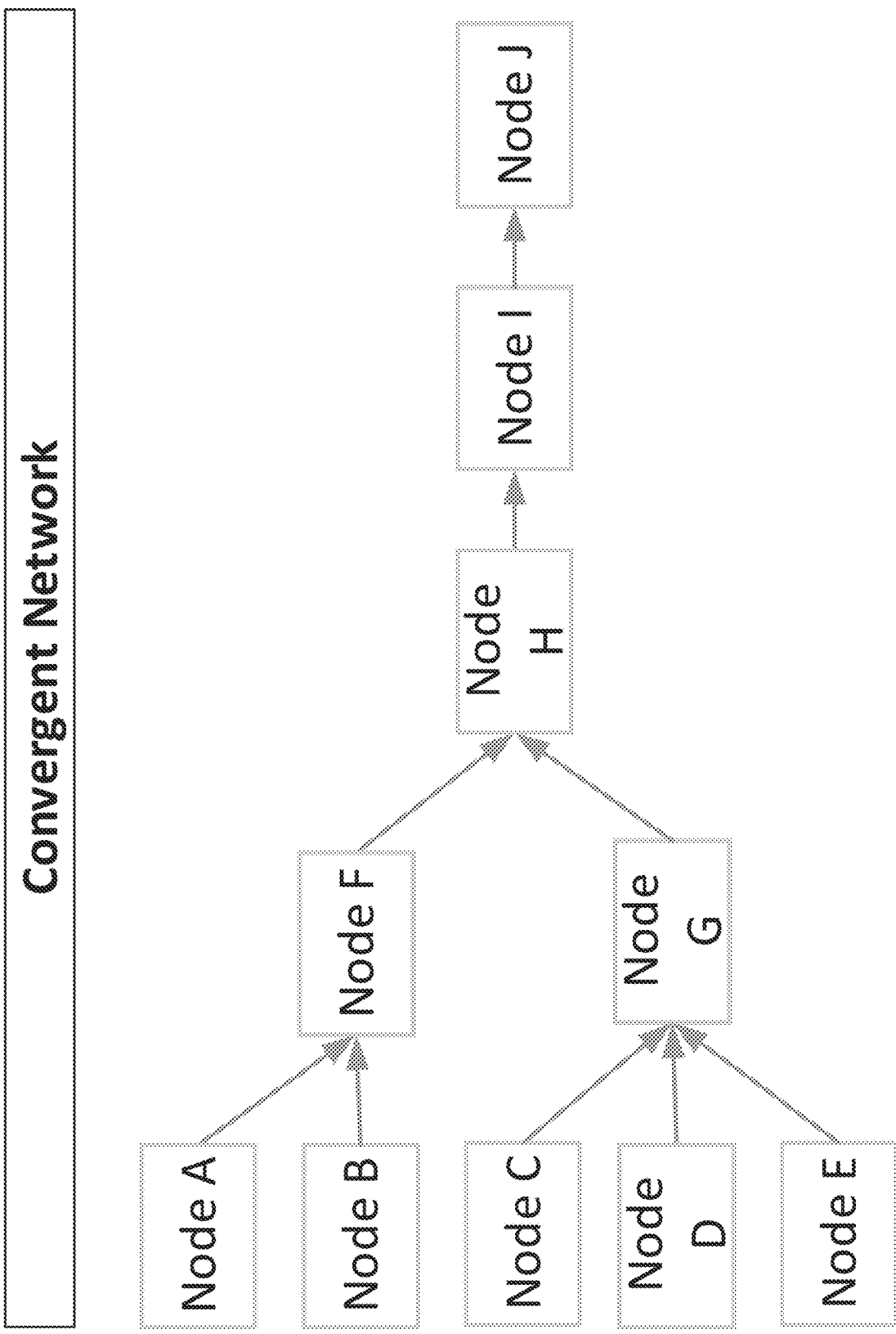
FIG. 13A schematically illustrates a convergent node-to-node network in accordance with certain embodiments described herein.
Figure 13B:
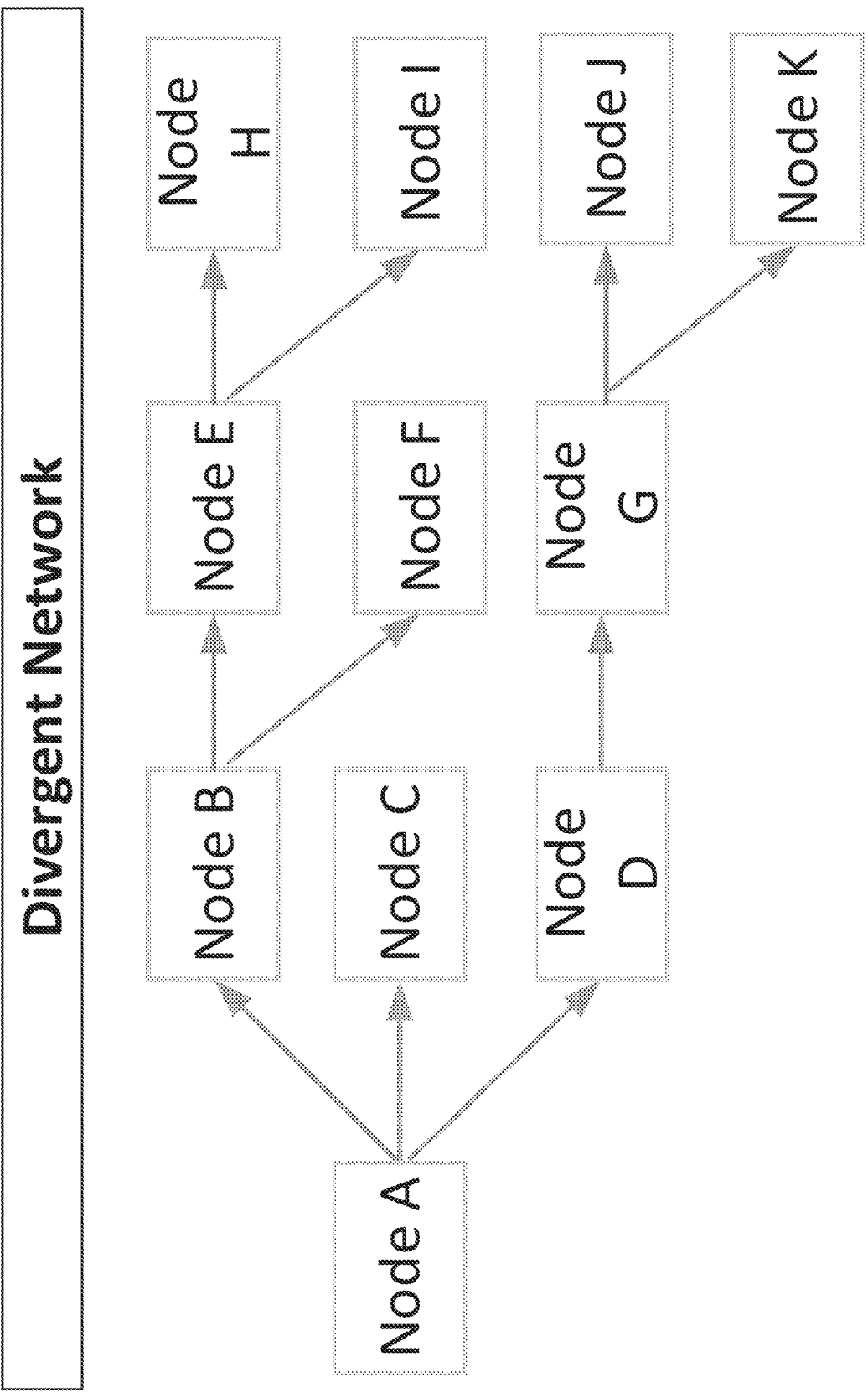
FIG. 13B schematically illustrates a divergent node-to-node network in accordance with certain embodiments described herein.

FIG. 13A schematically illustrates a convergent node-to-node network in accordance with certain embodiments described herein. The nodes are connected in a way that they continue to converge until the final node in the network. For example, an Apple Pie uses many ingredients that are prepared into two forms: a filling and a pie crust. These ingredients are assembled and then baked to transform them into an Apple Pie. FIG. 13B schematically illustrates a divergent node-to-node network in accordance with certain embodiments described herein. The nodes are connected such that they derive from one node and continue to have various forms. For example, a Fresh Apple can be cut in half to produce Apple Halves, the Apple Halves can have the seeds removed creating Seedless Apple Halves, and the Seedless Apple Halves can be cut in half to create Seedless Apple Quarters. The Fresh Apple can also be cored to create a Cored Apple. The Cored Apple can then be peeled into an Apple (Peeled & Cored). The network continues to diverge until all possible forms are connected via the node-to-node structure.

In certain embodiments, there are also combinations of a divergent network connected with a convergent network or a convergent network connected to a divergent network, ad infinitum. For example, for a divergent network connected to a convergent network, a Fresh Apple can be the beginning of a divergent network with all the various Apple derivative forms, and many of these forms (e.g., Seeded Sliced Apples) can be used in a convergent network (e.g., an Apple Pie). For example, for a convergent network connected to a divergent network, Making Bread can be a convergent network in which various flour mixes are combined to form a Bread Dough, and the Bread Dough is then baked, creating Baked Bread. The Baked Bread can then be made into Bread Crumbs which can be called out in a multitude of recipes, creating a divergent network into many recipes which use Bread Crumbs (e.g., crab cakes, breaded meats, breaded poultry, fillings, stuffing, etc.). In another example of a divergent network, Baked Bread can be sliced into Slices, which are then toasted in a toaster, creating Toasted Bread Slices. The Toasted Bread Slices are then buttered with a butter knife to create Toasted Buttered Bread Slices.

The food side of cooking is where the food is changed into a state useful for use in a recipe. The recipe can have certain food ingredients that are in a particular state to be used in the recipe, where they are transformed into a given final state. When starting with the Live/Fresh/Raw State of a given ingredient and then changing its form, there can be many different forms in which the changed ingredients can be used. For example, an Apple can be cut into halves, its seeds can be removed, it can be cut into quarters, or the Apple can be cored, then peeled and cut into peeled halves. The result of all the forms of an apple is a divergent network, where the network branches into more and more nodes. Each node can represent a possible ingredient which can be used directly into a recipe.

When starting with a recipe, all the ingredients can be provided in the forms dictated by the recipe before cooking. The French call this Mise en Place, which is everything ready and in place. The recipe can call out the item in a state. A recipe can start with one or more ingredients which can be combined together into one final form by the end of the recipe. Recipes can start with many things that then become one, which can be a convergent network, with all the nodes and ingredients leading to one final ingredient. This is like assembling a car, where thousands of parts produce one single item.

Figure 14:
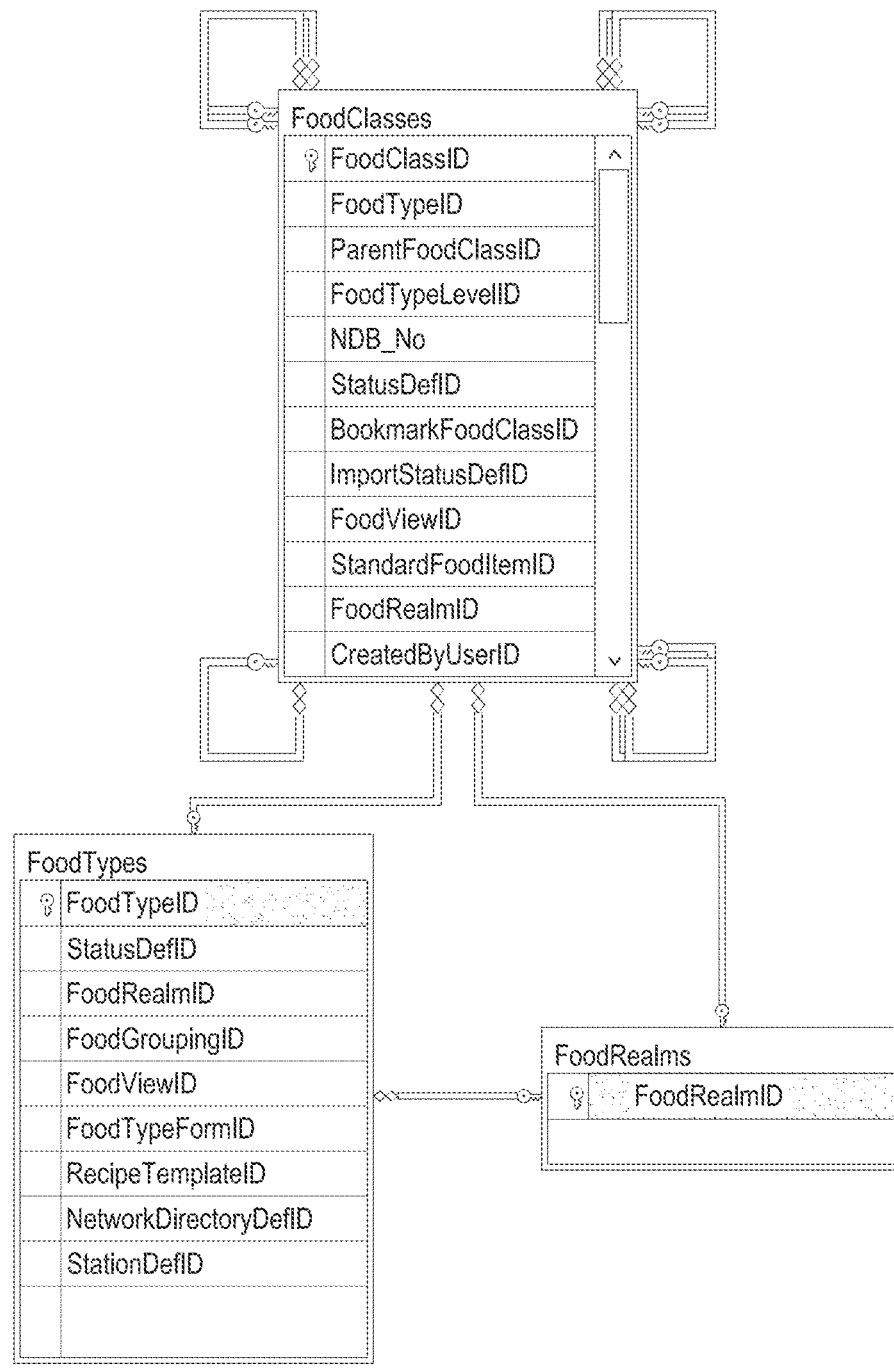
FIG. 14 schematically illustrates an example set of database tables in accordance with certain embodiments described herein.

FIG. 14 schematically illustrates an example set of database tables in accordance with certain embodiments described herein. The computer database splits the dbo.FoodClasses table (and corresponding dbo.FoodTypes table) into two halves, marked with foreign key connection to dbo.FoodRealms. Food Classes with a single item ingredient can reside within the "Food" realm, and Food Classes with two or more ingredients can reside within the "Recipe" realm.

Figure 15A:
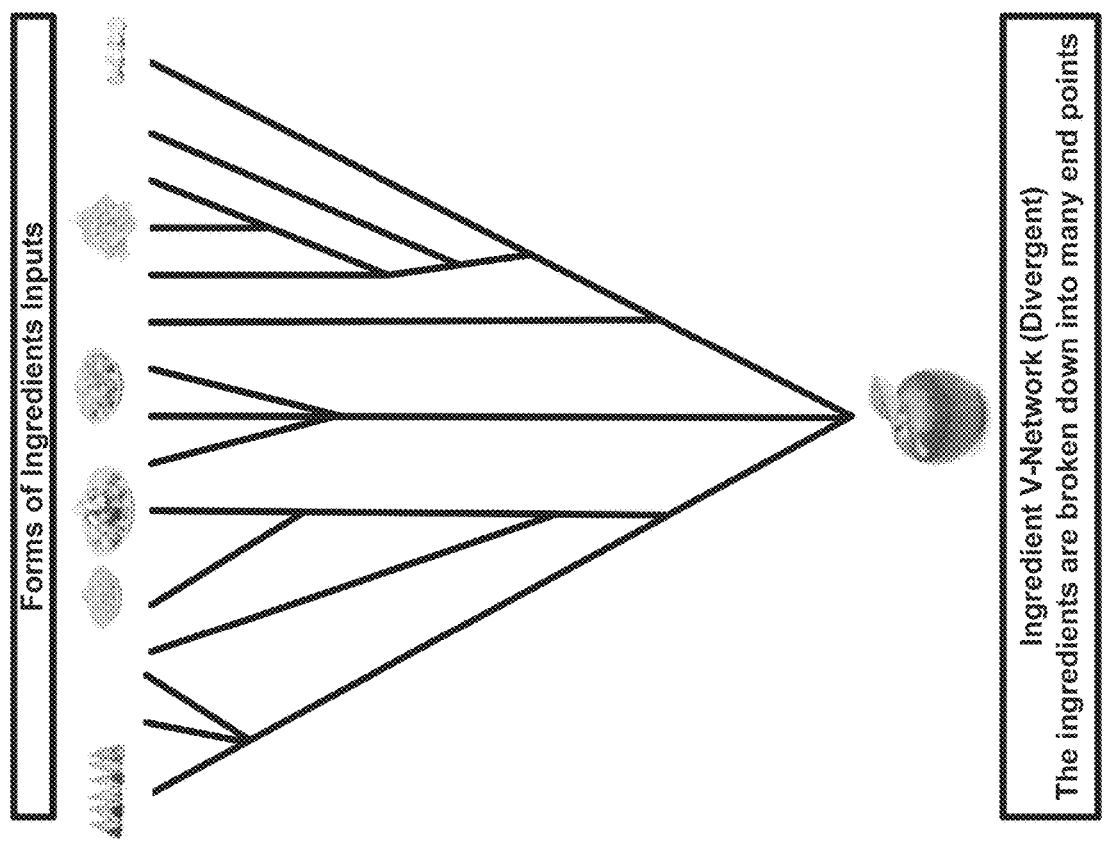
FIG. 15A schematically illustrates an example ingredient network (e.g., for Apple) having a V-network divergent structure in accordance with certain embodiments described herein.

FIG. 15A schematically illustrates an example ingredient network (e.g., for Apple) having a V-network divergent structure in accordance with certain embodiments described herein. Ingredients generally start in their Live, Fresh or Raw state. An ingredient can be used fresh or it can be prepared by hand or by tools to convert into a form useful in a recipe. For example, an Apple has an ingredient network in the shape a "V" (e.g., a V-network), where each form of the ingredient is different. The ingredient network can be divergent, where each form of the ingredient is a derivative of the raw form where it is still identifiable. In certain embodiments, the Food realm covers the ingredients and their basic forms for use in a recipe. For example, a raw New York Steak can be in the Food realm. Where the food item is cooked or mixed with other ingredients, then it can be part of the Recipe realm.

Figure 15B:
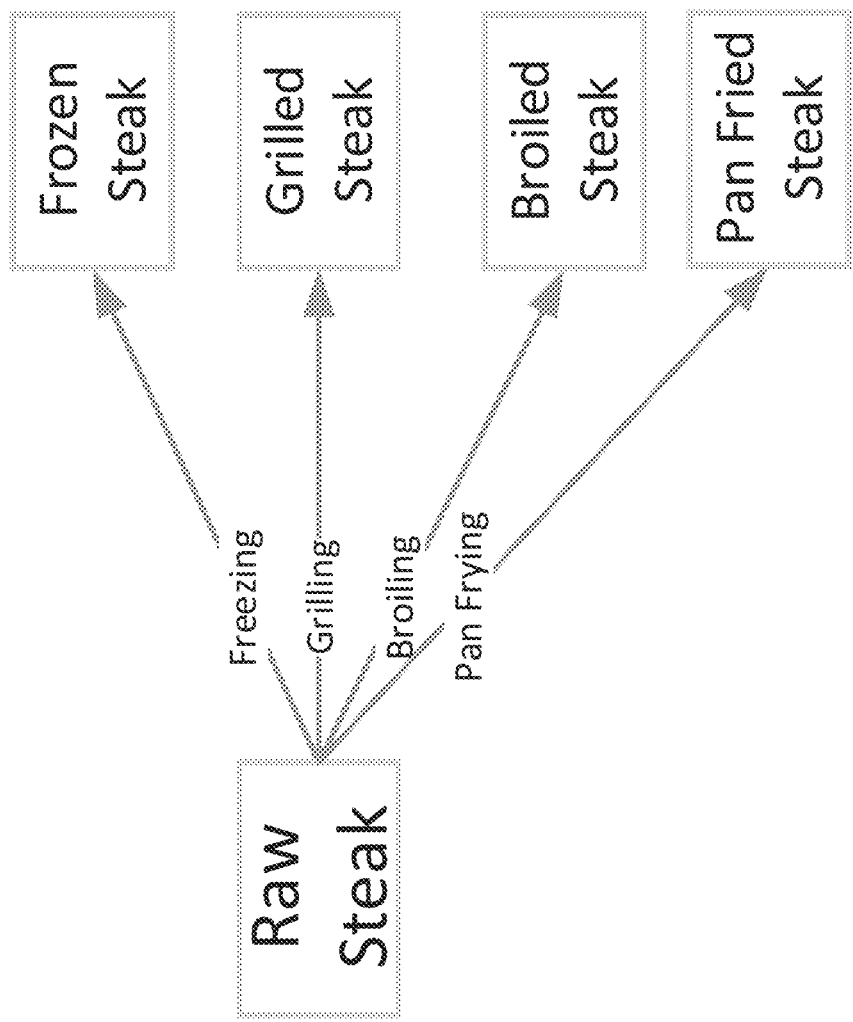
FIG. 15B schematically illustrates an example divergent temperature change network (e.g., for Steak) in accordance with certain embodiments described herein.
Figure 15C:
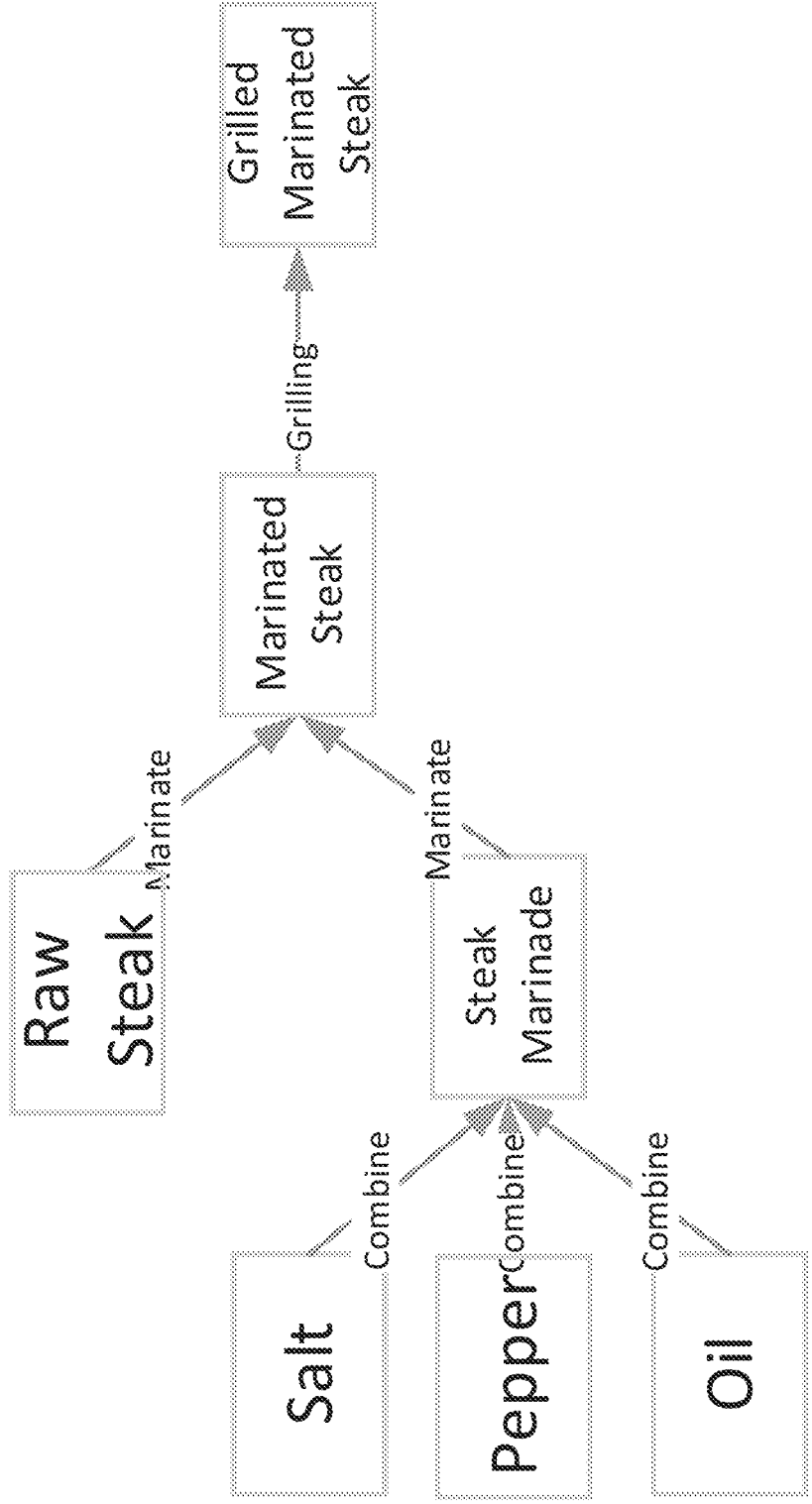
FIG. 15C schematically illustrates an example food item recipe convergent network in accordance with certain embodiments described herein.

FIG. 15B schematically illustrates an example divergent temperature change network (e.g., for Steak) in accordance with certain embodiments described herein. The raw New York Steak can be flash frozen, refrigerated or cooked, such as grilled, pan fried or broiled. This pivot can connect the Live, Fresh or Raw form to its possible cooking/freezing/refrigerating preparation methods. FIG. 15C schematically illustrates an example food item recipe convergent network in accordance with certain embodiments described herein. As shown in FIG. 15C, the raw steak can be part of the set of convergent steps to create a Grilled Marinated Steak. The other ingredients can connect into the recipe convergent network via flavoring methods prior to cooking as well (e.g., the New York Steak can be flavored by seasoning, rubbing, marinating, etc.). This preparation for flavoring can be on the recipe side which are generally convergent networks.

The Food realm can comprise divergent networks from a given raw/fresh/live ingredient, starting with the ingredient in its beginning Live, Fresh or Raw state, and all the derivative forms connected to this beginning state. The derivative forms also can be connected to their state where the temperature is changed (e.g., frozen, refrigerated, cellared, dried, cooked, etc.). There can also be derivative products produced by certain food processing techniques, which can be referred to as derivative food products. For example, Corn can be separated into its component germ, bran, starch, oil, etc., which are all derivatives of Corn and can form part of its divergent food network.

Figure 16A:
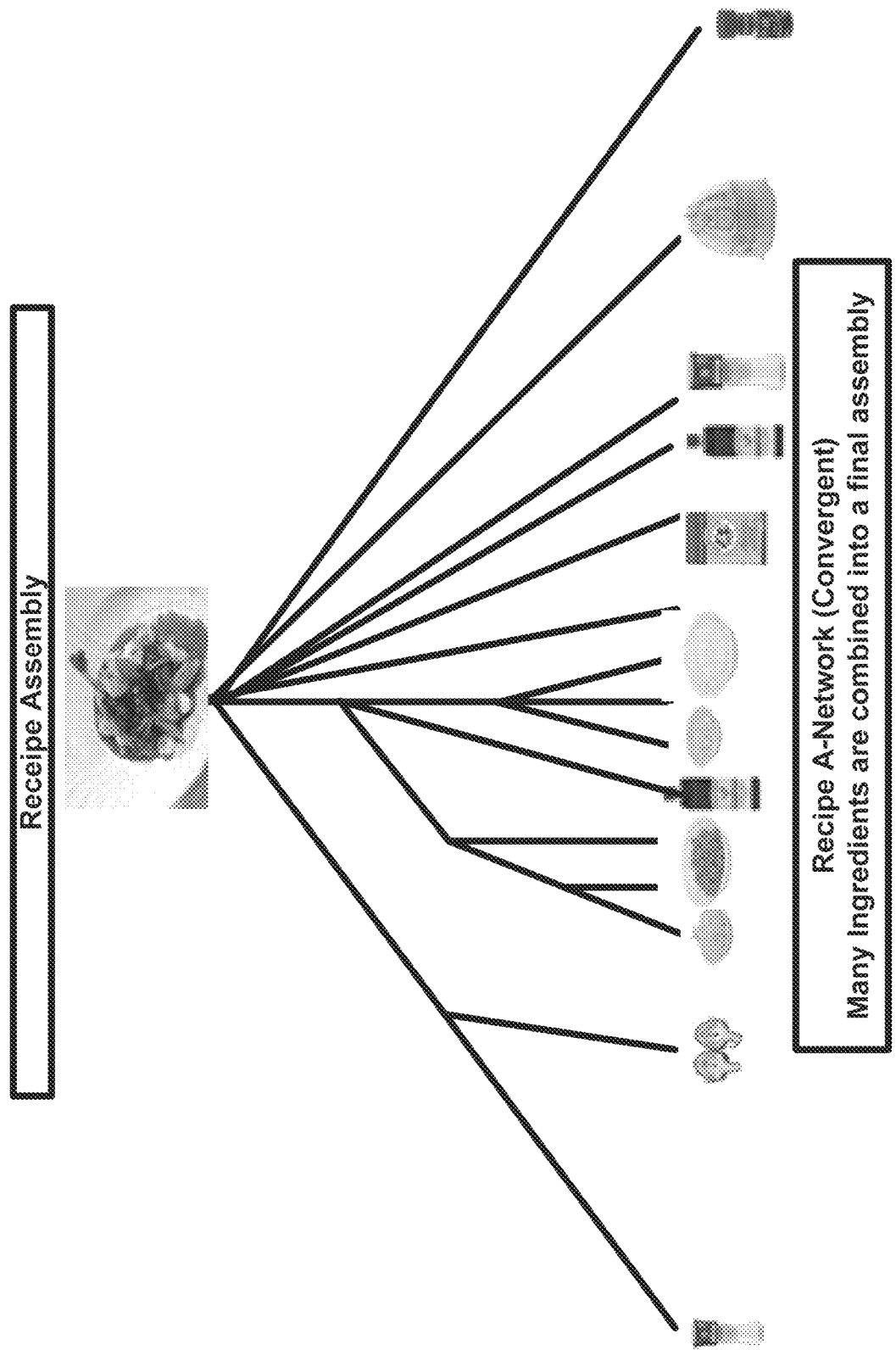
FIG. 16A schematically illustrates an example recipe network having an A-network convergent structure in accordance with certain embodiments described herein.

FIG. 16A schematically illustrates an example recipe network having an A-network convergent structure in accordance with certain embodiments described herein. Recipes can be the conversion of one item from one form to another, which changes its state and/or its temperature. Recipes are generally (but not always) a convergent network in which one or more ingredients can be used to make a final item (e.g., many ingredients can be combined and prepared in various ways into a final assembled dish). The dissimilar ingredients can be combined in various ways to form a final singular outcome. As shown in FIG. 16A, the network can be the shape of an "A," in which there are many inputs culminating in one final output (e.g., a convergent network).

Figure 16B:
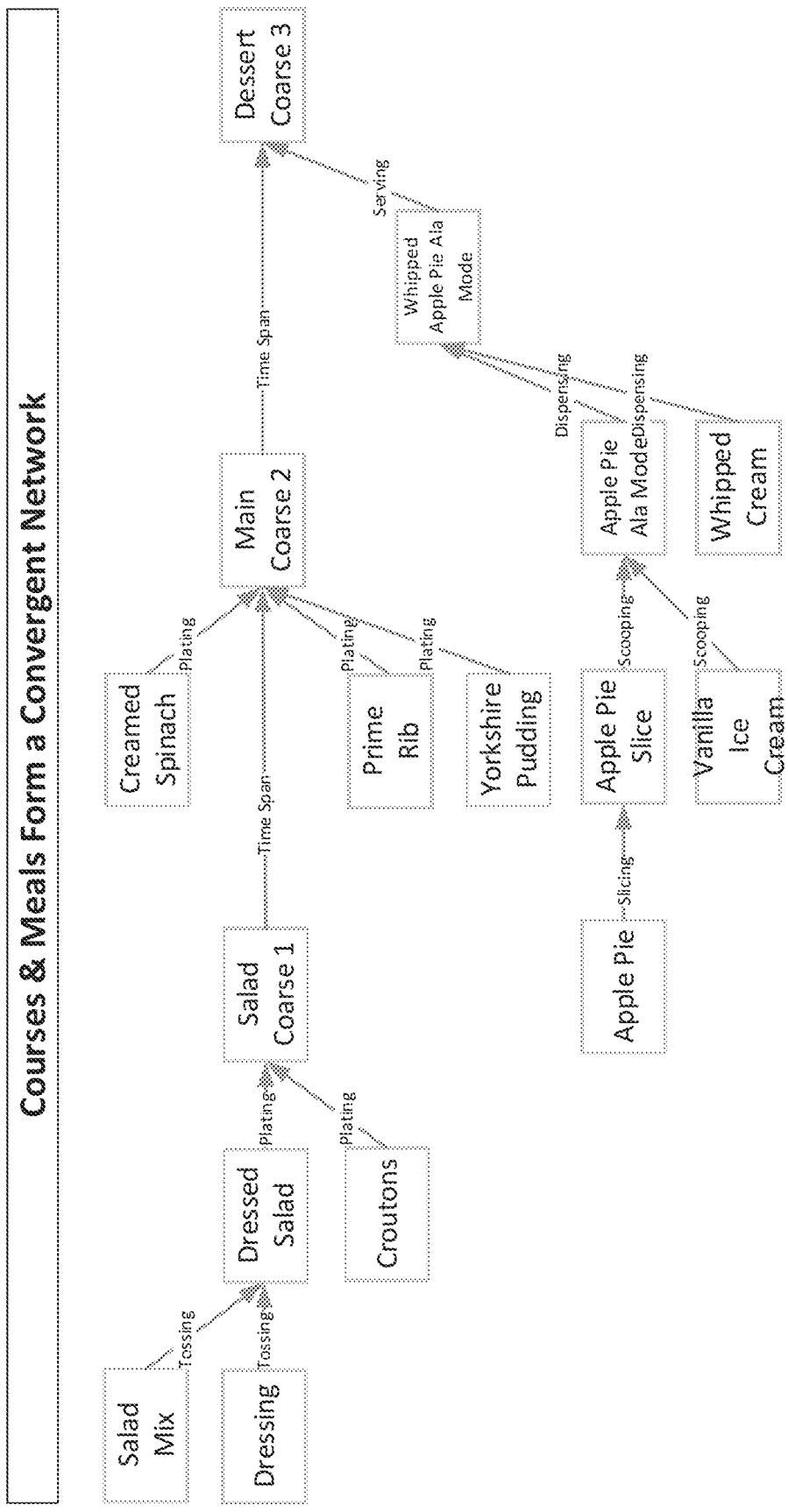
FIG. 16B schematically illustrates an example convergent network in which three courses form a meal in accordance with certain embodiments described herein.
Figure 17A:
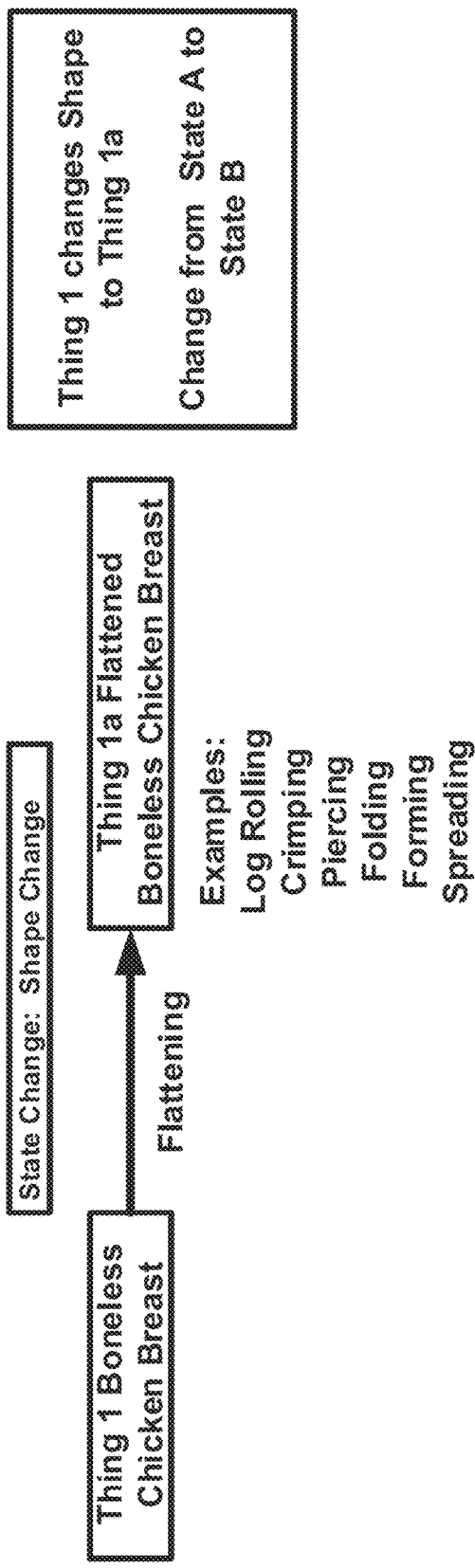
Figure 17B:
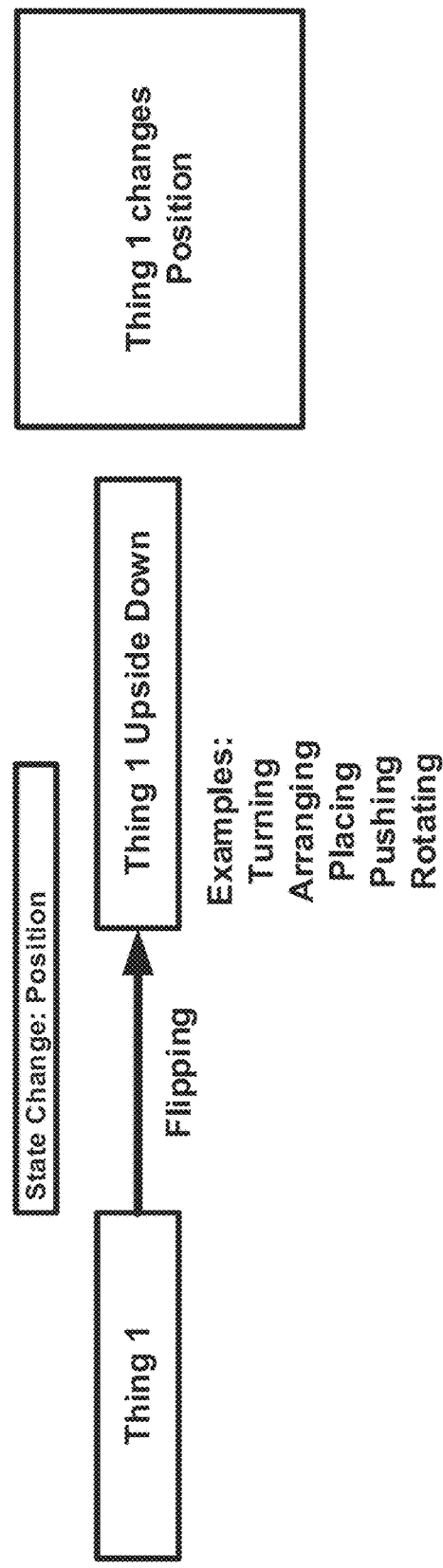
Figure 17C:
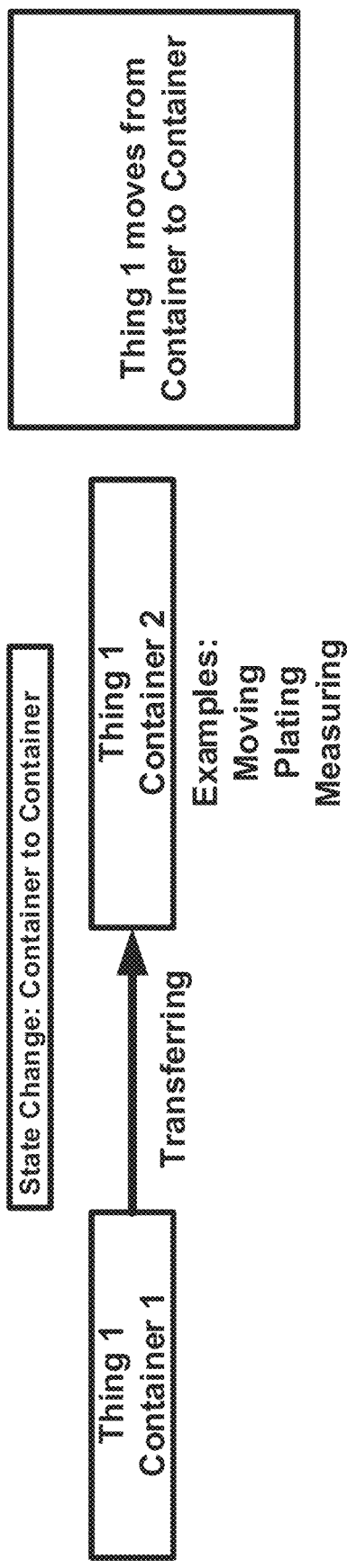
Figure 17D:
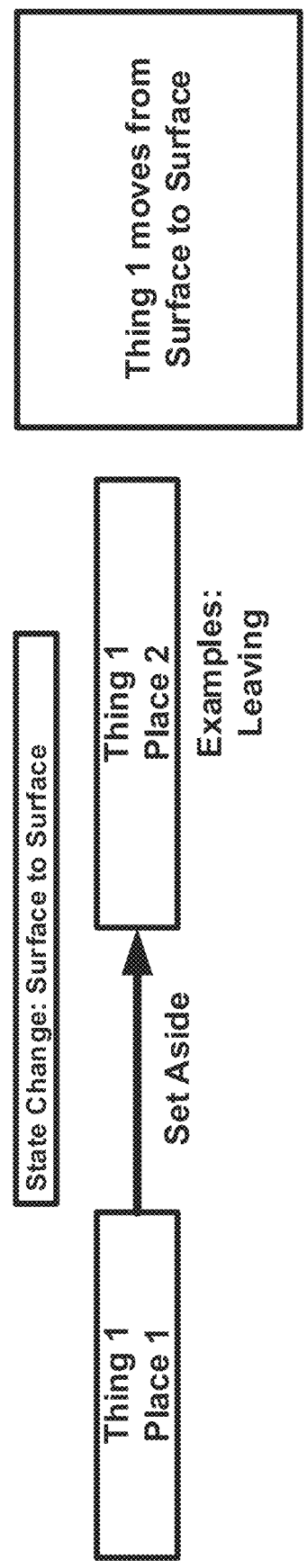
Figure 17G:
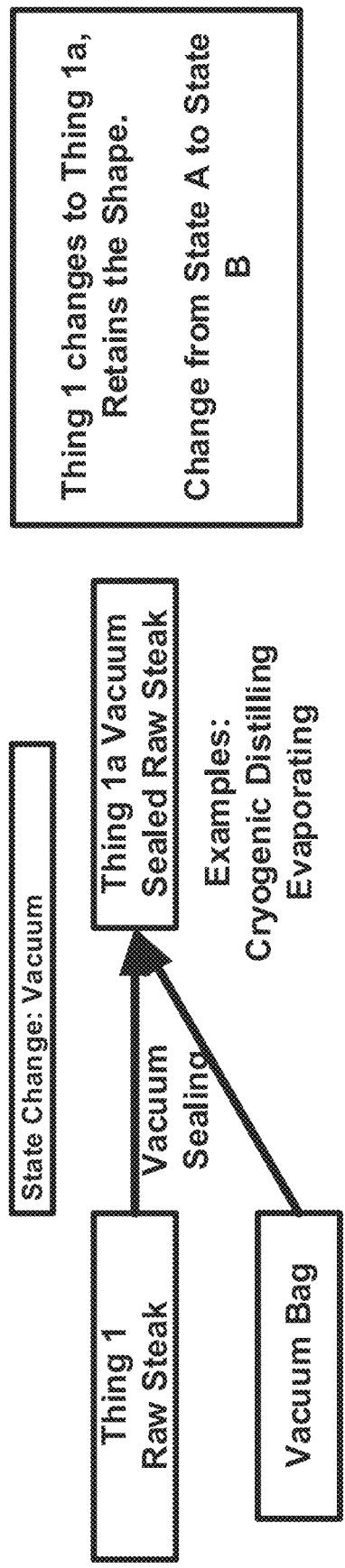
Figure 17H:
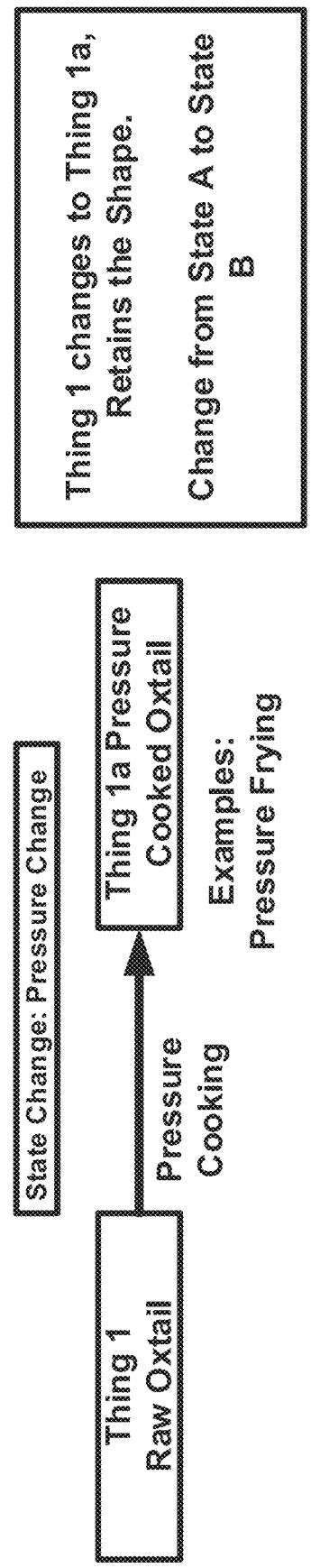
Figure 18C:
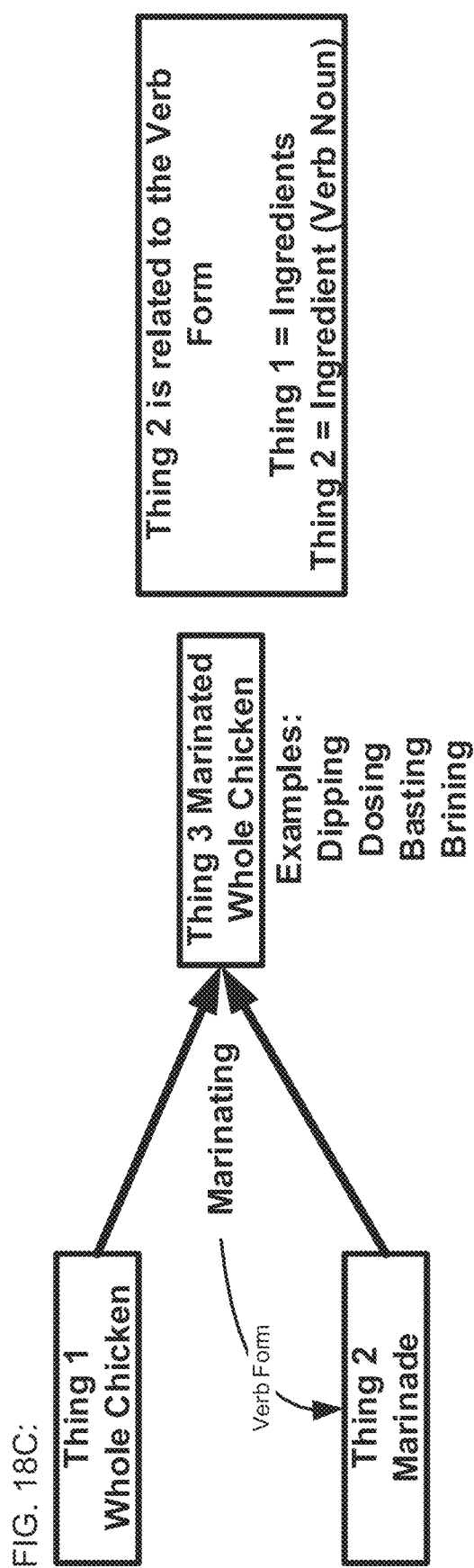
Figure 18D:
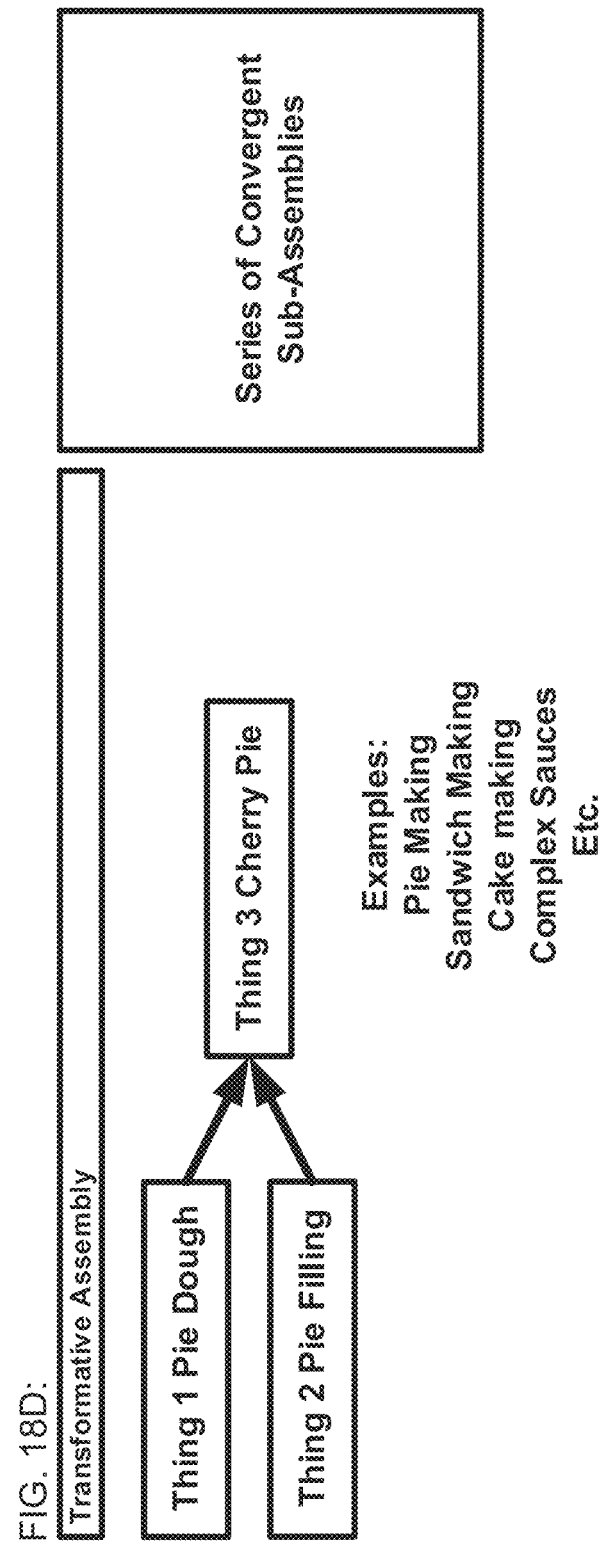
Figure 19A:
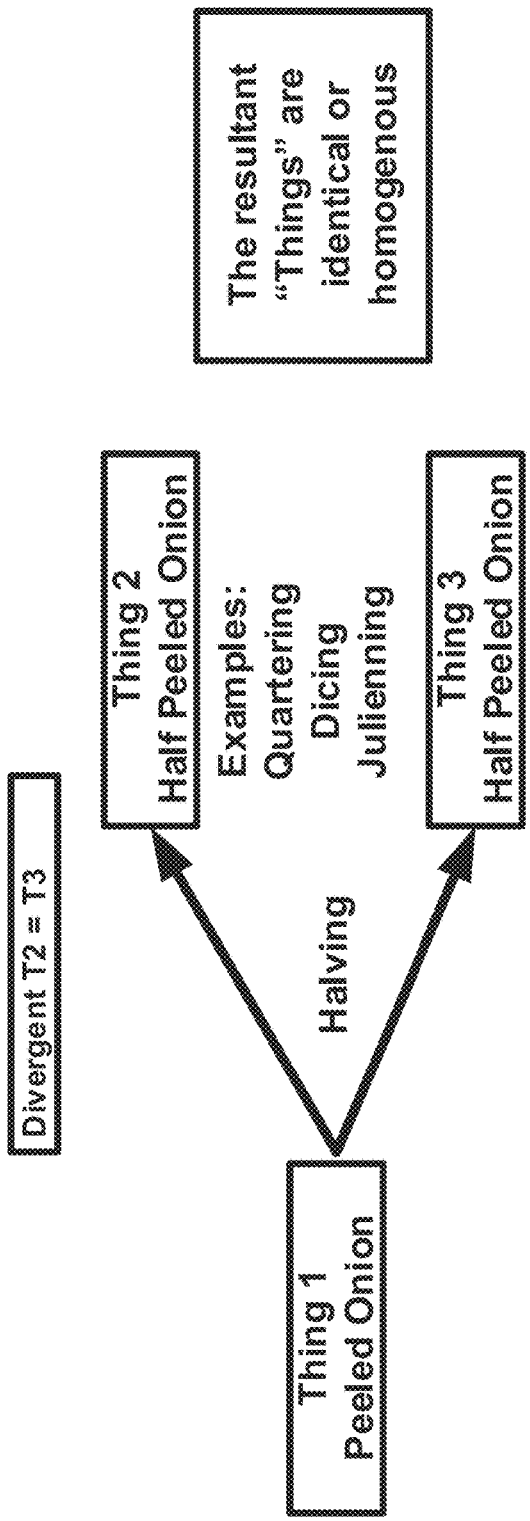
FIGS. 19A-19C schematically illustrate various examples of divergent node-to-node structures in accordance with certain embodiments described herein.
Figure 19B:
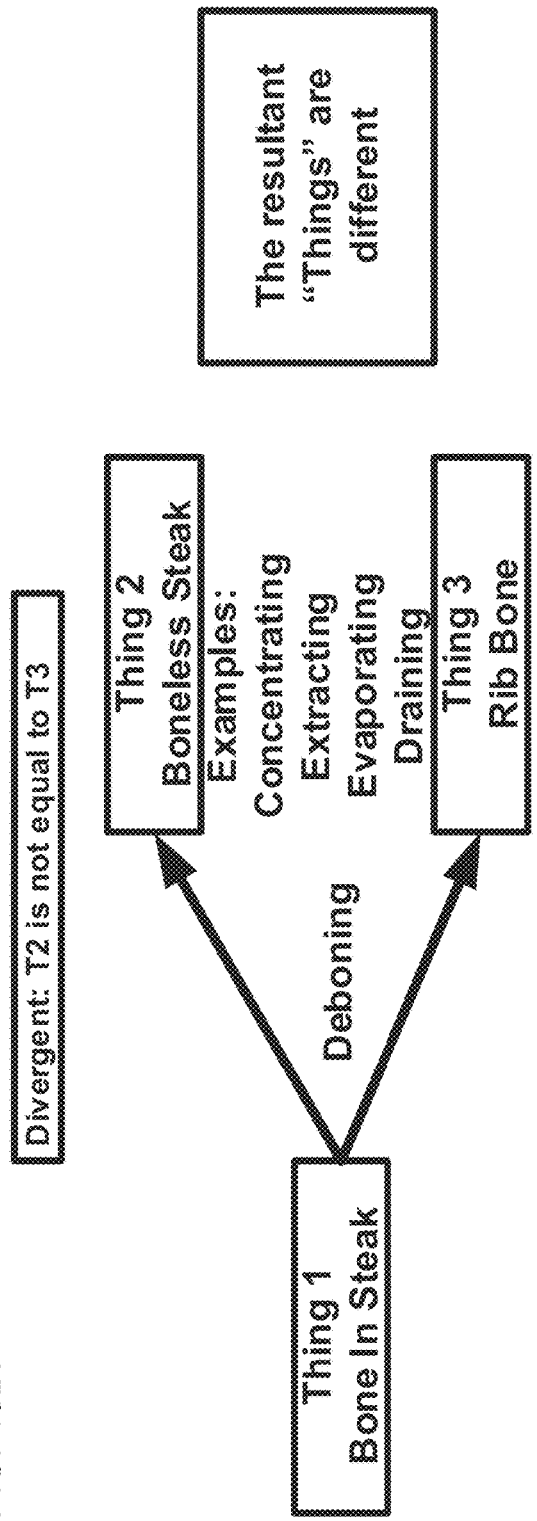
Figure 19C:
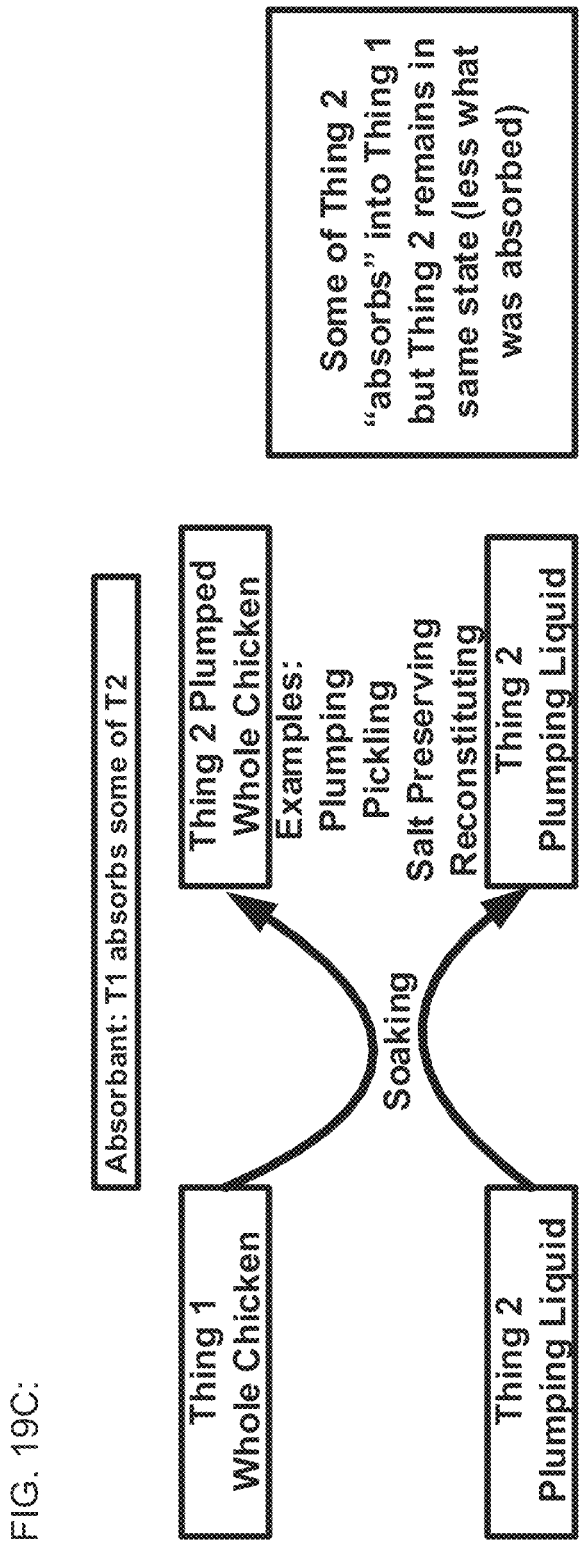

A meal can be another example of a convergent network, where a meal comprises various recipes. For example, Roasted Prime Rib with Yorkshire Pudding and Creamed Spinach can be a main dish for a meal. Each of the individual items can have its own recipe (e.g., recipes for Roasted Prime Rib, Yorkshire Pudding, and Creamed Spinach). Together, these three recipes can converge and form the main dish of the meal. A meal can also comprise one or more courses. Courses can be sequential servings of the overall meal. Each course can be a convergent network to form the course of that meal. FIG. 16B schematically illustrates an example convergent network in which three courses form a meal in accordance with certain embodiments described herein. The first course can be a salad, the second course can be a main dish, and the final course can be a dessert. Each course can comprise one or more recipes which can be performed to serve the course. The courses can be separated by a time span between them or can be served in parallel with one another.

FIGS. 17A-17H schematically illustrate various examples of state change node-to-node structures (e.g., changes of form, position, temperature, humidity, and/or pressure/vacuum) in accordance with certain embodiments described herein. FIGS. 18A-18D schematically illustrate various examples of convergent node-to-node structures in accordance with certain embodiments described herein. FIGS.

19A-19C schematically illustrate various examples of divergent node-to-node structures in accordance with certain embodiments described herein. As used herein, when referring to a thing being "related to the verb form" means that the noun form (e.g., the thing) and the verb form (e.g., the technique) may be based on the same root word and may be placed together, and when referring to a thing being "not related to the verb form" means that the form of the verb (e.g., technique) is not related to the form of either the input noun or the output noun.

Figure 20:
FIG. 20 schematically illustrates an example set of database tables that can plot recipes onto a calendar in accordance with certain embodiments described herein.

In certain embodiments, the nodes of the node-to-node structure or the one or more node-to-node segments of a recipe, course, or meal can be placed on a calendar or timeline, which can be used to set or coordinate a start time and/or finish time for using the recipe instruction step or steps. FIG. 20 schematically illustrates an example set of database tables that can plot recipes onto a calendar in accordance with certain embodiments described herein. In certain embodiments, the database can subsequently chart action items, their associated ingredients, and the equipment to be utilized on a User's Timeline. The node-to-node structure or segment can use a time duration for each of its techniques. The sum of the individual technique (e.g., step) times can enable the tasks to be scheduled on the timeline or started immediately. The nodes of the node-to-node structure or segment can be placed on a timeline or calendar either sequentially or in parallel to support making or scheduling a particular recipe or set of recipes.

Figure 21:
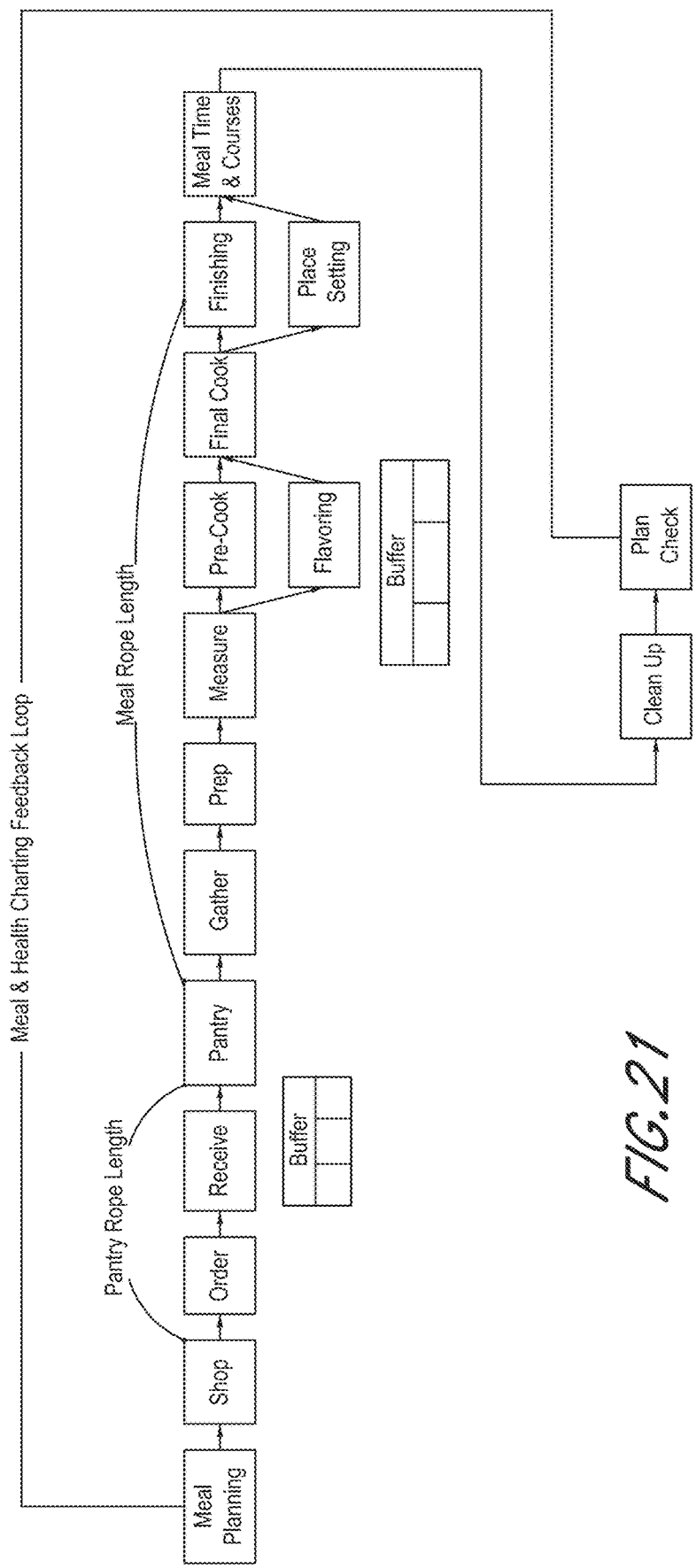
FIG. 21 schematically illustrates an example high level network in accordance with certain embodiments described herein.

FIG. 21 schematically illustrates an example high level network in accordance with certain embodiments described herein. At a high level, the network can be configured to repeat workflow, where the user can use one or more individual nodes based on how they want to use the software application. As shown in FIG. 21, a meal planning step can be at the highest level that connects with pantry management (e.g., shopping, ordering, receiving, pantry levels). From the pantry, the user can gather the ingredients from the pantry, prep them, measure them, cook and plate them as well as clean up. This network then can loop back to the meal planning.

Figure 22A:
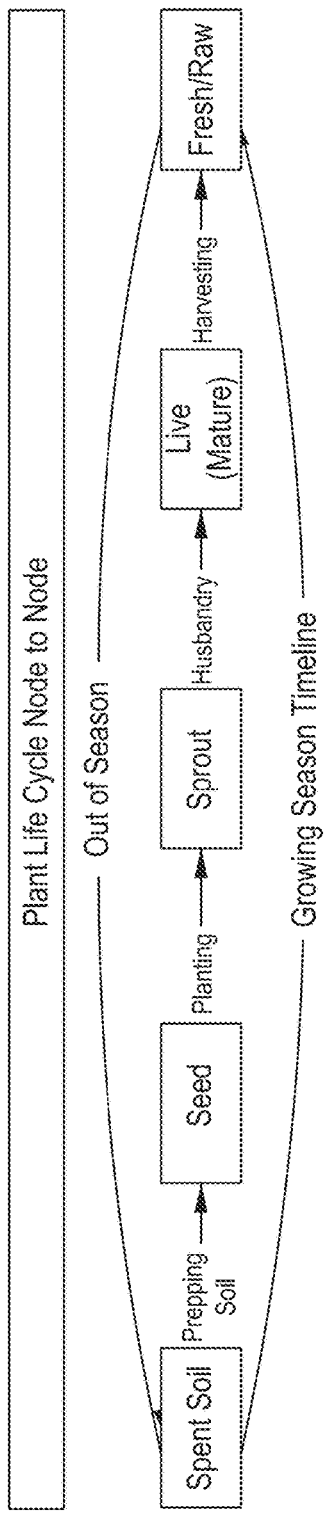
FIG. 22A-22C schematically illustrate the use of the node-to-node structure to model the cycle of life networks and its related seasonality in accordance with certain embodiments described herein.
Figure 22B:
Figure 22C:
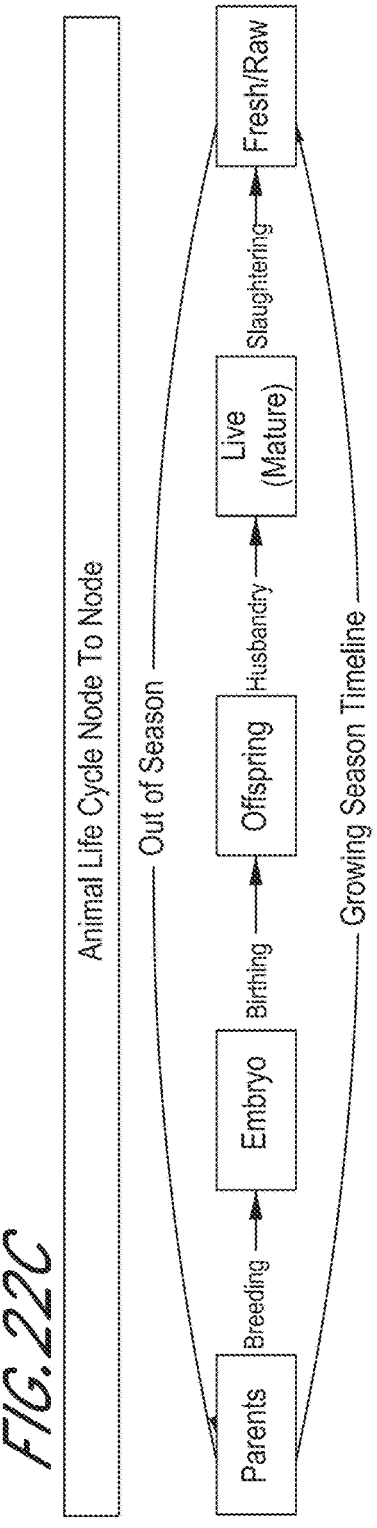

FIG. 22A-22C schematically illustrate the use of the node-to-node structure to model the cycle of life networks and its related seasonality in accordance with certain embodiments described herein. The plants and animals go through life cycles with node milestones, examples of which are shown in FIGS. 22A-22C. For example, FIG. 22A shows an example annual plant cycle, FIG. 22B shows an example perennial plant/tree cycle, and FIG. 22C shows an example animal cycle. The plant and animal life cycle node-to-node structure can show the perpetual growing cycles or regeneration life cycles.

Figure 23:
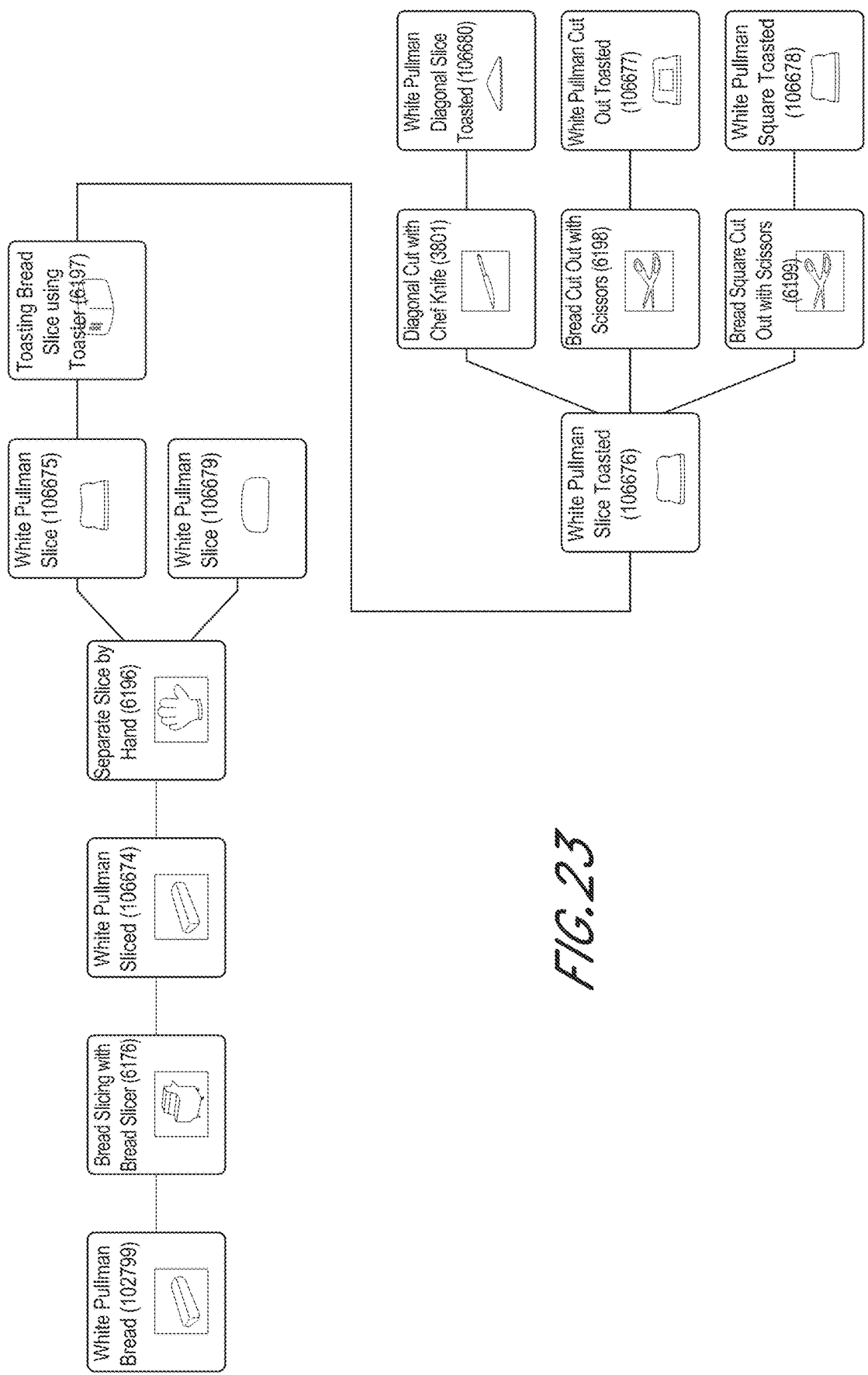
FIG. 23 schematically illustrates an example node-to-node structure with forms that can be derived from a loaf of bread in accordance with certain embodiments described herein.

In certain embodiments, the node-to-node structure can be used to tie all the forms and the activities together. The form can be connected via an "Action" to another form. Node A can be connected to Node B by a single verb (e.g., Noun A→Verb→Noun B) or by multiple verbs (e.g., Noun A→Verb1→Verb2, etc.→Noun B), with the verb action(s) changing the state of Noun A to the state of Noun B. FIG. 23 schematically illustrates an example node-to-node structure with forms that can be derived from a loaf of bread in accordance with certain embodiments described herein.

This node-to-node structure can be used throughout the network to standardize and harmonize the techniques and forms. There can be specific networks for cheese, oils, alcohol, baking, and all the cut forms in the food index. In certain embodiments, selected networks model how a product is made and can be kept as a standard. Most variations can be from the ingredient inputs and most food processing can follow the same basic steps with only a few variations (in what is practical).

Figure 24A:
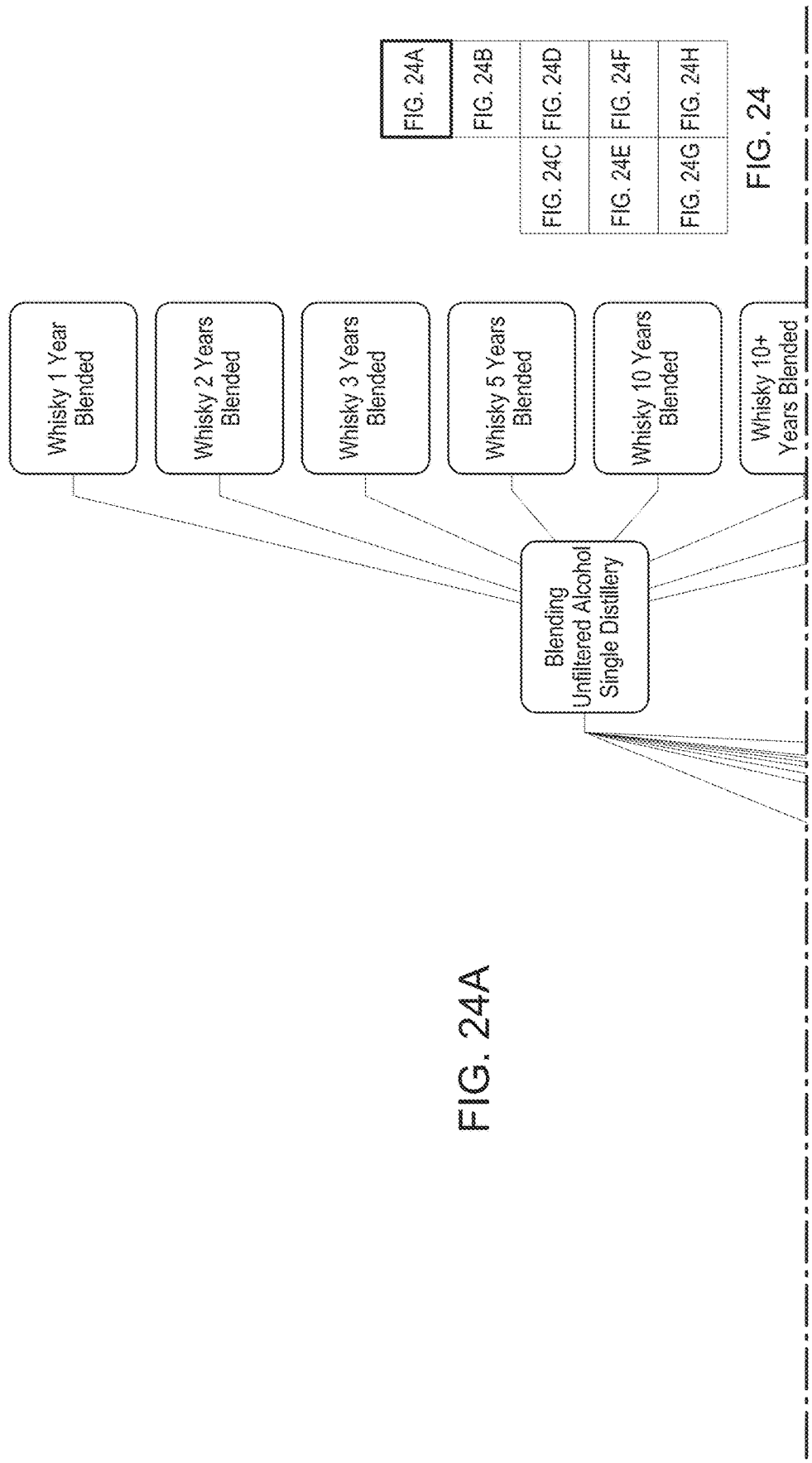
FIG. 24 schematically illustrates the node-to-node structure for whiskey in accordance with certain embodiments described herein.

All the recipes can form a web of networks as well. One output of a network can be an input into another network, providing the capability to scroll forward or backward through the network and providing traceability from beginning to end. As shown by FIG. 24, which schematically illustrates the node-to-node structure for Whiskey, the networks can become quite complex.

Figure 25:
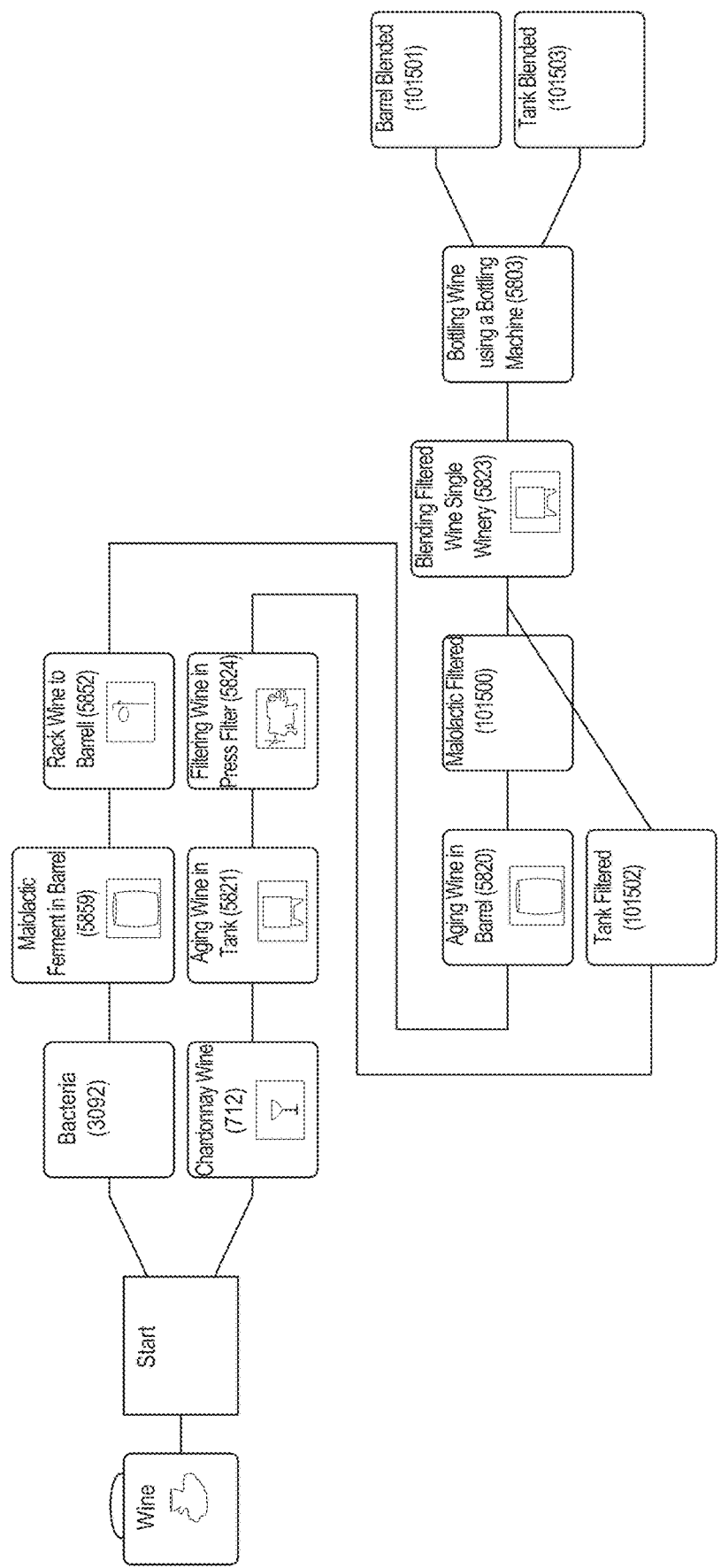
FIG. 25 schematically illustrates a node-to-node structure for the process industry of fermenting wine in accordance with certain embodiments described herein.

In certain embodiments, all foods can be connected via the node-to-node networks which comprise changes from State A to State B. The connector between A and B is the one or more actions to convert it from A to B, which can be referred to as a node-to-node structure or segment. For example, FIG. 25 schematically illustrates a node-to-node structure for the process industry of fermenting wine (e.g., white wine and variations) in accordance with certain embodiments described herein. As shown by FIG. 25, the ingredients can go through a few steps before a new intermediate product is formed.

Figure 26A:
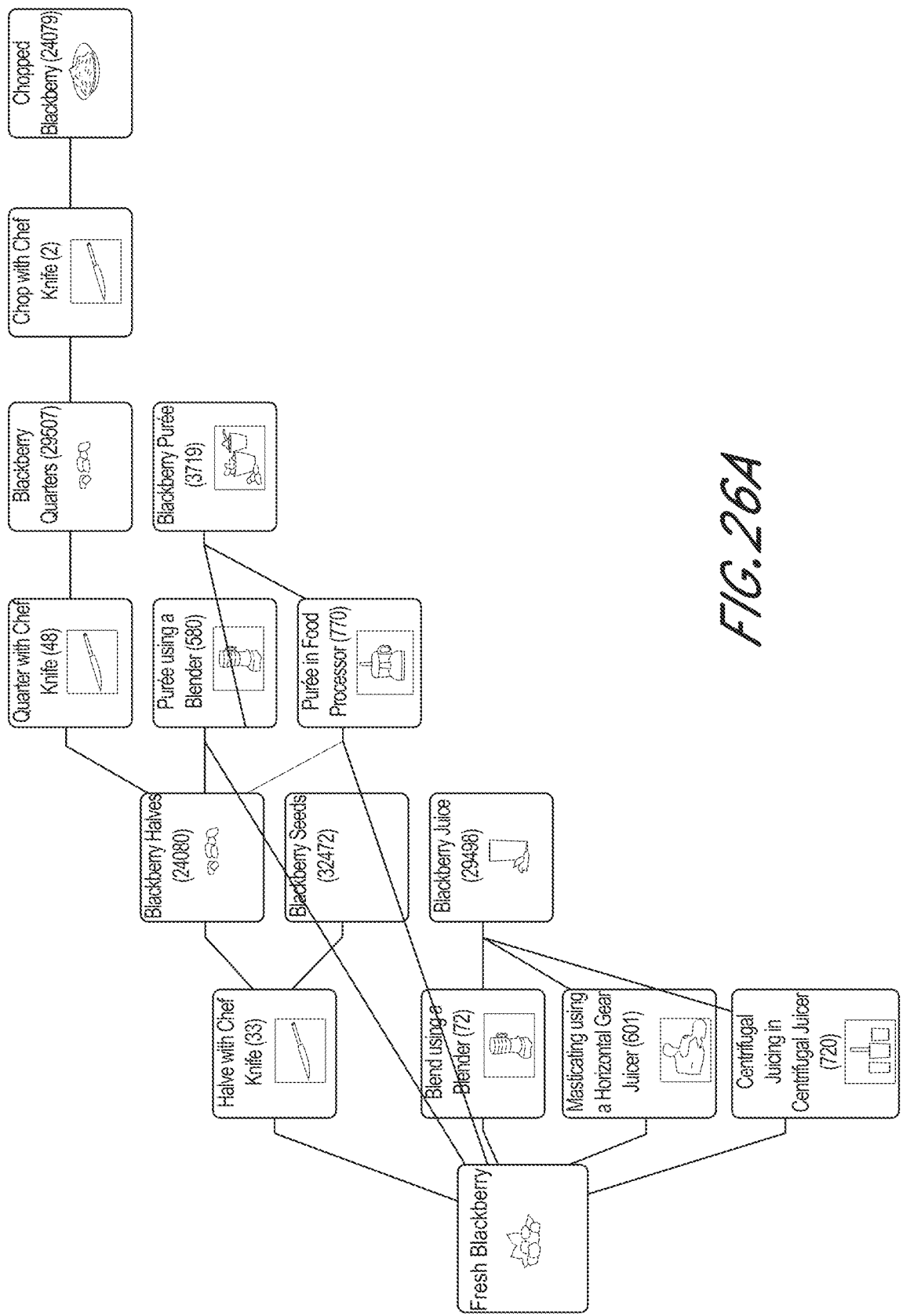
FIG. 26A schematically illustrates an example node-to-node structure for blackberry juice in accordance with certain embodiments described herein.
Figure 26B:
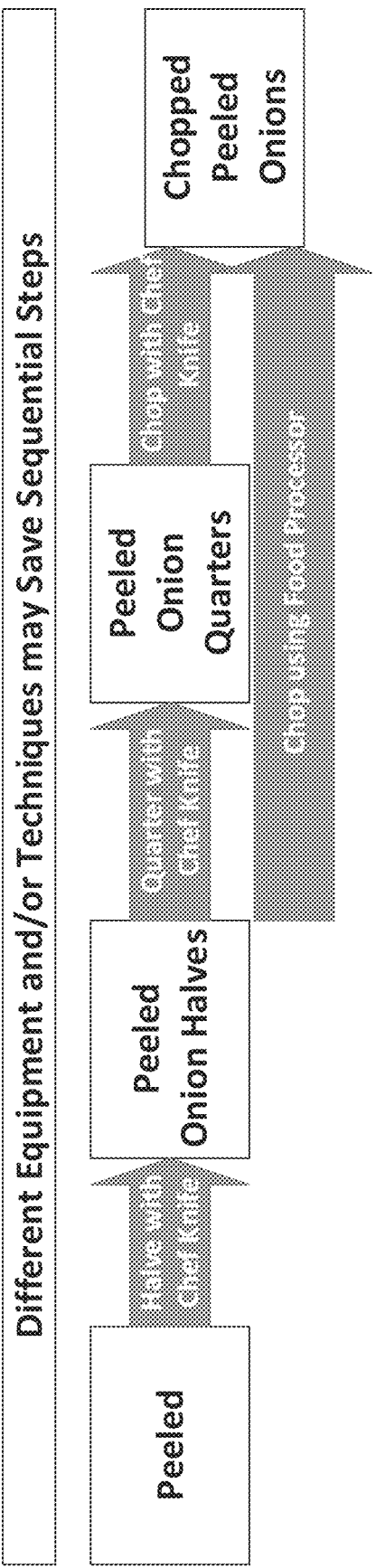
FIG. 26B schematically illustrates an example nod-to-node structure for chopped peeled onions in accordance with certain embodiments described herein.

In certain embodiments, there can be more than one way to process an ingredient. FIG. 26A schematically illustrates an example node-to-node structure for Blackberry Juice, in which the blackberries can be made into juice with a Blender, Centrifugal Juicer or with a Masticating Juicer. In certain embodiments, different equipment can skip steps where other types of equipment utilize more steps to be performed. For example, FIG. 26B schematically illustrates an example node-to-node structure for chopped peeled onions in accordance with certain embodiments described herein. A chef knife can be limited to making one slice at a time, with sequential cuts and/or steps, whereas a food processor can directly chop the onion halves, thereby skipping the sequential cutting steps when using a chef knife.

Figure 27A:
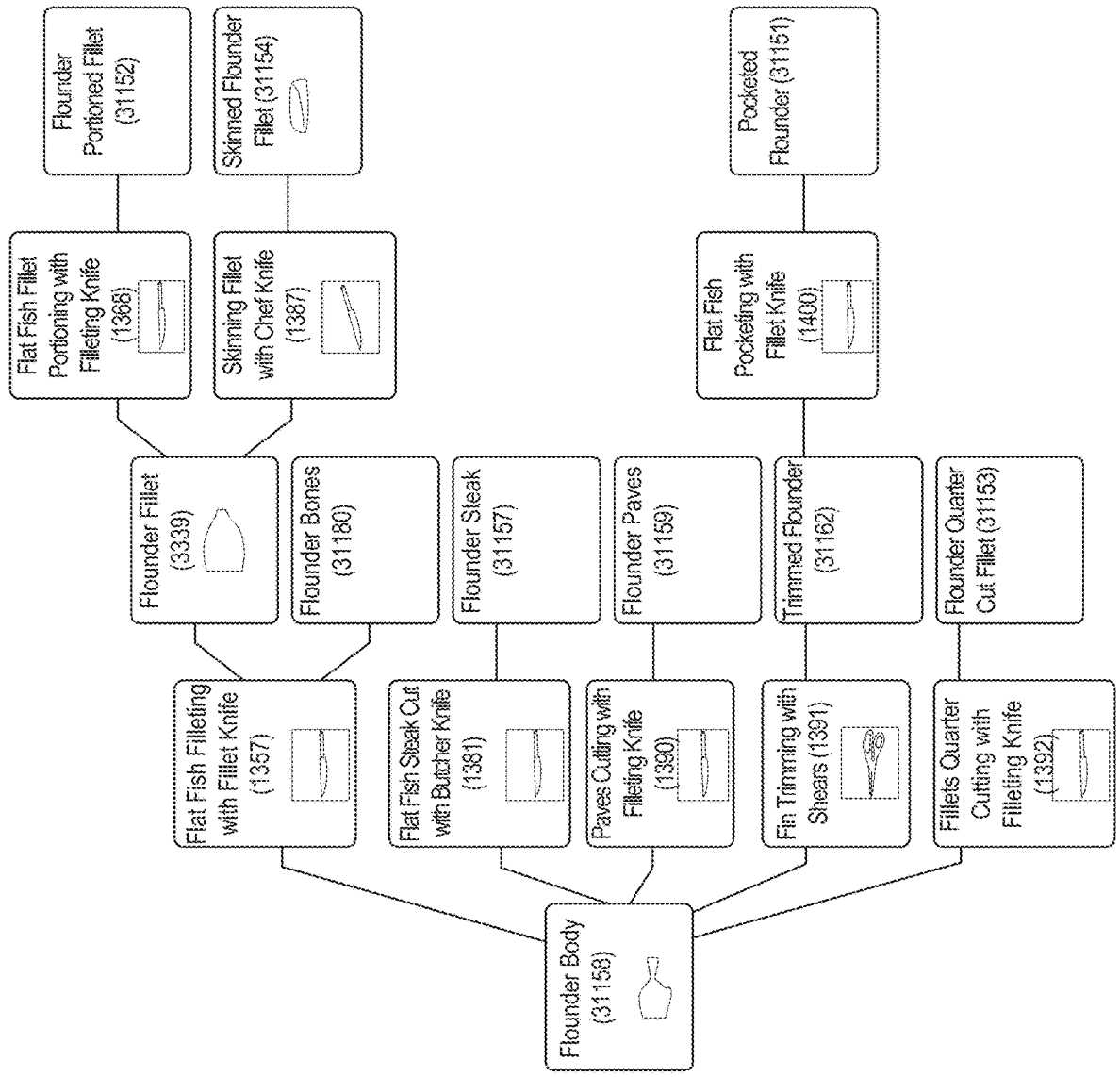
FIG. 27A schematically illustrates another example for a fresh fish cuts network in accordance with certain embodiments described herein.
Figure 27B:
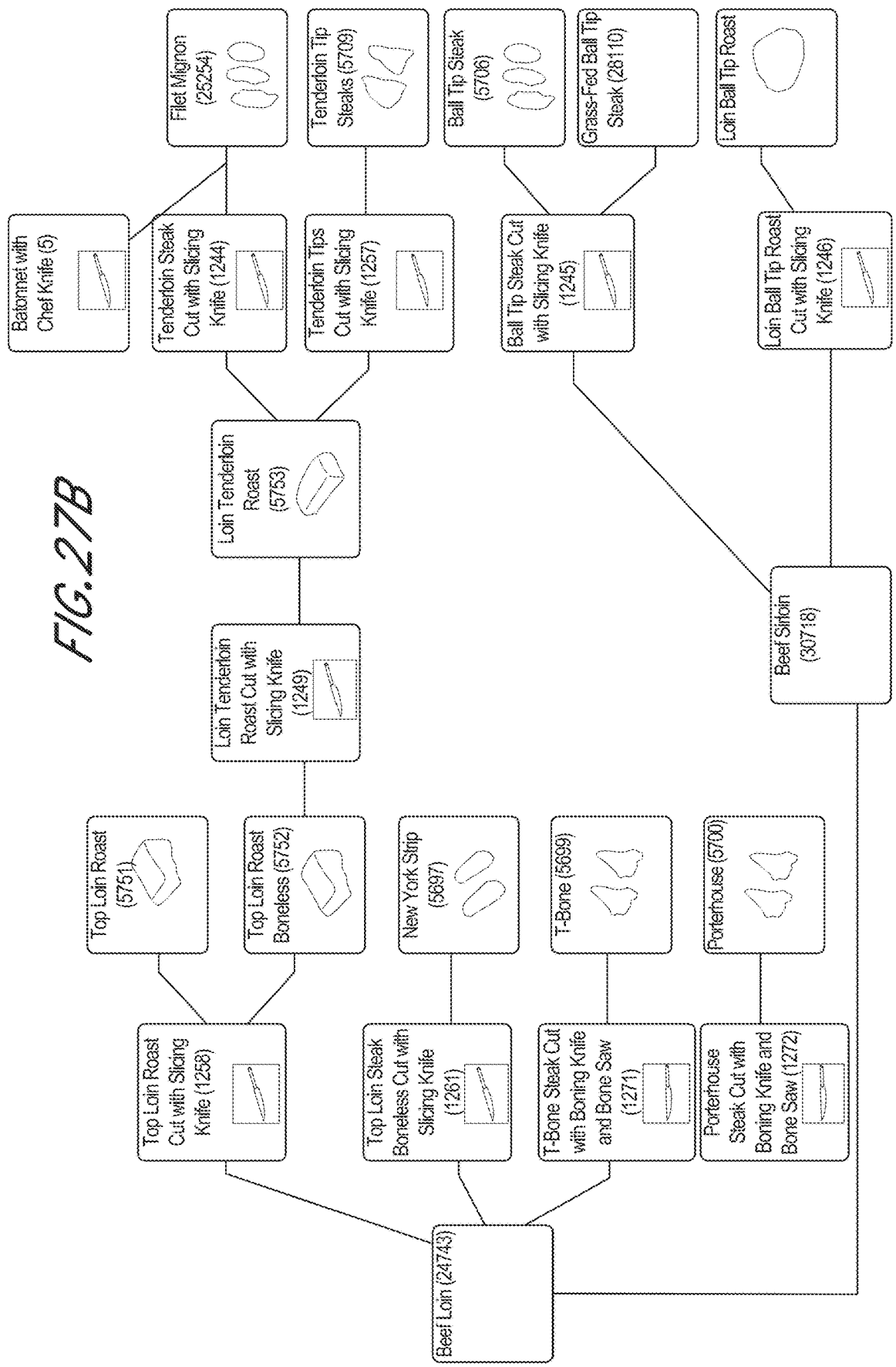
FIGS. 27B-27C schematically illustrate another example for a fresh meat cut network in accordance with certain embodiments described herein.
Figure 27C:
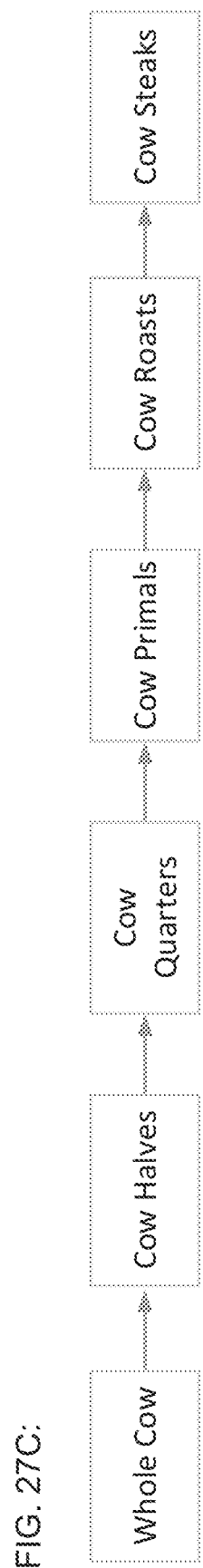
Figure 27D:
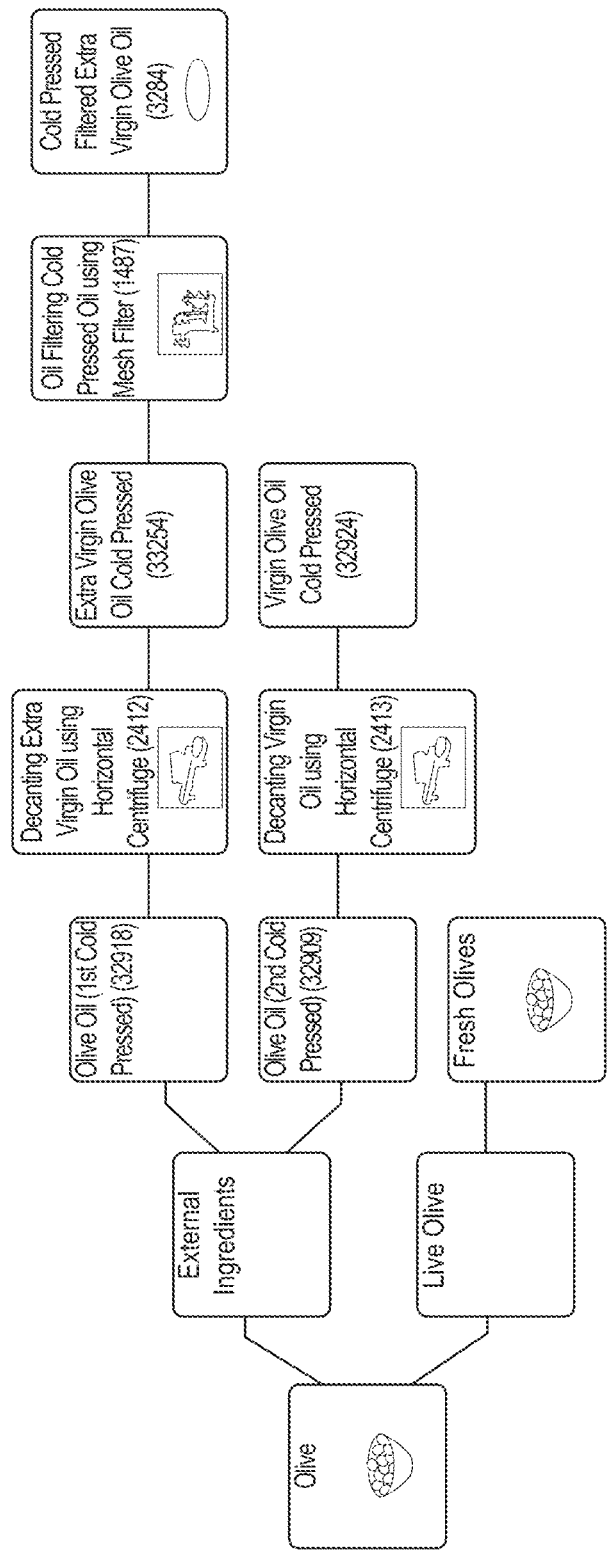
FIG. 27D schematically illustrate another example for a cold-pressed olive oil network in accordance with certain embodiments described herein.

FIG. 27A schematically illustrates another example for a fresh fish cuts network in accordance with certain embodiments described herein, which includes the flounder body and its derivative cuts. FIGS. 27B-27C schematically illustrate another example for a fresh meat cut network in accordance with certain embodiments described herein, which includes the whole cow network for beef. FIG. 27D schematically illustrate another example for a cold-pressed olive oil network in accordance with certain embodiments described herein.

Figure 28:
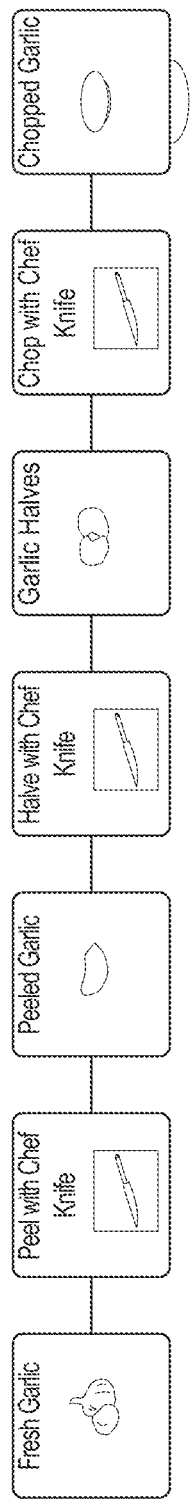
FIG. 28 schematically illustrates the example for chopped garlic in accordance with certain embodiments described herein.

In certain embodiments, the ingredient can be traced backward from a recipe via a modal (e.g., pop-up window) or other visual display which can track the ingredient back to its "Whole Fresh" State. This same process can trace it all the way back through to the vendor. This can be fully connected in the ordering, shipping, and/or pantry management process. The model can utilize the node-to-node structure to trace the steps of how the item was made, starting with its most basic raw material. For example, FIG. 28 schematically illustrates the example for Chopped Garlic in accordance with certain embodiments described herein. As shown in FIG. 28, the node-to-node structure can go step by step back to Fresh Garlic. By accessing the node-to-node structure of the computer database, the user can see all the processing steps for how the garlic was handled.

Figure 29A:
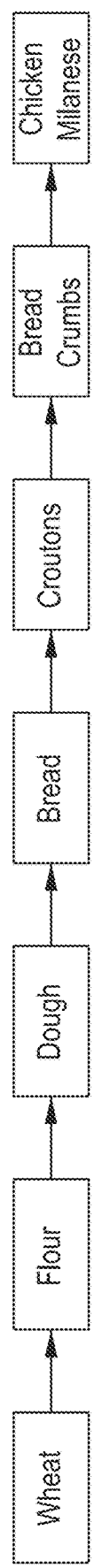
FIG. 29A schematically illustrates an example node-to-node network for Wheat in accordance with certain embodiments described herein.
Figure 29B:
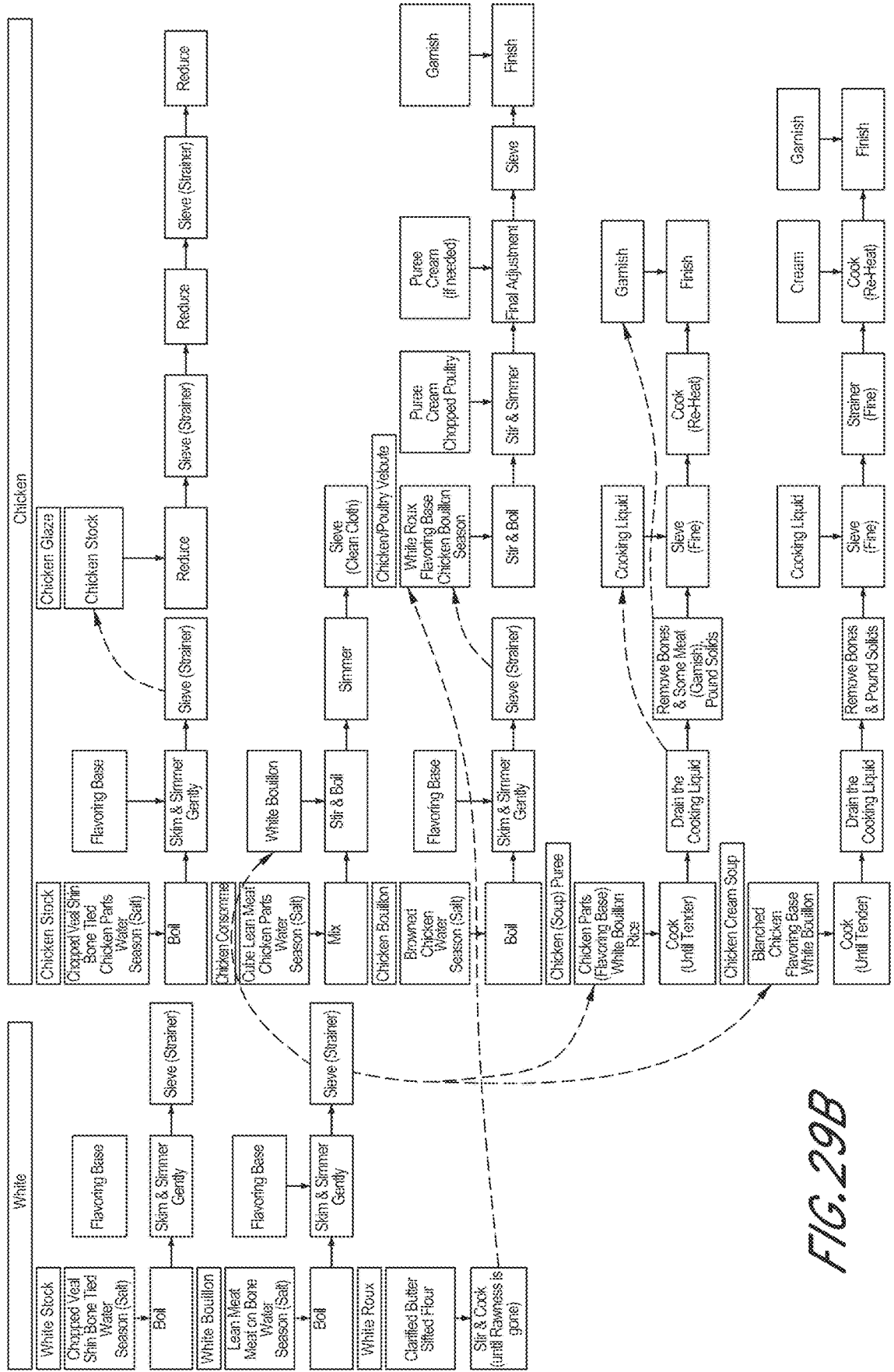
FIG. 29B schematically illustrates an example node-to-node structure for a series of traditional French Sauces in accordance with certain embodiments described herein.

In certain embodiments, a food item can be used as an input into other recipes in complex ways. For example, an item can be an ingredient in a recipe, the result of which may in turn become an ingredient in another recipe, and so on until the end of the chain. FIG. 29A schematically illustrates an example node-to-node network for Wheat in accordance with certain embodiments described herein. As shown in FIG. 29A, wheat can be turned into flour, made into a dough, baked into a bread, toasted into croutons, ground into bread crumbs, which are then used to coat a Chicken Milanese, all of which are shown in the node-to-node structure such that the wheat can be traced back through the chain from the Chicken Milanese. In certain embodiments, the node-to-node structure can connect multiple recipes by calling out the result of one recipe as an ingredient in another recipe. FIG. 29B schematically illustrates an example node-to-node structure (e.g., showing the states without the actions to make each recipe) for a series of traditional French Sauces in accordance with certain embodiments described herein. The French sauces can be included as individual recipes and/or as ingredients into other stocks, broths, or sauces. For example, White Bullion is an ingredient in Chicken Consomme, Chicken Cream Soup, and Chicken Soup; White Roux is an ingredient in Chicken Veloute or Chicken Stock; and Chicken Stock is an ingredient in Chicken Glaze.

In certain embodiments, the node-to-node segments of a recipe network can include the food derivatives and each action of the node-to-node segments can have a time duration and, if appropriate, temperature, speed, and pressure. For example, each node-to-node segment can have a time duration or rate which is dependent on the combination of equipment employed in the technique of the node-to-node segment (e.g., Chopping with a Chef Knife can have one rate, whereas Chopping with a Food Processor can have a different rate). The time of the recipe can be adjusted based on the techniques that are chosen.

In certain embodiments, the node-to-node structure can be used with generic instructions for generating various "how to" actions for multiple food classes, with the generic instruction set up once and then used over and over. For example, the action "Halving with a Chef Knife" is applicable to multiple food classes such as Fresh Fruit/Vegetable/ etc., each of which can be cut in half in a standardized manner. The generic instruction of how to halve with a chef knife is the same regardless of the food class (Apple, Pear, Orange, etc.); what changes is the name of the food class, not the technique. In certain such embodiments, the node-to-node structure can be used to generate instructions for different food classes by "substituting" the name of the food class into the same generic instruction (e.g., "Place 'food class' on the cutting board and hold with one hand. With the chef knife in the other hand, cut the 'food class' in half starting from its stem to produce two equal halves.").

In certain embodiments, the node-to-node structure can be used to enable call outs of recipes using different techniques/ equipment between nodes. For example, a number of different techniques can be used to get from the same node-to-node segment or to the same end result of a node. Multiple techniques can be used with the same starting node and same ending node (e.g., a whole fresh Carrot and be used to make Fresh Carrot Juice by Juicing using a Blender, Juicing using a Centrifugal Juicer, Juicing using a Masticating Juicer, Juicing using a Titurating Juicer, etc.). Multiple techniques can be used with different starting nodes and the same ending node (e.g., Chopped Onions can be produced starting with Peeled Onion Quarters and Chopping with a Chef Knife, starting with Peeled Onions Halves and Chopping with a Food Processor, or starting with Peeled Onions Quarters and Chopping with a Food Processor).

In certain embodiments, each node (e.g., noun in the noun-verb-noun structure) can specify that a unique form of a given food or recipe form. Since each node is unique, then synonyms can be used in order to match ingredients for that particular node. For example, the node-to-node system can include only one instance of Fresh Orange Halves, and can include a number of synonyms for this node including but not limited to: Fresh Orange Halves, Fresh Orange Half, Orange Halves, Orange Half, Half an Orange, etc. In certain embodiments, the node-to-node structure can include various modifiers that can be used to describe the Orange Halves, examples of which include but are not limited to: intrinsic attributes, quantity, size, form, packaging, and process/technique. For example, the modifiers for intrinsic apples can include: Origin, GMO/Non-GMO, Organic, Grade, and Variety (e.g., Origin: California Fresh Orange Halves; GMO: Non-GMO Fresh Orange Halves; Organic: Organic Fresh Orange Halves; Grade: Grade A Fresh Orange Halves; Variety: Valencia Fresh Orange Halves; Size: Large Fresh Orange Halves; Form: Round Fresh Orange Halves; Packaging: Fresh Orange Halves in Clamshell; Process/ Technique: Fresh Squeezed Orange Juice). The various modifiers can also be used in a multitude of combinations, and each version of the form can be parsed in order to determine the "Node" in which it belongs.

In certain embodiments, the same node-to-node segment can be used for different parts of other Food Categories or Recipes. Certain such embodiments can advantageously provide standardization by having the same step or series of steps replicated and used in other networks. For example, one can make juice from Fresh Orange Halves. One technique to perform this is Squeezing using an Arm Press Juicer. An example Instruction Set is as follows: "Place a cup under the juice spout and open the spout. Turn on the juicer. Place the <ingredients/> onto the top of the juicing cone and pull down the arm so that the half fits snuggly over and apply gentle pressure. Continue to apply pressure by slowly pressing the arm until the juice is extracted. Continue squeezing the <ingredients/> until the needed amount is obtained." This same example instruction set (for using an Arm Press Juicer) can also apply to other Fruits in the "Citrus" food grouping which includes, orange, lemon, lime, grapefruit, tangerine, etc. For example, the node-to-node network segment can be created once (e.g., for Oranges), and can then be replicated to all the other food items in the same Citrus Group. This standardization can enable the procedure to be done once and used many times within the node-to-node network. As new techniques/equipment are added, they can be added to the food or recipe node-to-node network by replication. Similarly, for multiple node-to-node segments, other foods/recipes that have the same properties can be grouped together and the node-to-node segment can be replicated into a new segment or can be spliced into an existing network, and can become standards that are easily rolled out to other members of a given food or recipe group. In certain embodiments, this replication can be performed at the network user (e.g., chef) level, while in certain other embodiments, this replication can be performed at the network administrator (e.g., global) level. Parts of the node-to-node network can include a series of verbs (e.g., techniques) which can be re-used or can produce a particular subassembly or final assembly. For example, a chef can keep a standard pie crust as a standard, including its related technique of making and forming, and the chef can then vary the pie filling to produce various pies while holding the standard pie crust constant. The same pie crust is then replicated for an apple pie, blueberry pie, marionberry pie, etc.

In certain embodiments, instructions from the node-to-node network can be given as generic descriptions to support the repeating segments. The instruction set can be presented to the user using multi-media, using images, graphics or video. The instructions set can also be used to guide the motions of human movements or robotic movements. As used herein, the term "robotic movements" has its broadest reasonable interpretation, including but not limited to, the action or series of actions performed by a robot or other mechanical or electromechanical device. For example, a robot can be programmed to perform repetitive tasks, techniques, or movements (e.g., pick and place, cutting, sawing, etc.), and once a technique (e.g., movement) is programmed (e.g., learned), then the robot can replicate such movement to be applied in other circumstances. For example, a standard technique (e.g., movement) may be applicable to multiple food classes in the node-to-node network. In certain embodiments, the node-to-node network provides a platform for using these techniques for any other food classes that use the same technique.

In certain embodiments, the node-to-node network groups techniques that are used throughout food preparation into standard "movements" or tasks, which can be used over and over. Alternatively, the robot would have to recognize that the new task is similar to one already programmed, which can be a daunting task since there are an infinite number of combinatorial sequences of techniques (e.g., movements). The robotic movements can be used in conjunction with the node-to-node repeating segments. The movements may be taught by using human motions using light point mirroring, for example. The movements can then be used as a standard node-to-node segment (e.g., instruction, which can then be used with other members of the same node-to-node category. A person or robot can be "certified" in knowing how to perform that node-to-node segment.

Since the node-to-node segments can be standard and repeatable, they can be used to train and set up levels of proficiency, for both human and robotic certification. For example, each node-to-node segment can define a level of proficiency to be obtained. Once obtained, then all the other foods/recipes that use the same node-to-node segment can also fall under the qualification. A person or a robot could be certified to perform a given node-to-node segment, and they then would qualify for all the other food/recipes that also have that same node-to-node segment. For example, a person or robot could be certified to be proficient with the Chef Knife to cut particular items in Half. If they can cut Oranges in Half, then they would be qualified to cut limes, lemons, tangerines, etc. in half as well. A person or robot could build up proficiencies to perform basic tasks that then build upon one another to perform more and more complex tasks. They start to gain proficiency in more and more parts of the food and recipe segments.

In certain embodiments, the node-to-node system is configured to enable a person or robot to master different techniques/equipment along with a means to track these activities and proficiencies. Certain such embodiments can advantageously provide a systematic method to train and certify the person or robot to have proficiency on individual parts of the total network. In contrast, prior methods perform training on one-offs, which is time consuming and redundant. In certain embodiments, the library of techniques along with their generic segments as described herein can create a set of standards that can be used to teach humans or robots and track their proficiencies or skill sets.

In certain embodiments, the node-to-node structure can be applied to other uses, e.g., food equipment repair, watch repair, phone repair, etc. These applications can utilize an item to be disassembled, the broken item removed and replaced, and then the item is reassembled. The disassembly can be a divergent network which creates many parts as the whole item is disassembled. The broken item is replaced, then the procedure can be done in reverse to re-assemble the item back into one piece. A total divergent network can be defined where all the parts can be disassembled into their component parts. Once the divergent network is defined, then all replacements of defective/broken parts can follow the divergent network, disassembling the requisite parts and replacing the defective parts. The item can then be reassembled by "flipping" the path in the divergent network the opposite way to create a convergent network. The items can then be reassembled following the network node by node until it converges back into the original item. Various devices (e.g., watches; cellular phones) that can be taken apart and either repaired or replaced can be follow this mirrored network (divergent back to convergent).

In certain embodiments, recipes can be dynamically generated (e.g., generated in real-time) using the node-to-node structure in various ways: (i) based on the status, state/form, or temperature of food/ingredients and their related quantity in the pantry, (ii) based on the equipment on hand in the kitchen at any given time, and/or (iii) based on the given skill set at the moment of the user/robot at time of recipe generation. These dynamic generation techniques can be used individually (e.g., one at a time), or in combination with one another.

With regard to the status, state/form, or temperature of food/ingredients in the pantry, the node-to-node network can enable the dynamic (e.g., real-time) generation of recipes based on the quantity of food items or ingredients on hand at the moment of generation. The pantry can change in real time with food items being withdrawn and replenished. When a recipe is generated, the system can use the node-to-node network to determine the state, temperature, and quantity of each ingredient available to be used for the recipe. This can affect the nodes (e.g., ingredients) to be used as the starting points of the recipe and what actions are used during the recipe (e.g., the actions used to prepare the ingredients for the recipe). The starting points can determine the series of steps and the corresponding times to prepare, measure, or otherwise have the food items ready for the recipe. For example, if one day, the user has chopped onions in their refrigerator (e.g., pantry), and chopped onions are required for the recipe, then the only prep time for the chopped onions is the gathering time to get it ready for the recipe. If the next time the recipe is used, there is only fresh (whole) onions, then in addition to the gather time, the prep time for the recipe can include the time for changing the fresh onion into chopped onions. For another example, the item could be fresh or frozen, and the prep time using the frozen item would include time to thaw, where the prep time for using the fresh item would not.

With regard to the equipment on hand, the node-to-node network can enable the dynamic (e.g., real-time) generation of recipes based on the kitchen equipment available to make the particular recipe. For example, the recipe may call out a food processor to make a given recipe one day. If on another day, the food processor is broken and no longer available, then a substitute equipment, like a chef knife would be called out. The time and steps utilized by the user to prepare a given set of ingredients with a chef knife would be different than that for a food processor.

With regard to the skills or proficiency of a given user or robot, the node-to-node network can enable dynamic (e.g., real-time) generation of recipes based on the techniques/equipment that the user has proficiency to use. For example, if the user has a food processor, but doesn't have the proficiency to use it, then the recipe would call out the technique that the user can use to make the recipe. The household members can each have different skill sets, which can be specified in the system. If for example, a child of 8 years old may not be allowed to carry out preparation steps utilizing knives, but can be skilled in gathering food items. The node-to-node system can task the child for the food gathering steps (e.g., guided step by step via the node-to-node system) for the items to be pulled from the pantry based on a pick list generated by the system. Household members or robots can be certified to carry out given node-to-node segments (e.g., main steps like gathering, prepping, specific techniques, or to operate or not operate specific kitchen equipment).

In certain embodiments, the node-to-node system supports integrating the calculating of item counts, weights, and volumes in the dynamically-generated recipes. As an example of the node-to-node network supporting item counts, an apple can produce 2 halves or 4 quarters. The recipe can call out 4 quarters, so the system knows that one apple is to be used. If the number of servings is changed on a recipe, then the system can connect the item counts based on the ingredients or the fresh, raw or live form. As an example of the node-to-node network supporting weights in which the system convert the weights from one disparate item to another, if 4 hamburger patties are to be used and each patty serving is ¼ lb., then the system knows that one pound of ground beef is to be used or one pound of top sirloin steak is to be ground into one pound of ground beef and formed into 4 quarter pound patties. As an example of the node-to-node network supporting volumes, the system can add up the volume of ingredients and present it either in terms of volume or convert it to weight and/or can use the volume to calculate the size of the containers that are to be used for a given recipe. For example, if the volume is 1 quart, then the system knows that only containers that are 1 quart or larger can be used for the recipe. Certain recipes can specify that the volume fills only a certain percentage of a container. For example, boiling pasta can use 4 quarts of water and 1½ tablespoons of Kosher Salt for each pound of pasta. However, the container can only be 2 thirds full, to avoid spilling the boiling water when the pasta is added. Therefore, the container can be specified to be 6 quarts or larger for each pound of pasta called out in the recipe. The user can specify the volume sizes of their containers and the specific container matching the recipe can be called out based on the volume requirements of the recipe.

In certain embodiments, variants of a node pair have the same starting and ending nodes as one another. Among the variants of a node pair, State A and State B are constant, but there are a multiplicity of methods/techniques that convert State A to State B. One variant can be set as a standard. The standard is then compared to the multiplicity of other methods/techniques, equipment or ingredients of converting something from State A to State B. In certain embodiments, a comparison can be made of a multiplicity of variants to the standard. Other variants are easily created using the standard and then varying one or more elements of the method/technique, equipment or ingredients. In certain embodiments, the node-to-node structure also enables node pairs or a series of nodes be used for other recipes, which, in certain embodiments, can provide a building block approach to building recipes.

Figure 30A:
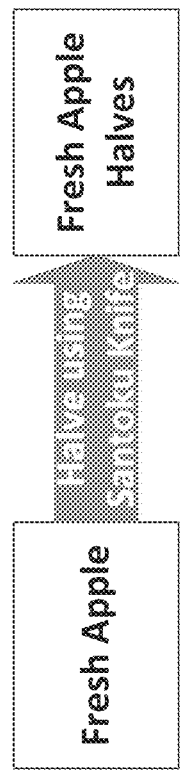
FIG. 30A schematically illustrates an example node pair for halving a fresh apple in accordance with certain embodiments described herein.

For example, FIG. 30A schematically illustrates an example node pair for halving a fresh apple in accordance with certain embodiments described herein. The example node pair of FIG. 30A can use a Chef Knife and can have multiple method/technique variations, one of which is a standard method/technique and others of which are multiple variant methods/techniques. For example, the standard method/technique can be: "Place the apple onto the cutting board with the stem side on top. Slice the Apple with the Chef Knife starting at the stem and cut straight down to produce two equal halves." A first variant can be: "Place the apple onto the cutting board with the stem side on bottom. Slice the Apple with the Chef Knife starting at the middle of the bottom and cut straight down to produce two equal halves." A second variant can be: "Place the apple onto the cutting board with the stem side on top. Slice the Apple with the Chef Knife holding the knife at a 45 degree angle. Start at the stem and cut downward to produce two equal halves."

Equipment can comprise tools, containers, appliances, work/cooking surfaces among many other items, which can be the basis for other variants (e.g., based on individual equipment variants or based on paired sets of equipment). For example, a knife can be paired with a cutting board. Chopped onions can be chopped with a knife and cutting board combination or a variant could be chopping with a food chopper on a work surface or a food processor on a work surface. The variants can be individual pieces and/or paired pieces of equipment.

Figure 30B:
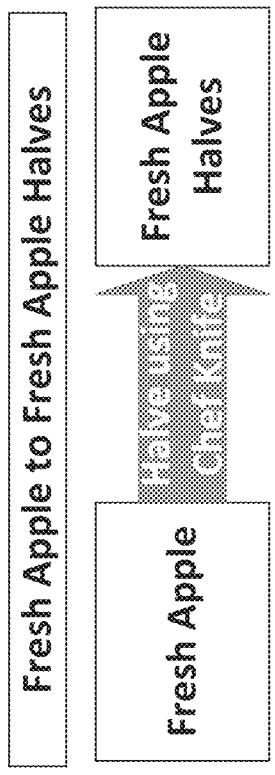
FIGS. 30B-30C schematically illustrate example node pairs for halving a fresh apple, with equipment variation from that of FIG. 30A, in accordance with certain embodiments described herein.
Figure 30C:
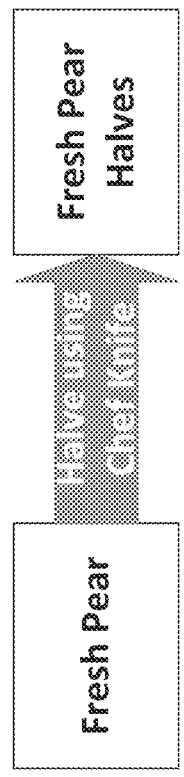

FIGS. 30B-30C schematically illustrate example node pairs for halving a fresh apple, with equipment variation from that of FIG. 30A, in accordance with certain embodiments described herein. The example node pair of FIG. 30A which uses a Chef Knife can be considered to be the standard method/technique: "Place the apple onto the cutting board with the stem side on top. Slice the Apple with the Chef Knife starting at the stem and cut straight down to produce two equal halves." The example node pair of FIG. 30B which uses a Santoku Knife can be considered to be a first variant: "Place the apple onto the cutting board with the stem side on top. Slice the Apple with the Santoku Knife starting at the stem and cut straight down to produce two equal halves." The example node pair of FIG. 30C which uses a Utility Knife can be considered to be a second variant: "Place the apple onto the cutting board with the stem side on top. Slice the Apple with the Utility Knife starting at the stem and cut straight down to produce two equal halves."

Figure 30D:
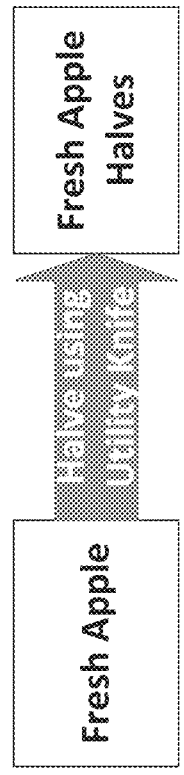
FIG. 30D schematically illustrates an example node pair for halving a fruit, with ingredient variation from that of FIG. 30A, in accordance with certain embodiments described herein.

FIG. 30D schematically illustrates an example node pair for halving a fruit, with ingredient variation from that of FIG. 30A, in accordance with certain embodiments described herein. The example node pair of FIG. 30A halves a fresh apple, and can be considered to be the standard: "Place the apple onto the cutting board with the stem side on top. Slice the Apple with the Chef Knife starting at the stem and cut straight down to produce two equal halves." The example node pair of FIG. 30D halves a fresh pear, and can be considered to be a first variant: "Place the pear onto the cutting board with the stem side on top. Slice the Pear with the Chef Knife starting at the stem and cut straight down to produce two equal halves."

In certain embodiments, there can be multi-element variants corresponding to a standard node-to-node conversion, such that the instruction set of a node-to-node conversion can have a multiplicity of variants that are handled by one standard instruction set. Text can be used in conjunction with the node-to-node system to provide specific valid variants to fill in the general categories (e.g., indicated by <category/>) and/or to utilize variations in the ingredient(s), technique, surface (cooking), container, and tools and to generate recipe directions provided to the user, e.g.:

With the <surface/> at medium heat. Place the <container/> on the heated surface and wait until it reaches temperature. Add in the <ingredient1/> and bring to temperature. Add the <ingredients2/> and cook the food quickly by <technique/> them using the <tool/> to cook them evenly. Continue until they are softened. with variants of the surface including Gas Range, Electric Range, Induction Range, etc.; variants of the container including Saute Pan, Fry Pan, Grill Pan, Omelet Pan, etc.; variants of the tool including Spoon, Spatula, Slotted Spoon, etc.; variants of the technique including Flipping, Tossing, etc.; variants of ingredients1 including Butter, Vegetable Oil, Lard, Canola Oil, Olive Oil, etc.; and variants of ingredients2 including Onions, Garlic, Carrots, Celery, etc.

In certain embodiments, the node to node system, by utilizing a standard and variants between two nodes, advantageously allows the two nodes to be used as a basis for generating multiple versions of the recipe instruction set (e.g., to be used in various recipes) in which one, two, or more of the elements are held constant while one, two, or more of the elements are varied, e.g.:

The equipment is held constant while either the ingredients and/or the method/technique is varied.

The ingredient is held constant while either the equipment and/or the method/technique is varied.

The technique/method is held constant while either the ingredients and/or the equipment is varied.

Figure 31:
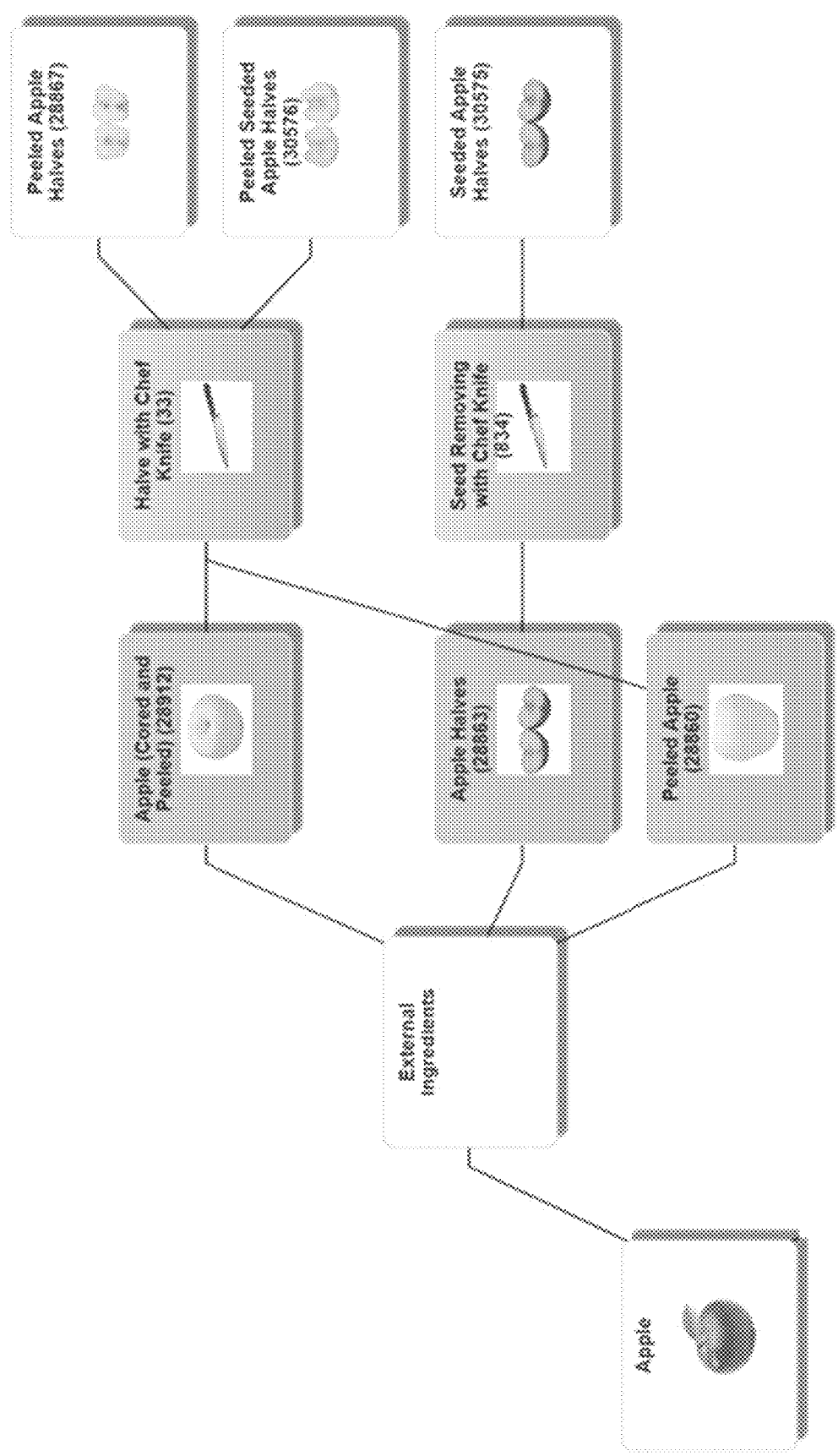
FIG. 31 schematically illustrates an example node-to-node V-network for a Fresh Apple in accordance with certain embodiments described herein.

In certain embodiments, the starting point node of a particular node-to-node network (e.g., a V-Network) is a given node corresponding to a particular element (e.g., ingredient). For example, FIG. 31 schematically illustrates an example node-to-node V-network for a Fresh Apple in accordance with certain embodiments described herein. The Fresh Apple is connected to all the derivative apple forms in its node-to-node network. The derivative forms can then be used as the inputs into a multiplicity of recipes where the fresh apple is used in its various forms.

In certain embodiments, the starting point node of a node-to-node network can be used to provide to the user (e.g., display to the user) a list of potential recipes that may be performed using the starting point node. For example, by having the same starting point node, one question (e.g., user-generated food-related query) that can be answered using the node-to-node network is: "What can I make with a Fresh Apple?" In answering this question posed by a user, the node-to-node network can be used to show a multitude of recipes which use a Fresh Apple via its multiplicity of Forms, (Halves, Seeded Halves, Peeled Halves, Peeled & Seeded Halves, Quarters, Seeded Quarters, Peeled Quarters, Peeled & Seeded Quarters, Slices, Seeded Slices, Peeled Slices, Peeled & Seeded Slices).

In certain embodiments, other nodes of the node-to-node network can be used to provide the user with a list of potential recipes that may be performed using the particular node. For example, using the node corresponding to Apple Form: Peeled & Seeded Slices, the node-to-node network can be used to provide the user (e.g., display to the user) with a multitude of recipes using this one form. Certain such embodiments advantageously enable a user to see the multiplicity of recipes from the perspective of any node within the node-to-node system.

As another example, a node-to-node network can connect a multiplicity of forms for the Loaf of Bread: Sliced Loaf, End Pieces, Slices, Loaf Halves, Loaf Sections, ¾ cut Loaf, Croutons, Bread Crumbs, etc. Using the node-to-node network, the Loaf of Bread can be connected to all the derivative forms in its network. The forms are then the inputs into a multiplicity of recipes where it is used in its various forms, and these recipes can be accessed in response to queries posed by the user. For example, the query "What can I make with a Loaf of Bread?" can be answered by providing (e.g., displaying to) the user with a multitude of recipes which use a Loaf of Bread via its multiplicity of forms, (e.g., Sliced Loaf, End Pieces, Slices, Loaf Halves, Loaf Sections, ¾ cut Loaf, Croutons, Bread Crumbs, etc.).

In certain embodiments, the system comprises a standard node-to-node network (e.g., V-Network) corresponding to a particular ingredient, in which the various forms of the ingredient are connected to one another, and the standard node-to-node network is used for other, different ingredients as well. For example, the system can comprise a standard node-to-node network corresponding to a fresh apple, connecting the various forms of the fresh apple to one another, and this node-to-node network can be used with (e.g., shared by) a fresh pear or other similar fruits. While apples and pears are slightly different shapes, they have the same characteristics in the methods, techniques, and equipment and the same derivative forms. For example, both apples and pears can be used in substantially the same forms, e.g., Halves, Seeded Halves, Peeled Halves, Peeled & Seeded Halves, Quarters, Seeded Quarters, Peeled Quarters, Peeled & Seeded Quarters, Slices, Seeded Slices, Peeled Slices, Peeled & Seeded Slices.

In certain embodiments, the node-to-node system advantageously enables a first node-to-node network (e.g., a standard network; a V-Network) to be created for one ingredient/food class (e.g., "apples"), and then the node-to-node network can be replicated as a second node-to-node network for another ingredient/food class (e.g., "pears"). The second network shares the same standards and variants between the nodes as does the first network. For another example, Pan Bread is the rectangular shaped, square cross-section bread that takes its form from a rectangular baking pan or Pullman baking pan. The Pan Bread network and its derivatives are all the same regardless of the particular variant of the bread (e.g., whether the bread is white, whole wheat, whole grain, 7 grain, 12 grain, sourdough, country potato, etc.). The derivative forms of Pan Bread can include, Whole Loaf, Sliced Loaf, End Piece, Slice, Halved Loaf, etc. The Pan Bread network can be replicated for any of the variants of the Pan Bread Loaf (e.g., such as white, whole wheat, whole grain, 7 grain, 12 grain, sourdough, country potato, etc.). The Pan Bread network also can share the same method/technique and equipment variants between the nodes.

In certain embodiments, the node-to-node system comprises general or generic node-to-node networks (e.g., V-networks) that apply to multiple ingredients, and such a generic node-to-node network is used as a standard (e.g., generic) network where a multiplicity of Food or Recipe Types use the identical network. For example, the Apple, Pear, and Quince are similar fruits of the Pome group, and the system can comprise a node-to-node network generically known as the Pome Network. For another example, the Pan Bread network can be considered to be a generic node-to-node network that applies to the multiplicity of breads made in a rectangular baking pan or a Pullman baking pan. Other bread networks can include the Baguette Network, the Round Bread Network, the Loaf Network, the Petit Loaf Network, 3 Braided Bread Network, 4 Braided Bread Network, etc.

Figure 32:
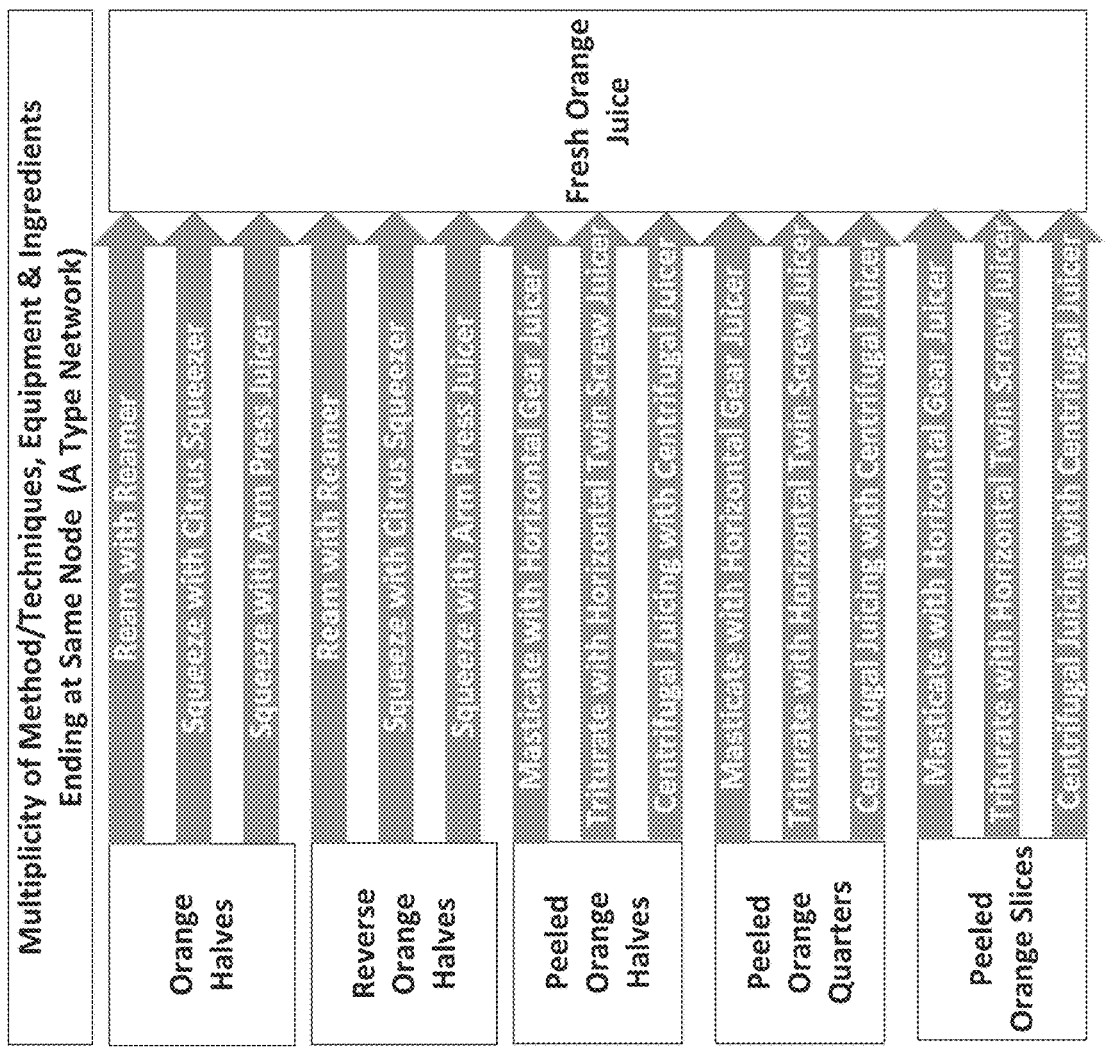
FIG. 32 schematically illustrates an example node-to-node network (e.g., A-network) for orange juice in accordance with certain embodiments described herein.

In certain embodiments, when the ending node is specified, there can be one or more node-to-node network segments that produce the same end node state (e.g., an A-Network). For example, FIG. 32 schematically illustrates an example node-to-node network (e.g., A-network) for orange juice in accordance with certain embodiments described herein. The end node of FIG. 32 is Fresh Orange Juice, and there is a multiplicity of equipment, ingredient forms, and method/techniques that can be employed to produce the Fresh Orange Juice. In certain embodiments, the node-to-node system utilizes one or more A-Networks to advantageously allow the two nodes to be used as a basis for generating multiple versions of the recipe instruction set (e.g., to be used in various recipes) in which one, two, or more of the elements are held constant while one, two, or more of the elements are varied. For example, the end node can be held constant while either the ingredients forms, the method/technique, and/or the equipment is varied. For another example, a user specifying their technique/methods can be shown recipes that are available using such technique/method. For still another example, a user specifying their equipment can be shown recipes that are available using such equipment.

In certain embodiments, the node-to-node system can advantageously be used to instruct a user (e.g., beginner user) via the methods and/or techniques of an A-Network, or to present the user with recipes utilizing a network segment previously learned by the user, as well as alternative network segments that are related to the network segment previously learned by the user. For example, if the beginner has learned to Halve an Apple with a Chef Knife, then they would also be proficient in using the same technique with a Santoku Knife or a Utility Knife, and the system could replicate the learned network segment, modified to include the changed tool, to present the user with recipes utilizing such alternative network segments. If the beginner has learned to Halve an Apple with a Chef Knife, then they would also be proficient in halving a Pear or Quince using the same technique, and the system could replicate the learned network segment, modified to include the changed ingredient, to present the user with recipes utilizing such alternative network segments. If the beginner has learned to Slice White Pan Bread with a Bread Knife, then they would also be proficient in using the same technique and Bread Knife to slice pan bread of whole wheat, whole grain, 7 grain, 12 grain, sourdough, country potato, etc., and the system can replicate the learned network segment, modified to include the changed ingredient, to present the user with recipes utilizing such alternative network segments. If the beginner has learned to Slice White Pan Bread with a Bread Knife, then they would also be proficient in using the same technique and a Utility Knife to slice pan bread of white, whole wheat, whole grain, 7 grain, 12 grain, sourdough, country potato, etc., and the system could replicate the learned network segment, modified to include the changed tool and/or ingredient, to present the user with recipes utilizing such alternative network segments.

In certain embodiments, the node-to-node system can advantageously be used to instruct (e.g., program) a robot to carry out recipes utilizing network segments that are related to a previously programmed network segment. For example, if the robot has been previously programmed to Slice White Pan Bread with a Bread Knife, then it would also be proficient in using the same technique and Bread Knife to perform alternative network segments such as to slice pan bread of whole wheat, whole grain, 7 grain, 12 grain, sourdough, country potato, etc., and the system can replicate the programmed network segment, modified to include the changed tool, to program the robot to carry out recipes utilizing these alternative network segments. If the robot has been previously programmed to Slice White Pan Bread with a Bread Knife, then it would also be proficient in using the same technique and a Utility Knife to perform alternative network segments such as to slice pan bread of white, whole wheat, whole grain, 7 grain, 12 grain, sourdough, country potato, etc., and the system can replicate the programmed network segment, modified to include the changed tool and/or ingredient, to program the robot to carry out recipes utilizing these alternative network segments.

In certain embodiments, the node-to-node network can advantageously use its replicated network segments to track the proficiency of chefs and robots. As skills are acquired (e.g., mastered by the user or programmed into the robot), then proficiency in using a given set of ingredients, ingredient groups, equipment, and/or methods/techniques within given sections of the node-to-node network can be tracked. As these skills are acquired, then the network segments and alternative network segments can be used to select (e.g., parse) recipes or preparations which are to be presented to the user (e.g., chef) or the robot. A robot may be used, for example, to prep vegetables (e.g., one Vegetable network at a time), as the robot gains proficiency in prepping vegetable networks, then it is able to change vegetables from State A to State B to State C, etc. The use of standard network segments or their variants can be used to show a multiplicity of recipes or their sub-sections that are to be carried out by the user or the robot.

In certain embodiments, the node-to-node system can advantageously record (e.g., track; trace) which network segments are known by a chef or robot, thereby enabling the node-to-node system to delegate particular network segments to a given resource (e.g., user of a plurality of users; chef; robot) that has proficiency in those network segments. In certain embodiments, the node-to-node system advantageously shows and/or selects a multiplicity of recipes based on the proficiency of the chef(s) and/or robot(s) participating in the preparation, cooking or other tasks of the recipe and/or its courses, and/or the meal.

In certain embodiments, a recipe can be considered to be either a single recipe or a multiplicity of recipes. An example challenge for someone writing a recipe is to what level of specificity the writer should call out to explain when writing a recipe. For example, if the recipe calls out Chopped Onion, does the recipe writer need to explain how to chop onions? For another example, if the recipe calls out a Toasted White Bread Slice, does the recipe writer need to explain how to toast a slice of white bread? Expressed differently, this example challenge for writing recipes can be considered to be knowing what is the starting point to prepare each ingredient and to what level of detail is required to explain the recipe to the user. This level of detail also varies depending on the level of skill of the person that the recipe is written for. A beginner may need more detailed explanation than that of a professional chef. The recipe writer then generally decides who the audience is for the recipe when writing it. If they put in too much detail, the professional chefs will balk. If the concepts are too advanced, then a beginner will be lost.

Using conventional systems, standards for recipes are very difficult to create or utilize, since the starting point of the recipe depends on the audience that the recipe writer is trying to explain. The starting point is also dependent on the starting state of the ingredient(s), the techniques/methods, and equipment involved. Conventionally, each recipe is typically written as a stand-alone entity, although some cook books may reference a sub-component as another recipe found elsewhere in the cook book.

In contrast, in certain embodiments, the node-to-node system does not write a recipe based on only one method/technique using a specific piece of equipment or set of equipment. The node-to-node system of certain embodiments advantageously breaks this limitation and enables many variants of methods/techniques and/or equipment to be used based on the one base recipe. The node-to-node system of certain such embodiments are advantageously adaptive to the user by a much wider audience customized to their equipment or preferred techniques without altering the outcome of the recipe.

The node-to-node system of certain embodiments advantageously solves problems encountered by conventional systems by including standard node-to-node networks for each parent food (e.g., a Fresh Apple; White Pan Bread) and including all of the derivative forms and/or prepared/cooked forms of these standard node-to-node networks, enabling a chef to call out the exact form/preparation required to be used directly into the recipe.

For example: the recipe ingredients for Baked Cherry Pie can be: 1 lb. rolled pastry dough and 2 cups Cherry Filling, and the instructions for the recipe can be the assembly, baking and cooling of the cherry pie. In certain embodiments, the node-to-node system does not have to call out the making of the rolled pastry dough or how to make the cherry filling. Those procedures can be specified by separate nodes and separate recipes. If the node-to-node system is being used to present a specific recipe variant (e.g., having one or more variant ingredients, methods/techniques/equipment from that of a standard recipe) for the rolled pastry dough or the cherry filling, then the node-to-node system can advantageously generate the specific recipe variant using a standard node-to-node network and modifying it to reflect the variant element (e.g., a variant of the rolled pastry dough and/or a variant of the cherry filling). In this way, certain embodiments advantageously leverage the node-to-node system to be able to present alternative recipes (e.g., different from the standard recipes utilizing the standard node-to-node networks) to the user even though the alternative recipes have not been explicitly inputted to the system previously.

In certain embodiments, a recipe writer functionality of the node-to-node system is configured to create variants of a standard node-to-node network (e.g., the standard Rolled Pastry Dough network and/or the standard cherry filling network) in creating recipes to be presented to the user. Each variant can call out the form and/or state of the ingredients that are used directly into the recipe being made. The user can utilize the node-to-node system of certain embodiments to create their own variant node-to-node networks that differ from the standard or variant node-to-node networks in the node-to-node system.

In certain embodiments, the user can work backwards from the final recipe (e.g., End Node) to call out exactly how each and every ingredient(s) is to be made based on their own variants as needed. These can be stored in memory by the node-to-node system as the user's "standard" preferences and can be re-used as needed. For example, the recipe writer functionality of the node-to-node system may use the same rolled pastry dough in the apple pie, blueberry pie, raspberry pie, boysenberry pie, etc. recipes presented to the user, but the rolled pastry dough can reflect the particular user's desired variants to the standard recipe or node-to-node network for rolled pastry dough.

In certain embodiments, the recipe generated by the node-to-node system and presented to the user is configured based on the level of detail that the particular user needs. For example, an experienced chef may only need to glance at the ingredient list to know what to do. Whereas, a beginner may want to know how to prepare each and every ingredient, step by step. The node-to-node network of certain embodiments enables a beginner to get instruction from the beginning state of each ingredient or other relevant state as they require or desire. For example, if the beginner doesn't know how to chop onions, then the recipe can be expanded to start at a Fresh Onion and to take them step by step to having chopped onions. In certain embodiments in which the user also has their pantry items and quantity levels entered into the system, then the system configures the recipe based on the state of the ingredients in the user's pantry. For example, if a Fresh Onion exists in the user's pantry, then the system can configure the recipe to include the time, methods, and equipment to produce chopped onions. If chopped onions exist in the pantry, then the system can configure the recipe to include the existing chopped onions along with the time for gathering them.

In certain embodiments, the node-to-node system advantageously presents a virtual accordion for recipes to the user by which the user can expand out each ingredient and its preparation as needed. For example, if the user needs a step-by-step recipe for chopped onions, then the user can have this portion of the recipe unfold into the steps to chop an onion.

In certain embodiments, the node-to-node system is also configured to be used for kitchen management of the tools and equipment used for food preparation, handling, cooking, serving and clean up. The principal behind node-to-node kitchen management of certain such embodiments is "Everything has a Place and Every Place has a Thing." Kitchen Management of tools and equipment can keep the tools and equipment in a proper condition for use with food. For example, bowls, pans, tools, serving plates, glasses, etc. are desired to be cleaned prior to being used to prepare, cook or serve food. Furthermore, the kitchen equipment is desired to be stored when not in use in its clean state. For example, kitchen equipment can be kept in their stored locations when not in use.

The folding of kitchen equipment is taking the tools and equipment, cleaning them properly and putting them in their proper place. If the items are clean and in their proper place, this is the "Folded" position. The user can designate the kitchen equipment on hand and can specify its proper storage area. To prepare, cook, and serve a meal requires that the tools and equipment are unfolded. They are gathered and placed in a proper place in order to be used for one or more recipes, and once the tools and equipment are used to prepare, cook and serve the meal, then they are in a soiled condition and may be left in many different locations. This is the unfolded position.

In certain embodiments, the node-to-node system advantageously tracks the equipment as it is used step-by-step and the quantities to be used in order to gather, prepare, cook, serve, bus, clean and place the equipment back into their "Folded" State. In certain embodiments, the node-to-node system is configured to scale recipes based on the number of individuals and their servings for a recipe and/or course and/or meal, and the kitchen management is tied to the recipes and their required equipment and/or substitutes. For example, if 5 people are attending a meal and soup is being served, the system can allocate 5 soup bowls and 5 soup spoons for that dish, and the recipe and its tools and equipment can be scaled for 5 people. For example, the stock pot volume can be scaled to match the volume of liquid needed for the soup for 5 people. If Champagne is going to be served for 5 adults for the first course of the meal, then the system allocates 5 champagne glasses, a champagne bucket with ice and kitchen towel. Courses of the meal are connected in the meal planning functionality of the nodeto-node system, with the required plateware, silverware and glassware being related to their recipes for serving the meal.

In certain embodiments, the node-to-node system advantageously enables portions of the recipe networks to be assigned to one or more resources (e.g., users; chefs). Each discrete node-to-node segment corresponding to a task can be configured to be assignable to a resource, with each node-to-node segment comprising the time, temperature, pressure, speed, ingredients, equipment, and the method/technique providing a resource with all the relevant information to carry out the task. The system of certain embodiments stores in memory and can access from memory the sections of the node-to-node network (e.g., tasks) that any particular resource is capable of performing, advantageously enabling the system to delegate the tasks in order to optimize the recipes to be prepared and synchronized for the food to be prepared at a desired time. The system of certain embodiments can assign the resources to particular tasks, depending on the capabilities of the resources, to schedule the tasks and resources to work on different recipes to prepare the food for a desired time.

In certain embodiments, the node-to-node system is configured to work with a meal planner which specifies given recipes to be performed on a given day at a given time. The node-to-node system can be configured to coordinate the timing of tasks for one or more resources based on the task dependencies and the resource availability. The system furthermore can be configured to coordinate the tasks and the resources based on the resource's capabilities to prepare the food for a desired time. For example, kitchen tasks may include gathering food items, ingredients from the pantry, retrieving equipment for preparing and cooking the food, preparing the ingredients to the desired state, cooking the recipes, plating, serving, busing, cleaning, drying and putting back equipment in its proper place and storing left over food. Some of these tasks can be assigned by the node-to-node system to some resources (e.g., assigning retrieving, cleaning, and putting back equipment to household children and assigning cooking, plating, and serving to household adults).

In certain embodiments, the node-to-node system is configured to perform pantry management which can include the step-by-step processes which connect meal planning, pantry quantity levels, shopping lists, purchasing, obtaining from food vendors and storing the food in their relevant pantry locations. For example, the meals can be placed on a calendar on the day and time desired, and the node-to-node pantry management can allocate the pantry items to the meal calendar. A shopping list can be generated for items not available in the pantry. The shopping lists can all be connected via node-to-node segments from the vendor to the pantry. The time needed to obtain any given item from a vendor can be used to determine when the item(s) need to be purchased in order to arrive in time for the meal. Food items can have a particular shelf life which can be factored into when the food item is shipped and/or how frequently the food item is to be purchased so it is fresh. In some cases, there is not enough time to obtain the item from a particular vendor via shipping, so the shopping list may request that the item be delivered by a local market or picked up at a local market.

In certain embodiments, some or all of the recipes (e.g., homemade recipes; industrial recipes) of the node-to-node network can have full traceability (e.g., information provided to the user regarding the food at each step of the processing) through each of their standard or variant processing node-to-node steps, thereby providing the traceability and transparency which are desirable for a safe and effective food supply chain. The node-to-node segments can comprise the time, temperature, pressure and speed along with the method/technique, ingredients, and equipment used to process any part of the recipe. The node-to-node system can include the Farm to Table networks of foods and recipes. The traceability can include the step-by-step process and the passing of the ingredient/food's attributes and nutrition levels through the system whether it is homemade, farmstead, artisan, commercially or industrially produced. In certain embodiments, the node-to-node system advantageously supports the integration with third party sources of traceability, whether manual, automated, block-chain, rfid or other digital forms. The information can be passed through the node-to-node system to provide traceability of the ingredients. Traceability elements may include, origin, batch number, lot number, processing entities or personnel, transportation, storage, along with processing conditions or codes. This information can be utilized for both consumers and for the tracing back of potentially contaminated food for recall.

In certain embodiments, the food quality parameters are also fully traceable through the node-to-node network. For example, the Parent food may have various attributes, e.g., organic, GMO free, Extra Fancy Grade and be grown in Washington. These attributes can be passed through the node-to-node network and included in any recipe accessing the node-to-node network. For example, the attributes of the Red Delicious Fresh Apple in a user's pantry can be passed through the node-to-node network for apples to the final recipe made by the user. The nutrition and anti-nutrition of a given ingredient can also be passed through the node-to-node network and provided to the user by the node-to-node system. The system of certain embodiments can also make adjustments to the nutrition based on certain processing thresholds. For example, if a method/techniques is known to decrease water soluble vitamins at a given temperature, pressure or speed, then the reduction of those vitamins can be denoted by the node-to-node network accordingly. For another example, if soaking beans reduces their Lectin Levels (anti-nutrient), then the lectin level in the node-to-node network can be adjusted in the node-to-node section corresponding to the soaking of the beans. The capability of tracking food quality parameters can be extended out by the node-to-node network of certain embodiments to each of the products and/or vendors that make such products. For example, chickens may be butchered and then they may be either Air Chilled or Chilled in a Water Bath. The node-to-node network for chicken can track these types of processing differences. The user can then use the system to specify which attributes of their chicken they want (e.g., Organic Chicken that is Pasture Raised and Air Chilled).

The example matrix below shows some of the possible variations of the elements that make up a meal kit based on the node-to-node structure.

| Matrix Possibilities for Source of Meal Elements | | | | | | | | | | |
|---|---|---|---|---|---|---|---|---|---|---|
| | Ingredients | | Recipes | | Techniques | | Equipment | | Resources | |
| Entity | User | Chef | User | Chef | User | Chef | User | Chef | User | Chef |
| Restaurant | | | | | | | | | | |
| Food Provider | | | | | | | | | | |
| Meal Kit | | | | | | | | | | |
| User | | | | | | | | | | |
| Chef | | | | | | | | | | |
| Dietician | | | | | | | | | | |

The node-to-node structure of certain embodiments supports a multiplicity of entities specifying user, their own or third party ingredients, recipes, techniques, equipment and resources to perform the work. For example, at one end of the spectrum, a user could purchase a fully prepared meal from a restaurant. The meal and all its related elements are sourced, and cooked to the state that the user will consume it. At the other end of the spectrum, a user could source their own food, make it from scratch using their own resources, techniques, and equipment.

The node-to-node structure of certain embodiments advantageously enables tracking and providing the user with information (e.g., instructions) regarding a virtually unlimited variety of interactions. For example, a meal kit maker could use some of the ingredients supplied by the meal kit maker and ingredients contained in the user's pantry. The meal kit could be cooked by the user or a third party chef could be employed to prepare the meal. The third party chef could in turn use the user's kitchen equipment or bring some or all of their own.

In still more examples, a celebrity chef could recommend a series of recipes that are put on the user's meal calendar. These recipes may be endorsed by a particular dietician to be "Paleo" certified in alignment with their diet. The celebrity chef may endorse specific food products which are part of the recipes which the user purchases and maintains in their pantry. The chef may work with a meal kit company to provide meal kits for preparation by the user, but uses some of the food products contained in the user's pantry.

The recurring nature of the node-to-node structure of certain embodiments advantageously enables the meal kit company to set up and provide instructions for the proper techniques on how to make the meal. The meal kit company may use the node-to-node system of certain embodiments to assign certain products in the user's pantry, such as condiments like ketchup, mustard, etc. to compliment a given series of meal plans. The meal kit company may also have other ingredients (e.g., wild salmon) come directly from an endorsed food provider and the meal kit company can provide the rest of the ingredients or other elements of the meal in their meal kit. The node-to-node structure of certain embodiments facilitates an unprecedented marketplace for sourcing and configuring ingredients, food, recipe, methods/techniques, equipment by users, food providers, chefs, dieticians and recipe providers. These entities are able to use the node-to-node structure of certain embodiments to cross-pollinate their efforts into new, unprecedented and unending alliances. In certain embodiments, the user has unprecedented choice, selection, and value in whether to make, buy or make/buy combos for their food and dietary needs.

In certain embodiments, the node-to-node system comprises half States and half Actions, with each action leading to a new state. The node-to-node structure is organized in relation to actions, which are taken step by step to get to the goal of the end node—a meal, a dessert a completed recipe. The node-to-node system of certain embodiments advantageously enables various degrees of action to be taken. Some users may want all the actions taken for them and only enjoy the end node. Others want to interact with their ingredients and equipment or other chefs. The actions of the node-to-node structure in certain embodiments can form the basis of the experience that users have. The node-to-node system of certain embodiments can be a platform for taking action based on the user's level of preferences. The node-to-node system of certain embodiments comprises descriptions, videos, images at each of its nodes, which can contain standard descriptions, videos, images, but also can have variants contributed by the community at large. The node-to-node system of certain embodiments enables stories to be told by its community, helping people to learn the actions to take to learn about their food, its quality, its origin, its processing, its history and its nutrition. The node-to-node system of certain embodiments enables the kitchen of action, as the internet of action. The set of actions contained in the node-to-node system of certain embodiments forms an intelligence to help users learn, develop their skills, interact with their food, equipment and community.

Each chef learns rules of thumb of how to prepare, cook, serve and preserve food. These are generally ways, methods, techniques, etc. where from experience knowledge is gained. These rules of thumb are generally passed from one another through word of mouth or may sometimes be written down. The rules of thumb are generally passed around in small circles and some may be trade secrets of particular chefs. In certain embodiments, the node-to-node system enables the codification of rules of thumb to be incorporated into the methods, techniques, rules, guidelines or other appropriate knowledge (e.g., to help chefs from making common mistakes). Since the node-to-node network of certain embodiments is a recurring structure, these rules of thumb can be incorporated in given nodes, network segments or the methods/techniques between the nodes or between a series of nodes, planning courses, recipes or meals. For example, some categories of rules of thumb may include but are not limited to: Until Rules (e.g., cook until it solidifies), Timing Rules (e.g., after 2 minutes of simmering, turn down the heat), Incompatible Rules (e.g., don't mix cream and oil), Not Repeating Rules (e.g., don't have a cream soup in the same meal as a cream sauce), Substitution Rules (e.g., use 1 cup milk or use ½ cup evaporated milk mixed with ½ cup water).

In certain embodiments, the node-to-node system includes or is connectable to a meal planner, thereby enabling the node-to-node system to schedule recurring calendared meals, snacks, supplements, etc. on a recurring basis. The node-to-node system of certain embodiment is configured to be used to backward schedule from the time the item on the meal plan is needed with the minimum order quantity, shelf life, and planned future recurrence on the meal planner. In certain embodiments, the node-to-node system with a meal planner creates a recurring subscription system.

For example, users can schedule meal kits to have them on particular days throughout the year. The system can then coordinate the timing of the meal kits, provide their equipment and pantry pick lists, assign resources to prepare the required elements of the meal, allocate the dinnerware, silverware, glassware, etc. for serving the meal to the proper resource and synchronize these activities to be ready for the time on the meal calendar. The food in certain embodiments comes from the meal kit company, from other third party food providers, or is held on a recurring replenishment inventory in the user's pantry. The meal can be prepared by the household members or a third party chef could cook and serve the meal. In certain embodiments, the user schedules their supplements to be taken during the day and they are alerted to when each supplement and its quantity is scheduled to be taken. The meal planner can work in conjunction with the node-to-node system to schedule replenishment based on the container quantity, lead time and shelf life of the supplement(s) being taken. Food Items and/or meal kits can be placed on any number of recurrence cycles based either on the meal planner or on a min/max inventory system. Each item making up a recipe can be connected to its preparation techniques to prepare, cook, and serve the recipe and/or meal.

Figure 33:
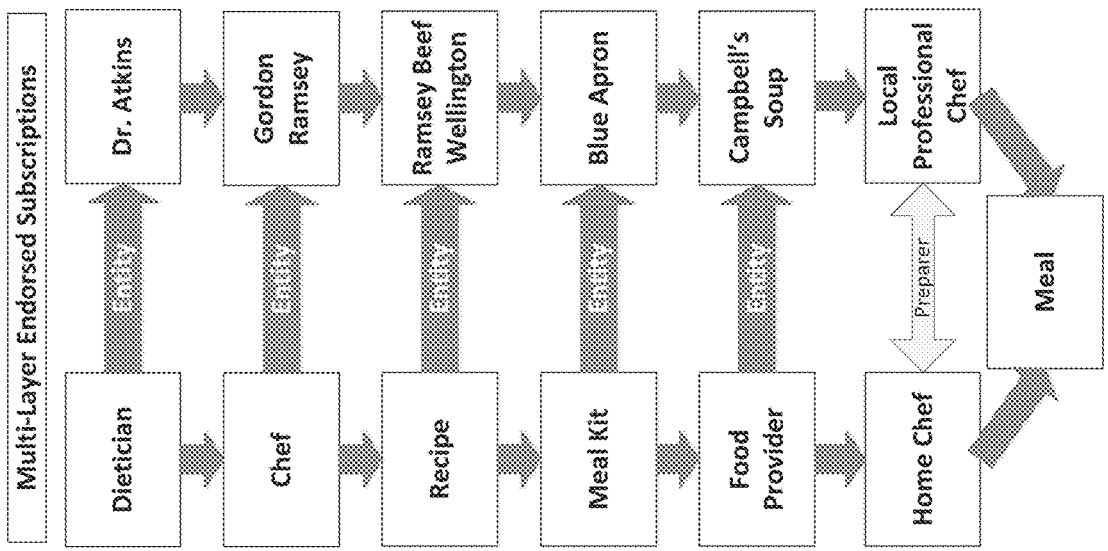
FIG. 33 schematically illustrates some example multi-layer endorsed subscriptions in accordance with certain embodiments described herein.

In certain embodiments, the node-to-node system enables a multi-layer endorsements for recipe subscriptions. FIG. 33 schematically illustrates some example multi-layer endorsed subscriptions in accordance with certain embodiments described herein. For example, dieticians may endorse certain chefs and/or their recipes that are compatible with their dietary advice. Chefs can put together recipes to constitute a given series of meal kits. The meal kits can endorse certain food product suppliers which provide ingredients for the meal kits. The meal kits can endorse certain local chefs which prepare, cook and/or serve the meal to the subscriber.

Dieticians, Chefs and Meal Kit Providers can endorse certain food products from particular food vendors. These endorsed food products can be the ingredients in the series of recipes that constitute a given series of meal kits over a subscription. The meal kits are not limited to coming in one package. In certain embodiments, the node-to-node system enables the meal kit to be expanded to include the subscriber's pantry. For example, the meal kit company may strategically assign meal kit ingredients in the user's pantry. This capability of the node-to-node system in certain embodiments opens up the very definition of a meal kit and enables virtually any one with recipes to create meal kits across the spectrum of food, equipment, chef resources, recipe types, etc.

More and more appliances are being connected to the internet. The appliances are becoming smart appliances with embedded computer chips, but also they are increasingly being connected to the internet. In certain embodiments, the node-to-node system enables these devices to be connected onto the node-to-node networks, with each node comprising the pressure, temperature, speed, time and the method/technique to employ step-by-step to make any and all recipes. The node-to-node system of certain embodiments has a multiplicity of equipment and paired equipment at each node, which can be the perfect platform for connecting and interacting with food and recipes for smart appliances.

An appliance manufacturer can set up their own variants in the node-to-node system of certain embodiments to better optimize their particular appliance's operation. The user can select the preferences of the equipment for particular recipes. The node-to-node system of certain embodiments can then coordinate and synchronize the activities of the human, robot, and appliance/equipment resources to plan and carry out the tasks to prepare the recipes, and/or courses and or meals. The smart appliances can be scheduled along with the other resources based on the task dependencies and the resource dependencies to prepare, cook, and serve the meal for the desired time.

Grading and Scoring Food

Certain embodiments described herein advantageously provide users with scoring values of possible foods based on the food's ingredients (e.g., constituents), attributes, and/or nutrition levels. By organizing predetermined values for the foods in a database (e.g., a node-to-node system as described herein), certain embodiments can calculate at least one food scoring parameter indicative of the food (e.g., a nutrition quotient, an attribute quotient, an ingredient quotient, and/or a total quotient). For example, the at least one food scoring parameter can comprise an "ABB Score" (Avoid, Better, Best Score) for the foods which is indicative of the properties of the ingredients, their intrinsic attributes, quality, preparation methods, and/or nutrition levels. In certain such embodiments, the system and method calculate individual ABB Scores for single ingredients and/or an overall ABB Score for the combined ingredients (e.g., to assist users in deciding which foods to use in recipes). When a single ingredient is called out on a recipe or a universal product code (UPC), certain embodiments described herein calculate the food score for the ingredient.

As described more fully herein, certain embodiments include one or more of the following:

Database structure (e.g., node-to-node structure as described herein) using top-level identifications, cascading down to subclasses, with the subclasses expressed in a mosaic model with three primary connections: ingredients (input), steps (process), and aliases (output).

Traceability model using the node-to-node network to show users the evolution of each food and its nutrition levels, with connectors representing actions of converting from a state A to a state B (e.g., from a "whole fresh" state to a processed state).

Reporting nutrition levels in terms of "per calorie unit."

Certain embodiments described herein includes a system (e.g., an app; a website; a computer program) or a method that provides food scoring which is indicative of (e.g., weighs) one or more properties of the foods, including but not limited to, the quality of the ingredients, their attributes, processing methods, and the nutrition levels of the food item/product. For example, a whole food with solid attributes which is minimally processed that maintains nutrition levels will score high, while food products with unknown attributes, poor quality ingredients, and harsh processing methods that lower the nutrition level will score low. For example, a website can show the Best in Class for each food class, and/or can rank the members of the food class from Best to Worst (e.g., by their score from 100 to 0).

In certain embodiments, the score of a food product can range from 100 (e.g., the highest possible score value) to one or zero (e.g., the lowest possible score value). For example, beginning from an initial score of 100, the food product's score can be reduced (e.g., by deducting points from the score) for various properties of the food product, including but not limited to the choices of ingredient(s), unspecified attributes, the processing methods employed and the product's nutrition levels. The scoring of certain embodiments is designed to reflect properties of the food products in some or all of the following characteristics or "pillars": Ingredient (s); Attributes (e.g., which can include processing methods); and Nutrition Levels. An intermediate "Nutrition Level" score (e.g., nutrition quotient) can be generated which is indicative of the nutrition level characteristics of the food, an intermediate "Attributes score" (e.g., attribute quotient) can be generated which is indicative of the attributes characteristics of the food, and an intermediate "Ingredient score" (e.g., ingredient quotient) can be generated which is indicative of the ingredient characteristics of the food. In certain such embodiments, two or more of these intermediate scores can be combined with one another (e.g., weighted relative to each other) to provide a "total score" (e.g., total quotient) to the user. The relative weights of the intermediate scores can be adjusted globally, thereby affecting all food/recipe classes equally. Certain embodiments advantageously provide a standardized scoring approach across all categories of food, which can be simple and easy to understand.

In certain embodiments, the food scoring system provides one or more scores that are indicative of one or more answers to one or more of the following questions:

What is in the food? (e.g., ingredient quotient);

What are the nutrients and/or anti-nutrients in the food? (e.g., nutrition quotient);

What is the traceability/pedigree of the food? How is the food made? (e.g., attribute quotient).

In certain embodiments, the food scoring system utilizes at least one relational computer database of food-related information (e.g., having a node-to-node structure), as described herein with regard to FIGS. 1 and 2. The database can include tables having a top-level records for parent foods and lower-level records for derivative forms of the parent food of the table. In certain embodiments, a parent food is a live, fresh, raw, or whole plant, animal, or culture (e.g., the most basic form found where the food is not a living item). For example, the parent food can be a naturally occurring material that has been extracted or gathered, an artificially created material, or water in its various forms.

In certain embodiments, derivative forms of the parent food are processed at a given pressure, temperature or speed. For certain cases, the processing does not affect the nutrition properties of the derived form. For example, derivative food forms can be divided (e.g., an Apple cut into Apple halves) or separated (e.g., an Orange squeezed into orange juice and separated from the peel/rind). A division can keep the per calorie nutrition intact where a separation can change the per calorie nutrition of the separated derivatives. For certain other cases, a derivative food item is processed in such a way that the processing does affect the nutrition properties of the derived form. For example, a steak that is cooked well done can have its nutrition affected by the application of heating the steak above a given temperature.

In certain embodiments, two or more ingredients can be combined, and the combination of ingredients can create a nutrition equal to the weight and/or volume of the combined ingredients. In certain cases, processing of a multi-ingredient combination (e.g., at a given pressure, temperature, or speed) does not affect at least some of the nutrition properties of the combined ingredients. For example, some types of processing do not change the per calorie nutrient level of the combined ingredients. In certain other cases, processing of the combined ingredients does affect the nutrition properties of the combined ingredients. For example, a seasoned steak that is cooked well done can have its nutrition affected by the application of heating the seasoned steak above a given temperature.

In certain embodiments, the combined ingredients can be divided. For example, a bread dough can be divided into two portions, and the division of the bread dough does not change the per calorie nutrition properties of the bread dough. In certain embodiments, the combined ingredients can be separated (e.g., into dissimilar portions). For example, the fermented mash or wash for making whisky can be distilled, which separates the ethanol from the wash, and which changes the per calorie nutrition of both the wash and the ethanol.

Figure 34:
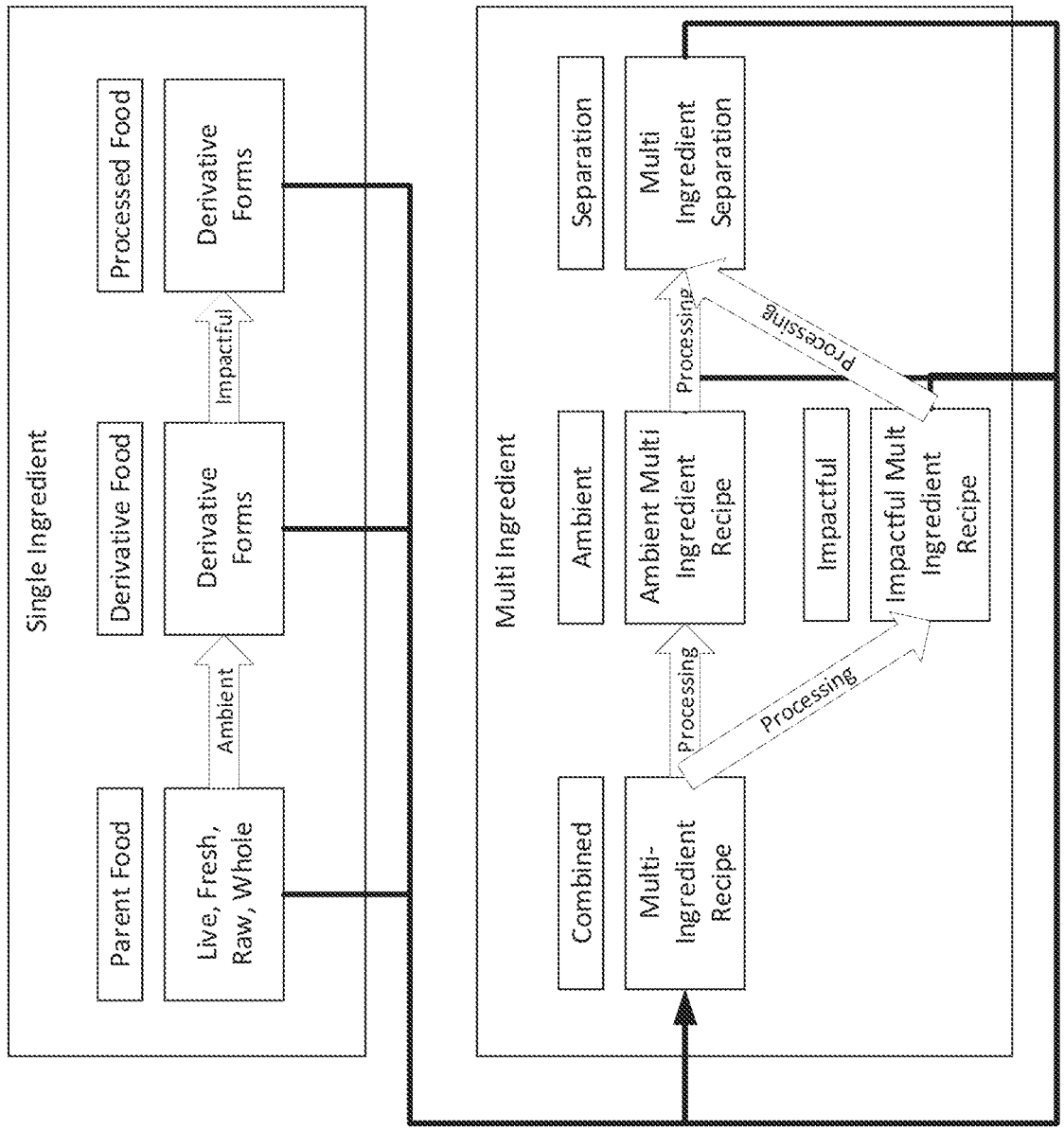
FIG. 34 shows an example of the relationships between single ingredients and multiple ingredients in accordance with certain embodiments described herein.

FIG. 34 shows an example of the relationships between single ingredients and multi-ingredients (e.g., recipes) in accordance with certain embodiments described herein. The nature of recipes is a recursive relationship where ingredients can be combined, processed, and/or separated in various combinations and repeated ad infinitum. Certain embodiments described herein can calculate scores and/or scoring factors that are indicative of these ingredients and/or recipes.

FIGS. 35A-35E schematically illustrate various scenarios in which single ingredients are processed in accordance with certain embodiments described herein. FIGS. 36A-36E schematically illustrate various scenarios in which multiple ingredients are processed in accordance with certain embodiments described herein. FIG. 37 illustrates various example combinations of factors relevant for the score calculation for single ingredients, based on ingredient type or category and type of processing in accordance with certain embodiments described herein.

Figure 35A:
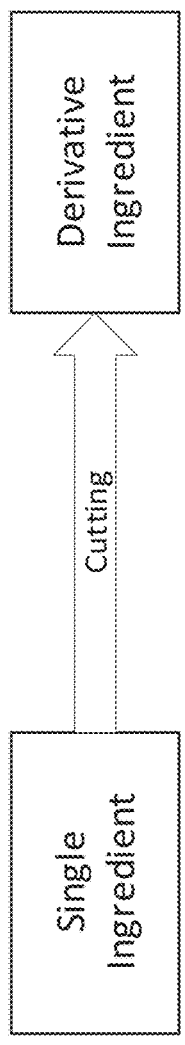
FIGS. 35A-35E schematically illustrate various scenarios in which single ingredients are combined in accordance with certain embodiments described herein.

FIG. 35A shows a single ingredient being processed into a derivative ingredient at ambient conditions in accordance with certain embodiments described herein. For example, a Fresh Apple can be cut into two Fresh Apple Halves. In this case, the attributes of the Fresh Apple are passed intact (e.g., unaffected by the processing) to the Fresh Apple Halves and the nutrition levels are also passed intact (e.g., unaffected by the processing). The scoring of the derivative ingredients can be based on the attributes and the nutrition levels (e.g., method B or C of FIG. 37). For example, the Food and Drug Administration (FDA) nutrition levels for the parent food can be used for the derivative food (method B of FIG. 37). For another example, for a food that is a Consumer Packaged Goods (CPG), the CPG nutrition levels (e.g., including the nutrition levels for some of nutrients), supplemented with the FDA nutrition levels (e.g., including the nutrition levels for some other nutrients), can be used for the derivative food (method C of FIG. 37).

Figure 35B:
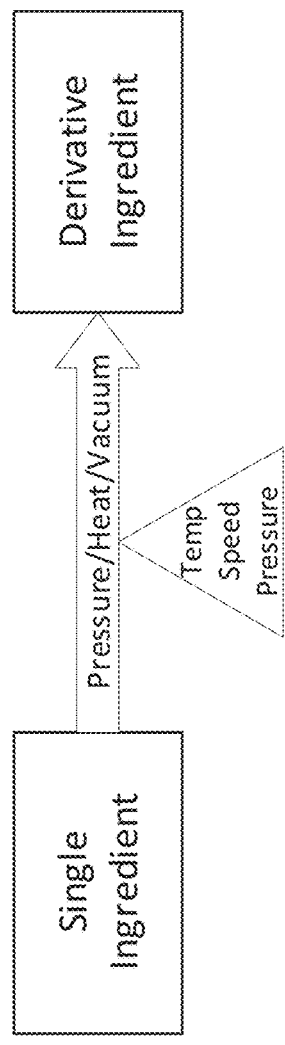
Figure 35C:
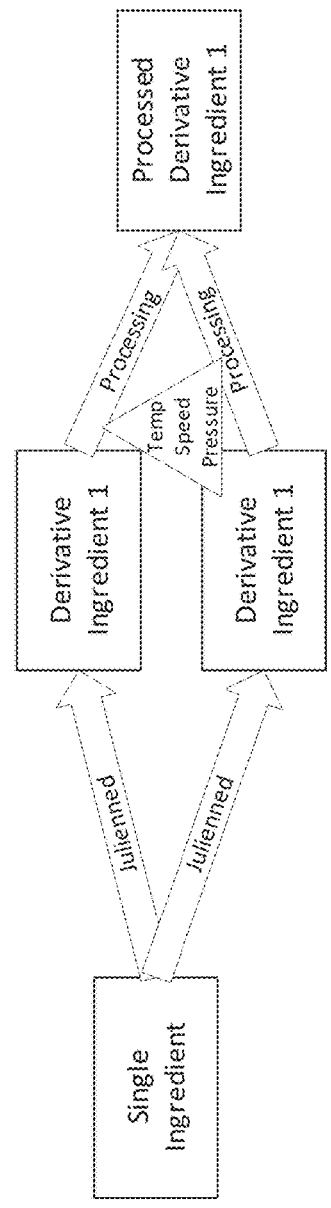

FIG. 35B shows a single ingredient being processed into a derivative ingredient at impactful conditions in accordance with certain embodiments described herein. For example, a Steak can be cooked well done (e.g., steak cooked until reaching an internal temperature of 160 F). In this case, the attributes of the Steak are passed intact (e.g., unaffected by the processing) to the well done steak, but the nutrition levels are impacted (e.g., reduced) by the higher processing temperature. FIG. 35C shows a single ingredient being processed into similar derivative ingredients and then further processed at impactful conditions (e.g., conditions that affect the nutrition levels of the single ingredient) in accordance with certain embodiments described herein. For example, a Fresh Potato can be julienned into Fresh Julienned Potatoes, during which the attributes and nutrition levels are passed intact (e.g., unaffected by the processing) and then deep fried until reaching an internal temperature of 170 F, impacting the nutrition levels for the processed derivative ingredient.

In certain embodiments, the nutrition levels for the derivative ingredients (e.g., the food in the derivative state) of FIGS. 35B and 35C are available from other sources (e.g., from nutrition information from the FDA, which can be included in the lower-level records for the derivative ingredients), and the scoring of the derivative ingredients can be based on the attributes and the FDA nutrition levels (e.g., method B of FIG. 37). In certain other embodiments, the nutrition levels for the derivative ingredients are not available from other sources and are not included in the lower-level records for the derivative ingredients, but can be calculated, e.g., by using the FDA nutrition levels of the parent food and accessing an impact chart or look-up table with factors for calculating the derivative ingredient nutrition levels based on the impactful parameter (e.g., temperature) of the impactful processing technique (e.g., method D of FIG. 37). For example, for a CPG food, the CPG nutrition levels (e.g., including the nutrition levels for some of nutrients), supplemented with the FDA nutrition levels (e.g., including the nutrition levels for some other nutrients), can be used for the derivative food (method C of FIG. 37). For another example, for a CPG food, the nutrition levels for the derivative ingredients can be calculated, e.g., by using the CPG nutrition levels supplemented with the FDA nutrition levels and accessing an imp[act chart or look-up table with factors for calculating the derivative ingredient nutrition levels based on the impactful parameter (e.g., temperature) of the impactful processing technique (e.g., method E of FIG. 37).

Figure 35D:
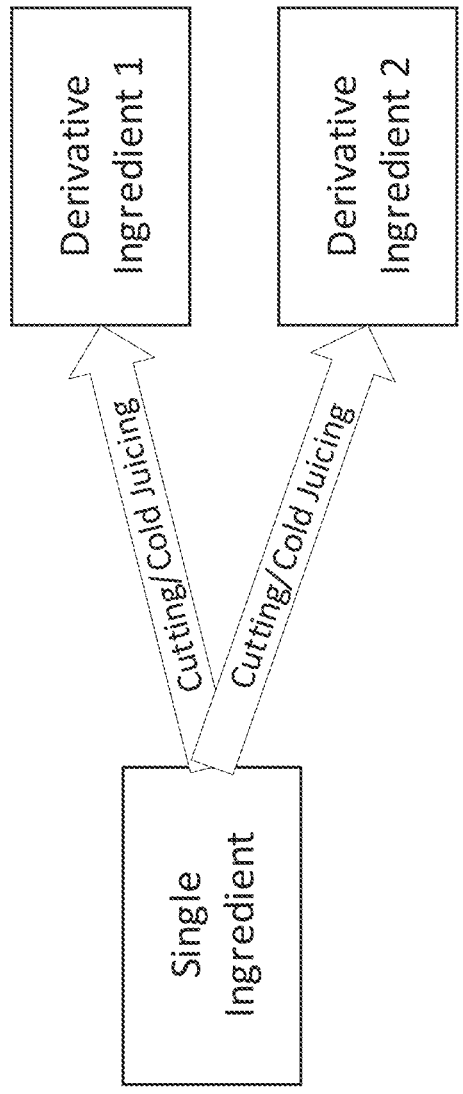

FIG. 35D shows a single ingredient being processed into two dissimilar derivative ingredients at ambient conditions in accordance with certain embodiments described herein. For example, a Fresh Orange Half can be cold juiced at ambient temperature to produce Cold Pressed Orange Juice (e.g., derivative ingredient 1) and the Orange Rind/Peel Half (e.g., derivative ingredient 2). In this case, the attributes are passed to both derivative ingredients intact (e.g., unaffected by the processing), but the nutrition levels of the two dissimilar derivative ingredients are affected (e.g., have different nutrition levels from one another and from the original ingredient). In certain embodiments, the nutrition levels for one or both of the ingredients are available from other sources (e.g., from FDA nutrition information, which can be included in the lower-level records for the derivative ingredients), and the scoring of the derivative ingredients can be based on the attributes and the FDA nutrition levels (e.g., method B of FIG. 37). In certain other embodiments, one of the derivative ingredients is not available from other sources and is not included in the lower-level record for the derivative ingredient, but the nutrition levels can be calculated, e.g., by subtracting the one derivative ingredient's nutrition levels from the single ingredient's nutrition levels to yield the nutrition levels of the second derivative ingredient.

Figure 35E:
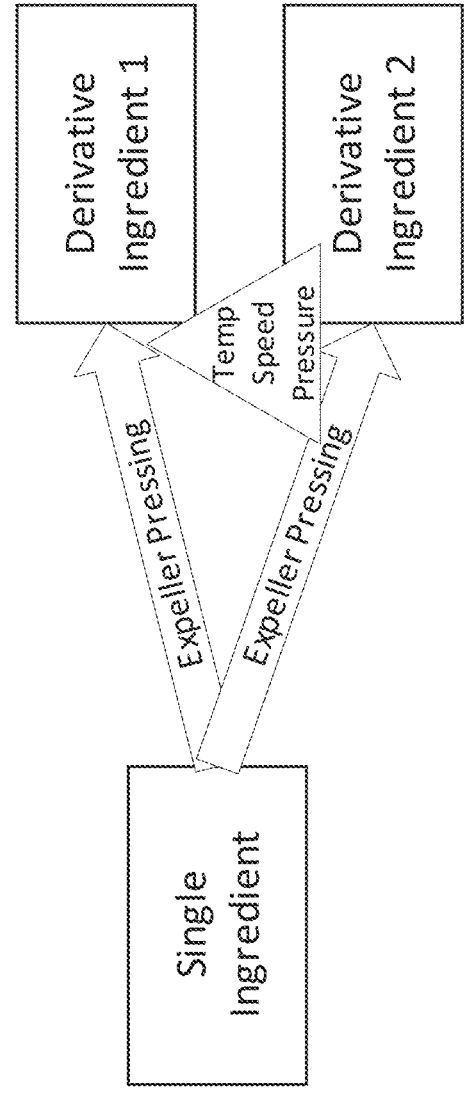

FIG. 35E shows a single ingredient being processed into two dissimilar derivative ingredients at impactful conditions in accordance with certain embodiments described herein. For example, Olives can be expeller pressed, generating high heat to produce Olive Oil and Olive Press Cake. In this case, the attributes are passed to both derivative ingredients intact (e.g., unaffected by the processing), but the nutrition levels are affected by the high heat. In certain embodiments, the nutrition levels for one or both of the ingredients are available from other sources (e.g., from FDA nutrition information, which can be included in the lower-level records for the derivative ingredients), and the scoring of the derivative ingredients can be based on the attributes and the FDA nutrition levels (e.g., method B of FIG. 37). In certain other embodiments, the nutrition levels for the two processed derivative ingredients are not available from other sources and are not included in the lower-level records for the derivative ingredients, but can be calculated, e.g., by using the FDA nutrition levels of the parent food and accessing an impact chart or look-up table with factors for calculating the derivative ingredient nutrition levels based on the impactful parameter (e.g., temperature) of the impactful processing technique (e.g., method D of FIG. 37).

Figure 36A:
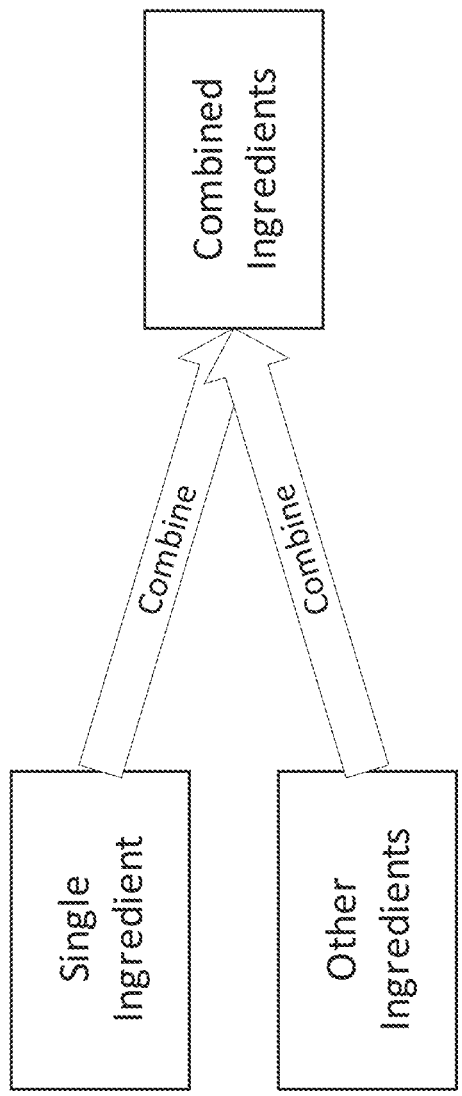

FIG. 36A shows dissimilar ingredients being combined into a new combination at ambient conditions in accordance with certain embodiments described herein. For example, Salt, Pepper, and Granulated Garlic can be combined to make a Seasoned Salt. In certain embodiments, methods A or B of FIG. 37B can be used for calculating the scores for the combined ingredients.

Figure 36B:
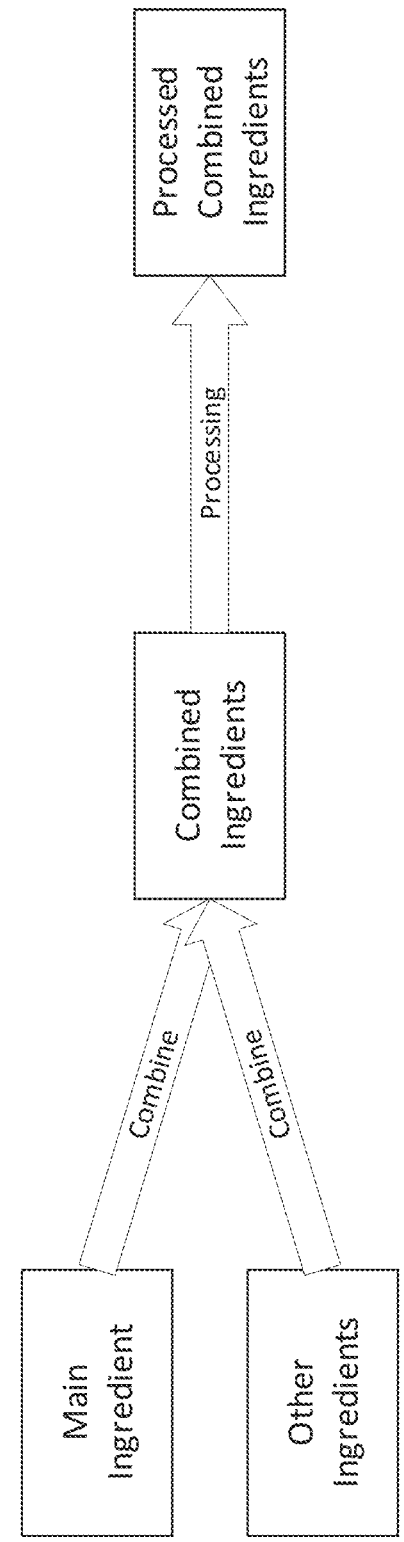

FIG. 36B shows a main ingredient (e.g., single ingredient) retaining its basic form in the recipe and combined with other ingredients and processed at ambient conditions in accordance with certain embodiments described herein. For example, a steak (e.g., main ingredient) can be seasoned and the addition of the seasoning can affect its nutrition levels. The seasoned steak can then be cooked to rare (e.g., reaching an internal temperature of 120 F), such that the nutrition levels are not impacted.

FIG. 36C shows a main ingredient (e.g., single ingredient) combined with other ingredients at impactful conditions in accordance with certain embodiments described herein. For example, a Steak (e.g., main ingredient) can be seasoned and the addition of the seasoning can affect its nutrition levels. The seasoned steak can then be cooked to well done (e.g., reaching an internal temperature of 170 F), such that the nutrition levels are impacted.

FIG. 36D shows dissimilar ingredients being combined into a new combination and processed at ambient conditions in accordance with certain embodiments described herein. For example, Shredded Lettuce can be combined with many other chopped or shredded vegetables and Salad Dressing to form a Salad, and the Salad can be tossed (e.g., processed) to mix in the Salad Dressing and evenly coat the Salad components.

Figure 36E:
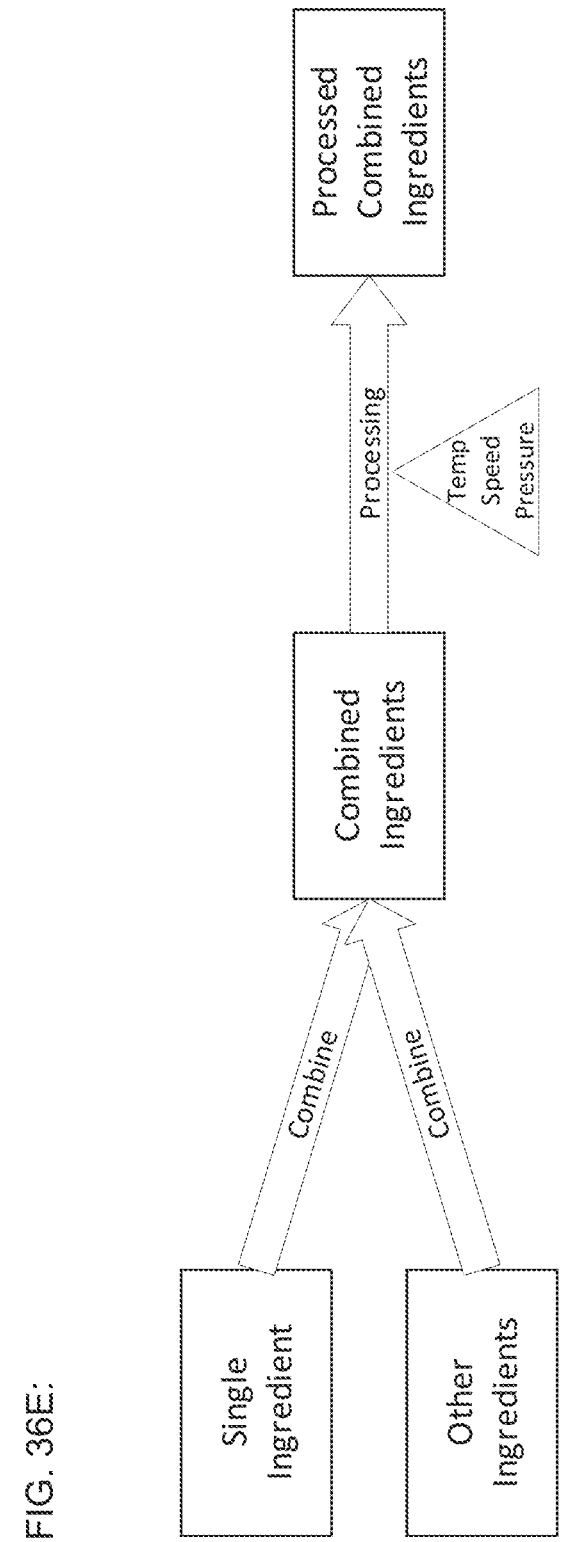

FIG. 36E shows dissimilar ingredients combined into a new combination and processed at impactful conditions in accordance with certain embodiments described herein. For example, whisky can be made by combining water, malted barley, and yeast, and the combination can be fermented and then distilled at 173 F (which affects the nutrition levels) in order to evaporate the ethanol alcohol.

In each of FIGS. 36A-36E, the nutrition levels can be calculated for the combined ingredients (e.g., in a recipe, the quantity or weight of the ingredients is known). In certain such embodiments, the scoring does not utilize the attributes, while in certain other embodiments, the attributes for each of the incoming ingredients are used to determine the attributes and the scoring of the combined ingredients. For example, for a Consumer Packaged Goods (CPG) of a manufacturer, the nutrition levels can be obtainable from the manufacturer, a sub-set of the FDA information (if available) corresponding to the CPG, or both. For another example, the nutrition levels can be supplemented with predetermined standard recipe values for the missing nutrition levels based on a predetermined standard recipe for that recipe/food class. In certain embodiments, the nutrition levels for some or all of the ingredients are obtainable from other sources (e.g., from FDA nutrition information) and/or are included in the lower-level records for the processed combined ingredients. In certain other embodiments, the nutrition levels for the processed combined ingredients are not obtainable from other sources and are not included in the lower-level records for the processed combined ingredients, but can be calculated, e.g., by accessing an impact chart or look-up table with factors for calculating the nutrition levels based on the impactful parameter (e.g., temperature) of the impactful processing technique.

In certain embodiments, at least one of the nutrition quotient and the attribute quotient is based on two parameters: a base score and an impact factor. For example, the nutrition quotient can be based on a plurality of substance base scores, each substance base score indicative of a nutrition value (e.g., between 100 for the best nutrition value and 0 for the worst nutrition value) of a corresponding substance (e.g., nutrient; anti-nutrient) of the food product, and a plurality of substance impact factors, each substance impact factor indicative of a relative effect of the corresponding substance on the nutrition value of the food product. For another example, the attribute quotient can be based on a plurality of attribute base scores, each attribute base score (e.g., between 100 for the closest to a natural state of the food and 0 for the farthest from a natural state of the food) indicative of a corresponding attribute of the food product, and a plurality of attribute impact factors, each attribute impact factor indicative of a relative importance of the corresponding attribute.

In certain such embodiments, the substance impact factors represent the nutrient density of the corresponding substances. The more sources (e.g., either major sources or minor sources) that a given food class has, the higher the nutrient density relative to other foods. For example, sources can be given a substance impact factor of 25 for major sources, a substance impact factor of 10 for minor sources, and a substance impact factor of 1 for not being either a major or minor source. The more sources for a given vitamin, mineral, fat, etc., the higher the impact factor. Also, by virtue of the substance impact factors, the more of a nutrient that is lost from a major or minor source can greatly impact the nutrition quotient for the food item. For example, it can be desirable that a food processor not lose the most vital sources of which the food item has, and the substance impact factors can be assigned to ensure that the resultant nutrition quotient is indicative of any such nutrient loss.

In certain embodiments, the impact factors are used as a weighting of the corresponding base scores. For example, when calculating the nutrition quotient for a food item, each of the substance base scores can be multiplied by the corresponding substance impact factor to get an extended score and then summing these extended scores and dividing the sum by a sum of the impact factors to derive the nutrition quotient for the food item. Similarly, the attribute quotient and the ingredient quotient can be calculated using the corresponding base scores and impact levels. The overall score can then be calculated by averaging the nutrition quotient, attribute quotient, and ingredient quotient (e.g., summing the extended scores across the individual ingredients and then dividing the summed extended scores by the sum of the impact factors).

Nutrition

Figure 38:
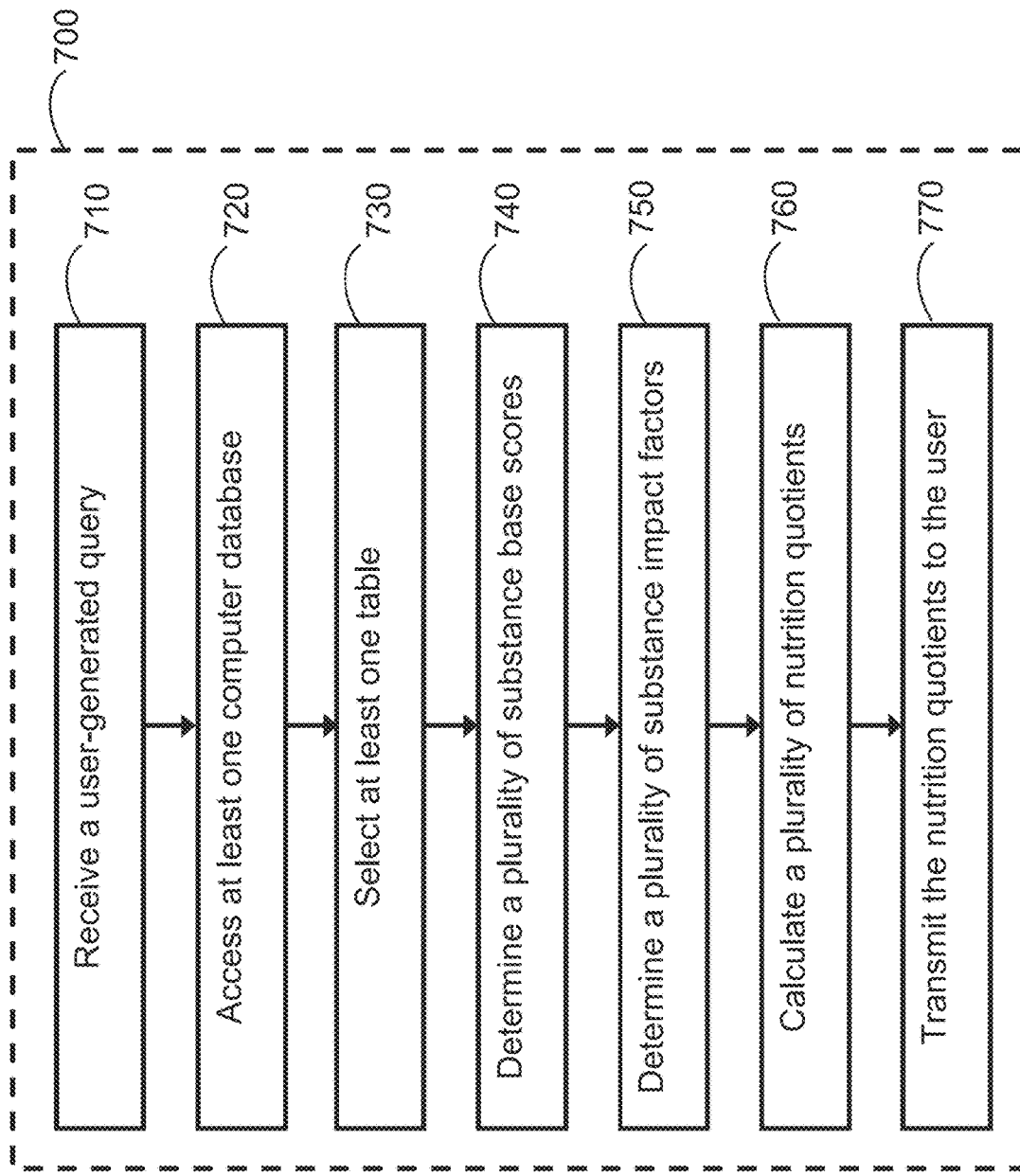
FIG. 38 is a flow diagram of an example method of providing food-related information to a user in accordance with certain embodiments described herein.

FIG. 38 is a flow diagram of an example method 700 (e.g., performed by the example computer system 100) of providing food-related information to a user (e.g., to a user computing device 150) in accordance with certain embodiments described herein. In certain embodiments, a software application is running on the user computing device 150, the software application configured to receive the food-related information transmitted from the computer system 100 to the user computing device 150 and to present the received food-related information to the user.

In an operational block 710, the example method 700 comprises receiving a user-generated query regarding at least one food (e.g., food product). In an operational block 720, the example method 700 further comprises accessing, in response to the query, at least one computer database comprising, inter alia, a plurality of tables (e.g., branches) (e.g., stored by the at least one memory device 120 of the computer system 100). Each table of the plurality of tables comprises a top-level record corresponding to a subject of the table and a plurality of lower-level records that correspond to food members (e.g., food products) of the subject of the table. Each lower-level record of the plurality of lower-level records comprising a plurality of nutrition values ($N_n$), with each nutrition value indicative of an amount per calorie in the food member of a corresponding substance (n) of a plurality of substances.

In certain embodiments, receiving the user-generated query regarding the at least one food (e.g., a user-generated food-related query from one of the plurality of user computing devices 150) in the operational block 710 and accessing, in response to the query, the at least one computer database in the operational block 720 can be performed as described herein with regard to FIGS. 1 and 2. For example, the at least one computer database can comprise a relational database of food-related information (e.g., having a node-to-node structure), as described herein, and receiving the user-generated query regarding the at least one food can comprise generating, in response to the query, a subject identifier indicative of the at least one food of the query, as described herein. In certain embodiments, the user-generated query includes information regarding the user's particular diet constraints (e.g., number of calories; amount of sugar; amount of salt) which can be used to provide food scores tailored to the user.

In certain embodiments, the substances of the food products (e.g., food members) comprise nutrients (e.g., substances that provide nourishment that facilitates growth and the maintenance of life) and anti-nutrients (e.g., substances which hinder the absorption of nutrients or can be hazardous to long term health). Examples of nutrients include, but are not limited to, calories, fats, carbohydrates, proteins, amino acids, vitamins, minerals, sterols, alcohol, and water. Certain embodiments described herein calculate a score (e.g., nutrition quotient) for the food product which takes the existence and/or effects of at least one nutrient into account (e.g., raising the score if such nutrients and/or their effects are present).

Examples of anti-nutrients include, but are not limited to, phytates, lectins, gluten, sulfites, sulfates, nitrates, nitrites, butylated hydroxytoluene (BHT), other substances which hinder or affect normal digestion, chemical fertilizers, biocides, pesticides, heavy metals, persistent organic pollutants (POPs), and other chemicals or toxins found in certain food classes. Some anti-nutrients can have minute exposures, but can have negative health benefits over a longer time span. Some anti-nutrients are found naturally within food, like gluten, which is a lectin found in wheat. Other anti-nutrients are man-made or man-caused, such as pollutants like heavy metals found in some species of fish. Certain embodiments described herein calculate a score (e.g., nutrition quotient) for the food product which takes the existence and/or effects of at least one anti-nutrient into account (e.g., lowering the score if such anti-nutrients and/or their effects are present).

FIG. 39A-39C show a table of 169 substances in accordance with certain embodiments described herein. At least some of the substances of FIGS. 39A-39C comprise nutrients and at least some of the substances of FIGS. 39A-39C are caloric quantities (e.g., total calories; calories from carbohydrates; calories from fat) which are not rigorously substances, but can be included in the calculation of the nutrition quotient as described herein. Certain embodiments described herein utilize nutrient levels of some or all the nutrients. For example, certain embodiments described herein can present users with a score (e.g., nutrition quotient) of a selected food or recipe that is based on the food's or recipe's nutrient levels of the 160 nutrients measured by the Food and Drug Administration (FDA) plus nine combined and calculated values. The 160 FDA nutrients can be grouped into three groups: (i) nutrients a user seeks to get enough of (e.g., a recommended daily allowance), (ii) nutrients a user seeks to minimize, and (iii) nutrients a user seeks to maintain in balance. In certain embodiments, the plurality of substances comprises only a subset of the nutrients listed in FIG. 39A-39C. For example, the substances can include one or more vitamins (e.g., vitamin A, vitamin C), one or more minerals (e.g., calcium, iron, sodium), protein, one or more fats (e.g., saturated fat, total fat, trans fat), one or more carbohydrates (e.g., total carbohydrates, fiber, sugars), and one or more sterols (e.g., cholesterol). In certain embodiments, the nutrition information of the lower-level record further includes the total number of calories and/or the number of calories from fat.

For example, the table below shows example nutrition values (per 100 grams) for a plurality of substances of three different varieties of Apples in accordance with certain embodiments described herein. For each substance, the recommended daily allowance (RDA) and the amounts can be obtained from the FDA.

In an operational block 730, the example method 700 further comprises selecting at least one table of the plurality of tables. Each selected table comprises a lower-level record corresponding to a food of the at least one food. For example, selecting the at least one table can comprise using the subject identifier generated in response to the query and retrieving the one or more tables (e.g., from the at least one memory device 120 of the computer system 100) that include the lower-level record that corresponds (e.g., matches) the subject identifier. For example, if the subject identifier is "Fuji Apple," the selected table includes a lower-level record corresponding to "Fuji Apple," a top-level record corresponding to "Apple," and other lower-level records corresponding to other types of apples (e.g., "Granny Smith Apple," "Gala Apple").

In an operational block 740, the example method 700 further comprises determining, for each food member of the at least one selected table, a plurality of substance base scores ($SB_n$). Each substance base score is indicative of a comparison of the nutrition value ($N_n$) of the corresponding substance in the food member to a nutrition value ($N_n^*$) of the corresponding substance in a benchmark food member of the table of the food member. For example, if the top-level record of the selected table corresponds to "Apple," a plurality of substance base scores is determined for each type of apple having a lower-level record in the table (e.g., plurality of substance base scores $SB_n$ for Fuji Apples, plurality of substance base scores $SB_n$ for Granny Smith Apples, plurality of substance base scores $SB_n$ for Gala Apples, etc.).

In certain embodiments, the benchmark food product (e.g., food member) of the table of the food product can be the live/fresh/raw/whole food form of the parent food class of the food product corresponding to the subject identifier, and the nutrition values ($N_n$) of the food product can be

| | | Top-level: Apple | | |
|---|---|---|---|---|
| | Recommended Daily Allowance (RDA) | Organic Apple, Granny Smith Amount (per 100 g) | Organic Apple, Gala Amount (per 100 g) | Organic Apple, Fuji Amount (per 100 g) |
| Vitamin A, RAE | 900 µg | 5 µg | 1 µg | 2 µg |
| Calcium | 1000 mg | 5 mg | 7 mg | 7 mg |
| Iron | 18 mg | 0.15 mg | 0.12 mg | 0.1 mg |
| Sodium | 2300 mg | 1 mg | 1 mg | 1 mg |
| Protein | 50 g | 0.44 g | 0.25 g | 0.2 g |
| Total Lipid (Fat) | 78 g | 0.09 g | 0.12 g | 0.18 g |
| Carbohydrates, by difference | 275 g | 13.61 g | 13.68 g | 15.22 g |
| Fiber, total dietary | 28 g | 2.8 g | 2.3 g | 2.1 g |
| Calories | 2000 | 58 | 57 | 63 |

In certain embodiments, the nutrition information (e.g., the nutrition values $N_n$) for the food products in the at least one computer database are obtained (e.g., received) from one or more sources, including but not limited to: an FDA database; a database or communication from the producer of the food product (e.g., the company manufacturing and/or marketing the food product); or other public or private database; derived (e.g., inherited) from the FDA nutrition information for the food class which contains the food product; calculated by the weight and/or volume of the ingredient(s) of the food product.

compared to the nutrition values ($N_n^*$) of the live/fresh/raw/whole food form of the parent food class of the food product. For some foods and processes (e.g., subjected to heat, speed, friction, pressure), the nutrition values can be modified (e.g., nutrition can be lost) due to the processing or can be unaffected by the processing. Certain levels of pressure, temperature, or speed can have a positive impact on the nutrition values as applied to some foods and can have a negative impact on the nutrition values as applied to other foods. For example, heating vegetables above a certain temperature can reduce their water-soluble nutrients, while soaking beans can reduce their lectins which could otherwise inhibit the absorption of nutrients by the body. The conditions of how something is made or processed can affect the nutrient or anti-nutrient properties, and certain embodiments described herein calculate a score for the food product which takes these effects into account.

Certain embodiments described herein calculate the modified nutrition values for the affected nutrient, anti-nutrient, and/or nutrient category and these nutrition values and/or the comparison of these nutrition values to the nutrition values for the live/fresh/raw/whole food form of the parent food can be transmitted to be presented to the user. The comparison (e.g., difference, ratio, or other calculated value) can be calculated for each nutrient, anti-nutrient, and/or category of nutrients and a score (e.g., substance base score) can be assigned based on the comparison to the parent food. For example, the nutrition values for Apple Sauce can be compared to those of Fresh Apple to see if the food product (Apple Sauce) gained, lost, or maintained its nutrition values due to the processing from its parent food class form (Fresh Apple).

In certain embodiments, each nutrient, anti-nutrient, and/or category of nutrients can be given a score (e.g., substance base score) based on how close the food product is to the nutrition value of the original form in the category of its parent food class form. A reduction of nutrient levels can correlate to a lower score, while a reduction of anti-nutrient levels can correlate to a higher score. For example, Red Kidney Beans have up to 70,000 Lectin Units, while pressure-cooked Red Kidney Beans have up to 700 Lectin Units, which is a thousand-fold reduction, and this reduction can be reflected in the score for pressure-cooked Red Kidney Beans. In certain embodiments, the frequency of intake of any particular nutrient and/or anti-nutrient, along with their associated nutrition values, can be transmitted to be presented to the user.

In certain embodiments, the substance base score is indicative, at least in part, of the anti-nutrient levels (e.g., levels of pollutants, fertilizers, and other toxins of which the consumer should be aware). For example, a commercial apple can have a high potential level of pesticides: 99% of commercial apples tested positive for at least one biocide residue. Typical biocides detected for apples include diphenylamine (0.002 ppm) and imidacloprid (0.003 ppm). The FDA tolerance for these biocides are 1 ppm and 0.5 ppm, respectively. For other anti-nutrients, there are no tolerances set. These and other pesticide levels are documented in the USDA Pesticide Data Program, and certain embodiments described herein can access such data for use in calculating the scores for food products (e.g., the score can be indicative of a comparison of the pesticide level of the food product with a predetermined exposure level, with higher scores indicative of lower pesticide levels and lower scores indicative of higher pesticide levels). Heavy metals and persistent organic pollutants (POPs) accumulate and build up in fatty acids. For example, older fish may be exposed to mercury or other heavy metals where they accumulate and build up in the fish's fatty acids, and these substances can be passed to the consumer at the top of the food chain. For another example, arsenic in rice can range from 1 to 200 ppb, with each dish of rice giving the consumer about 200 ppb of arsenic. Documented values of these and other heavy metal and/or POP levels can be accessed by certain embodiments described herein (e.g., by accessing appropriate databases) for use in calculating the scores for food products (e.g., the score can be indicative of a comparison of the metal and/or POP level of the food product with a predetermined exposure level, with higher scores indicative of lower metal and/or POP levels and lower scores indicative of higher metal and/or POP levels). Some commercial food products may contain many of the by-products of their industrialization, including but not limited to, pollutants, biocides, and chemical fertilizers. These anti-nutrients can be quantified on a per serving basis or a per item consumed basis. In certain embodiments, the anti-nutrition score (e.g., a substance base score for only the anti-nutrients) can be shown along with the nutrition score (e.g., a substance base score for only the nutrients) to highlight the balance of nature and industrialization of the food chains such that the user can see the nutrition and anti-nutrition factors for each of the food ingredients.

In certain embodiments, the substance base score ($SB_n$) for a nutrient of a food product can be dependent on a ratio ($N_n/N_n^*$) of the nutrition value ($N_n$) for the nutrient in the food product to the nutrition value ($N_n^*$) of the nutrient in a benchmark food product related to the food product (e.g., in a benchmark food product of the table of the food product). In certain embodiments, the substance base score ($SB_n$) for an anti-nutrient of a food product can be dependent on a ratio ($N_n^*/N_n$) of the nutrition value ($N_n^*$) of the anti-nutrient in a benchmark food product related to the food product (e.g., in a benchmark food product of the table of the food product) to the nutrition value ($N_n$) for the anti-nutrient in the food product.

For example, the substance base scores ($SB_n$) for a nutrient can be given by:
for $[100 \times (N_n/N_n^*)] \geq 100$, $SB_n = 100$;
for $100 > [100 \times (N_n/N_n^*)] > 0$, $SB_n = [100 \times (N_n/N_n^*)]$; and
for $[100 \times (N_n/N_n^*)] = 0$, $SB_n = 1$.
In this example, the substance base score for nutrients is restricted to be within a range of 1 to 100.

For another example, the substance base scores ($SB_n$) for an anti-nutrient can be given by:
for $[100 \times (N_n^*/N_n)] \geq 100$, $SB_n = 100$;
for $100 > [100 \times (N_n^*/N_n)] > 0$, $SB_n = [100 \times (N_n^*/N_n)]$; and
for $[100 \times (N_n^*/N_n)] = 0$, $SB_n = 1$.
In this example, the substance base score for anti-nutrients is restricted to be within a range of 1 to 100.

In certain embodiments, the benchmark food product (e.g., food member) of the selected table of the food product can be identified by calculating, for each food product of the selected table, a benchmarking quotient (BQ) given by: $BQ = \Sigma_n(N_n/DDA_n)/\Sigma_n(1)$ and identifying the food product of the selected table having the largest benchmarking quotient as the benchmark food product, where $\Sigma_n(N_n/DDA_n)$ is a sum over the plurality of substances of the nutrition values ($N_n$) divided by the dietary daily allowance of the substance per calorie ($DDA_n$) and $\Sigma_n(1)$ is the number of substances. In certain embodiments, one or more of the top-level record and the lower-level records of the table comprising the lower-level record of the food product includes a foreign key that points to (e.g., provides a link) to the record of the benchmark food product.

For example, not all varieties of Apple have the same nutrition (e.g., a Fuji Apple has less nutrition than does a Golden Delicious Apple), and the variety of Apple with the best nutrition (e.g., more of the nutrients and less of the anti-nutrients) will have the largest benchmarking quotient and can then be the benchmark food product for the Apple table (e.g., the standard or "best-in-class" of the food class). For another example, certain breeds of cows produce milk with an A-2 Caesin which is easy to digest and has more calcium and other nutrients than does the milk from other cow breeds (e.g., Holstein cows which are the most populous cow in America). The breeds producing the "best"

profile can be used as the standard, and all Milk can then be compared to this standard. As the nutrient content of any other type of Milk varies from that of the benchmark food product for the Milk network (e.g., the "best-in-class"), then the score of the other type of Milk will be lower than that of the benchmark Milk, reflecting a lesser amount of nutrients gained per calorie consumed and/or a higher amount of anti-nutrients gained per calorie consumed.

Where there are multiple FDA nutrition profiles for the same food or recipe class, then certain embodiments described herein can use the one that has the best nutrition profile as the "gold standard." As new FDA nutrition profiles are completed, then those that have the best nutrition can become the new "gold standard." This way, as new information is developed and it is superior to the other ones, then it can be promoted to the "gold standard" to which the others are compared.

In an operational block 750, the method 700 further comprises determining, for each food member of the at least one selected table, a plurality of substance impact factors ($SIF_n$). Each substance impact factor is indicative of the nutrition value ($N_n*$) of the corresponding substance in the benchmark food member relative to a dietary daily allowance per calorie ($DDA_n$) of the corresponding substance. In certain embodiments, the dietary daily allowance of the substance per calorie ($DDA_n$) corresponds to a diet having a predetermined number of calories per day (e.g., 2,000 calories per day; 2,500 calories per day; 1,500 calories per day). In certain embodiments, standard values of the dietary daily allowances of the substances per calorie ($DDA_n$) are used (e.g., based on a standard diet of 2,000 calories per day; based on the diet not including any non-standard constraints such as a diabetes-compatible diet or a low-salt diet). In certain other embodiments, the values of the dietary daily allowances of the substances per calorie ($DDA_n$) are tailored to particular users or to particular groups of users (e.g., low-calorie diets for users looking to lose weight; diabetes-compatible diets for diabetic users; low-salt diets for users looking to reduce blood pressure). For example, information regarding the user's particular diet constraints can be received along with or separately from the user-generated query regarding at least one food.

In certain embodiments, the substance impact factor ($SIF_n$) for a nutrient of a benchmark food product can be calculated to be equal to the ratio ($SIF_n = N_n*/DDA_n$) of the nutrition value ($N_n*$) of the nutrient in the benchmark food product and the dietary daily allowance per calorie ($DDA_n$) of the nutrient. In certain embodiments, the substance impact factor ($SIF_n$) for an anti-nutrient of a benchmark food product can be calculated to be equal to the ratio ($SIF_n = DDA_n/N_n*$) of the dietary daily allowance per calorie ($DDA_n$) of the anti-nutrient and the nutrition value ($N_n*$) of the anti-nutrient in the benchmark food product. In certain other embodiments, the substance impact factors for a substance in the food product are calculated using the nutrition values ($N_n$) of the substance in the food product itself rather than the nutrition value ($N_n*$) of the substance in the benchmark food product (e.g., $SIF_n = N_n/DDA_n$ for nutrients and $SIF_n = DDA_n/N_n$ for anti-nutrients). In certain other embodiments, determining one or more substance impact factors for one or more nutrients and/or anti-nutrients of a food product comprises accessing a pre-assigned value of the substance impact factor.

In certain embodiments, the substance impact factors reflect whether the food product is a major source, minor source, or insignificant source of the substance (e.g., a major, minor, or insignificant source of a specific vitamin or mineral), and the substance impact factors are pre-assigned correspondingly. Major sources can have larger substance impact factors (e.g., assigned a substance impact factor of 25) than do minor sources (e.g., assigned a substance impact factor of 10), and minor sources can have larger substance impact factors than do insignificant sources (e.g., assigned a substance impact factor of 1), such that substance impact factors reflect a measure of the food's overall nutrition. If a food product provides an amount of a specific vitamin or mineral that is significantly higher than the user's average recommended daily amount (RDA) per calorie, then the substance impact factor of the food product for that specific vitamin or mineral can be larger than the substance impact factors of the food product for other vitamins or minerals. In this way, certain embodiments advantageously provide a score which differentiates major, minor, and insignificant sources of substances (e.g., vitamins and minerals) and which is indicative of whether those nutrition levels have been affected by the processing of the food product. For example, an Orange can be a major source of Vitamin C and an insignificant source of Vitamin D, so the substance impact factor for Vitamin C ($SIF_{VitC}$) in the Orange can be higher than the substance impact factor for Vitamin D ($SIF_{VitD}$) in the Orange. Because $SIF_{VitC}$ is larger than $SIF_{VitD}$, loss of Vitamin C during the processing of the Orange to make Orange Juice will have a larger effect (e.g., have a greater weight in the calculation) on the score (e.g., nutrition quotient) for the Orange Juice than will loss of Vitamin D during the processing.

In an operational block 760, the method 700 further comprises calculating, for each food member of the at least one selected table, a nutrition quotient (NQ) given by: $NQ = \Sigma_n(SB_n \times SIF_n)/\Sigma_n(SIF_n)$, where $\Sigma_n(SB_n \times SIF_n)$ is a sum over the plurality of substances of the products of the substance base scores multiplied by the substance impact factors and $\Sigma_n(SIF_n)$ is a sum over the plurality of substances of the substance impact factors. For example, the table below shows an example calculation of the nutrition quotient for an "Organic Apple, Granny Smith" in accordance with certain embodiments described herein.

| Organic Apple, Granny Smith | | | | |
|---|---|---|---|---|
| Substance | Amount/ calorie | $SB_n$ | $SIF_n$ | Extended Score ($SB_n \times SIF_n$) |
| Vitamin A, RAE | 0.09 μg | 99 | 1 | 99 |
| Vitamin C- Ascorbic Acid | 0 g | 100 | 1 | 100 |
| Calcium | 0.09 mg | 99 | 1 | 99 |
| Iron | 0 mg | 99 | 1 | 99 |
| Sodium | 0.02 mg | 100 | 1 | 100 |
| Protein | 0.01 g | 99 | 1 | 99 |
| Fatty Acids, total saturated | 0 g | 100 | 1 | 100 |
| Total Fat | 0 g | 100 | 1 | 100 |
| Trans Fat | 0 g | 100 | 1 | 100 |
| Carbohydrate | 0.23 g | 100 | 2 | 200 |
| Dietary Fiber | 0.05 g | 99 | 3 | 297 |
| Sugars | 0.16 g | 100 | 1 | 100 |
| Calories from Fat | 0 g | 100 | 1 | 100 |
| Cholesterol | 0 g | 100 | 1 | 100 |
| $SIF_n$ Sum; Extended Score Sum | | | 17 | 1693 |

Nutrition Quotient: (1693/17) = 100

In an operational block 770, the method 700 further comprises transmitting (e.g., from the computer system 100 to the user computing device 150 via the internet 140), in response to the query, the nutrition quotients for the food members of the at least one selected table, to the user (e.g., to the user computing device 150).

Ingredient Attributes

In certain embodiments, a food can be a single-ingredient food (e.g., Granny Smith Apple; Filet Mignon) or a multi-ingredient food (e.g., tomato sauce; milk), and the ingredient score of the food can be indicative of the food classes of the ingredients of the food. The ingredients can be organized to be within a plurality of main categories. For example:

Water: colorless liquid found in seas, lakes, rivers, and rain; forms the basis of the fluids for all living organisms.

Plants: organisms that typically grow in a permanent site and absorb water and inorganic substances and synthesize nutrients by photosynthesis (e.g., trees, grass, ferns, herbs, shrubs, moss, ferns).

Animals: organisms that feed on organic matter and are typically able to move and have specialized sense organs and nervous systems that respond to stimuli in their environment.

Cultures: small organisms that are the simplest forms of life (e.g., bacteria, mold, yeast, other microorganisms) that exist everywhere, including human skin and human digestive tracts; many types are essential for animals to digest and absorb nutrients.

Naturally Occurring: non-organic substances that have formed through natural processes over large time scales; sources of organic or inorganic substances and materials (e.g., salt; minerals).

Hydrocarbons: compounds of carbon and hydrogen materials produced over a large time scale from decomposed organic matter; generally found as crude oil; can be either naturally occurring or man-made.

Artificial (or Synthetic): substances and compounds that are manufactured or replicated by man; some do not naturally exist, while others may be produced by replicating natural forces.

Figure 40B:
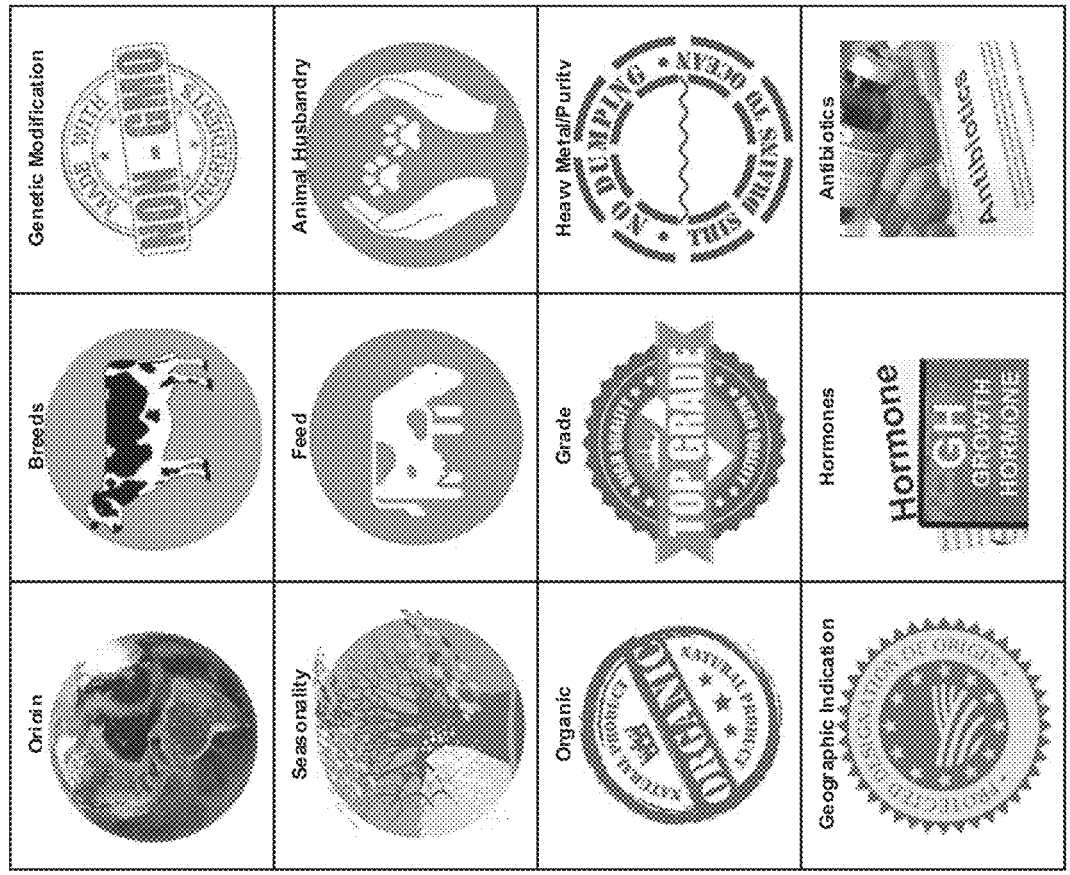
FIG. 40B illustrates a graphical representation of the twelve intrinsic attributes for the "animals" ingredient category in accordance with certain embodiments described herein.

In certain embodiments, a food can have a plurality of attributes, which can be intrinsic attributes or extrinsic attributes. In certain embodiments, each of the categories of ingredients can have a corresponding set of standard intrinsic attributes. For example, FIG. 40A shows twelve global attributes and the corresponding standard intrinsic attributes for each of the ingredient categories (e.g., Water, Plant, Animal, Culture, Hydrocarbon, Naturally Occurring, Artificial) in accordance with certain embodiments described herein. FIG. 40B illustrates a graphical representation of the twelve intrinsic attributes for the "animals" ingredient category in accordance with certain embodiments described herein. Each ingredient category can have its own range of attributes or variables. For example, FIG. 40C illustrates a graphical representation of the example intrinsic attribute values for a specific Consumer Package Goods (CPG) within a Universal Product Code (UPC) (e.g., beef filet mignon) in accordance with certain embodiments described herein.

In contrast to intrinsic attributes, extrinsic attributes are not part of the essential nature of the ingredient category, but are external to the food. An example extrinsic attribute for a food is the packaging in which the food is placed. Extrinsic attributes can have a positive effect, negative effect, or neutral or no effect on the nutritional properties of the food. For an example of a positive effect, bottle-conditioned beer continues to ferment after it has been packaged, thereby continuing to enhance its overall nutrient levels. For an example of a negative effect, cans that are lined with bisphenal A ("BPA"), an industrial chemical, may have the BPA leach into the food products, thereby potentially adversely affecting human health. For another example of a negative effect, Teflon® coatings may transfer into foods through use, and the repeated exposure over many weeks, months, or years may build up in the body. For an example of a neutral effect, glass containers are not known to leach into the food contained therein and have no net effect on the food. In certain embodiments, extrinsic attributes have an attribute base score $(AB_m)$ that is indicative of the influence of the corresponding attribute value on the food's nutritional properties and has an attribute impact factor $(AIF_m)$ indicative of the relative importance of the corresponding attribute as compared to the other attributes of the food. For example, various attribute values of the "packaging" external attribute can have the following attribute base scores and attribute impact factors:

| Extrinsic Attribute Value | Impact | Attribute Base Score $(AB_m)$ | Attribute Impact Factor $(AIF_m)$ |
|---|---|---|---|
| BPA-lined can | Negative | 25 | 5 |
| Glass container | Neutral | 100 | 1 |
| Bottle-conditioned | Positive | 100 | 5 |

Figure 41A:
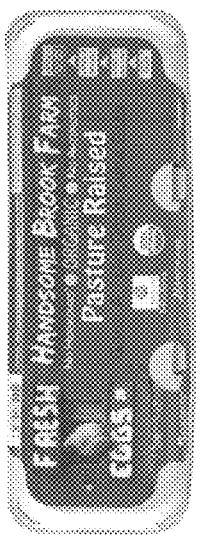

In certain embodiments, the system is configured to display a scorecard for the food product to the user, the scorecard showing the logos for the various attributes for the ingredient category (e.g., animal; plant; etc.) and the attribute base score $(AB_m)$ for each attribute (m). FIGS. 41A-41C illustrate a graphical representation of an example scorecard for an example food (e.g., Handsome Brook Farm Grade A organic pasture-raised large chicken eggs) in accordance with certain embodiments described herein. The example scorecard of FIGS. 41A-41C show twelve attributes for the food product, along with the attribute values, the attribute base scores $(AB_m)$ for each of the attribute values, the attribute impact factors $(AIF_m)$ for each of the attributes, and the extended score $(AB_m \times AIF_m)$ for each of the attributes for the food product. For each attribute, the attribute value can have a corresponding attribute base score which is indicative of an influence of the corresponding attribute value on the food's nutritional properties.

For example, FIG. 41D illustrates a graphical representation of example attribute base scores corresponding to various attribute values for the "husbandry" attribute for chickens in accordance with certain embodiments described herein. In this example, the attribute base score for the "pasture-raised" attribute value equals 100 while the attribute base score for the "caged" attribute value equals 40, indicating that food from "pasture-raised" chickens has more desirable nutritional properties than does food from "caged" chickens. Some attributes can be neutral with respect to the nutritional properties (e.g., can have little or no impact on the nutrition level or quality), while other attributes can directly affect the nutritional properties of the food. In certain embodiments, an attribute impact factor $(AIF_m)$ for each attribute can be used to indicate the relative importance of the attribute as compared to the other attributes of the food. For example, certain breeds of animals can be assigned more relative importance in a given food class in which one or more breeds are more nutritious or have better characteristics than other breeds for a given product class (e.g., the composition of milk differs for different cow breeds, with some having a higher fat content that is better for cream and butter; the nutrition of meat differs for different cow breeds, with some, such as piedmont cattle, having higher nutritional properties than other breeds). In these examples, the "breed" attribute can have a higher attribute impact factor which indicates the relative importance of the "breed" attribute as compared to the other attributes of the food. FIGS. 42A-42D schematically illustrate example beef attribute values in accordance with certain embodiments described herein.

In certain embodiments, each lower-level record of the plurality of lower-level records of the tables of the at least one computer database further comprises a plurality of attribute values, a plurality of attribute base scores ($AB_m$), and a plurality of attribute impact factors ($AIF_m$). Each attribute value is indicative of an attribute of the food member, and each attribute base score is indicative of an influence of the corresponding attribute value on the food member's degree of natural state (e.g., indicative of the deviation of the attribute value from a predetermined "idealized most natural version" of the attribute), and each attribute impact factor is indicative of a relative importance of the corresponding attribute as compared to the other attributes of the food member. For example, referring to FIG. 41D, the "idealized most natural version" of the husbandry attribute for chicken can be "pasture-raised," so the attribute base score for that attribute value can equal 100. The attribute value of "humanely-raised" can equal 75 (e.g., a relatively small deviation from the "idealized most natural version"), the attribute value of "cage-free" can equal 60 (e.g., a larger deviation from the "idealized most natural version"), and the attribute value of "caged" can equal 40 (e.g., the largest deviation from the "idealized most natural version").

In certain such embodiments, the method further comprises calculating (e.g., for each food member of the at least one selected table) an attribute quotient (AQ) given by: $AQ=\Sigma_m(AB_m \times AIF_m)/\Sigma_m(AIF_m)$, where $\Sigma_m(AB_m \times AIF_m)$ is a sum over the plurality of attributes of the products of the attribute base scores multiplied by the attribute impact factors and $\Sigma_m(AIF_m)$ is a sum over the plurality of attributes of the attribute impact factors. For example, for the food product of FIGS. 41A-41C, the attribute quotient is equal to $AQ=\Sigma_m(AB_m \times AIF_m)/\Sigma_m(AIF_m)$, with $\Sigma_m(AB_m \times AIF_m)=2688$ and $\Sigma_m(AIF_m)=35$, so $AQ=2688/35=77$.

The following table provides an example calculation of an attribute quotient for a food product (e.g., sunflower oil) from a particular food manufacturer in accordance with certain embodiments described herein:

| Attribute | Attribute Value | $AB_m$ | $AIF_m$ | Extended Score |
|---|---|---|---|---|
| Oil Grade | Pure | 65 | 1 | 65 |
| Oil Batch Size | Large | 10 | 1 | 10 |
| Organic | No | 80 | 1 | 80 |
| Oil Hydrogenation | Not Hydrogenated | 100 | 1 | 100 |
| Sunflower Seed Variety | Unspecified | 70 | 1 | 70 |
| Nut Product | Oil | 100 | 1 | 100 |
| Origin Certification | Unspecified | 70 | 1 | 70 |
| Oil Temperature | Solvent Extraction | 5 | 5 | 25 |
| Oil Form | Liquid | 100 | 1 | 100 |
| Sunflower Seed Origin | Unspecified | 70 | 1 | 70 |
| Oil Flavor | None | 100 | 1 | 100 |
| Package Type | Bottle | 100 | 1 | 100 |
| $AIF_m$ Sum; Extended Score Sum | | | 16 | 890 |

Attribute Quotient: (890/16) = 55

The following table provides another example calculation of an attribute quotient for a food product (e.g., Organic Apple, Granny Smith) in accordance with certain embodiments described herein:

| Attribute | Attribute Value | $AB_m$ | $AIF_m$ | Extended Score |
|---|---|---|---|---|
| Plant Organic | Organic | 100 | 5 | 500 |
| Plant Feed | Organic | 100 | 5 | 500 |
| Fruit Husbandry | Field Farmed | 100 | 5 | 500 |
| Apple Variety | Granny Smith | 100 | 1 | 100 |
| Apple Grade | Unspecified | 1 | 3 | 3 |
| Pesticides | Organic | 100 | 5 | 500 |
| Apple GMO | Organic | 100 | 5 | 500 |
| Apple Origin | USA | 80 | 1 | 80 |
| Plant Seasonality | Seasonal | 100 | 3 | 300 |
| Geo Indication | Unspecified | 0 | 0 | 0 |
| $AIF_m$ Sum; Extended Score Sum | | | 33 | 2983 |

Attribute Quotient: (2983/33) = 90

In certain embodiments, the method further comprises transmitting (e.g., from the computer system 100 to the user computing device 150 via the internet 140), in response to the query, the attribute quotients for the food members of the at least one selected table, to the user (e.g., to the user computing device 150).

Equalization

In certain embodiments, a total quotient is calculated for the food product by averaging the nutrition quotient and the attribute quotient (e.g., by adding the nutrition quotient and the attribute quotient and dividing by two). In certain other embodiments, an equalization calculation is applied to each of the nutrition quotient and the attribute quotient for this averaging. In certain embodiments, the equalization is used to account for a disparity between the number of attributes that were used to calculate the attribute quotient and the number of substances that were used to calculate the nutrition quotient. In certain embodiments, averaging using the equalization provides the same result as does averaging by adding the nutrition quotient and the attribute quotient and dividing by two, while in certain other embodiments, the results of these two calculations are different from one another.

In certain embodiments, a nutrition component of the equalization comprises (i) subtracting the sum of the nutrition impact factors from a large number (e.g., 100,000), (ii) multiplying the difference from (i) by the nutrition quotient, and (iii) summing the product from (ii) to the nutrition extended score sum. In certain embodiments, an attribute component of the equalization comprises (i) subtracting the sum of the attribute impact factors from a large number (e.g., 100,000), (ii) multiplying the difference from (i) by the attribute quotient, and (iii) summing the product from (ii) to the attribute extended score sum. The equalization further comprises summing the summed values from (iii) of the nutrition component of the equalization and from (iii) of the attribute component of the equalization and dividing the resulting sum by the sum of the two large numbers.

For example, the following two tables provide an example calculation of the nutrition component of the equalization and the attribute component of the equalization for a food product (e.g., Organic Apple, Granny Smith) in accordance with certain embodiments described herein:

| Organic Apple, Granny Smith | | | |
|---|---|---|---|
| Nutrition Equalization Component | | | |
| Nutrition Impact Factor Sum ($NIF_{sum}$); | | 17 | 1693 |
| Nutrition Extended Score Sum | | | |
| Apply Equalization: NQ × (100000-$IF_{sum}$) | 100 | 99983 | 9998300 |
| | | 100,000 | 9,999,993 |

| Organic Apple, Granny Smith | | | |
|---|---|---|---|
| Attribute Equalization Component | | | |
| Attribute Impact Factor Sum ($IF_{sum}$); | | 33 | 2983 |
| Attribute Extended Score Sum | | | |
| Apply Equalization: AQ × (100000-$AIF_{sum}$) | 90 | 99967 | 8,997,030 |
| | | 100,000 | 9,000,013 |

The equalization averaging for this example is then:

$$\{[NQ \times (100000-IF_{sum})]+[AQ \times (100000-AIF_{sum})]\}/200,000=95.$$

Per Calorie Unit of Measure

Certain embodiments described herein advantageously report the amount of a substance (e.g., nutrient; anti-nutrient) that is being delivered to the body, by calorie. The delivery of nutrients can be analogized to the delivery of packages. If the boxes being delivered are empty, then the cost of the delivery (e.g., the calories) are, in effect, wasted. However, if the recipient is receiving high quality products in the boxes (e.g., high levels of nutrients), then the cost of the delivery is worthwhile. A daily caloric budget (e.g., 2,000 calorie/day) can be considered as the budget to be spent on shipping of nutrients to the body. If the caloric budget is spent on junk food with little to no nutrition value (e.g. only empty boxes are being delivered), then the caloric cost does not justify the delivery. However, if the food has high quality nutrition, vitamins, minerals, etc., then the caloric cost makes sense.

Figure 43:
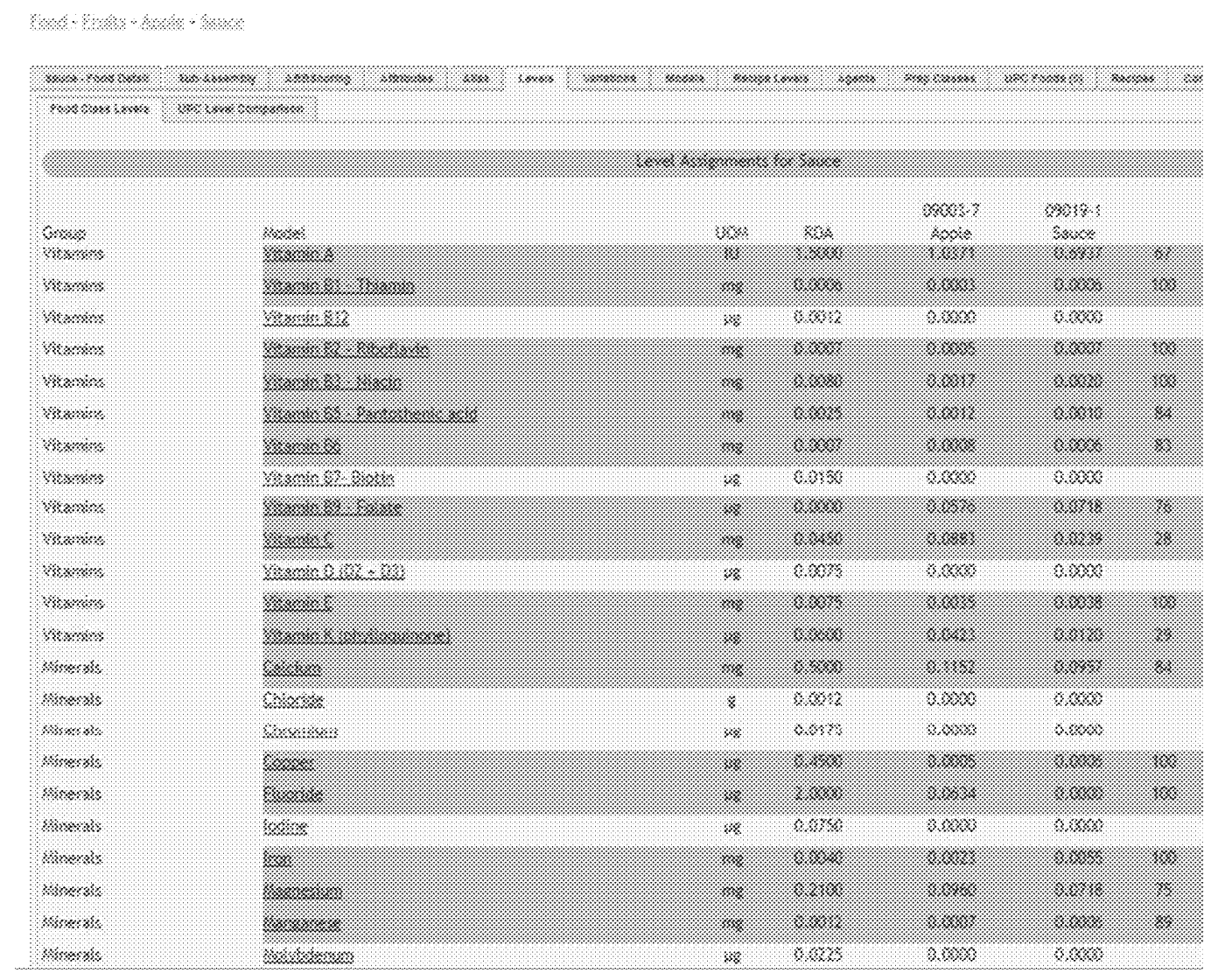

FIG. 43 schematically illustrates the nutrients for Apple Sauce and Fresh Apple expressed in terms of the recommended daily allowance (RDA) per calorie in accordance with certain embodiments described herein. Certain embodiments described herein advantageously provide a comparison of what the live/whole/raw/fresh state form of the food contains versus its derivative forms. This comparison is of interest to users because the goal of the food is to provide the nutrients of the original food, not lose them along the way. For example, Fresh Apple has 1.037 IU of Vitamin A per calorie while Apple Sauce has 0.6937 IU of Vitamin A per calorie, which equates to Apple Sauce containing 67% of the Vitamin A per calorie as does Fresh Apple.

Food Traceability Modals

Certain embodiments described herein utilize node-to-node networks, as described herein, to connect the various ingredients and food products. The node-to-node networks change ingredients from State A to State B. The connector between A and B is the action to convert it from A to B. It is possible to have more than one activity before a State change occurs. Process industries like beer brewing, may go through a few steps before a new intermediate product is formed.

The modals of certain embodiments show each of the processing steps that a particular food went through to get into a given form. Each of the processing steps can show the pressure, temperature, and/or speed at which the food was processed. When the food is processed in ambient conditions and not separated, then its nutrition levels will pass intact. However, if the food is separated or processed under impactful conditions, then its nutrition level is impacted. The result can show that the food quality score was reduced. Alternatively, the food nutrition and the food quality score could be enhanced by fortification (e.g., the addition of vitamins and minerals to food products), which can be used when a processing method destroys the vitamins or minerals. For example, the nutrition of the food can be decimated by certain processing methods or where parts of the food are removed to yield a given derivative product. In certain embodiments, fortification is handled in two parts: (i) the processing method where it is known to destroy the nutrition and will score lower, and (ii) the quality of the vitamins and minerals that are added back into the food which can be scored as individual ingredients into the food product.

Figure 44A:
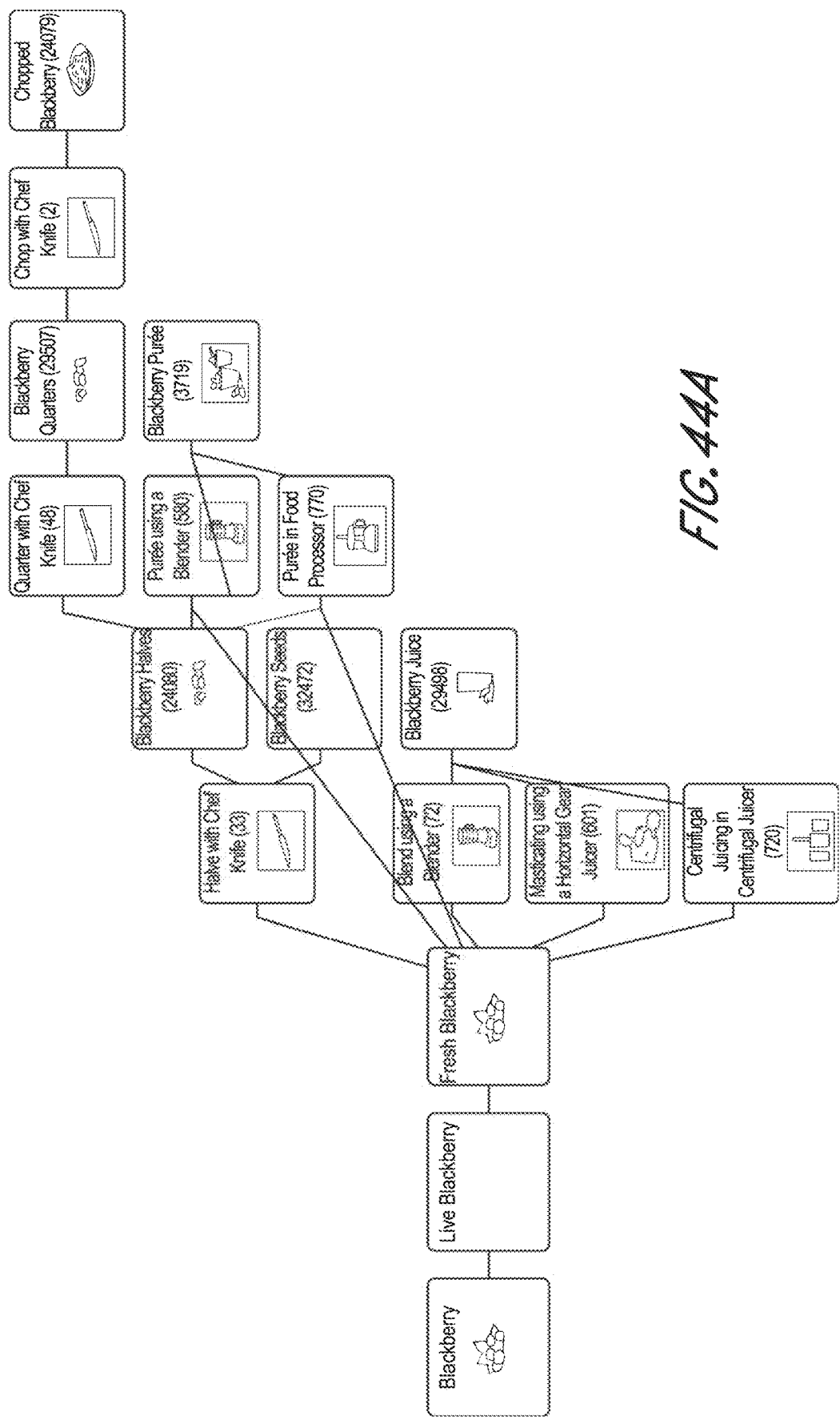
FIGS. 44A-44E schematically illustrate example modals for various foods in accordance with certain embodiments described herein.
Figure 44B:
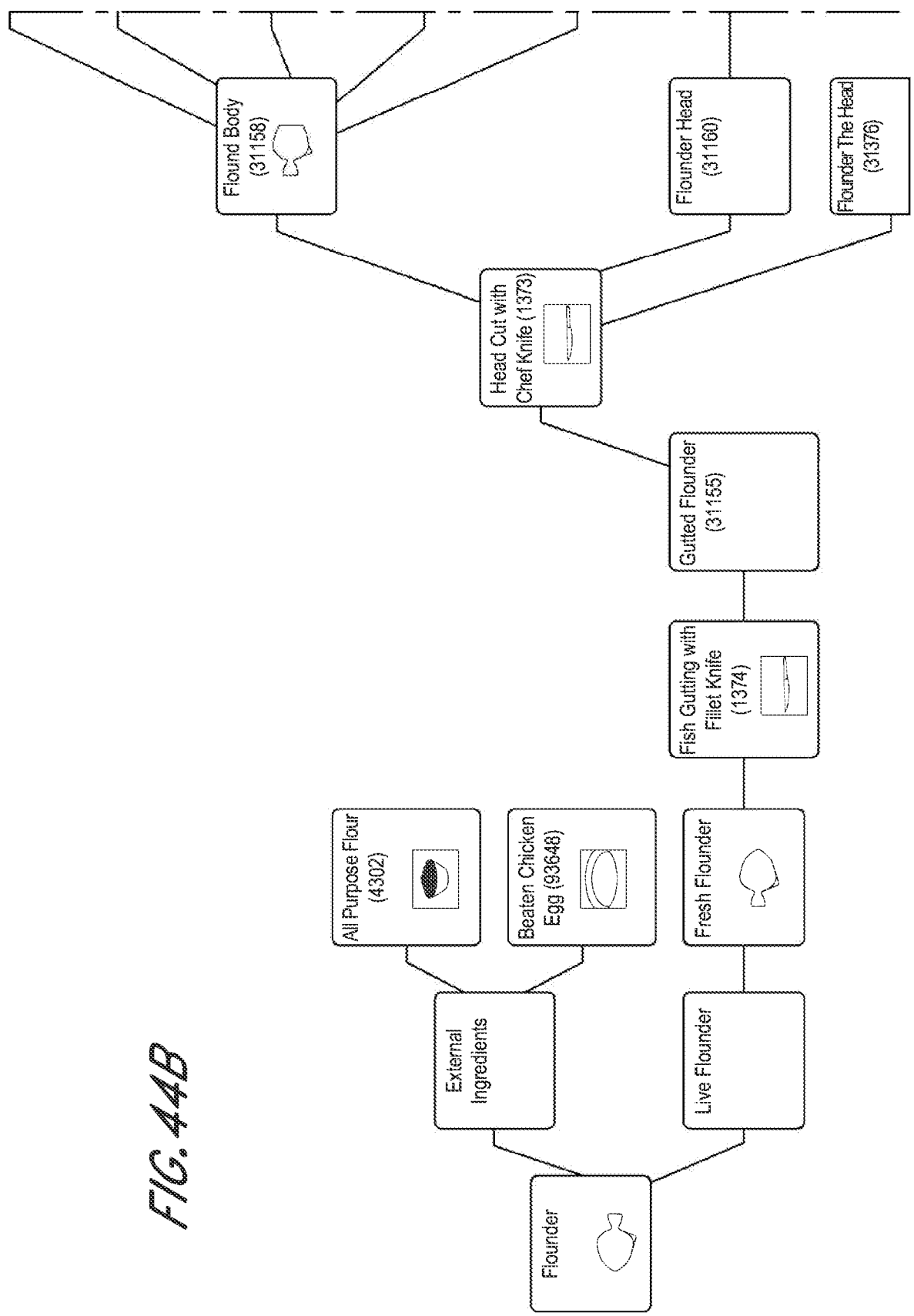
Figure 44B:
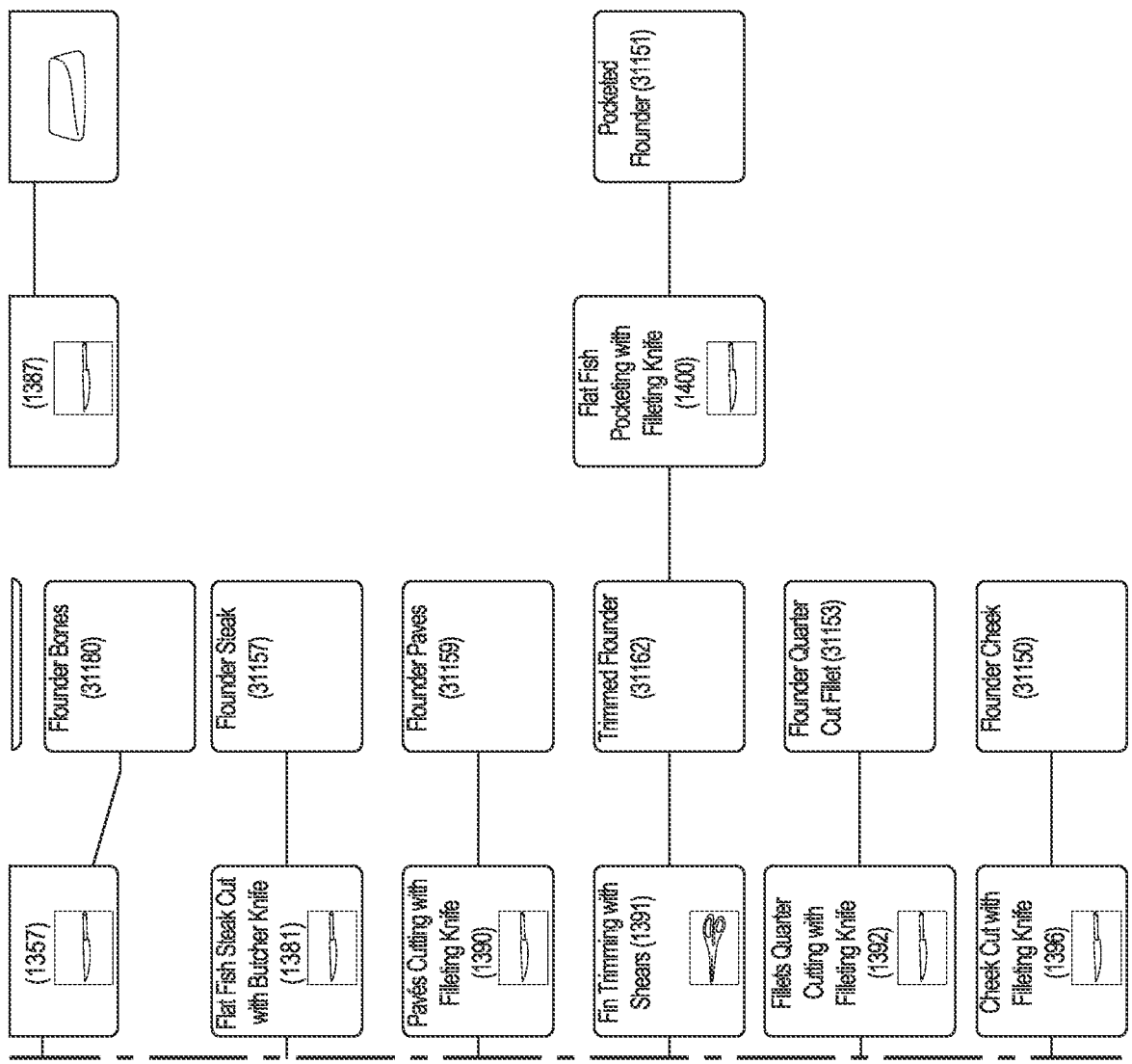
Figure 44C:
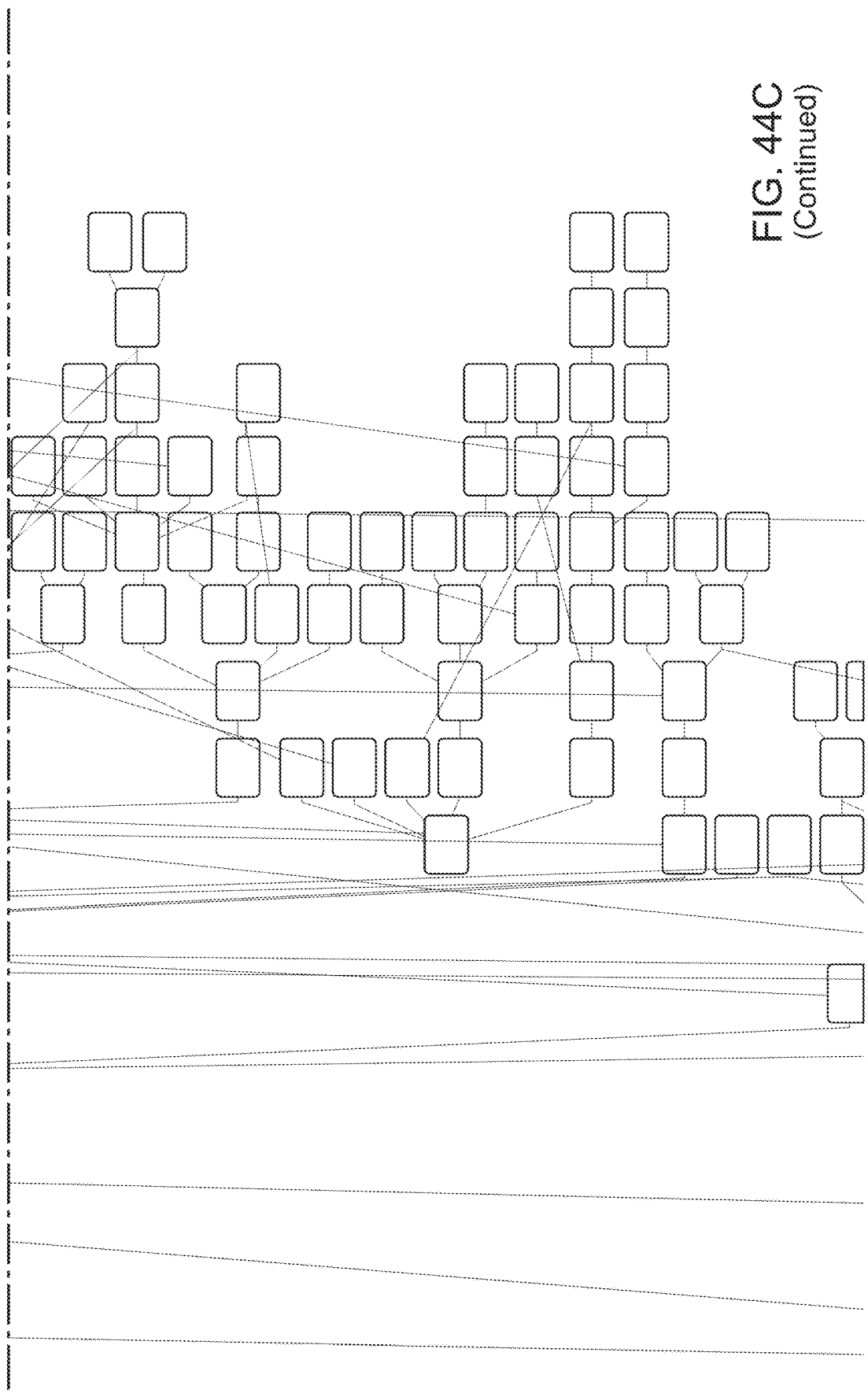
Figure 44D:
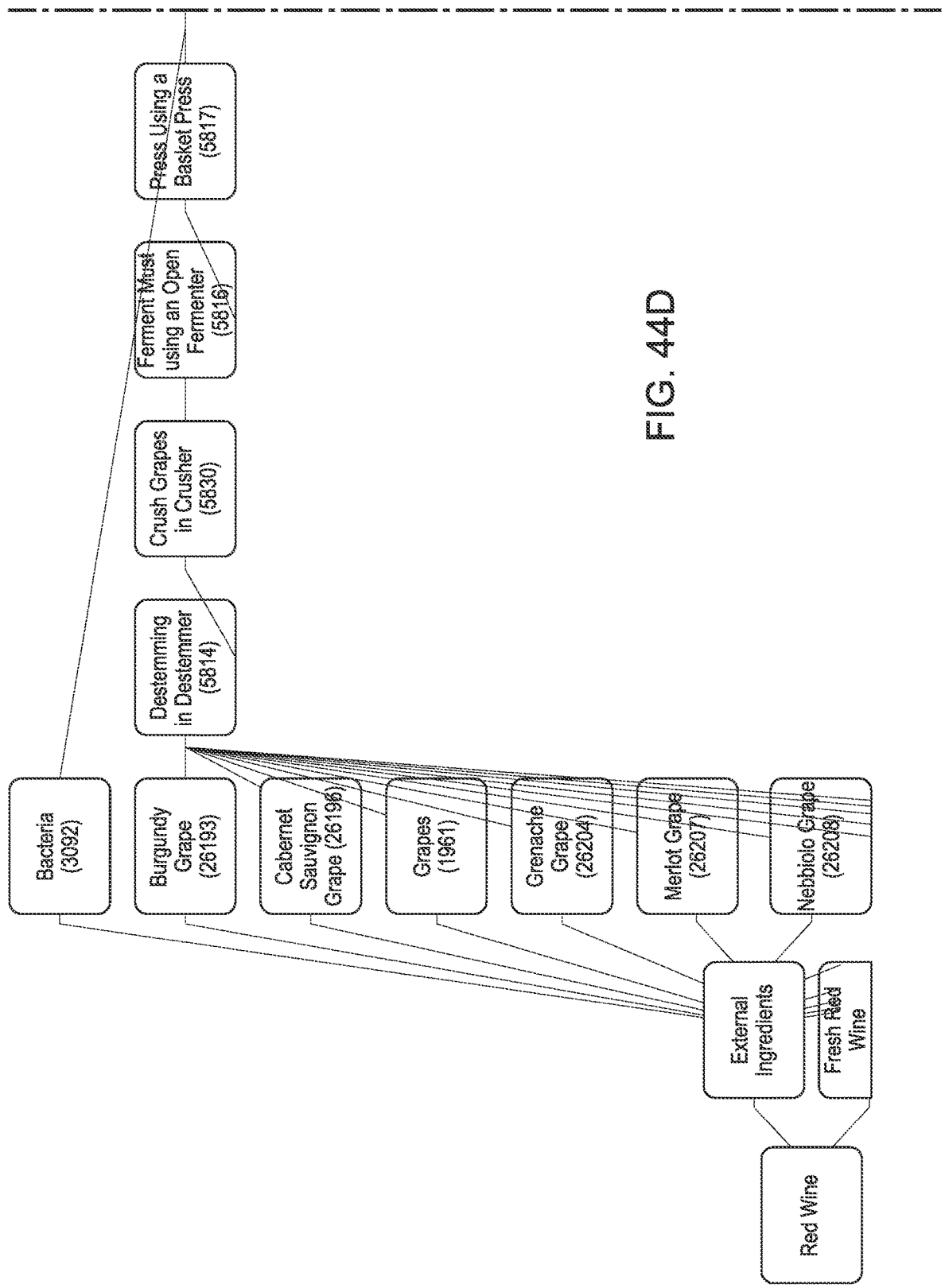
Figure 44D:
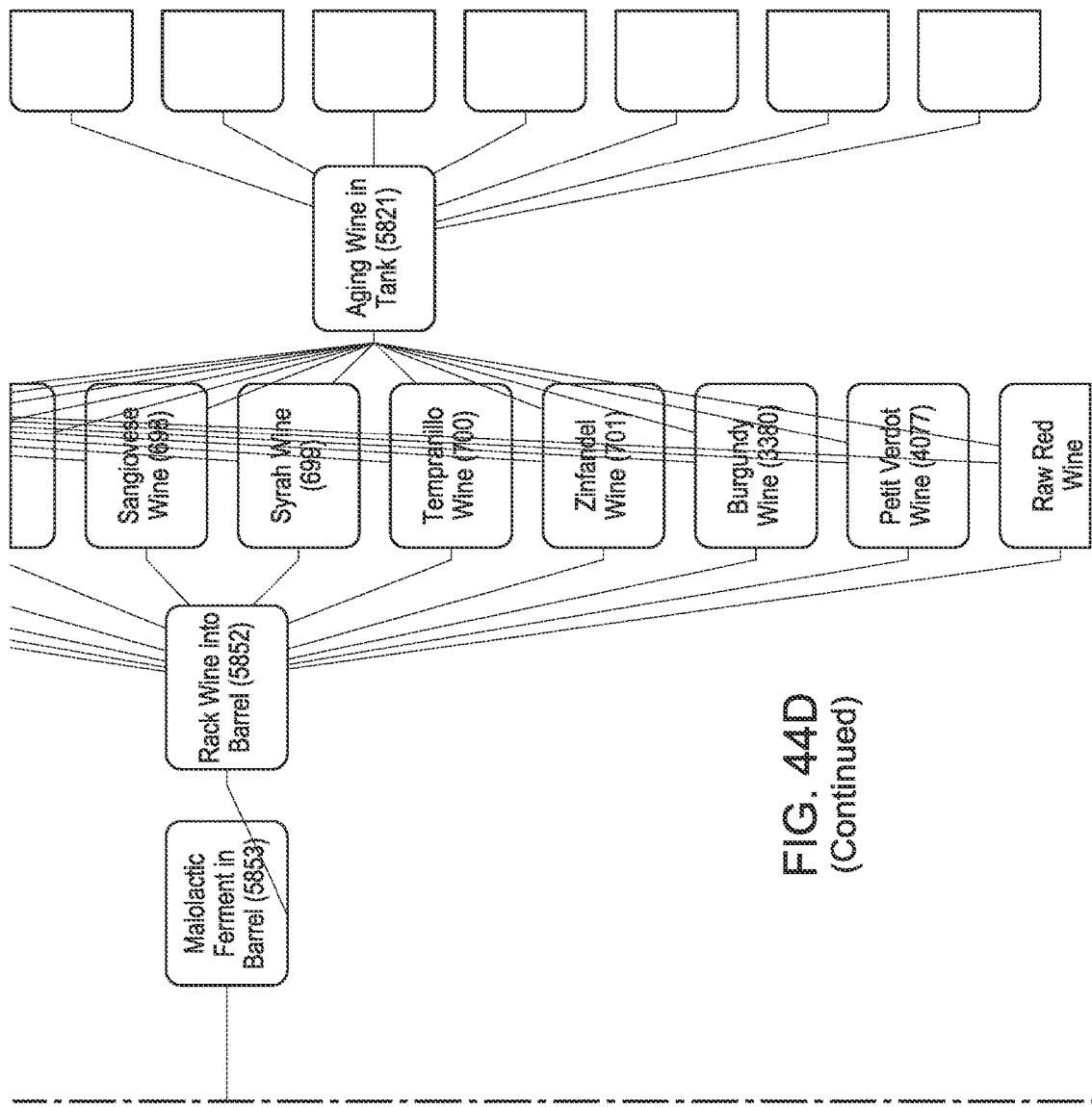
Figure 44E:
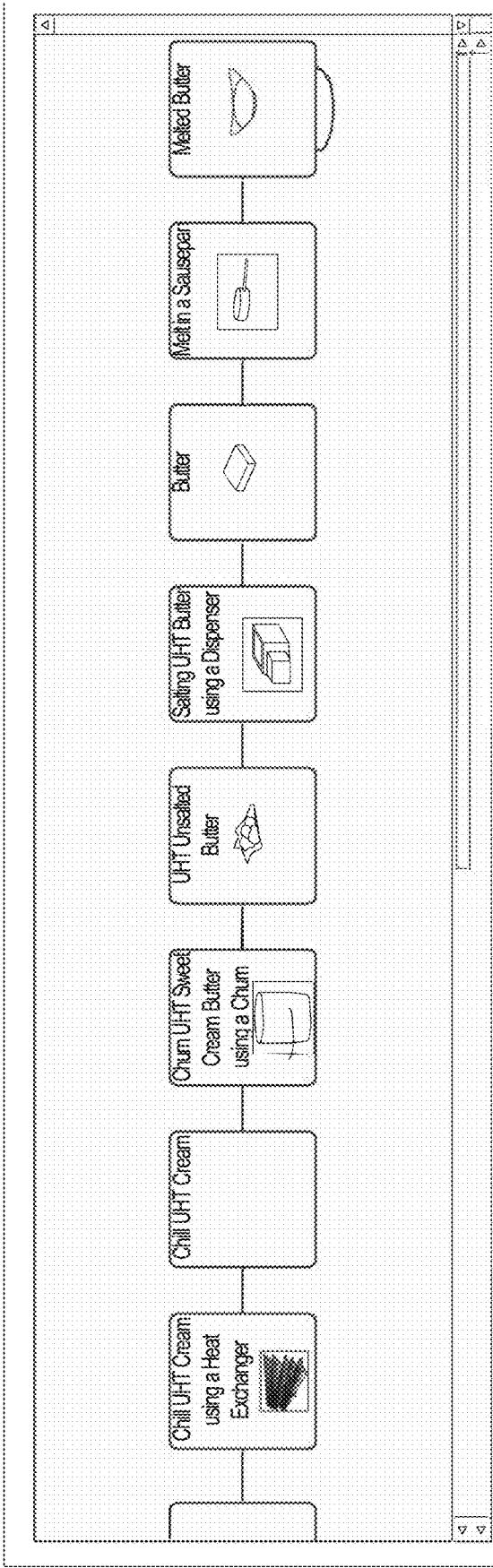

FIGS. 44A-44D schematically illustrate example modals for various foods in accordance with certain embodiments described herein. FIG. 44A shows an example modal for the Blackberry fresh fruit cuts network in accordance with certain embodiments described herein. FIG. 44B shows a portion of an example modal for the Flounder fresh fish cuts network in accordance with certain embodiments described herein. FIG. 44C shows a portion of an example modal for the Beef fresh meats cuts network in accordance with certain embodiments described herein. FIG. 44D shows a portion of an example modal for the Red Wine recipe network in accordance with certain embodiments described herein. FIG. 44E shows a portion of an example modal for Melted Butter in accordance with certain embodiments described herein.

In certain embodiments, the modal displays the ingredient such that the ingredient can be traced back from a recipe to its live/whole/raw/fresh state and/or to the vendor. For example, the modal can trace the steps of how the item was made, starting with its most basic raw material (e.g., for melted butter, the modal goes step-by-step back to Fresh Milk), allowing the user to see all the processing steps for how the item was made. In certain embodiments, the modals are displayed with one or more sliders configured to allow the user to move along the network to view various portions of the network. In certain embodiments, the food quality score changes as it goes from the fresh/whole/raw/live state to whatever derivative forms are part of its network, and the modal is configured to show where in the path that the derivative food lost some, most or all of its nutrients in the network.

Certain embodiments described herein provide information to the user regarding how the nutrition of the derivative products compares to the parent class foods from which the derivative products are made. Some of the derivative products are the result of pressure, temperature, speed, friction, separation, etc. which can negatively impact the nutrition of the food item. For example, Milk can be separated into Cream and Whey, which have different nutrition levels compared to Milk. The Whey can be made into Curds or it can be made into Whey Powder. For another example, Oil can be squeezed or extracted out of certain food items. The extraction (e.g., separation) means that other parts of the food item are no longer present, and some of these derivative food items can become very out of balance from the original food product. For another example, Fresh White Corn has a ratio of Omega-6 to Omega-3 of 33:1, while Corn Oil has a ratio of Omega-6 to Omega-3 of 46:1. Corn is already extremely high in Omega-6 compared to Omega-3, but making the Corn Oil makes it even more out of balance.

In certain embodiments described herein, every food name is taken literally. For example, if the manufacturer only lists "Corn" as an ingredient and there are no other intrinsic attributes in the ingredient list or on the package denoting any other quality parameters, then certain embodiments assume that it is the lowest grade/quality of that product category. For another example, if ground beef is called out, then it can receive the lowest of all intrinsic attributes scores. Of the twelve intrinsic attributes for beef, it can score as "Unspecified" in each. If the label says U.S. Beef, then the Origin score could be USA which would raise its score from "Unspecified."

The food manufacturers have an informational advantage over the consumer, and they will market their products by promoting the good attributes (e.g., making the good attributes prominent on the packaging and marketing materials) and hiding the bad attributes (e.g., by not specifying the real intrinsic attributes, they can pass off low quality industrial food). Certain embodiments described herein advantageously account for this lack of information to the consumer by assuming the worst and not hoping for the best. Certain embodiments described herein automatically punishes lack of disclosure (e.g., by defaulting to the lowest attribute value for any nondisclosed attribute) from a food manufacturer and rewards traceability and disclosure, thereby putting the consumer in the front seat and rewarding the best manufacturers.

Certain embodiments described herein include methods which are performed by computer hardware, software or both, comprising one or more modules or engines (e.g., hardware or software programs that perform a specified function; can be used in operating systems, subsystems, application programs, or by other modules or engines). The hardware used for certain embodiments described herein can take a wide variety of forms, including processors, network servers, workstations, personal computers, mainframe computers and the like. The hardware running the software will typically include one or more input devices, such as a mouse, trackball, touchpad, and/or keyboard, a display, and computer-readable memory media, such as one or more random-access memory (RAM) integrated circuits and data storage devices (e.g., tangible storage, non-transitory storage, flash memory, hard-disk drive). It will be appreciated that one or more portions, or all of the software code may be remote from the user and, for example, resident on a network resource, such as a LAN server, Internet server, network storage device, etc.

The software code which configures the hardware to perform in accordance with certain embodiments described herein can be downloaded from a network server which is part of a local-area network or a wide-area network (such as the Internet) or can be provided on a tangible (e.g., non-transitory) computer-readable medium, such as a CD-ROM or a flash drive. Various computer languages, architectures, and configurations can be used to practice the various embodiments described herein. For example, one or more modules or engines can be provided by one or more processors of one or more computers executing (e.g., running) computer code (e.g., one or more sets of instructions which are executable by the one or more processors of one or more computers). The computer code can be stored on at least one storage medium accessible by the one or more processors, as can other information (e.g., data) accessed and used by the one or more processors while executing the computer code.

Any process descriptions, elements, or blocks in the flow diagrams described herein and/or depicted in the attached figures should be understood as potentially representing modules, engines, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art. It will further be appreciated that the data and/or components described above may be stored on a computer-readable medium and loaded into memory of the computing device using a drive mechanism associated with a computer readable storing the computer executable components such as a CD-ROM, DVD-ROM, or network interface further, the component and/or data can be included in a single device or distributed in any manner. Accordingly, computing devices may be configured to implement the processes, algorithms and methodology of the present disclosure with the processing and/or execution of the various data and/or components described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although commonly used terms are used to describe the systems and methods of certain embodiments for ease of understanding, these terms are used herein to have their broadest reasonable interpretation, as described in more detail herein. Although various aspects of the disclosure are described with regard to illustrative examples and embodiments, one skilled in the art will appreciate that the disclosed embodiments and examples should not be construed as limiting. It should be emphasized that many variations and modifications may be made to the above-described embodiments, the elements of which are to be understood as being among other acceptable examples. All such modifications and variations are intended to be included herein within the scope of this disclosure.

What is claimed is:

1. A method of providing food-related information to a user, the method comprising:
   receiving, from a user computing device of a plurality of user computing devices, a user-generated query regarding at least one food;
   accessing, in response to the query, at least one computer database comprising a plurality of tables, each table of the plurality of tables comprising:
   a top-level record corresponding to a subject of the table; and
   a plurality of lower-level records that correspond to food members of the subject of the table, each lower-level record of the plurality of lower-level records comprising a plurality of nutrition values ($N_n$), each nutrition value indicative of an amount per calorie in the food member of a corresponding substance (n) of a plurality of substances;
   selecting at least one table of the plurality of tables, each selected table comprising a lower-level record corresponding to a food of the at least one food;
   determining, for each food member of the at least one selected table, a plurality of substance base scores ($SB_n$), each substance base score indicative of a comparison of the nutrition value ($N_n$) of the corresponding substance in the food member to a nutrition value ($N_n^*$) of the corresponding substance in a benchmark food member of the table of the food member;

determining, for each food member of the at least one selected table, a plurality of substance impact factors ($SiF_n$), each substance impact factor indicative of the nutrition value ($N_n^*$) of the corresponding substance in the benchmark food member relative to a dietary daily allowance of the corresponding substance per calorie ($DDA_n$) of the corresponding substance;

calculating, for each food member of the at least one selected table, a nutrition quotient (NQ) given by: $NQ=\Sigma_n(SB_n \times SIF_n)/\Sigma_n(SIF_n)$, where $\Sigma_n(SB_n \times SIF_n)$ is a sum over the plurality of substances of the products of the substance base scores multiplied by the substance impact factors and $\Sigma_n(SIF_n)$ is a sum over the plurality of substances of the substance impact factors; and transmitting, in response to the query, the nutrition quotients for each of the food members of the at least one selected table to the user computing device.

2. The method of claim 1, wherein the substances in the food member comprise nutrients and anti-nutrients.

3. The method of claim 2, wherein the substance base score ($SB_n$) for a nutrient is given by:
for $[100 \times (N_n/N_n^*)] \geq 100$, $SB_n=100$;
for $100 > [100 \times (N_n/N_n^*)] > 0$, $SB_n=[100 \times (N_n/N_n^*)]$; and
for $[100 \times (N_n/N_n^*)]=0$, $SB_n=1$.

4. The method of claim 2, wherein the substance base score ($SB_n$) for an anti-nutrient is given by:
for $[100 \times (N_n^*/N_n)] \geq 100$, $SB_n=100$;
for $100 > [100 \times (N_n^*/N_n)] > 0$, $SB_n=[100 \times (N_n^*/N_n)]$; and
for $[100 \times (N_n^*/N_n)]=0$, $SB_n=1$.

5. The method of claim 1, further comprising identifying the benchmark food member of each selected table by:
calculating, for each food member of the selected table, a benchmarking quotient (BQ) given by: $BQ=\Sigma_n(N_n/DDA_n)/\Sigma_n(1)$, where $\Sigma_n(N_n/DDA_n)$ is a sum over the plurality of substances of the nutrition values ($N_n$) divided by the dietary daily allowance of the substance per calorie ($DDA_n$) and $\Sigma_n(1)$ is the number of substances; and
identifying the food member of the selected table having the largest benchmarking quotient as the benchmark food member.

6. The method of claim 1, wherein the dietary daily allowance of the substance per calorie ($DDA_n$) corresponds to a diet having 2,000 calories per day.

7. The method of claim 1, wherein each lower-level record of the plurality of lower-level records further comprises a plurality of attribute values, a plurality of attribute base scores ($AB_m$), and a plurality of attribute impact factors ($AIF_m$), each attribute value indicative of an attribute of the food member, each attribute base score indicative of an influence of the corresponding attribute value on the food member's degree of natural state, and each attribute impact factor indicative of a relative importance of the corresponding attribute as compared to the other attributes of the food member, the method further comprising:
calculating, for each food member of the at least one selected table, an attribute quotient (AQ) given by: $AQ=\Sigma_m(AB_m \times AIF_m)/\Sigma_m(AIF_m)$, where $\Sigma_m(AB_m \times AIF_m)$ is a sum over the plurality of attributes of the products of the attribute base scores multiplied by the attribute impact factors and $\Sigma_m(AIF_m)$ is a sum over the plurality of attributes of the attribute impact factors.

8. The method of claim 7, further comprising transmitting, in response to the query, the attribute quotients for each of the food members of the at least one selected table, to the user.

9. The method of claim 7, further comprising:
calculating, for each food member of the at least one selected table, a total quotient equal to an average of the attribute quotient and the nutrition quotient; and
transmitting, in response to the query, the total quotients for the food members of the at least one selected table, to the user computing device.

10. The method of claim 7, wherein the at least one food comprises a single ingredient.

11. A computer system for providing food-related information to a user, the system comprising:
at least one processor configured to provide food-related information to a plurality of user computing devices in response to food-related queries received from the plurality of user computing devices; and
at least one memory device in operative communication with the at least one processor, the at least one memory device operative to store at least one computer database comprising a plurality of tables, each table of the plurality of tables having a food-related subject, each table of the plurality of tables comprising a top-level record corresponding to the subject of the table and a plurality of lower-level records that correspond to members of the subject of the table, each lower-level record of the plurality of lower-level records comprising a plurality of nutrition values ($N_n$), each nutrition value indicative of an amount per calorie in the food member of a corresponding substance (n) of a plurality of substances,
the at least one processor configured to:
receive a user-generated query regarding at least one food from a user computing device of the plurality of user computing devices;
access, in response to the query, the at least one computer database;
select at least one table of the plurality of tables, each selected table comprising a lower-level record corresponding to a food of the at least one food;
determine, for each food member of the at least one selected table, a plurality of substance base scores ($SB_n$), each substance base score indicative of a comparison of the nutrition value ($N_n$) of the corresponding substance in the food member to a nutrition value ($N_n^*$) of the corresponding substance in a benchmark food member of the table of the food member;
determine, for each food member of the at least one selected table, a plurality of substance impact factors ($SIF_n$), each substance impact factor indicative of the nutrition value ($N_n^*$) of the corresponding substance in the benchmark food member relative to a dietary daily allowance of the corresponding substance per calorie ($DDA_n$) of the corresponding substance;
calculate, for each food member of the at least one selected table, a nutrition quotient (NQ) given by: $NQ=\Sigma_n(SB_n \times SIF_n)/\Sigma_n(SIF_n)$, where $\Sigma_n(SB_n \times SIF_n)$ is a sum over the plurality of substances of the products of the substance base scores multiplied by the substance impact factors and $\Sigma_n(SIF_n)$ is a sum over the plurality of substances of the substance impact factors; and transmit, in response to the query, the nutrition quotients for each of the food members of the at least one selected table to the user computing device.

12. The system of claim 11, wherein the substances in the food member comprise nutrients and anti-nutrients.

13. The system of claim 12, wherein the substance base score ($SB_n$) for a nutrient is given by:
for $[100 \times (N_n/N_n^*)] \geq 100$, $SB_n = 100$;
for $100 > [100 \times (N_n/N_n^*)] > 0$, $SB_n = [100 \times (N_n/N_n^*)]$; and
for $[100 \times (N_n/N_n^*)] = 0$, $SB_n = 1$.

14. The system of claim 12, wherein the substance base score ($SB_n$) for an anti-nutrient is given by:
for $[100 \times (N_n^*/N_n)] \geq 100$, $SB_n = 100$;
for $100 > [100 \times (N_n^*/N_n)] > 0$, $SB_n = [100 \times (N_n^*/N_n)]$; and
for $[100 \times (N_n^*/N_n)] = 0$, $SB_n = 1$.

15. The system of claim 11, wherein the at least one processor is further configured to identify the benchmark food member of each selected table by:
calculating, for each food member of the selected table, a benchmarking quotient (BQ) given by: $BQ = \Sigma_n(N_n/DDA_n)/\Sigma_n(1)$, where $\Sigma_n(N_n/DDA_n)$ is a sum over the plurality of substances of the nutrition values ($N_n$) divided by the dietary daily allowance of the substance per calorie ($DDA_n$) and $E_n(1)$ is the number of substances; and
identifying the food member of the selected table having the largest benchmarking quotient as the benchmark food member.

16. The system of claim 11, wherein the dietary daily allowance of the substance per calorie ($DDA_n$) corresponds to a diet having 2,000 calories per day.

17. The system of claim 11, wherein each lower-level record of the plurality of lower-level records further comprises a plurality of attribute values, a plurality of attribute base scores ($AB_m$), and a plurality of attribute impact factors ($AIF_m$), each attribute value indicative of an attribute of the food member, each attribute base score indicative of an influence of the corresponding attribute value on the food member's degree of natural state, and each attribute impact factor indicative of a relative importance of the corresponding attribute as compared to the other attributes of the food member, the at least one processor further configured to:
calculate, for each food member of the at least one selected table, an attribute quotient (AQ) given by: $AQ = \Sigma_m(AB_m \times AIF_m)/\Sigma_m(AIF_m)$, where $\Sigma_m(AB_m \times AIF_m)$ is a sum over the plurality of attributes of the products of the attribute base scores multiplied by the attribute impact factors and $\Sigma_m(AIF_m)$ is a sum over the plurality of attributes of the attribute impact factors.

18. The system of claim 17, wherein the at least one processor is further configured to transmit, in response to the query, the attribute quotients for the food members of the at least one selected table, to the user computing device.

19. The system of claim 17, wherein the at least one processor is further configured to:
calculate, for each food member of the at least one selected table, a total quotient equal to an average of the attribute quotient and the nutrition quotient; and
transmit, in response to the query, the total quotients for the food members of the at least one selected table, to the user computing device.

20. A non-transitory computer storage having stored thereon a computer program that instructs a computer system to provide food-related information by at least:
receiving, from a user computing device of a plurality of user computing devices, a user-generated query regarding at least one food;
accessing, in response to the query, at least one computer database comprising a plurality of tables, each table of the plurality of tables comprising:
a top-level record corresponding to a subject of the table; and
a plurality of lower-level records that correspond to food members of the subject of the table, each lower-level record of the plurality of lower-level records comprising a plurality of nutrition values ($N_n$), each nutrition value indicative of an amount per calorie in the food member of a corresponding substance (n) of a plurality of substances;
selecting at least one table of the plurality of tables, each selected table comprising a lower-level record corresponding to a food of the at least one food;
determining, for each food member of the at least one selected table, a plurality of substance base scores ($SB_n$), each substance base score indicative of a comparison of the nutrition value ($N_n$) of the corresponding substance in the food member to a nutrition value ($N_n^*$) of the corresponding substance in a benchmark food member of the table of the food member;
determining, for each food member of the at least one selected table, a plurality of substance impact factors ($SIF_n$), each substance impact factor indicative of the nutrition value ($N_n^*$) of the corresponding substance in the benchmark food member relative to a dietary daily allowance of the corresponding substance per calorie ($DDA_n$) of the corresponding substance;
calculating, for each food member of the at least one selected table, a nutrition quotient (NQ) given by: $NQ = \Sigma_n(SB_n \times SIF_n)/\Sigma_n(SIF_n)$, where $\Sigma_n(SB_n \times SIF_n)$ is a sum over the plurality of substances of the products of the substance base scores multiplied by the substance impact factors and $\Sigma_n(SIF_n)$ is a sum over the plurality of substances of the substance impact factors; and
transmitting, in response to the query, the nutrition quotients for each of the food members of the at least one selected table to the user computing device.

* * * * *

UNITED STATES PATENT AND TRADEMARK OFFICE
CERTIFICATE OF CORRECTION

PATENT NO. : 10,942,932 B2
APPLICATION NO. : 16/296028
DATED : March 9, 2021
INVENTOR(S) : Daniel Edwin Doble et al.

It is certified that error appears in the above-identified patent and that said Letters Patent is hereby corrected as shown below:

In the Claims

In Column 63, Line 8, Claim 1, delete "($SiF_n$)" and insert --($SIF_n$)--.

In Column 65, Line 24 (Approx.), Claim 15, delete "$E_n$" and insert --$\Sigma_n$--.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*